United States Patent
Borrajo

(10) Patent No.: US 11,767,528 B2
(45) Date of Patent: Sep. 26, 2023

(54) TARGETED TRANS-SPLICING USING CRISPR/CAS13

(71) Applicant: MASSACHUSETTS INSTITUTE OF TECHNOLOGY, Cambridge, MA (US)

(72) Inventor: Jacob Borrajo, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 108 days.

(21) Appl. No.: 16/994,230

(22) Filed: Aug. 14, 2020

(65) Prior Publication Data

US 2021/0071178 A1 Mar. 11, 2021

Related U.S. Application Data

(60) Provisional application No. 62/985,633, filed on Mar. 5, 2020, provisional application No. 62/888,210, filed on Aug. 16, 2019.

(51) Int. Cl.
  *C07H 21/04* (2006.01)
  *C12N 15/113* (2010.01)
  *C12N 9/22* (2006.01)

(52) U.S. Cl.
  CPC .............. *C12N 15/113* (2013.01); *C12N 9/22* (2013.01); *C12N 2310/20* (2017.05)

(58) Field of Classification Search
  None
  See application file for complete search history.

(56) References Cited

FOREIGN PATENT DOCUMENTS

| WO | WO2010012472 A1 | 2/2010 |
| WO | WO2013025461 A1 | 2/2013 |
| WO | WO2018071663 A1 | 4/2018 |
| WO | WO2019040664 A1 | 2/2019 |
| WO | WO0009734 A2 | 2/2020 |

OTHER PUBLICATIONS

Coady et al. "Restoration of SMN function: delivery of a trans-splicing RNA re-directs SMN2 pre-mRNA splicing." Molecular Therapy 15.8 (2007): 1471-1478.*
Koonin, Eugene V., Kira S. Makarova, and Feng Zhang. "Diversity, classification and evolution of CRISPR-Cas systems." Current opinion in microbiology 37 (2017): 67-78.*
PCT Application No. PCT/US20/46523, International Search Report and Written Opinion, dated Nov. 4, 2020, 17 pages.
Haroon Butt et al., Efficient CRISPR/Cas9-Mediated Genome Editing Using a Chimeric Single-Guide RNA Molecule, Frontiers in Plant Science, vol. 8, Aug. 24, 2017.
Silvana Konermann et al., Transcriptome Engineering with RNA-Targeting Type VI_D CRISPR Effectors, CELL, vol. 173, No. 3, Apr. 19, 2018, pp. 665-676.

* cited by examiner

*Primary Examiner* — Kimberly Chong
(74) *Attorney, Agent, or Firm* — Lathrop GPM LLP; Laura A. Labeots

(57) ABSTRACT

This disclosure provides compositions and methods of using these compositions to mediate a targeted trans-splicing event on a pre-mRNA in a cell.

19 Claims, 23 Drawing Sheets

Specification includes a Sequence Listing.

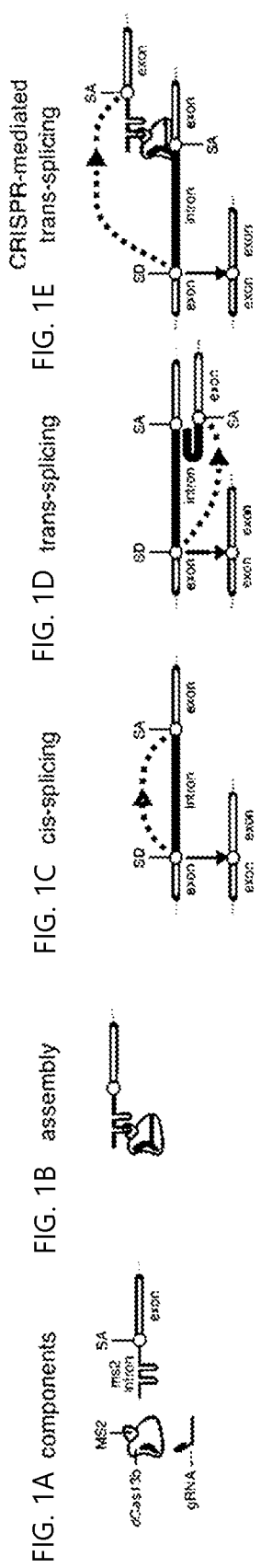

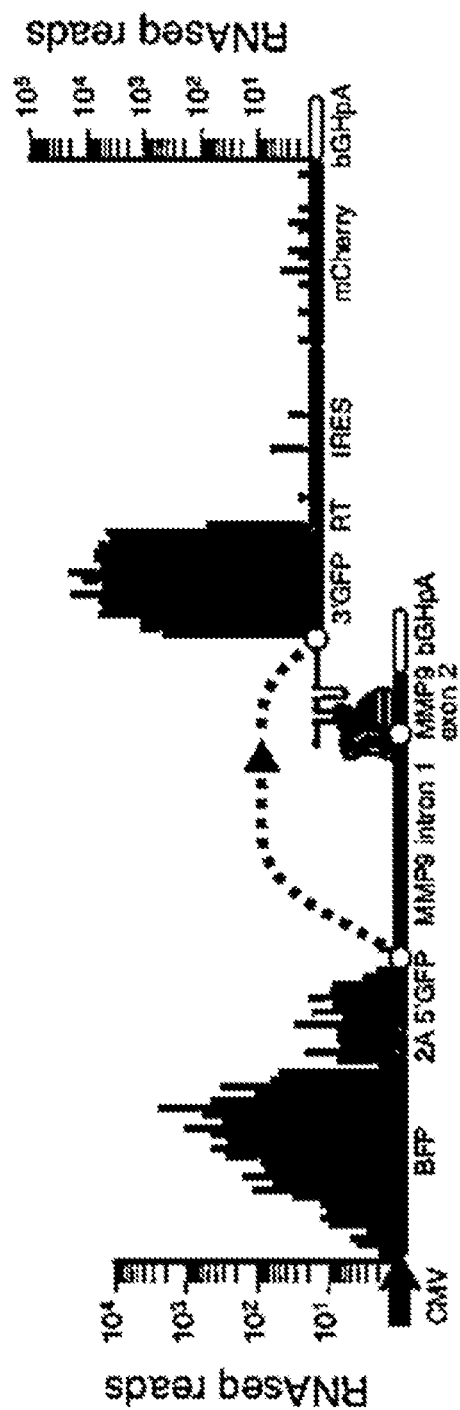
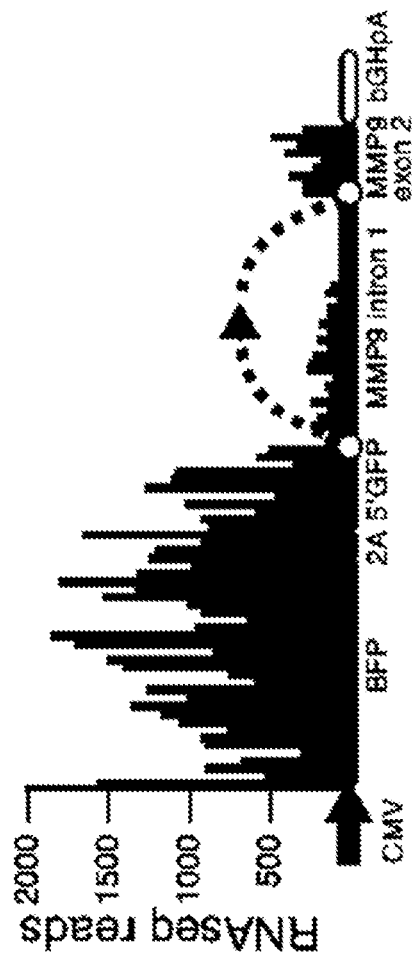
FIG. 4A
FIG. 4B

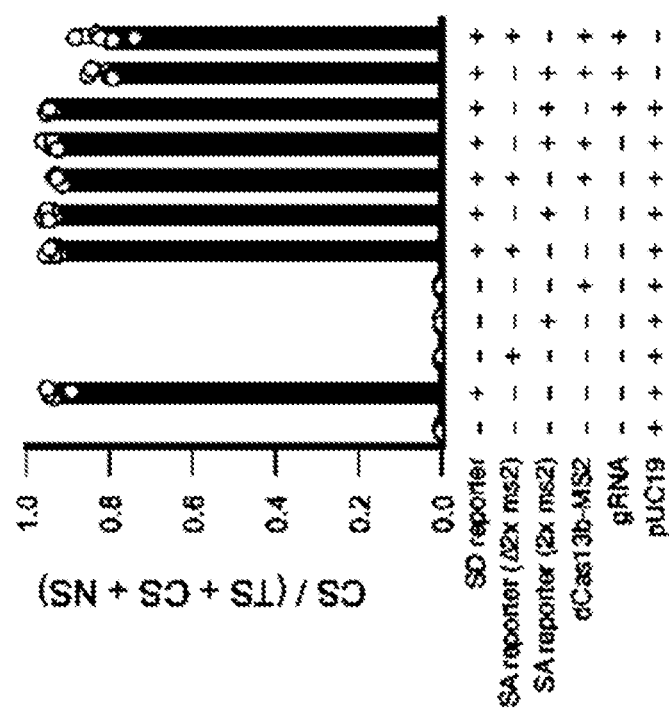

TARGETED TRANS-SPLICING USING CRISPR/CAS13

RELATED APPLICATION

This application claims priority to U.S. Provisional Application No. 62/888,210, filed on Aug. 16, 2019, and 62/985,633, filed on Mar. 5, 2020, each of which is incorporated by reference herein in its entirety.

STATEMENT REGARDING FEDERALLY SPONSORED RESEARCH

This invention was made with Government support under Grant No. HL141005 awarded by the National Institutes of Health (NIH). The Government has certain rights in the invention.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Aug. 14, 2020, is named 706829_083474-007PC_ST25.txt and is 475,491 bytes in size.

FIELD

The present disclosure relates to the field of CRISPR/Cas-mediated trans-splicing of nucleic acids for the treatment of disease.

BACKGROUND

Trans-splicing is a form of RNA processing where exons from two different primary pre-mRNA transcripts are joined end to end and ligated. This process is a promising strategy to treat various diseases using the spliceosome ribonucleoprotein complex. However, the efficiency and the specificity of trans-splicing of the current systems need to be improved upon to provide a more effective therapeutic strategy.

CRISPR/Cas systems have been used to edit genomic loci to treat diseases and disorders. This leads to a permanent edit to the DNA. The present invention provides a CRISPR/Cas system to target a trans-splicing element to a desired pre-mRNA sequence, and allows for the option of transient RNA repair while improving both the specificity and the efficiency of trans-splicing events.

SUMMARY

This disclosure provides methods and compositions for mediating a targeted trans-splicing event on a pre-mRNA in a cell. In one aspect, targeted trans-splicing system comprises: a nucleic acid-targeting CRISPR/Cas system; a nucleic acid guide; a specific RNA-binding domain; and a repair template comprising a splice donor and/or acceptor and an RNA sequence that hybridizes under physiological conditions to the specific RNA-binding domain.

In various embodiments, the nucleic acid guide is a RNA guide. In various embodiments, the nucleic acid guide is a DNA guide. In various embodiments the trans-splicing system comprises one nucleic acid guide. In various embodiments, the trans-splicing system comprises more than one nucleic acid guide. In various embodiments, the nucleic acid guides recognize multiple targets. In various embodiments, the nucleic acid guide targets a splice acceptor (SA) site. In various embodiments, the nucleic acid guide targets a splice donor (SD) site. In various embodiments, the nucleic acid guide targets a region near a splice site. In various embodiments, the nucleic acid guide targets a region within 200 nucleotides of a splice site. In various embodiments, the nucleic acid guide targets a region less than or equal to 100 nucleotides from a splice site. In various embodiments, the more than one nucleic acid guides target one nucleic acid of interest. In various embodiments, the more than one nucleic acid guides target multiple nucleic acids of interest.

In various embodiments, the CRISPR/Cas system comprises a Cas13 polypeptide. In various embodiments, the Cas13 is a nuclease-inactive Cas13 polypeptide (dCas13). In various embodiments, the Cas13 is a nuclease-active Cas13 polypeptide. In various embodiments, the specific RNA-binding domain comprises a viral protein. In various embodiments, the viral protein is a MS2 binding protein. In various embodiments, the viral protein is a λN protein. In various embodiments, the viral protein is a PP7 coat protein. In various embodiments, the viral protein is a QBeta coat protein.

In various embodiments, the viral protein is covalently bound to the CRISPR/Cas system. In various embodiments, the viral protein is not covalently bound to the CRISPR/Cas system. In various embodiments, the viral protein and CRISPR/Cas system is a fusion protein.

In one embodiment, the trans-splicing system comprises one repair template. In one embodiment, the trans-splicing system comprises more than one repair template. In various embodiments, the repair template is introduced as DNA. In various embodiments, the repair template is delivered as RNA.

In various embodiments, the repair template is expressed as RNA. In various embodiments, the repair template comprises a splice acceptor. In various embodiments, the repair template comprises a splice donor. In various embodiments, the repair template comprises one or more splice sites. In various embodiments, the repair template comprises an exon. In various embodiments, the repair template comprises more than one exon. In various embodiments, the repair template comprises an intron. the repair template comprises more than one intron. In various embodiments, the repair template comprises one or multiple sequences that hybridize to the target nucleic acid of interest. In various embodiments, at least one portion of the repair template comprises a ms2 hairpin that specifically binds to the MS2 binding protein. In various embodiments, the repair template comprises a boxB hairpin that specifically binds to the λN protein. In various embodiments, the repair template comprises a PP7 hairpin that specifically binds to the PP7 coat protein. In various embodiments, the repair template comprises a QBeta hairpin that specifically binds to the QBeta coat protein.

In various embodiments, the targeted trans-splicing system further comprises a cell. In various embodiments, at least one portion of the trans-splicing system is introduced into the cell.

In various embodiments, expression and/or activity of at least one portion of the trans-splicing system is transient. In various embodiments, the activity of at least one portion of the trans-splicing system is regulated by a small molecule. In various embodiments, the small molecule is selected from abscisic acid (ABA), rapamycin (or rapalog), FK506, Cyclosporine A, FK1012, Gibberellin3-AM, FKCsA, AP1903/AP20187, and Auxin. In various embodiments, the at least one portion is a Cas13 protein. In various embodiments, the Cas13 protein further comprises a small molecule binding domain. In various embodiments, the Cas13 protein and the small molecule binding domain are linked by a glycine-serine linker. In various embodiments, the small molecule binding domain is an ABA-binding domain. In various embodiments, the ABA-binding domain comprises an ABI1 polypeptide.

In various embodiments, the targeted trans-splicing system further comprises a viral protein. In various embodiments, the viral protein further comprises a small molecule binding domain. In various embodiments, the viral protein and the small molecule binding domain are linked by a glycine-serine linker. In various embodiments, the small molecule binding domain is an ABA-binding domain. In various embodiments, the ABA-binding domain comprises a PYL1 polypeptide. In various embodiments, the addition of ABA induces targeted trans-splicing of a target pre-mRNA.

In various embodiments, delivery of at least one portion of the trans-splicing system to the cell is viral. In various embodiments, the virus is a retrovirus, adenovirus, adeno-associated virus, herpes simplex virus, anellovirus, or baculovirus. In various embodiments, delivery of at least one portion of the trans-splicing system to a cell is non-viral. In various embodiments, the non-viral delivery system is selected from a cationic lipid vehicle, electroporation, calcium phosphate transfection, mechanical transfection, and nanoparticle delivery.

In various embodiments, the CRISPR/Cas system is targeted to a nucleic acid. In various embodiments, the nucleic acid is RNA. In various embodiments, the nucleic acid is DNA. In various embodiments, the CRISPR/Cas system is associated with RNA in the cell. In various embodiments, the RNA is a pre-mRNA. In various embodiments, the CRISPR/Cas system is associated with DNA in the cell. In various embodiments, the CRISPR/Cas system is not associated with DNA in the cell. In various embodiments, the CRISPR/Cas system mediates trans-splicing of pre-mRNA in the nucleus of the cell. In various embodiments, the CRISPR/Cas system mediates trans-splicing of pre-mRNA in the cytoplasm of the cell.

In various embodiments, the trans-splicing occurs in dividing cells. In various embodiments, the trans-splicing occurs in post-mitotic cells. In various embodiments, post-mitotic cells are neurons, myocytes, or adipocytes.

In various embodiments, expression of at least one portion of the trans-splicing system is inducible. In various embodiments, activity of at least one portion of the trans-splicing system is inducible.

In another aspect, provided herein is a method of mediating a targeted trans-splicing event on a pre-mRNA in a cell, the method comprises introducing at least one portion of a targeted trans-splicing CRISPR/Cas system into the cell. In one aspect, the CRISPR/Cas system comprises: a nucleic acid-targeting CRISPR/Cas system; a nucleic acid guide that specifically hybridizes to a nucleic acid locus of interest; a specific RNA-binding domain; and a repair template comprising a splice donor and/or a splice acceptor and an RNA sequence that hybridizes under physiological conditions to the specific RNA-binding domain.

In one embodiment, the nucleic acid guide comprises RNA. In another embodiment, the nucleic acid guide comprises DNA.

In one embodiment, a single nucleic acid guide is introduced into the cell. In another embodiment, multiple nucleic acid guides are introduced into the cell.

In one embodiment, the multiple nucleic acid guides target one nucleic acid of interest. In another embodiment, the multiple nucleic acid guides target more than one nucleic acid of interest.

In various embodiments, the nucleic acid guide targets a splice acceptor (SA) site. In other embodiments, the nucleic acid guide targets a splice donor (SD) site.

In various embodiments, the nucleic acid guide targets a region near the splice site.

In various embodiments, the nucleic acid guide targets a region within 200 nucleotides of the splice site. In other embodiments, the nucleic acid guide targets a region less than or equal to 100 nucleotides of the splice site.

In various embodiments, a plurality of nucleic acid guides is delivered to a plurality of cells. In various embodiments, the CRISPR/Cas system comprises a Cas13 polypeptide.

In various embodiments, the Cas13 polypeptide is a Cas13b polypeptide. In various embodiments, the Cas13b polypeptide is a nuclease-inactive Cas13b (dCas13b). In various embodiments, the Cas13b polypeptide is a nuclease-active Cas13b.

In various embodiments, the specific RNA-binding domain comprises a viral protein. In various embodiments, the viral protein is a MS2 binding protein. In various embodiments, the viral protein is a $\lambda$N protein.

In various embodiments, the viral protein is a PP7 coat protein. In various embodiments, the viral protein is a QBeta coat protein.

In various embodiments, the viral protein is covalently bound to the CRISPR/Cas system. In various embodiments, the viral protein is not covalently bound to the CRISPR/Cas system. In various embodiments, the viral protein and CRISPR/Cas system is a fusion protein.

In various embodiments, the trans-splicing system comprises one splice acceptor repair template. In various embodiments, the trans-splicing system comprises more than one splice acceptor repair template. In various embodiments, the trans-splicing system comprises one splice donor repair template.

In various embodiments, the trans-splicing system comprising more than one splice donor repair template.

In various embodiments, the repair template comprises a ms2 hairpin that specifically binds to the MS2 binding protein. In various embodiments, the repair template comprises a boxB hairpin that specifically binds to the $\lambda$N protein.

In various embodiments, the repair template comprises a PP7 hairpin that specifically binds to the PP7 coat protein. In various embodiments, the repair template comprises a QBeta hairpin that specifically binds to the QBeta coat protein.

In various embodiments, expression of at least one portion of the trans-splicing system is transient. In various embodiments, the activity of at least one portion of the trans-splicing system is transient. In various embodiments, the activity of at least one portion of the trans-splicing system is regulated by a small molecule. In various embodiments, the small molecule is selected from abscisic acid (ABA), rapamycin (or rapalog), FK506, Cyclosporine A, FK1012, Gibberellin3-AM, FKCsA, AP1903/AP20187, and Auxin.

In various embodiments, at least one portion of the trans-splicing system comprises a Cas13 polypeptide. In various embodiments, the Cas13 polypeptide further comprises a small molecule binding domain.

In various embodiments, the Cas13 polypeptide and the small molecule binding domain are linked by a glycine-serine linker. In various embodiments, the small molecule binding domain is an ABA-binding domain.

In various embodiments, the ABA-binding domain comprises an ABI1 polypeptide. In various embodiments, the method further comprises a viral protein. In various embodiments, the viral protein further comprises a small molecule binding domain. In various embodiments, the viral protein and the small molecule binding domain are linked by a glycine-serine linker.

In various embodiments, the small molecule binding domain is an ABA-binding domain.

In various embodiments, the ABA-binding domain comprises a PYL1 polypeptide.

In various embodiments, the addition of ABA induces targeted trans-splicing of a target pre-mRNA.

In various embodiments, delivery of at least one portion of the trans-splicing system to a cell is viral.

In various embodiments, the virus is a retrovirus, adenovirus, adeno-associated virus, herpes simplex virus, anellovirus or baculovirus.

In various embodiments, delivery of at least one portion of the trans-splicing system to a cell is non-viral.

In various embodiments, the non-viral delivery system is selected from a cationic lipid vehicle, electroporation, calcium phosphate transfection, mechanical transfection, and nanoparticle delivery.

In various embodiments, the CRISPR/Cas system associates with RNA in the cell.

In various embodiments, the RNA is a pre-mRNA.

In various embodiments, the CRISPR/Cas system associates with DNA in the cell.

In various embodiments, the CRISPR/Cas system does not associate with DNA in the cell.

In various embodiments, the CRISPR/Cas system mediates trans-splicing of pre-mRNA in the nucleus of the cell.

In various embodiments, the CRISPR/Cas system mediates trans-splicing of pre-mRNA in the cytoplasm of the cell.

In various embodiments, the CRISPR/Cas system mediates trans-splicing of a pre-mRNA at intron-exon junctions.

In various embodiments, wherein the CRISPR/Cas system mediates trans-splicing of a pre-mRNA at exon-intron junctions.

In various embodiments, the splice repair template does not comprise a splice acceptor.

In various embodiments, the splice repair template does not comprise a splice donor.

In various embodiments, the splice repair template comprises both a splice acceptor and a splice donor.

In various embodiments, the CRISPR/Cas system mediates trans-splicing of a pre-mRNA at the 5' end of the pre-mRNA. In various embodiments, the CRISPR/Cas system mediates trans-splicing of a pre-mRNA at the 3' end of the pre-mRNA. In various embodiments, the CRISPR/Cas system mediates trans-splicing of a pre-mRNA at an internal site within a pre-mRNA. In various embodiments, the CRISPR/Cas system mediates trans-splicing of a pre-mRNA within the 3' untranslated region (UTR). In various embodiments, the CRISPR/Cas system mediates trans-splicing of a pre-mRNA within the 5' untranslated region (UTR).

In various embodiments, the cell is a dividing cell. In various embodiments, the cell is a post-mitotic cell.

In various embodiments, the post-mitotic cell is selected from the group consisting of a neuron, myocyte, and adipocyte.

In various embodiments, expression of at least one portion of the trans-splicing system is inducible.

In various embodiments, activity of at least one portion of the trans-splicing system is inducible.

In various embodiments, the cell is in a subject suffering from a disease or disorder.

In various embodiments, the disease or disorder is a neurodegenerative, neurological, or neuromuscular disease or disorder.

In various embodiments, the neurodegenerative, neurological, or neuromuscular disease or disorder is selected from the group consisting of spinal muscular atrophy, Rett Syndrome, Angelman syndrome, Parkinson's disease, Alzheimer's disease, Huntington's disease, frontotemporal dementia, lysosomal storage diseases, multiple sclerosis, and amyotrophic lateral sclerosis (ALS).

In yet another aspect, disclosed herein is a targeted trans-splicing system comprising: a nucleic acid binding protein domain; a specific RNA-binding domain; and a repair template comprising a splice donor and/or a splice acceptor and an RNA sequence that hybridizes under stringent conditions to the specific RNA-binding domain.

In various embodiments, the nucleic acid binding protein domain targets a splice acceptor (SA) site. In various embodiments, the nucleic acid binding protein domain targets a splice donor (SD) site. In various embodiments, the specific RNA-binding domain comprises a viral protein. In various embodiments, the viral protein is a MS2 binding protein. In various embodiments, the viral protein is λN protein. In various embodiments, the viral protein is a PP7 coat protein. In various embodiments, the viral protein is a QBeta coat protein. In various embodiments, the viral protein is covalently bound to the nucleic acid binding protein domain. In various embodiments, the viral protein is not covalently bound to the nucleic acid binding protein domain. In various embodiments, the viral protein and nucleic acid binding protein domain is a fusion protein.

In various embodiments, the trans-splicing system comprises one splice acceptor repair template. In various embodiments, the trans-splicing system comprises more than one splice acceptor repair template. In various embodiments, the trans-splicing system comprises one splice donor repair template. In various embodiments, the trans-splicing system comprises more than one splice donor repair template. In various embodiments, the trans-splicing system comprises a repair template comprising a splice donor and/or a splice acceptor. In various embodiments, at least one portion of the repair template comprises a ms2 hairpin that specifically binds to the MS2 binding protein. In various embodiments, the splice repair template comprises a boxB hairpin that specifically binds to the λN protein. In various embodiments, the splice repair template comprises a PP7 hairpin that specifically binds to the PP7 coat protein. In various embodiments, the splice repair template comprises a QBeta hairpin that specifically binds to the QBeta coat protein.

In various embodiments, the targeted trans-splicing system further comprises a cell. In various embodiments, at least one portion of the trans-splicing system is introduced into the cell.

In various embodiments, expression and/or activity of at least one portion of the trans-splicing system is transient. In various embodiments, the activity of at least one portion of the trans-splicing system is regulated by a small molecule. In various embodiments, the small molecule is selected from abscisic acid (ABA), rapamycin (or rapalog), FK506, Cyclosporine A, FK1012, Gibberellin3-AM, FKCsA, AP1903/AP20187, and Auxin. In various embodiments, at least one portion is the nucleic acid binding protein domain.

In various embodiments, the nucleic acid binding protein domain further comprises a small molecule binding domain. In various embodiments, the nucleic acid binding protein domain and the small molecule binding domain are linked by a glycine-serine linker. In various embodiments, the small molecule binding domain is an ABA-binding domain. In various embodiments, the ABA-binding domain comprises an ABI1 polypeptide. In various embodiments, the trans-splicing system further comprises a viral protein. In various embodiments, the viral protein further comprises a small molecule binding domain. In various embodiments, the viral protein and the small molecule binding domain are linked by a glycine-serine linker. In various embodiments, the small molecule binding domain is an ABA-binding domain. In various embodiments, the ABA-binding domain comprises a PYL1 polypeptide. In various embodiments, the addition of ABA induces targeted trans-splicing of a target pre-mRNA.

In various embodiments, delivery of at least one portion of the trans-splicing system to the cell is viral. In various embodiments, the virus is a retrovirus, adenovirus, adeno-associated virus, herpes simplex virus, anellovirus, or baculovirus. In various embodiments, delivery of at least one portion of the trans-splicing system to a cell is non-viral. In various embodiments, the non-viral delivery system is selected from a cationic lipid vehicle, electroporation, calcium phosphate transfection, mechanical transfection, and nanoparticle delivery.

In various embodiments, the nucleic acid binding protein domain is targeted to DNA. In various embodiments, the nucleic acid binding protein domain is targeted to RNA. In various embodiments, the nucleic acid binding protein domain is associated with RNA in the cell. In various embodiments, the RNA is a pre-mRNA. In various embodiments, the nucleic acid binding protein domain is associated with DNA in the cell. In various embodiments, the nucleic acid binding protein domain is not associated with DNA in the cell.

In various embodiments, the system mediates trans-splicing of pre-mRNA in the nucleus of the cell. In various embodiments, the system mediates trans-splicing of pre-mRNA in the cytoplasm of the cell. In various embodiments, the system mediates trans-splicing of a pre-mRNA at intron-exon junctions. In various embodiments, the nucleic acid binding protein domain mediates trans-splicing of a pre-mRNA at exon-intron junctions. In various embodiments, the splice repair template does not comprise a splice donor. In various embodiments, the splice repair template does not comprise a splice acceptor. In various embodiments, the splice repair template comprises both a splice acceptor and a splice donor.

In various embodiments, the system comprises multiple splice templates. In various embodiments, the multiple splice templates comprise splice repair templates that comprise a splice acceptor and splice repair templates that comprise a splice donor. In various embodiments, at least some of the multiple splice repair templates comprise a splice acceptor and a splice donor.

In various embodiments, the system mediates trans-splicing of a pre-mRNA at the 5' end of the pre-mRNA. In various embodiments, the system mediates trans-splicing of a pre-mRNA at the 3' end of the pre-mRNA. In various embodiments, the system mediates trans-splicing of a pre-mRNA at an internal site within a pre-mRNA. In various embodiments, the system replaces the 5' or the 3' end of the target mRNA.

In various embodiments, the target mRNA is a pre-mRNA. In various embodiments, the system comprises replacing one or more exons of the target mRNA, excluding the first and last exon of the target mRNA. In various embodiments, the nucleic acid binding protein domain mediates trans-splicing of a pre-mRNA within the 3' untranslated region (UTR). In various embodiments, the nucleic acid binding protein domain mediates trans-splicing of a pre-mRNA within the 5' untranslated region (UTR).

In various embodiments, the trans-splicing occurs in dividing cells. In various embodiments, the trans-splicing occurs in post-mitotic cells. In various embodiments, the post-mitotic cells are neurons, myocytes, or adipocytes.

In various embodiments, expression of at least one portion of the trans-splicing system is inducible. In various embodiments, activity of at least one portion of the trans-splicing system is inducible. In various embodiments, the nucleic acid binding protein domain is a domain from a zinc finger nuclease (ZFNs) or a Pumby module, or is an RNA recognition motif.

BRIEF DESCRIPTION OF THE FIGURES

FIG. 1A-1E illustrates the components of the CRISPR/Cas system, cis- and trans-splicing that can occur within a pre-mRNA, and the CRISPR-mediated trans-splicing.

FIG. 4A is RNAseq mapping of RNAseq libraries to demonstrate trans-splicing. FIG. 4B illustrates validation that there was cis-splicing of the SD reporter.

FIG. 8 illustrates induction of the trans-splicing complex with a small molecule.

FIG. 9 is a measurement of trans-splicing at splice junctions. FIG. 9C is a plot of spliced reads that were cis-spliced for all transfection conditions.

FIG. 10 is an illustration of strategies for targeted trans-splicing.

FIG. 11 illustrates a strategy for internal exon repair.

DETAILED DESCRIPTION

Figure 2A:
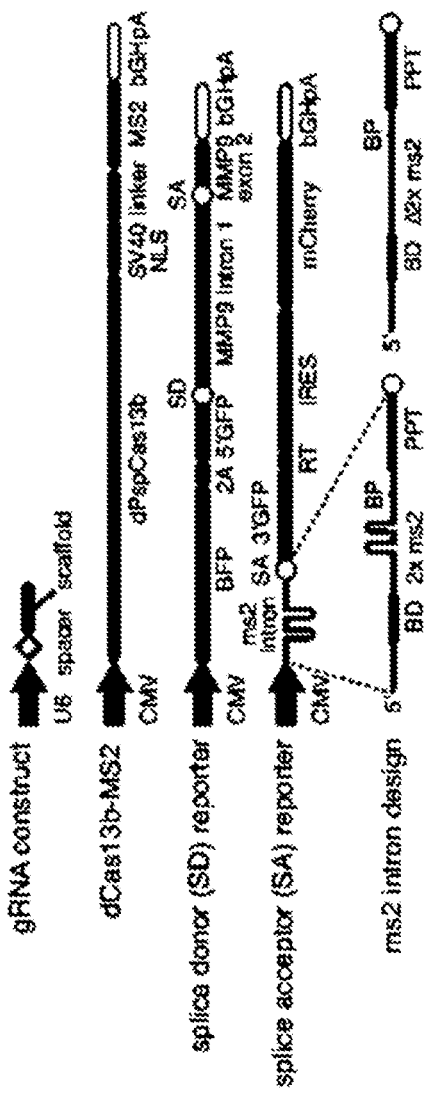
FIG. 2A illustrates the DNA constructs encoding the endoribonuclease-inactive Cas13 (dCas13b)-MS2 fusion protein, the gRNA construct, the splice donor (SD) and splice acceptor (SA) reporters, and the ms2 intron design.

This disclosure provides compositions and methods of using these compositions to mediate a targeted trans-splicing event on a pre-mRNA in a cell. In various embodiments, the targeted trans-splicing event is mediated by a CRISPR/Cas system. In various embodiments, the CRISPR/Cas system that mediates a targeted trans-splicing event is used to treat a neurodegenerative disease or disorder. These compositions and methods include a trans-splicing event mediated by a CRISPR/Cas system comprising a nuclease-inactive Cas13.

As used within the Claims, the Summary, and the Detailed Description herein, the term "a" or "an" entity refers to one or more of that entity; for example, "a cell" is understood to represent one or more cells.

Furthermore, "and/or" where used herein is to be taken as specific disclosure of each of the two specified features of components with or without the other. Thus, the term "and/or" as used in a phrase such as "A and/or B" herein is intended to include "A and B," "A or B," "A" (alone), and "B" (alone).

It is understood that wherever aspects are described herein with the language "comprising," otherwise analogous aspects described in terms of "consisting of" are also provided.

The term "near a splice site" means within 500 bp of a splice site.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition, and may include, for example, minimal changes or improvements in one or more measurable markers of the disease or condition being treated.

The terms "patient," "subject," "individual," and the like are used interchangeably herein, and refer to any animal, or cells thereof whether in vitro or in situ, amenable to the methods described herein. In certain non-limiting embodiments, the patient, subject, or individual is a human.

In aspects of the invention the terms "guide nucleic acid, "RNA guide," "DNA guide," and "single guide nucleic acid," are used interchangeably and refer to the polynucleotide sequence comprising the guide sequence, and the tracr sequence. In certain embodiments, the guide nucleic acid comprises only a crispr RNA (crRNA). The term "guide sequence" refers to a 10-80 bp sequence within the RNA or DNA guide that specifies the target site. In aspects of the invention, the terms "guide sequence" and "spacer" are used interchangeably. In aspects of the invention, the terms "direct repeat" and "scaffold" are used interchangeably.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. In some embodiments, stringent conditions include hybridization in 6× sodium chloride/sodium citrate (SSC) at about 45° C., followed by one or more washes in 0.2×SSC, 0.1% SDS at 50-65° C. Other examples of stringent conditions are known to those skilled in the art and can be found in Current Protocols in Molecular Biology, Ausubel et al., eds., John Wiley & Sons, Inc. (1995), sections 2, 4, and 6, the teachings of which are hereby incorporated by reference herein. Additional stringent conditions can be found in Molecular Cloning: A Laboratory Manual, Sambrook et al., Cold Spring Harbor Press, Cold Spring Harbor, N.Y. (1989), chapters 7, 9, and 11, the teachings of which are hereby incorporated by reference herein.

As used herein, the term "physiological condition" typically refers to biologic parameters that are valid for an animal, specifically a mammal, more specifically a human. The term may relate to biochemical and biophysical parameters commonly found in mammals, especially in the human body (especially body fluids). The "physiological condition" may relate to parameters found in a sick mammal or human patient, as well as that corresponding parameters found in a healthy body. For example, a sick mammal or human patient may have a high but "physiological" temperature condition when the mammal or the human is suffering from a fever. Regarding "physiological conditions" the most important parameters are temperature (37° C. for human body), pH (7.35-7.45 for human blood), osmotic pressure (280-300 mmol/Kg H2O) and, if necessary, protein content (66-85 g/l serum). However, those skilled in the art will appreciate that these parameters may vary. For example, such temperature, pH, osmotic pressure, and protein content may be different in a given body or tissue, such as blood or cerebrospinal fluid (Klinke (2005) Physiologic, 5th ed., Georg Thieme Verlag, Stuttgart). "Physiological condition" can also refer to conditions in a buffer system, solvent, and/or excipient that mimic conditions in an animal.

"Hybridization" or "hybridizes" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these.

As used herein, "expression" refers to the process by which a polynucleotide is transcribed from a DNA template (such as into a mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide," "peptide," "protein," and "enzyme" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. as used herein the term "amino acid" includes natural and/or unnatural or synthetic amino acids, including glycine and both the D or L optical isomers, and amino acid analogs and peptidomimetics.

The term "nucleic acid" or nucleic acid sequence" refers to a deoxyribonucleic or ribonucleic oligonucleotide in either single- or double-stranded form. The term encompasses nucleic acids, i.e., oligonucleotides, containing known analogues of natural nucleotides. The term also encompasses nucleic-acid-like structures with synthetic backbones, see, e.g., Eckstein, Biomed Biochim Acta. 1991; 50(10-11):S114-7; Baserga et al. Genes Dev. 1992 Jun.; 6(6):1120-30; Milligan et al., Nucleic Acids Res. 1993 Jan. 25; 21(2):327-33; WO 97/03211; WO 96/39154; Mata, Toxicol Appl Pharmacol. 1997 May; 144(1):189-97; Strauss-Soukup, Biochemistry. 1997 Aug. 19; 36(33): 10026-32; and Samstag, Antisense Nucleic Acid Drug Dev. 1996 Fall; 6(3):153-6.

"Inducible" as used herein refers to inducing expression or activity of a protein or a system, e.g., the trans-splicing system of the instant application. Known inducible gene expression systems have been designed to allow for chemically induced activation of an inserted nucleic acid sequence, resulting in gene overexpression or repression. Inducing activity of a protein or system can include release of a molecule to allow for activity or the addition of an effector molecule to induce activity of a protein or system.

The term "nuclease-inactive" is used to describe a Cas enzyme which no longer has nuclease activity. In some embodiments, a Cas enzyme that no longer has nuclease activity can have a small amount of residual activity. In some embodiments, this small amount of residual activity is less than 5, 1, 0.1, 0.05, 0.01 or 0.005% of wild type nuclease activity of the Cas enzyme. A nuclease-inactive Cas protein may interchangeably be referred to as a "dCas" protein, e.g., dCas13b. In some embodiments, the dCas protein can be a dCas13b protein. In some embodiments, a polynucleotide sequence set forth in SEQ ID NOs: 1, 62, 71, 74, 77, 80, 83, 86, or 89 encodes a dCas13b protein. In some embodiments, dCas13b corresponds to, or comprises in part or in whole, the amino acid sequence set forth as SEQ ID NOs: 2, 63, 72, 75, 78, 81, 84, 87, or 90. In some embodiments, the dCas protein can be a dCas13a protein. In some embodiments, a dCas13a protein is encoded by a polynucleotide sequence set forth in any one of SEQ ID NOs: 17, 20, 23, 26, 29, 32, 35, 38, 41, 44, 47, 50, 53, 56, or 59. In some embodiments, dCas13a corresponds to, or comprises in part or in whole, any one of the amino acid sequence set forth as SEQ ID NOs: 18, 21, 24, 27, 30, 33, 36, 39, 42, 45, 48, 51, 54, 57, or 60. In some embodiments, the dCas protein can be a dCas13d protein. In some embodiments, the dCas13d protein is encoded by the polynucleotide sequence set forth in SEQ ID NO: 65. In some embodiments, the dCas13d protein corresponds to, or comprises in part or in whole, the amino acid sequence set forth in SEQ ID NO: 66. Nuclease-inactive Cas proteins may be variants having mutations which result in nuclease activity inactivated.

"Targeted" is used to describe a molecule, protein, or complex that comprise a targeting moiety which specifically binds to one or more targets associated with a specific pre-mRNA of interest.

As used herein, the term "RNA-binding" is used to describe a molecule, protein, nucleic acid, or complex that specifically binds to RNA.

"Pre-mRNA" refers to a precursor mRNA and is an RNA which contains both exons and intron(s). Pre-mRNA is a type of primary transcript that becomes a messenger RNA after processing. It is synthesized from a DNA template in the cell nucleus by transcription. In some embodiments, RNA is from a mammalian cell. In other embodiments, the RNA is from the mitochondria of a mammalian cell.

The phrase "associates with DNA" refers to nucleic acids, systems, proteins, and molecules that may bind or be in the same vicinity as DNA.

The term "post-mitotic" refers to a non-replicating cell, such as a cell of the nervous system, bone marrow cells, muscle cells, liver cells, and the like. Cells of the nervous system include neurons, glial cells, etc. that is no longer capable of undergoing mitosis.

The term "non-dividing cells" refers to a cell that does not frequently undergo mitosis. Many non-dividing cells may be blocked at any point in the cell cycle (e.g., G0/G1, G1/S, G2/M), as long as most of the cells are not actively dividing. In some embodiments, non-dividing cells are from tissue types that do not frequently divide. Examples of non-dividing cells in the body include, but are not limited to, neuronal, muscle (myocytes), liver, skin, heart, lung, adipose, and bone marrow cells, and their derivatives. "Dividing cells" would be a cell that frequently actively undergoes mitosis. In some embodiments, dividing cells are from tissue types that do not frequently divide. Examples of dividing cells in the body include, but are not limited to, epithelial cells and hematopoietic cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. Diseases and disorders include spinal muscular atrophy, Rett Syndrome, Angelman syndrome, Parkinson's disease, Alzheimer's disease, Huntington's disease, frontotemporal dementia, lysosomal storage diseases, multiple sclerosis, and amyotrophic lateral sclerosis (ALS).

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, herpes simplex virus, anellovirus, baculovirus, retroviral vectors, and the like.

The term "specifically binds," or the like, means that a given molecule forms a complex with another molecule that is relatively stable under physiologic conditions. Methods for determining whether a given molecule specifically binds to another molecule are well known in the art and include, for example, equilibrium dialysis, surface plasmon resonance, and the like. For example, an RNA hairpin that "specifically binds" a viral protein, as used herein, includes RNA hairpins that bind viral proteins or a portion thereof with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or about 0.5 nM, as measured in a surface plasmon resonance assay.

"Variant" as used herein means a polypeptide or nucleotide sequence that differs from a given polypeptide or nucleotide sequence in amino acid or nucleic acid sequence by the addition (e.g., insertion), deletion, or conservative substitution of amino acids or nucleotides, but that retains the biological activity of the given polypeptide (e.g., a variant nucleic acid could still encode the same or a similar amino acid sequence). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol., 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Variant" also can be used to describe a polypeptide or fragment thereof that has been differentially processed, such as by proteolysis, phosphorylation, or other post-translational modification, yet retains its biological activity or antigen reactivity. Use of "variant" herein is intended to encompass fragments of a variant unless otherwise contradicted by context.

Alternatively or additionally, a "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present disclosure may also be derived from homologs, orthologs, or paralogs of the parent molecule or from artificially constructed variant, provided that the variant exhibits at least one biological activity of the parent molecule, i.e. is functionally active.

Alternatively, or additionally, a "variant" as used herein, can be characterized by a certain degree of sequence identity to the parent polypeptide or parent polynucleotide from which it is derived. More precisely, a protein variant in the context of the present disclosure exhibits at least 80% sequence identity to its parent polypeptide. A polynucleotide variant in the context of the present disclosure exhibits at least 70% sequence identity to its parent polynucleotide. The term "at least 70% sequence identity" is used throughout the specification with regard to polypeptide and polynucleotide sequence comparisons. This expression preferably refers to a sequence identity of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) available e.g. on http://www.ebi.ac.uk/Tools/clustalw/or on http://www.ebi.ac.uk/Tools/clustalw2/index.html or on http://npsa-pbil.ibcp.fr/cgi-bin/npsa_automat.pl?page=/NPSA/npsa_clustalw.html. Preferred parameters used are the default parameters as they are set on http://www.ebi.ac.uk/Tools/clustalw/or http://www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:I54-I62) or Markov random fields. When percentages of sequence identity are referred to in the present application, these percentages are calculated in relation to the full length of the longer sequence, if not specifically indicated otherwise.

Trans-Splicing

Figure 7:
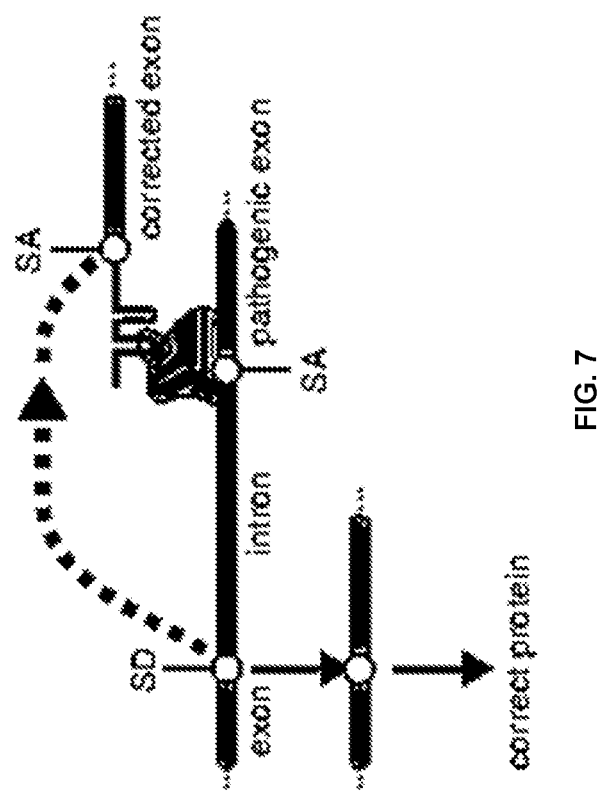
FIG. 7 is a schematic that illustrates the components of the CRISPR/Cas system in trans-splicing in the context of correcting a pathogenic exon.

A number of gene therapy techniques have been devised to address specific pathologies. These different approaches range from gene supplementation using viral vectors to genome editing using CRISPR/Cas9 technology. However, there are times when these approaches are not applicable or effective to achieve significant therapeutic effect. Currently, there are efforts to address this problem by repairing mutant transcripts to make clean transcripts without altering gene expression levels by exploiting the spliceosome to catalyze therapeutic trans-splicing events. (See, e.g., FIG. 7).

Splicing is a reaction found in the nucleus of eukaryotic cells catalyzed by the spliceosome, a large ribonucleoproteic complex. Splicing results in the elimination of introns in the pre-mRNA. This reaction is considered cis-splicing as it involves a donor site, a branch point, and an acceptor site located on the same RNA molecule.

The spliceosome can also catalyze trans-splicing events. Unlike cis-splicing, trans-splicing occurs between two different RNA molecules. The molecular process is the same, except that the final mRNA is composed of the first exon(s) of the first pre-mRNA and the exon(s) of another, thus creating a chimeric molecule. With the discovery of naturally occurring trans-splicing, it was demonstrated to be useful for bioengineering purposes. In 1999, Puttaraju et al. (Nature Biotech., 17:246-52) demonstrated the ability of diverting trans-splicing to induce repair of an endogenous mRNA using exon exchange mediated by an artificial RNA capable of inducing trans-splicing in cell culture. Subsequent studies showed the feasibility of using this in vivo, leading to the functional restoration of mutant cystic fibrosis transmembrane conductance regulator (CFTR) in a human bronchial xenograft model system. This led to the study of and use of the spliceosome-mediated RNA trans-splicing, or SMaRT system, as a gene therapy strategy. While this technology has been used to mediate repair of various mRNA sequences associated with disease, there are drawbacks and limitations to the SMaRT technology.

There are some important drawbacks to the current SMaRT technology that one must take into account. One drawback of the SMaRT technology is the specificity of the molecule. Theoretically, off-target trans-splicing with random mRNAs should be processed by nonsense mediated decay or nonstop decay, it is essential to validate the specificity of the pre-mRNA trans-splicing molecule for the target sequence and limit nonspecific events. It has been found that increasing the length of the binding domain sequence up to 153 bases dramatically decreases the probability of finding the entire and exact corresponding sequence in a human genome and increases efficiency. Another drawback is the efficiency of the system. With certain diseases, even a low level of expression of the mutated protein will lead to a diseased phenotype.

CRISPR/Cas

The present disclosure includes compositions and methods that comprise a targeted trans-splicing system comprising a nuclease-inactive CRISPR/Cas system, a nucleic acid guide, a specific RNA-binding domain, and a repair template comprising an RNA sequences that hybridizes under stringent conditions to the specific RNA-binding domain. Clustered regularly interspaced short palindromic repeats, known more widely as CRISPR, and a family of enzymes known as Cas (CRISPR-associated) proteins is a prokaryotic immune system that confers resistance to foreign genetic elements such as those present within plasmids and phages that provides a form of acquired immunity. Recently, CRISPR/Cas systems have been developed as tools used in basic molecular biology research, the development of biotechnology products, and treatment of disease. These systems have been widely adopted for mediating targeted DNA cleavage which in turn drives targeted gene disruption through non-homologous end joining (NHEJ) or precise gene editing through template-dependent homology-directed repair (HDR).

In certain embodiments, the CRISPR/Cas system described herein comprises a Cas13 enzyme encoded by a polynucleotide sequence of any one of SEQ ID NOs: 1, 17, 20, 23, 26, 29, 32, 35, 38, 41, 44, 47, 50, 53, 56, 59, 62, 65, 71, 74, 77, 80, 83, 86, or 89 or variants thereof. In certain embodiments, the CRISPR/Cas system comprises a Cas13 enzyme comprising an amino acid sequence of any one of SEQ ID NOs: 2, 18, 21, 24, 27, 30, 33, 36, 39, 42, 45, 48, 51, 54, 57, 60, 63, 66, 72, 75, 78, 81, 84, 87, or 90 or variants thereof. Cas13 enzymes are classified as Type VI CRISPR-Cas systems and have two Higher Eukaryotes and Prokaryotes Nucleotide-binding (HEPN) endoRNase domains that mediate precise RNA cleavage with a preference for targets with protospacer flanking site motif observed biochemically and in bacteria. Three Cas13 protein families have been identified to date. Cas13a, previously known as C2c2, can be adapted as tools for nucleic acid detection. Cas13b has been used for both RNA editing and nucleic acid detection, and is unique among the type VI CRISPR effectors in its linear domain architecture and CRISPR RNA (crRNA) structures. Cas13 enzymes are programmable in nature, and makes them an attractive starting point to develop tools for RNA binding and perturbation applications (Cox et al. (2017) Science. 358:1019-1027, incorporated by reference herein in its entirety).

The term "nucleic acid binding protein domain" refers to a domain of a protein that is capable of targeting a specific nucleic acid sequence. In some embodiments, the nucleic acid sequence is DNA. In other embodiments, the nucleic acid sequence is RNA. In some embodiments, the nucleic acid binding protein domain specifically binds to a splice acceptor or a splice donor site. Some examples of nucleic acid binding protein domains include, but are not limited to, zinc finger nucleases (ZFNs), and Pumby modules (Adamala et al. (2016) Proc Natl Acad Sci. 113(19):E2579-E2588, incorporated by reference herein in its entirety), or humanized CRISPR, e.g., CRISPR-Cas-Inspired RNA Targeting System (CIRTS) (Rauch et al. (2019) Cell. 178(1): P122-134, incorporated by reference herein in its entirety), or RNA recognition motif (Maris et al. (2005) The FEBS journal 272: 2118-2131).

The RNA-targeting systems, the vector systems, the vectors and the compositions described herein may be used in various RNA-targeting applications, altering or modifying synthesis of a gene product, such as a protein, RNA cleavage, RNA editing, RNA splicing; trafficking of target RNA, tracing of target RNA, isolation of target RNA, visualization of target RNA, etc.

The term "splice donor" refers to the 5' end of the intron.

The term "splice acceptor" refers to the 3' end of the intron.

The term "repair template" refers to a nucleic acid molecule with comprising a desired sequence to be spliced to a nucleic acid locus of interest. In some embodiments, the desired sequence to be spliced is an exon. In some embodiments, the repair template further comprises one or more introns.

In certain embodiments, the nucleic acid guide is a RNA guide. In certain embodiments, the nucleic acid guide is a DNA guide. In some embodiments, the guide nucleic acid, such as a guide RNA or gRNA, is a specific sequence that recognizes the target pre-mRNA of interest and directs the Cas protein to said pre-mRNA. In some embodiments, the guide nucleic acid targets the DNA locus where transcription is occurring. Generally, the guide nucleic acid is made of two components—a crispr RNA (crRNA), which is a 17-20 nucleotide sequence complementary to the target sequences, and a tracr RNA, which serves as a binding scaffold for the Cas nuclease. More recently, the crRNA and tracr RNA components have been fused into one molecule to create a single guide RNA (sgRNA). In certain embodiments, the trans-splicing system comprises one nucleic acid guides. For currently characterized CRISPR/Cas13 systems, a crispr RNA (crRNA) is comprised of a spacer and a direct repeat. For Cas13b, the spacer is 5' and the direct repeat is the 3' of the crRNA. For Cas13b, crRNA and guide RNA can be used interchangeably. For Cas13a and Cas13d, the spacer is 3' and the direct repeat is the 5' of the crRNA (Zhang F (2019). Development of CRISPR-Cas systems for genome editing and beyond. Quarterly Reviews of Biophysics 52, e6, 1-31. https://doi.org/10.1017/S0033583519000052, incorporated by reference herein in its entirety). In certain embodiments, the trans-splicing system comprises more than one nucleic acid guide. In certain embodiments, more than one nucleic acid guides are in an array operably linked to one promoter, which are then cleaved and processed by Cas13. In some embodiments, an array has direct repeats between multiple spacers wherein each spacer targets a different nucleic acid. In certain embodiments, more than one nucleic acid guides are expressed by separate promoters, such as U6 promoters. In certain embodiments, the guide RNAs have a direct repeat (e.g., SEQ ID NOs: 10, 19, 22, 25, 28, 31, 34, 37, 40, 43, 46, 49, 52, 55, 58, 61, 64, 67, 73, 76, 79, 82, 85, 88, and 91) at the 5' end, and a spacer at the 3' end. In other embodiments, the guide RNAs have a direct repeat (e.g., SEQ ID NOs: 10, 19, 22, 25, 28, 31, 34, 37, 40, 43, 46, 49, 52, 55, 58, 61, 64, 67, 73, 76, 79, 82, 85, 88, and 91) at the 3' end, and a spacer at the 5' end. In other embodiments, spacers are flanked by direct repeats (e.g., SEQ ID NOs: 10, 19, 22, 25, 28, 31, 34, 37, 40, 43, 46, 49, 52, 55, 58, 61, 64, 67, 73, 76, 79, 82, 85, 88, and 91). In certain embodiments, the direct repeats have at least 70% (e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) sequence identity with the direct repeat nucleic acid sequences of SEQ ID NOs: 10, 19, 22, 25, 28, 31, 34, 37, 40, 43, 46, 49, 52, 55, 58, 61, 64, 67, 73, 76, 79, 82, 85, 88, or 91. In certain embodiments, the nucleic acid guides recognize multiple targets. In certain embodiments, the instant disclosure provides nucleic acid guide sequences having at least 70% (e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) sequence identity with the nucleic acid sequence of SEQ ID NO: 11 or 12.

The invention uses nucleic acids to bind target RNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In certain embodiments, the specific RNA binding domain of the CRISPR/Cas system comprises a viral protein fused to the Cas protein. The term "viral protein" can be used to describe a protein of viral origin that is bound to the Cas protein that binds to a hairpin of the splice acceptor template. Coat proteins of single-stranded RNA bacteriophages are translational repressors of viral replicase. They accomplish this by specifically binding an RNA hairpin that encompasses the replicase start codon. Some examples would be the coat proteins of RNA phages MS2, λN, QBeta, and PP7 (e.g. SEQ ID NOs: 5-9). In certain embodiments, the specific RNA binding domain comprises an amino acid sequence of any one of SEQ ID NOs: 6, 7, 8, or 9, or variants thereof. The term "binding", or the like, means that a viral protein forms a complex with a corresponding hairpin that is relatively stable under physiologic conditions. In certain embodiments, the instant disclosure provides hairpin sequences having at least 70% (e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) sequence identity with any one of the nucleic acid sequences of SEQ ID NOs: 13-16.

In certain embodiments, the viral protein is covalently bound to the CRISPR/Cas system. In certain embodiments, the viral protein is not covalently bound to the CRISPR/Cas system. In certain embodiments, the viral protein and CRISPR/Cas system is a fusion protein. As used herein, the term "covalently bound" refers to a chemical bond that involves the sharing of electrons between atoms. The term "fusion protein" refers to proteins created through the joining of two or more genes that originally coded for separate proteins.

In some embodiments, the specific RNA binding domain of the CRISPR/Cas system comprises an RNA binding protein that is not of viral origin.

In certain embodiments, the trans-splicing system comprises one repair template. In certain embodiments, the trans-splicing system comprises more than one repair template.

In certain embodiments, the trans-splicing system comprises a nucleic acid guide-binding protein domain comprising a nuclease-inactive CRISPR/Cas system.

In certain embodiments, expression and/or the activity of the trans-splicing system is transient. "Transient expression" refers to the temporary expression of genes that are expressed for a time after a nucleic acid has been introduced into eukaryotic cells. In some embodiments, transient expression of the trans-splicing system may be controlled with a small molecule. As used herein, the term "small molecule" refers to a a non-nucleic acid/non-amino acid molecule. As used herein, the term "small molecule binding domain" refers to a portion of a molecule, often a protein, that specifically binds to a given small molecule. These can include a tet-ON or tet-OFF system or chemogetic control using synthetic transcription factors and protease inhibitors. For example, dCas13-NLS-NS3-MS2 remains active and uncleaved in the presence of BILN-2061. (Tague et al., Nature Methods, Volume 15, pages 519-522 (2018) and Wagner et al. Nature Chemical Biology, Volume 14, pages 1043-1050 (2018), incorporated by reference herein in their entireties). In some embodiments, transient expression of the trans-splicing system can be controlled by degradation of the delivery particle. In some embodiments, expression of the trans-splicing system may be controlled with a light-activated transcription factor (Konermann et al., Nature, Volume 500, pages 472-476 (22 Aug. 2013), incorporated by reference herein in its entirety). In some embodiments, assembly of the trans-splicing system may be controlled with a small molecule, e.g., chemically induced dimerization. Examples include, dCas13-NLS-FKBP and FKBP-NLS-MS2, assembled by FK1012; dCas13-NLS-FKBP and CNA-NLS-MS2, assembled by FK506; and dCas13-NLS-FRB and MS2-FKBP transiently assembled by rapamycin, and rapidly disassembled by FK506. (Braun et al., Nature Communications, DOI: 10.1038/s41467-017-00644-y, incorporated by reference herein in its entirety). Additional examples include dCas13-NLS-ABI1 and PYL1-MS2, assembled by abscisic acid (Gao et al., Nature Methods, DOI: https://doi.org/10.1038/nmeth.4042, incorporated by reference herein in its entirety). Other examples of small molecules and their chemically induced systems are included in Stanton et al. (Science, DOI: http://dx.doi.org/10.1126/science.aao5902, incorporated by reference herein in its entirety). In some embodiments, activity of the trans-splicing system can be controlled using a small molecule to degrade the system. In some embodiments, the small molecule binding domain may be linked to the CRISPR system via a self-cleaving peptide. In some embodiments, the self-cleaving peptide is a 2A self-cleaving peptide. Some examples include, but are not limited to, T2A, P2A, E2A, and F2A sequences.

In some embodiments, assembly of the trans-splicing system is mediated by a SunTag (Tanenbaum et al., Cell, 2014, DOI: https://doi.org/10.1016/j.cell.2014.09.039). In some embodiments, assembly of the trans-splicing system is mediated by hairpins on the guide RNA, either native or modified, such as the SAM system (Konermann et al., Nature, 2015, DOI: 10.1038/nature14136).

In some embodiments, transient expression is performed by delivering the trans-splicing system as RNA as shown in Hewitt et al., Science Translational Medicine 30 Jan. 2019: Vol. 11, Issue 477, eaat9143, incorporated by reference herein in its entirety. In some embodiments, the trans-splicing system assembly can be controlled via light. For example, dCas13-NLS-CRY2 and CIB1-NSL-MS2 are assembled by 466 nm light. (Konermann et al. (2013)). In some embodiments, transient expression is performed by delivering the trans-splicing system with an episomal or non-integrating virus. These viruses include Ad5, AAV, HSV-1, or baculovirus. In some embodiments, activity of the trans-splicing system is mediated by conditionally active inteins, such as inteins that undergo protein splicing in the presence of 4-hydroxytamoxifen (4-HT) or other small molecules. In some embodiments, activity of the trans-splicing system is controlled by 4-HT by including a 4-HT sensitive intein into Cas13 at a location that disrupts Cas13 activity until 4-HT mediated protein splicing has taken place, similar to Davis et al. (Nature Chemical Biology, 2015, DOI: https://doi.org/10.1038/nchembio.1793).

Delivery

In some embodiments, the nucleic acid introduced into the eukaryotic cell is a plasmid DNA or viral vector.

Preferably, delivery is in the form of a vector which may be a viral vectors, such as a lenti- or baculo- or adeno-viral/adeno-associated viral vectors, but other means of delivery are known (such as yeast systems, microvesicles, gene guns/means of attaching vectors to gold nanoparticles) and are provided. The viral vector may be selected from a variety of families/genera of viruses, including, but not limited to Myoviridae, Siphoviridae, Podoviridae, Corticoviridae, Lipothrixviridae, Poxviridae, Iridoviridae, Adenoviridae, Polyomaviridae, Papillomaviridae, Mimiviridae, Pandoravirusa, Salterprovirusa, Inoviridae, Microviridae, Parvoviridae, Circoviridae, Hepadnaviridae, Caulimoviridae, Retroviridae, Cystoviridae, Reoviridae, Birnaviridae, Totiviridae, Partitiviridae, Filoviridae, Orthomyxoviridae, Deltavirusa, Leviviridae, Picornaviridae, Marnaviridae, Secoviridae, Potyviridae, Caliciviridae, Hepeviridae, Astroviridae, Nodaviridae, Tetraviridae, Luteoviridae, Tombusviridae, Coronaviridae, Arteriviridae, Flaviviridae, Togaviridae, Virgaviridae, Bromoviridae, Tymoviridae, Alphaflexiviridae, Sobemovirusa, or Idaeovirusa.

A vector may mean not only a viral or yeast system (for instance, where the nucleic acids of interest may be operably linked to and under the control of (in terms of expression, such as to ultimately provide a processed RNA) a promoter), but also direct delivery of nucleic adds into a host cell. While in herein methods the vector may be a viral vector and this is advantageously AAV, other viral vectors as herein discussed can be employed, such as lentivirus. For example, baculoviruses may be used for expression in insect cells. These insect cells may, in turn be useful for producing large quantities of further vectors, such as AAV or lentivirus adapted for delivery of the present invention. Also envisaged is a method of delivering the present CRISPR enzyme comprising delivering to a cell mRNA encoding the CRISPR enzyme. It will be appreciated that in certain embodiments the CRISPR enzyme is truncated, and/or comprised of less than one thousand amino acids or less than four thousand amino acids, and/or is a nuclease or nickase, and/or is codon-optimized, and/or comprises one or more mutations, and/or comprises a chimeric CRISPR enzyme, and/or the other options as herein discussed.

In some embodiments, expression of a nucleic acid sequence encoding a CRISPR enzyme may be driven by a promoter. In some embodiments, a single promoter drives expression of a nucleic acid sequence encoding a CRISPR enzyme and one or more of the guide sequences. In some embodiments, the CRISPR enzyme and guide sequence(s) are operable linked to and expressed from the same promoter. In some embodiments, the CRISPR enzyme and guide sequence(s) are expressed from different promoters. For example, the promoter(s) can be, but are not limited to, a UBC promtoer, a PGK promoter, an EF1A promoter, a CMV promoter, an EFS promoter, a SV40 promtoer, and a TRE promoter. The promoter may be a weak or a strong promoter. The promoter may be a constitutive promoter or an inducible promoter. In some embodiments, the promoter can also be an AAV ITR, and can be advantageous for eliminating the need for an additional promoter element, which can take up space in the vector. The additional space freed up by use of an AAV ITR can be used to drive the expression of additional elements, such as guide sequences. In some embodiments, the promoter may be a tissue specific promoter.

In some embodiments, an enzyme coding sequence encoding a CRISPR enzyme is codon-optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a Cas protein correspond to the most frequently used codon for a particular amino acid.

In some embodiments, a vector encodes a Cas protein comprising one or more nuclear localization sequences (NLSs), such as about or more than about 1, 2, 3, 4, 5, 6, 7, 8, 9, 10, or more NLSs. In some embodiments, the Cas protein comprises about or more than 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., one or more NLS at the amino-terminus and one or more NLS at the carboxy terminus), When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, bur other types of NLS are known. In some embodiments, the NLS is between two domains, for example between the Cas13 protein and the viral protein. The NLS may also be between two functional domains separated or flanked by a glycine-serine linker.

In general, the one or more NESS are of sufficient strength to drive accumulation of the Cas protein in a detectable amount in the nucleus of a eukaryotic cell. In general, strength of nuclear localization activity may derive from the number of NLSs in the Cas protein, the particular NLS used, or a combination of these factors. Detection of accumulation in the nucleus may be performed by any suitable technique. For example, a detectable marker may be fused to the Cas protein, such that location within a cell may be visualized, such as in combination with a means for detecting the location of the nucleus (e.g., a stain specific for the nucleus such as DAPI). Examples of detectable markers include fluorescent proteins (such as green fluorescent proteins, or GFP; RFP; CFP), and epitope tags (HA tag, FLAG tag, SNAP tag). Cell nuclei may also be isolated from cells, the contents of which may then be analyzed by any suitable process for detecting protein, such as immunohistochemistry, Western blot, or enzyme activity assay, Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR complex activity), as compared to a control not exposed to the CRISPR complex, or exposed to a Cas protein lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, ClustalX, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 3.5, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay.

In some aspects, the invention provides methods comprising delivering one or more polynucleotides, such as one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a Cas protein in combination with (and optionally complexed) with a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-8313 (1992); Navel and Feigner, TIBTECH 11:211-217 (1993); Mitani and Caskey, TIBTECH 11:162-166 (1993); Dillon, TIBTECH 11:167-175 (1993); Miller, Nature 357: 455-460 (1992), Van Brunt, Biotechnology 6(10):1149-1154 (1988); Vigne, Restorative Neurology and Neuroscience 8:35-36 (1995); Kremer and Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

The CRISPR/Cas system as described herein, can be delivered using adeno-associated virus (AAV), lentivirus, adenovirus, or other viral vector types, or combinations thereof. Cas protein(s) and one or more guide RNAs can be packaged into one or more viral vectors. In some embodiments, the targeted trans-splicing system is delivered via AAV as a split intein system, similar to Levy et al, (Nature Biomedical Engineering, 2020. DOI: https://doi.org/10.1038/s41551-019-0501-5). In other embodiments, the targeted trans-splicing system can be delivered via AAV as a trans-splicing system, similar to Lai et al. (Nature Biotechnology, 2005, DOI: 10.1038/nbt1153). In some embodiments, the viral vector is delivered to the tissue of interest by, for example, an intramuscular injection, while other times the viral delivery is via intravenous, transdermal, intranasal, oral, mucosal, intrathecal, intracranial or other delivers' methods. Such delivery may be either via a single dose, or multiple doses. One skilled in the art understands that the actual dosage to be delivered herein may vary greatly depending upon a variety of factors, such as the vector chosen, the target cell, organism, or tissue, the general condition of the subject to be treated, the degree of transformation/modification sought, the administration route, the administration mode, the type of transformation/modification sought, etc.

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues. Viral-mediated in vivo delivery of Cas13 and guide RNA provides a rapid and powerful technology for achieving precise mRNA perturbations within cells, especially in post-mitotic cells and tissues.

In certain embodiments, delivery of the trans-splicing system to a cell is viral. In certain embodiments, the virus is a retrovirus, adenovirus, adeno-associated virus, herpes simplex virus, anellovirus, or baculovirus.

In certain embodiments, delivery of the trans-splicing system to a cell is non-viral. In certain embodiments, the non-viral delivery system is selected from a cationic lipid vehicle, electroporation, calcium phosphate transfection, transfection through membrane disruption using mechanical shear forces, mechanical transfection, and nanoparticle delivery.

Preferably, the vector is a viral vector, such as a lend-, baculo-, or adeno-viral/adeno-associated viral vectors, but other means of delivery are known (such as yeast systems, microvesicles, gene guns/means of attaching vectors to gold nanoparticles) and are provided. In some embodiments, one or more of the viral or plasmid vectors may be delivered via liposomes, nanoparticles, exosomes, microvesicles, or a gene-gun.

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

In another embodiment, minimal non-primate lentiviral vectors based on the equine infectious anemia virus (EIAV) are also contemplated, especially for ocular gene therapy (see, e.g., Balagaan, J gene Med 2006: 8:275-285, Published online 21 Nov. 2005 in Wiley InterScience (www.interscience.wiley.com). DOI: 10.1002/jgm.845). In another embodiment, RetinoStat, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) may be modified for the CRISPR-Cas system of the present invention.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for delivery to the brain, see, e.g., US Patent Publication Nos. US20110293571, US20040013648; US20070025970, US20090111106, and U.S. Pat. No. 7,259,015.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386; 4,946,787; and 4,897,355; and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g., in vitro or ex vivo administration) or target tissues (e.g., in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-289 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183; 4,217,344; 4,235,871; 4,261,975; 4,485,054; 4,501,728; 4,774,085; 4,837,028; and 4,946,787).

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. Cell lines are available from a variety of sources known to those with skill in the art (see, e.g., the American Type Culture Collection (ATCC) (Manassas, VA)), In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rate, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tract mate sequence which in turn hybridizes to a tracr sequence.

With recent advances in crop genomics, the ability to use CRISPR/Cas systems to perform efficient and cost effective gene editing and manipulation will allow the rapid selection and comparison of single and multiplexed genetic manipulations to transform such genomes for improved production and enhanced traits. In this regard, reference is made to US patents and publications: U.S. Pat. No. 6,603,061—*Agrobacterium*-Mediated Plant Transformation Method: U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morell et al "Crop genomics: advances and application" Nat Rev Genet. 2011 Dec. 29; 13(2):85-96 are also herein incorporated by reference in their entirety.

Any components of the instant CRISPR/Cas system can be delivered in the form of RNA. Cas and/or viral protein mRNA can be generated using in vitro transcription. For example, Cas mRNA can be synthesized using a PCR cassette containing the following elements: T7 promoter-Kozak sequence (GCCACC)-Cas13-3' UTR from beta globin-poly A tail (a string of 120 or more adenines). The cassette can be used for transcription by T7 polymerase. Guide RNAs can also be transcribe using in vitro transcription from a cassette containing T7 promoter-GG-guide RNA sequence.

The components of the instant CRISPR/Cas system may be delivered simultaneously using nanoparticles or lipid envelopes. For example, Su X, Fricke J, Kavanaugh D G, Irvine D J ("In vitro and in vivo mRNA delivery using lipid-enveloped pH-responsive polymer nanoparticles" Mole Phar. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self-assembling bioadhesive polymers are contemplated, which may be applied to oral delivery of peptides, intravenous delivery of peptides and nasal delivery of peptides, all to the brain. Other embodiments, such as oral absorption and ocular deliver of hydrophobic drugs are also contemplated. The molecular envelope technology involves an engineered polymer envelope which is protected and delivered to the site of the disease (see, e.g., Mazza, M, et al. ACSNano, 2013, 7(2):1016-1026; Siew, A., et al, Mal Pharm, 2012. 9(1):14-28; Lalatsa, A., et al. J Control Rel, 2012. 161(2):523-36; Lalatsa, A., et al., Mol Pharm, 2012. 9(6):1665-80; Lalatsa, A., et al, Mol Phar, 2012. 9(6):1764-74; Garrett, N. L., et al, J. Biophotonics, 2012. 5(56):458-68; Garrett, N. L., et al. J Raman Spect, 2012. 43(5):681-688; Ahmad, S., et al. J Royal Soc Interface 2010. 7:S423; 33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

US Patent Application 20110293703 relates to lipidoid compounds are also particularly useful in the administration of polynucleotides, which may be applied to deliver the CRISPR/Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Application 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofueling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolte complex capsules for cell encapsulation. The invention may also have many other biological applications such as antimicrobial coatings, DNA or siRNA delivery, and stem cell tissue engineering. The teachings of US Patent Application No. 20130302401 may be applied to the CRISPR/Cas system of the present invention.

In another embodiment, lipid nanoparticles (LNPs) are contemplated. In particular, an antitransthy retin small interfering RNA encapsulated in lipid nanoparticles (see, e.g., Coelho et al., N Engl J Med 2013; 369:819-29) may be applied to the CRISPR/Cas system of the present invention.

The charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular therapy, vol. 19, no. 12, pages 1286-22.00, December, 2011). Negatively charged polymers such as siRNA oligonucleotides may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminoproane (DLinKDMA), and 1,2-dilinoleyl-4-(2-dimethylaminoethyl)-11,31-dioxolane (DLinKC2-DMA).

Self-assembling nanoparticles with siRNA may be constructed with polyethyleneimine (PEI) that is PEGylated with an Arg-Gly-Asp (RGD) peptide ligand attached at the distal end of the polyethylene glycol (PEG), for example, as a means to target tumor neovasculature expressing integrins and used to deliver siRNA inhibiting vascular endothelial growth factor receptor-2 (VEGFR2) expression and thereby tumor angiogenesis (see, e.g., Schiffelers et al., Nucleic Acids Research, 2004. Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to her as nanoplexes.

Exosomes are endogenous nano-vesicles that transport RNAs and proteins which can deliver short interfering (si)RNA to the brain in mice. To reduce immunogenicity, Alvarez-Erviti et al, (2011, Nat Biotechnol 29: 341) used self-derived dendritic cells for exosome production.

In certain embodiments, the invention provides a method of treating or inhibiting a condition caused by a defect in a target sequence in a mRNA of interest in a subject (e.g., mammal or human) or a non-human subject (e.g., mammal) in need thereof comprising modifying the subject or a non-human subject by manipulation of the target sequence and wherein the condition is susceptible to treatment or inhibition by manipulation of the target sequence comprising providing treatment comprising: delivering a non-naturally occurring or engineered composition comprising an AAV or lentivirus vector system comprising one or more AAV or lentivirus vectors operably encoding a composition for expression thereof, wherein the target sequence is manipulated by the composition when expressed, wherein the composition comprises: (A) a non-naturally occurring or engineered composition comprising a vector system comprising one or more vectors comprising a targeted trans-splicing system comprising a non-natural nucleic acid guide-binding protein domina, a nucleic acid guide, a specific RNA-binding domain, and a repair template comprising a splice donor and/or splice acceptor and an RNA sequence that hybridizes under stringent conditions to the specific RNA-binding domain.

Targeting of Cells

The work herein supports the use of CRISPR/Cas systems to target pre-mRNA in post-mitotic cells through delivery of the CRISPR/Cas system to the appropriate location (i.e., to cells within the organs or tissues of interest) to mediate trans-splicing events to pre-mRNA.

In certain embodiments, the CRISPR/Cas system further comprises a cell. In certain embodiments, the CRISPR/Cas system is targeted to RNA. In certain embodiments, the CRISPR/Cas system is associated with RNA in the cell. In certain embodiments, the RNA is a pre-mRNA. In certain embodiments, the CRISPR/Cas system mediates trans-splicing of pre-mRNA at intron-exon junctions. In certain embodiments, the CRISPR/Cas system mediates trans-splicing of pre-mRNA at exon-intron junctions. In certain embodiments, the CRISPR/Cas system mediates trans-splicing of a pre-mRNA at the 3' end of the pre-mRNA. Examples of a sequence targeting the 3' end of a pre-mRNA may include, but is not limited to SEQ ID NO: 70, as disclosed herein. In certain embodiments, the CRISPR/Cas system mediates trans-splicing of pre-mRNA within the 3' untranslated region (UTR). Trans-splicing within the 3' UTR can lead to stronger translation of the resulting mRNA. In certain embodiments, the CRISPR/Cas system mediates trans-splicing of a pre-mRNA at na internal site within a pre-mRNA. Examples of a sequence targeting an internal site within a pre-mRNA may include, but is not limited to SEQ ID NO: 92, as disclosed herein. In various embodiments, the CRISPR/Cas system mediates trans-splicing of pre-mRNA within the 5' untranslated region (UTR). The 3' and 5' UTRs of mRNA are known to contain multiple regulatory elements and are critical for the stability and translation of mRNA into protein. Warren et al. (Cell Stem Cell, Volume 7, pages 618-630 (2010), incorporated by reference herein in its entirety) used an artificial 5' UTR containing a strong Kozak translation signal and the alpha globin 3' UTR to improve protein production during reprogramming of fibroblasts to induced pluripotent stem cells. In certain embodiments, the CRISPR/Cas system can mediate trans-splicing to provide a 3'UTR sequence to change the strength of translation, in some cases leading to stronger translation and significant increases in protein production. For example, 3' UTRs from genes including, but are not limited to, AGXT, ALB, APOA2, ASL, C3, CYP2E1, FBA, HPX, and/or ORM, can be used to change the strength of translation. Also, for example, 5' UTRs from genes including, but are not limited to, AGXT, ALB, APOA2, ASL, C3, CYP2E1, FBA, HPX, and/or ORM, can be used to change the strength of translation.

In certain embodiments, the CRISPR/Cas system is associated with DNA in the cell. In certain embodiments, the CRISPR/Cas system is not associated with DNA in the cell.

In certain embodiments, the trans-splicing system is introduced into the cell. In certain embodiments, the CRISPR/Cas system mediates trans-splicing of pre-mRNA in the nucleus of a cell. In certain embodiments, the CRISPR/Cas system mediates trans-splicing of pre-mRNA in the cytoplasm of a cell. In another aspect of the invention, provided herein is a method of mediating a targeted trans-splicing event on a pre-mRNA in a cell, the method comprising introducing a targeted trans-splicing CRISPR/Cas system into the cell, wherein the system comprises a nuclease-inactive nucleic acid-targeting CRISPR/Cas system, a nucleic acid guide that specifically hybridizes to a nucleic acid locus of interest, a specific RNA-binding domain, and a repair template comprising an RNA sequence that hybridizes under stringent conditions to the specific-RNA-binding domain.

Gene editing using Type II, and more recently Type V, CRISPR systems can be accomplished through either of two pathways: non-homologous end joining (NHEJ) or homology-directed repair (HDR). NHEJ does not require the cells to be actively dividing, however HDR is only active in dividing cells. In certain embodiments, the CRISPR/Cas system mediates trans-splicing of pre-mRNA in the nucleus of the cell. In certain embodiments, the CRISPR/Cas system mediates trans-splicing of pre-mRNA in the cytoplasm of the cell. The cell can be a dividing cell, or a post-mitotic cell. In certain embodiments, the post-mitotic cell can be simply one or post-mitotic cells, or an organ per se or a tissue within it. In certain embodiments, the post-mitotic cell can be selected from the group consisting of a neuron, myocyte, and adipocyte. The post-mitotic cells may be comprised within a vertebrate animal, either a patient (in the sense of an animal in need of trans-splicing mediated treatment) or a model organism, or may be in cell culture, an organoid, or other ex vivo tissue, such a "liver on a chip" for instance where hepatocytes are seeded and grown on a scaffold. With the development of 3-D printing techniques being applied to biology, printed tissues are within grasp and it is entirely feasible that liver cells or tissues printed I this way to create an organoid or onto a chip could also be targeted. Non-liver alternatives are also envisaged, particularly for other post-mitotic cells/tissues.

Thus, provided is a model organism comprising post-mitotic cells, such as neurons or kidney cells, to which the present CRISPR-Cas system has been delivered. Such collections may include post-mitotic organs, organoids, or cells populating a scaffold ('kidney on a chip').

In particular, such post-mitotic cells may express, or comprise polynucleotides capable of expressing, a Cas enzyme. As discussed herein, this has the advantage of providing a ready model for interrogating gene product function through targeted-trans-splicing of pre-mRNA. This is particularly useful in studying conditions of the post-mitotic cells, such as the kidney or brain, such as those listed herein, as well as broader conditions such as obesity.

Also provided is a method of inducing transcript perturbation in one or more post-mitotic cells, comprising transducing population of cells with a CRISPR/Cas system according to the present invention to thereby alter transcripts of a population of cells. The method may be ex vivo or in vitro, for instance in a cell culture or in an ex vivo or in vitro model (such as an organoid). Alternatively, the method may be in vivo, in which case it may also include isolating a population of cells from the subject, and transplanting the population of cells (back) into the subject. Transcript perturbation may be for one or more, or two or more, or three or more, or four or more genes. However, if the cells already comprise Cas, whether expressed as a protein or encoded by polynucleotides already comprised within the cells, then only the CRISPR polynucleotide needs to be delivered. The method may include extraction from and, optionally, re-insertion back into the post-mitotic cell. By delivering, it is meant actually physical delivery of the polynucleotides to the nucleus of the cell, but also transtection. Therefore, delivery should also be read as including transfection unless otherwise apparent.

Gene Therapy

Because the described invention can be used to mediate trans-splicing in a non-dividing cell, in certain embodiments the cell is in a subject suffering from a disease or disorder. In certain embodiments the disease or disorder is a neuro-degenerative, neurological, or neuromuscular disease or disorder. In certain embodiments, the disease or disorder is selected from the group consisting of spinal muscular atrophy, Rett Syndrome, Angelman syndrome, Parkinson's disease, Alzheimer's disease, Huntington's disease, frontotemporal dementia, lysosomal storage diseases, multiple sclerosis, and amyotrophic lateral sclerosis (ALS).

The approaches taken herein demonstrate that the instant invention can be applied to gene therapy. For instance, correction of one or more deficient genotypes (for example single point mutations) is achievable through the use of the present CRISPR-Cas system in the post-mitotic cells discussed herein. Monogenic conditions associated with the post-mitotic are particularly preferred and are exemplified herein.

Although one guide may be used, so-called multiplexing with two, three, four or more guides, is particularly useful in gene therapy where multiple defective genotypes are to be corrected (either multiple errors in a single gene or multiple errors spread across several genes.

Accordingly, in certain embodiments the invention provides a method of modifying post-mitotic cells of an organism, e.g., mammal including a human or a non-human mammal or organism by manipulation of a target sequence in a genomic locus of interest comprising delivering a non-naturally occurring or engineered composition comprising a viral or plasmid vector system comprising one or more viral or plasmid vectors operably encoding a composition for expression thereof, wherein the composition comprises: (A) a non-naturally occurring or engineered composition comprising a vector system comprising one or more vectors comprising a targeted trans-splicing system comprising a non-natural nucleic acid guide-binding protein domain, a nucleic acid guide, a specific RNA-binding domain, and a repair template comprising a splice donor and/or splice acceptor and an RNA sequence that hybridizes under stringen conditions to the specific RNA-binding domain.

The trans-splicing system as described herein can be used to interrogate the function of one or more genes in post-mitotic cells. This may be achieved through delivery and expression of the CRISPR/Cas system to the post-mitotic cell, wherein the guide(s) of the CRISPR/Cas system are designed to recruit the CRISPR/Cas system to the pre-mRNA target or targets of interest. Equally, where the CRISPR/Cas is already comprised within the post-mitotic cell, protein (transcribed) form, then delivery of the guides to the post-mitotic cell will suffice. Having a CRISPR/Cas system induced by a small molecule may be advantageous here. Where the CRISPR/Cas is already within the post-mitotic cell, in polynucleotide (untranscribed), then delivery of the guides to the post-mitotic cell as well as induction of transcription of the Cas9 polynucleotide will be necessary. Having the CRISPR/Cas system under the control of an inducible or repressible promoter, such as the tet (tetracycline) on-off system may be advantageous here.

One aspect that is particularly promising is the integration of CRISPR techniques with phenotypic assays to determine the phenotypic changes, if any, resulting from gene perturbations, especially knock downs. Use of the CRISPR/Cas system can be combined with biochemical, sequencing, electrophysiological, and behavioral analysis to study the function of the targeted genomic element.

This, in one aspect, there is provided a method of interrogating the function of one or more genes in a post-mitotic cell, comprising inducing an expression of a modulated mRNA and determining changes in phenotype due to one or more genes in the condition thereby interrogating the function of the one or more proteins translated from the modulated pre-mRNA.

The following applies broadly to appropriate aspects of the invention. The cell may be in a subject, such as a human, animal, or model organism, so that protein function is interrogated in vivo. however, it is also envisaged that the cell may be ex vivo, for instance in a cell culture or in a model organ or organoid. In some embodiments, the method may include isolation of a first population of cells from the subject, optionally culturing them and transducing them with one or more CRISPR/Cas systems. Further optional culturing may follow. Transplantation of the transduced cells back into the subject may then occur.

The cell may be from any of the tissues or organism described herein. The brain is one preferred example, providing for said method of interrogating the function of one or more gene products, such as pre-mRNA, wherein the post-mitotic cell is a brain cell, for instance a neuron. Particularly in vivo, this allows for the interrogation of mutated or modified protein function on animal behavior. The animal is preferably a mammal, for instance a rodent. Given the complexity of the nervous system, which consists of intricate networks of heterogeneous cell types, being able to efficiently edit pre-mRNAs of neurons in vivo enables direct testing of gene function in relevant cell types embedded in native contexts.

Kits

The present disclosure provides kits for carrying out a method. In one aspect, the invention provides kits containing any one or more of the elements disclosed in the above methods and compositions. In some embodiments, the kit comprises a vector system and instructions for using the kit. In some embodiments, the kit comprises a vector system comprising regulatory elements and polynucleotides encoding the CRISPR/Cas trans-splicing system. In some embodiments, the kit comprises a viral delivery system of the CRISPR/Cas trans-splicing system. In some embodiments, the kit comprises a non-viral delivery system of the CRISPR/Cas trans-splicing system. Elements may be provided individually or in combinations, and may be provided in any suitable container, such as a vial, a bottle, or a tube. In some embodiments, the kit includes instruction in one or more languages, for examples, in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element.

The invention is further described in detail by reference to the following experimental examples. These examples are included merely for purposes of illustration of certain aspects and embodiments of the present invention, and are not intended to limit the invention. Thus, the invention should in no way be construed as being limited to the following examples, but rather, should be construed to encompass any and all variation which become evident as a result of the teaching provided herein.

EXAMPLES

Example 1—Engineering of the CRISPR-Based Trans-Splicing System

A CRISPR-based trans-splicing system was engineered to comprise a guide RNA, such as a guide RNA (gRNA), an exon or a group of exons of interest conjugated to an engineered intron with ms2 hairpins, and a catalytically inactive Cas13b (dCas13b) linked to a MS2 binding protein (FIG. 1A). Assembly of the trans-splicing system relies on the dCas13b recognizing the gRNA scaffold, and the MS2 binding protein recognizing the ms2 hairpins of the engineered intron (FIG. 1B). Instead of inducing a cis-splicing reaction (FIG. 1C), the CRISPR-dCas13b system induces a trans-splicing event similar to the endogenous spliceosome-based reaction that is illustrated in FIG. 1D. In the CRISPR/Cas-based system, the trans-splicing event occurs when the above described CRISPR-dCas13b assembly binds to a pre-mRNA. When the dCas13b that is linked to a MS2 binding protein binds to the pre-mRNA, the cis-splice acceptor is blocked. The MS2 binding protein tethers a trans-splicing RNA molecule of interest, and with the binding of the dCas13b to the target pre-mRNA, directs the trans-splicing RNA to the pre-mRNA. This enables highly efficient trans-splicing (FIG. 1E).

Several DNA constructs were utilized to reduce CRISPR-mediated trans-splicing to practice (FIG. 2A). First, a U6 promoter-driven gRNA construct with a *Prevotella* sp. Cas13b (PspCas13b) RNA scaffold was used to drive expression of the gRNA in the cells. The dCas13b was linked to a MS2 binding protein via a SV40 nuclear localization signal (SV40 NLS) and glycine-serine linker. Bovine growth hormone polyadenylation signal (bGHpA) was used to allow for stable expression of the construct. A splice donor was used to generate expression of a pre-mRNA that could be assayed for trans-splicing. Blue fluorescent protein (BFP) was used as a marker to validate expression of the splice donor, and a self-cleaving p2A linker was used on truncated GFP (5' GFP). To ensure the splice acceptor would undergo trans-splicing, Matrix Metallopeptidase 9 (MMP9) intron 1 and exon 2 were placed downstream, followed by bGHpA to ensure stable expression. A splice acceptor reporter was designed, such that trans-splicing would generate a complete GFP, which could be observed by flow cytometry. The designed ms2 intron consists of i) a binding domain (BD) which hybridizes to MMP9 intron 1 in the splice donor reporter, ii) two ms2 loops, iii) a branch point (BP), and iv) a polypyrimidine tract (PPT), followed by v) a splice acceptor sequence. The second half of the truncated GFP was placed behind the ms2 intron, which was then followed by a reverse transcription primer binding site (RT), allowing for generation of next generation sequencing libraries (NGS) to validate trans-splicing via RNAseq. To confirm expression of the splice acceptor reporter, an internal ribosome entry site (IRES) was used to drive translation of mCherry, thus allowing mCherry measurement via flow cytometry independent of trans-splicing. Lastly, a ms2 null (Δ2x ms2) splice acceptor reporter was used to measure the effect of ms2 loops on CRISPR-mediated trans-splicing efficiency.

Figure 2B:
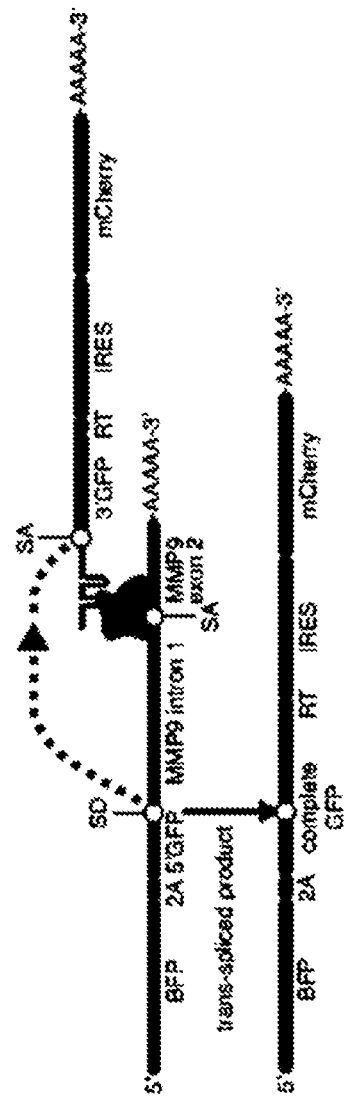
FIG. 2B illustrates the trans-splicing reporter assay.

Upon successful trans-splicing, the truncated GFP exons (5' GFP, 3' GFP) introduced by the splice donor and acceptor reporters are spliced together, generating a transcript that contains a complete GFP mRNA sequence capable of creating a functional GFP protein product (FIG. 2B). Cells were gated for BFP+ and mCherry+ using flow cytometry, to validate expression of both the splice donor (SD) and splice acceptor (SA) reporters respectively. From the gated double positive BFP+ mCherry+ population, trans-splicing activity was measured by the fraction of cells that were GFP+.

Example 2—Measuring CRISPR-Mediated Trans-Splicing

Figure 3A:
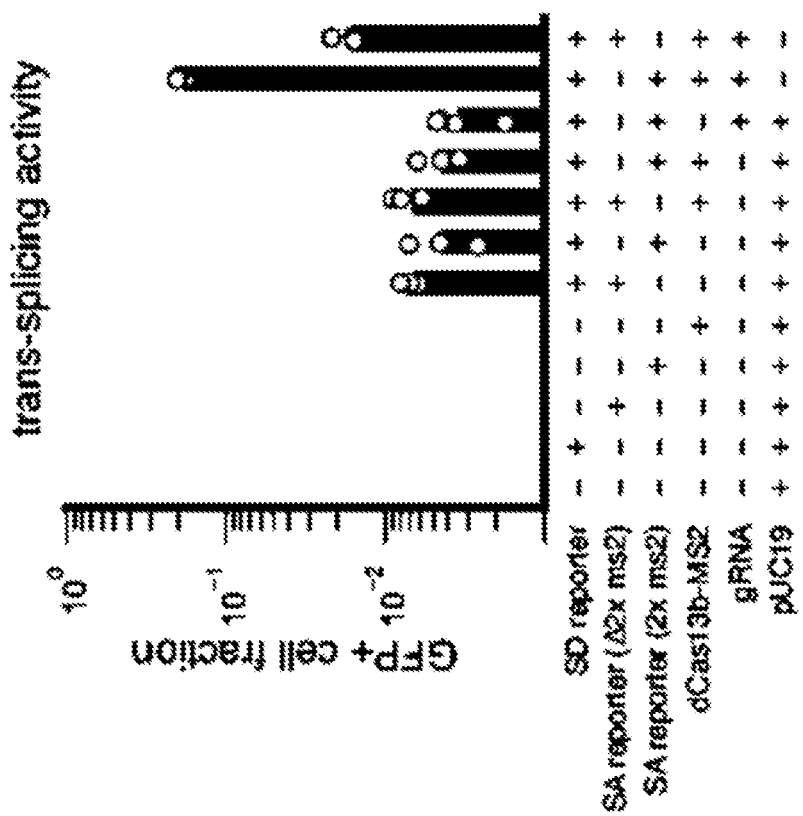
FIG. 3A illustrates the trans-splicing activity of the CRISPR/Cas system compared to negative controls in HEK193FT cells. Columns 1-5 represent activity in the negative controls. Column 11 is the activity of the CRISPR/Cas system.

HEK293FT cells were transfected in a 12-well plate format, with a total of 1250 ng of DNA and 4 uL of Lipofectamine 2000 per condition. Each construct was one fourth of the total DNA transfection, with the exception of pUC19, which was used as non-coding control DNA in conditions where less than four components were delivered. A total of 1250 ng of DNA was delivered. Media was changed 6 hours post-transfection, and the cells were analyzed via flow cytometry 48 hours after transfection. Negative controls (columns 1-5 of FIG. 3A) showed no detection of trans-splicing via the GFP reporter assay. Column 6, which represents the state-of-the-art for trans-splicing, led to detection of trans-splicing in 0.69%±0.08% (mean±SD, n=4) of BFP+ mCherry+ cells. CRISPR-mediated trans-splicing (column 11) led to detection of trans-splicing in 19.58%±1.01% (mean±SD, n=4) of BFP+ mCherry+ cells, which was a 28.03±1.45-fold increase. As expected, CRISPR-mediated trans-splicing had a significant decrease in efficiency when utilizing the ms2 null (Δ2x ms2) SA reporter (column 12). Interestingly, there was a significant increase in trans-splicing compared to the case where dCas13b-MS2 and a gRNA were not expressed (column 6) by 2.45±0.45-fold (p=0.00074), suggesting that binding dCas13b to the SA prevents cis-splicing, thereby promoting trans-splicing in contexts where there are no further exons for cis-splicing.

Figure 3B:
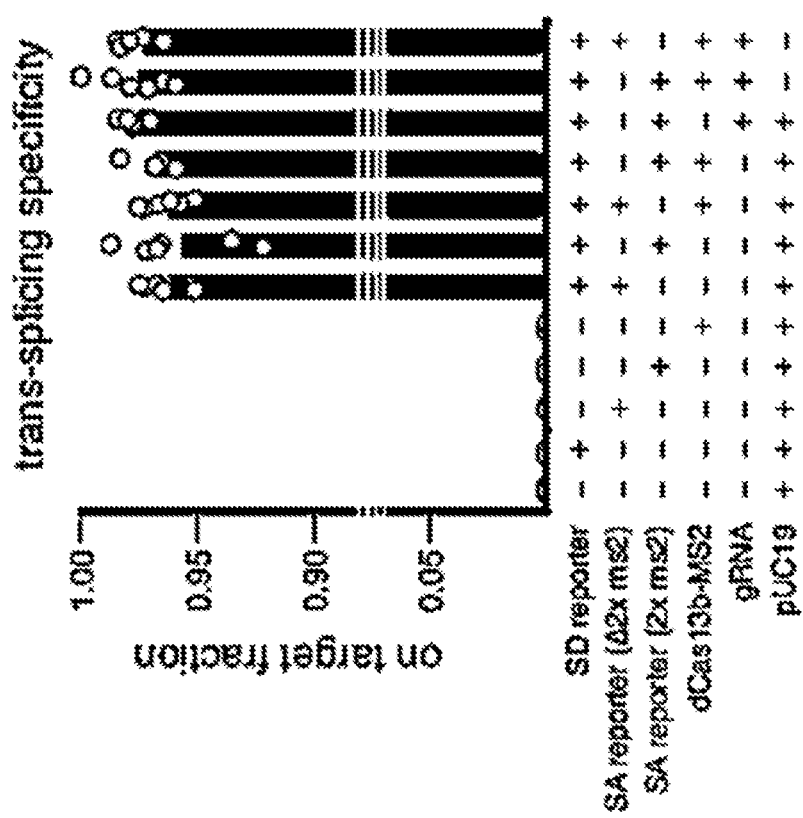
FIG. 3B illustrates the trans-splicing specificity of the CRISPR/Cas system. RNAseq libraries were created using primers that bind to the SA reporter mRNA, and on-target reactions of reads were calculated and plotted.

RNAseq libraries were created by carrying out reverse transcription on the SA reporter using a reverse transcription primer that binds to the RT site on the SA reporter mRNA. The RT site was designed to also carry a TruSeq adapter sequence, such that read 1 of the final library would be the 3' end of GFP. The read 2 sequencing adapter was randomly inserted via tagmentation. Reads were filtered by having read 1 match the 3' end of GFP. Read 2 was then aligned using BWA to a whole transcriptome reference concatenated with the SD and SA reporters. The on-target fraction (plotted) was calculated by dividing the number of reads that map to the SD reporter by the number of total reads that align to the transcriptome (including the SD reporter) but do not align to the SA reporter (FIG. 3B).

Example 3—Generation of RNAseq Library to Measure On-Target Trans-Splicing

RNAseq libraries generated by RT of the SA reporter were analyzed for mapping position of read 2. As expected, read 2 showed high mapping to the exonic region of the SD reporter, demonstrating trans-splicing. In contrast, only 1 read mapped to the MMP9 intron and MMP9 exon 2, which was likely from index-hopping or chimeric events (FIG. 4A).

To validate cis-splicing of the SD reporter, RNAseq libraries were generated by reverse transcription of the poly(A) tail. As expected, cis-splicing was observed as the number of reads was lower for the intronic region (MMP intron 1) and higher for the exonic regions (BFP-2A-5'GFP and MMP9 exon 2) (FIG. 4B).

Figure 5:
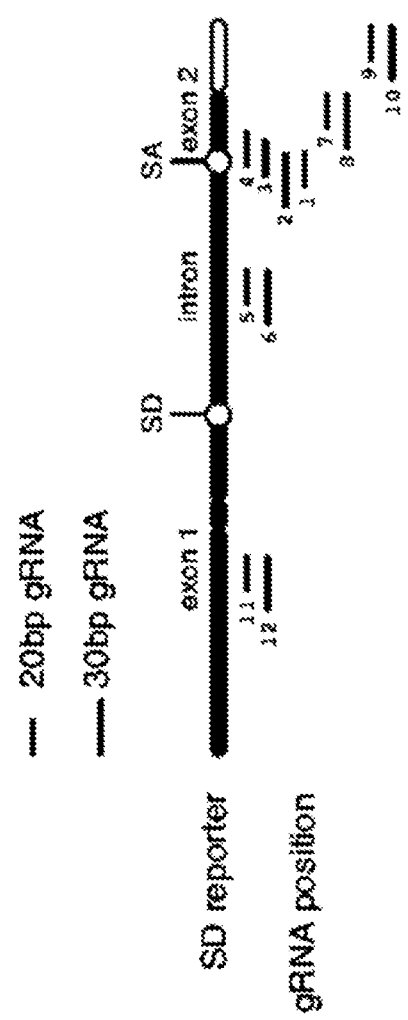
FIG. 5 is a schematic of gRNA target sites. Several gRNAs were designed to target different regions of the SD reporter.

To better understand the gRNA design constraints for CRISPR-mediated trans-splicing, several gRNAS were designed to target different regions of the SD reporter. gRNAS-1-4 targeted the SA site, while gRNAs 5 and 6 targeted the intron. gRNAs 7 and 8 targeted MMP9 exon 2, while gRNAs 9 and 10 targeted bGHpA. gRNAs 11 and 12 targeted BFP in the first exon (FIG. 5).

Figure 6A:
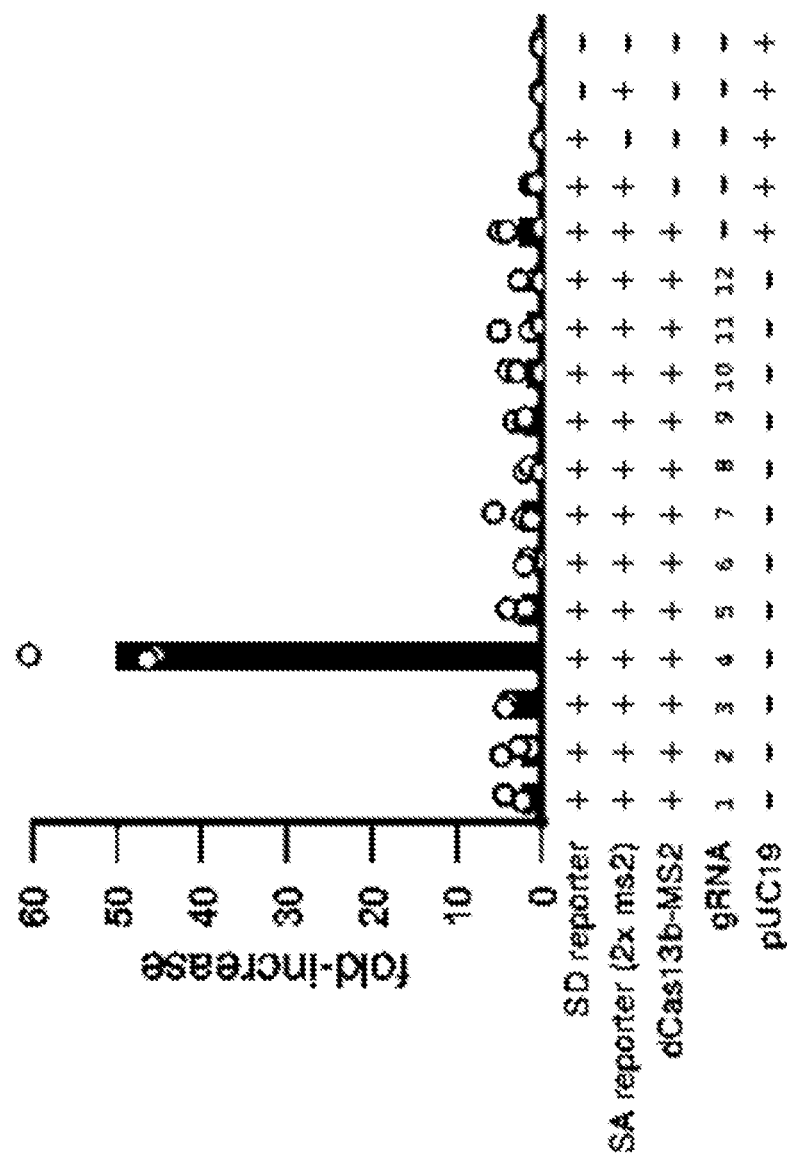
FIG. 6A illustrates fold-increase in targeted trans-splicing with dCas13b-MS2 as measured by using a truncated GFP trans-splicing reporter assay.

Targeted trans-splicing was measured by using the truncated GFP trans-splicing reporter assay. Flow cytometry was conducted on transfected cells with 3 biological replicates per condition. When using a gRNA that targets the splice acceptor site, CRISPR-mediated trans-splicing improved trans-splicing efficiency by ~50-fold with a gRNA designed to target the splice acceptor site. In this case, the most effective gRNA (gRNA 4) has 3' guide mapping to the splice acceptor site. As expected, targeting the CRISPR system to alternative regions of the SD reporter result in marginal gains in trans-splicing efficiency (FIG. 6A).

Figure 6B:
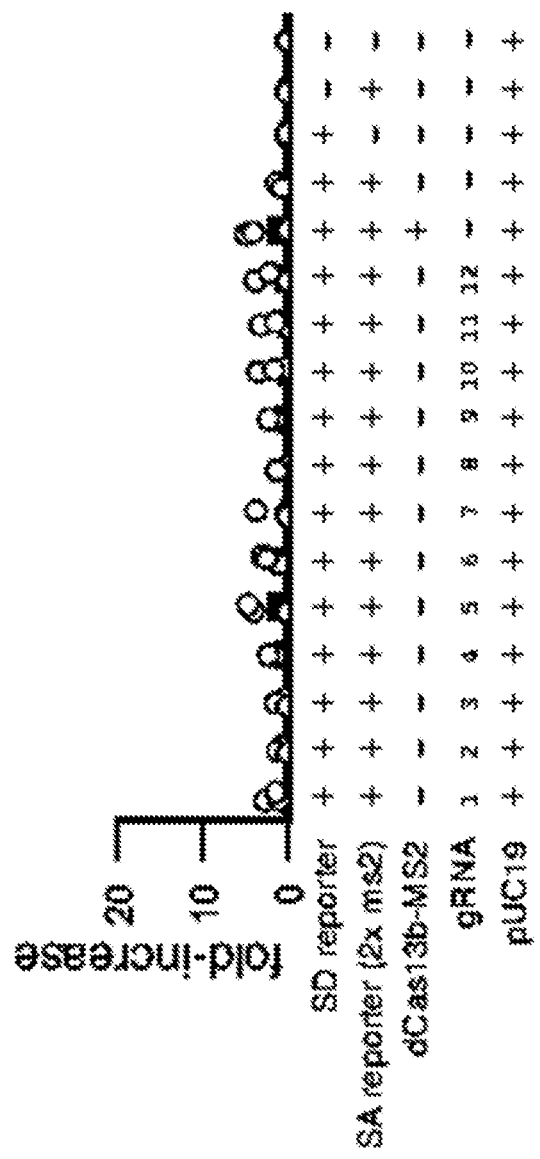
FIG. 6B illustrates the targeted trans-splicing without dCas13b-MS2.

Fold-increases in targeted trans-splicing are marginal when excluding dCas13b-MS2, as measured by the truncated GFP trans-splicing reporter assay (FIG. 6B). Flow cytometry was conducted on transfected cells with three biological replicates per condition.

Example 4—Trans-Splicing Induced by a Small Molecule

Figure 8A:
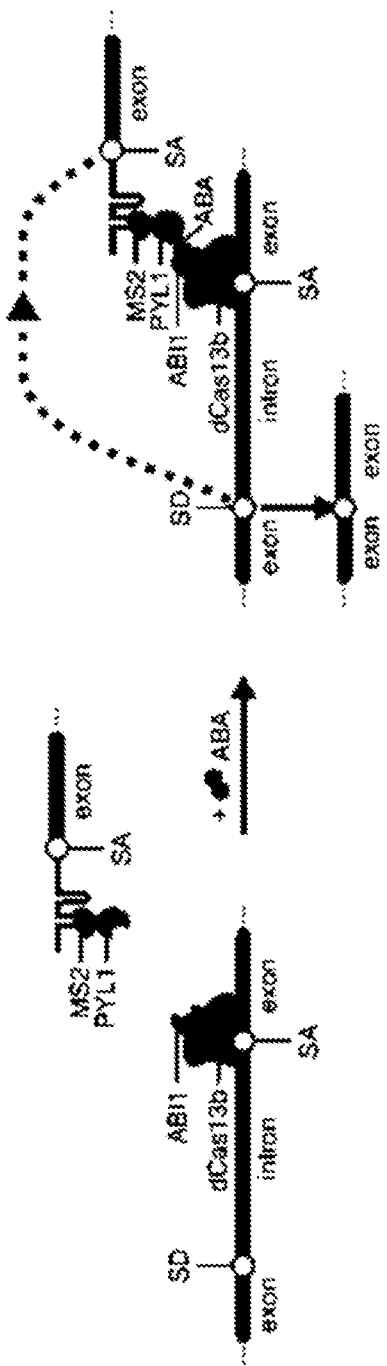
FIG. 8A illustrates a dCas13b polypeptide fused to abscisic acid (ABA)-binding protein ABI1, and MS2 fused to PYL1.

In order to test if the trans-splicing dCas13b complex could be modified to induce trans-splicing with a small molecule, dCas13b was fused to ABI1, and the MS2 was fused to PYL1, both via glycine-serine linkers (FIG. 8A). It was hypothesized that with this architecture, trans-splicing can be transiently induced via introduction of abscisic acid (ABA), as the machinery assembles in the presence of ABA. The construct delivered by a single expression cassette was a CMV-dPspCas13b-ABI1-2A-PYL1-MS2. A split GFP reporter was utilized to assay trans-splicing activity via GFP measurement through flow cytometry.

Figure 8B:
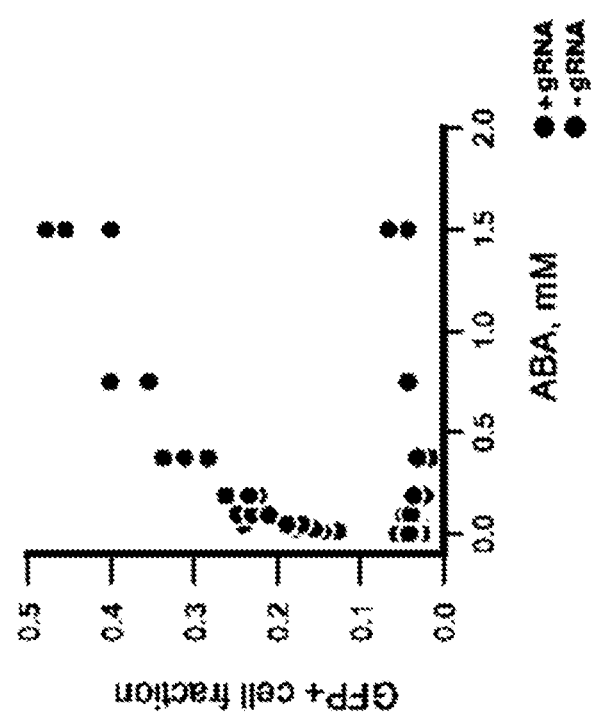
FIG. 8B is a graph demonstrating expression of GFP after induction of trans-splicing in the presence of a range of ABA concentrations, shown with a no guide control as a negative control.
Figure 8C:
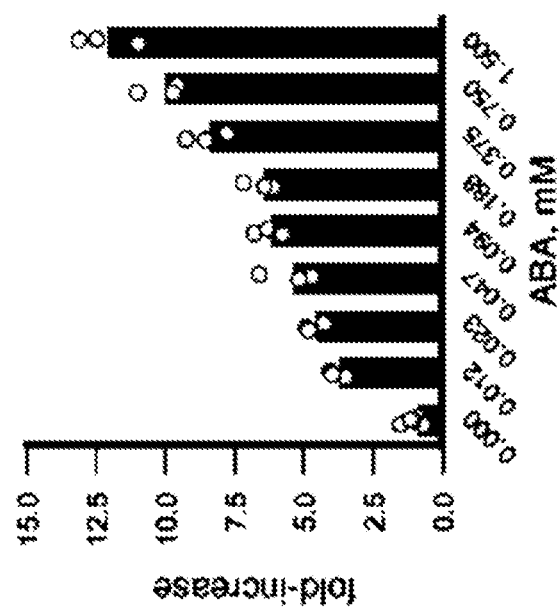
FIG. 8C demonstrates that ABA could control induced targeted trans-splicing by measuring fold-increase in expression of GFP with increasing concentrations of ABA (mM).

Using the construct as described above, the split GFP reporter was trans-spliced in the presence of 1.5 mM ABA, resulting in >40% of cells being GFP+ (FIG. 8B). HEK293FT cells were transfected using Lipofectamine 2000 per the manufacturer's instructions, and flow cytometry was conducted 72 hours after transfection. ABA was titrated across multiple samples, and 3 biological replicates per ABA concentration were measured via flow cytometry. To demonstrate that ABA could control the induced targeted trans-splicing, a split GFP reporter was trans-spliced in the presence of ABA, and the fold-change in GFP translation was tightly controlled by ABA concentration (FIG. 8C).

Example 5—Measuring Trans-Splicing at Splice Junctions

Figure 9A:
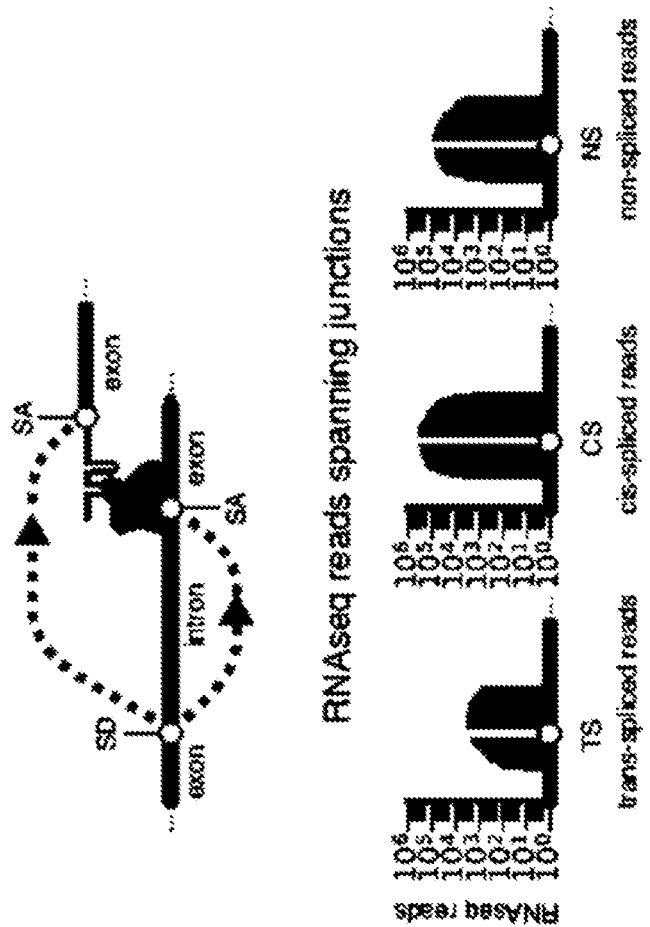
FIG. 9A illustrates RNAseq reads spanning possible junctions.

To measure exon junctions, full-length RNAseq was conducted on 293FT cells transfected with dCas13b-MS2, gRNA, and the split GFP reporter system (SD reporter, SA reporter with 2× ms2). Cells were gated for BFP+ and mCherry+ via flow cytometry, to validate expression of both the splice donor (SD) and splice acceptor (SA) reporters respectively, and were then sorted into TCL buffer to lyse the cells prior to RNAseq library construction. RNAseq reads spanning all possible junctions were filtered using regular expressions, and were subsequently mapped onto all possible junction sequences, namely, trans-spliced junctions (TS), cis-spliced junctions (CS), and non-spliced junctions (NS). The mapping positions were the plotted to illustrate reads spanning possible junctions (FIG. 9A).

Figure 9B:
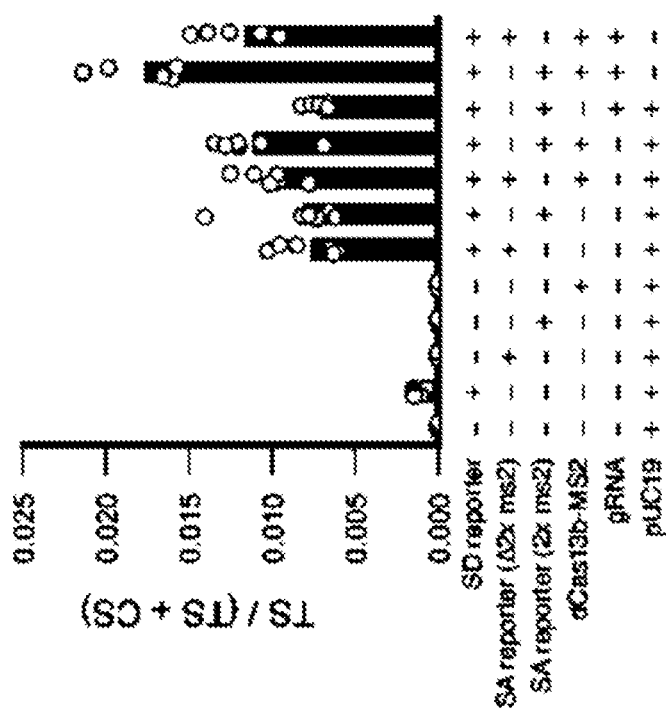
FIG. 9B is a plot of spliced reads that were trans-spliced for all transfection conditions.

Full length RNAseq reads spanning all possible junctions were filtered using regular expressions, and were subsequently mapped onto all possible junction sequences, namely, the trans-spliced junction (TS), cis-spliced junction (CS), and non-spliced junction (NS). A fraction of spliced reads that were trans-spliced were calculated and plotted for all transfection conditions (FIG. 9B). Full length RNAseq reads spanning all possible junctions were filtered using regular expressions, and were subsequently mapped onto all possible junction sequences, namely the TS, CS, and NS as above. Fractions of the spliced reads that were cis-spliced was calculated and plotted for all transfection conditions (FIG. 9C). Results how that the reporter undergoes efficient splicing, and that dCas13 inhibits cis-splicing in the presence of a targeting gRNA.

Example 6—Strategies for Targeted Trans-Splicing

Figure 10A:
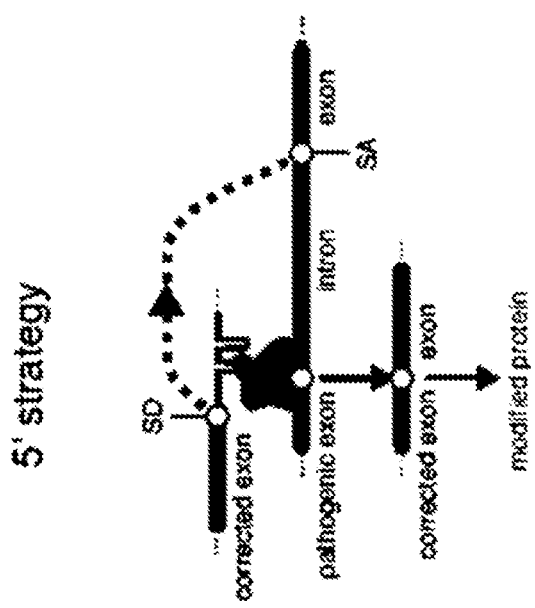
FIG. 10A illustrates a strategy for 5' targeting of trans-splicing.
Figure 10B:
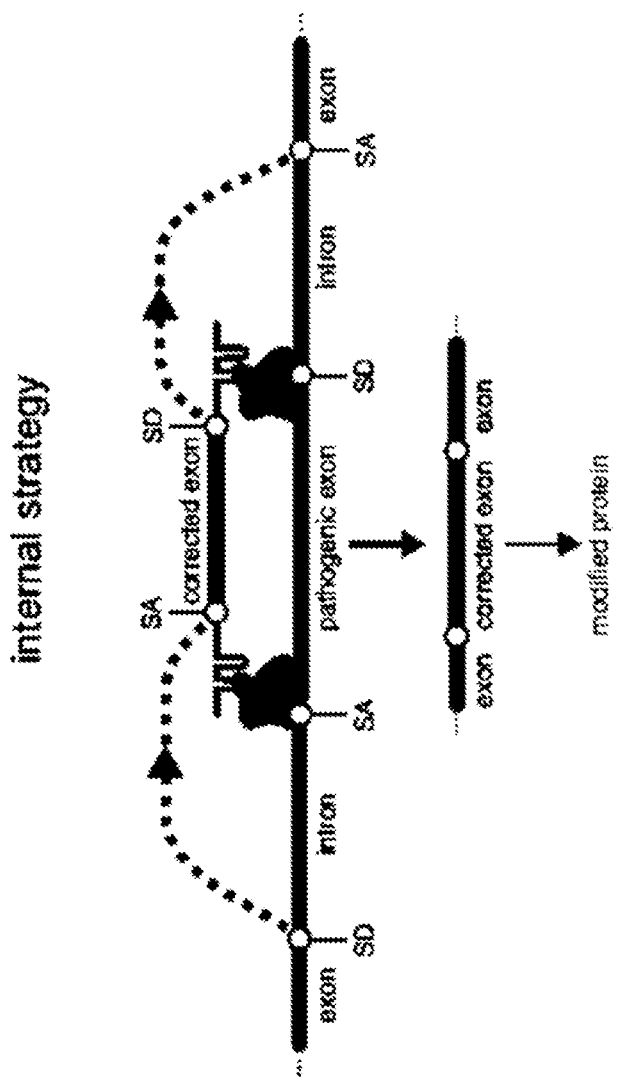
FIG. 10B illustrates an internal targeted trans-splicing strategy.
Figure 10C:
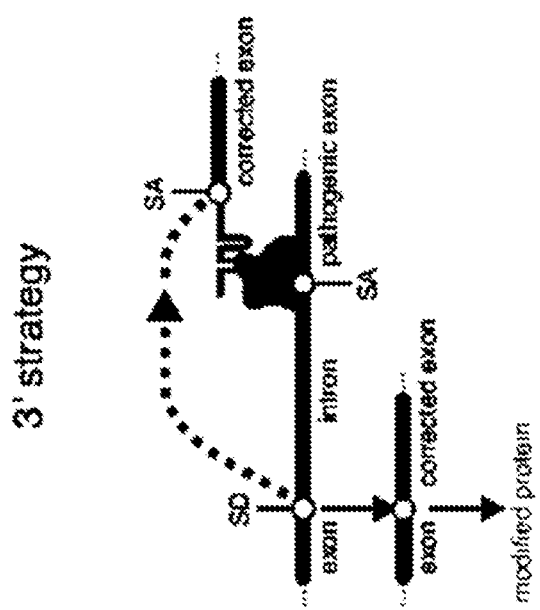
FIG. 10C illustrates a strategy for 3' trageting of trans-splicing.

FIG. 10A illustrates a strategy for 5' targeting of trans-splicing. For this strategy, a dCas13b-MS2 or analogue, can be targeted to a splice donor (SD), while simultaneously providing a 5' repair template for 5' correction or modification of RNA. Such a strategy may be advantageous when the correction or modification is near the 5' end of the mRNA. FIG. 10B illustrates an internal targeted trans-splicing strategy. A dCas13b-MS2 or analogue, can be targeted both to a splice acceptor, and a splice donor, while simultaneously providing a repair template with an exon, or group of exons, possessing both a splice acceptor and splice donor. FIG. 10C illustrates a strategy for 3' targeting of trans-splicing. For this strategy, a 3' repair template may be provided for 3' correction or modification of RNA, along with a dCas13b-MS2, or analogue, targeting a splice acceptor (SA). Such a strategy may be advantageous when the correction or modification is near the 3' end of the mRNA.

Example 7—Internal Exon Repair

Figure 11A:
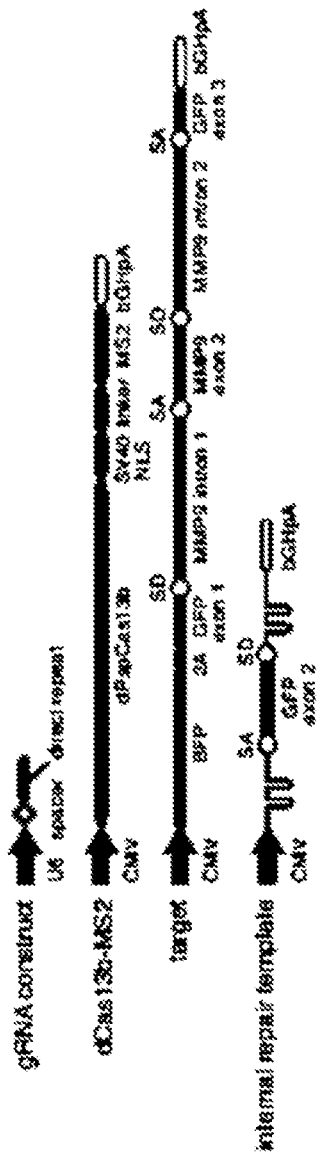
FIG. 11A illustrates dPspCas13b-MS2, gRNA, target and internal repair template constructs to test if CRISPR-mediated internal exon repair is possible.

FIG. 11A illustrates a construct to be used for internal exon repair. Standard gRNA constructs were used, along with CMV-dPspCas13b-MS2 to test whether internal exon repair is possible with CRISPR-mediated trans-splicing. GFP was split into three exons, and GFP exons 1 and 3 were utilized in the target RNA molecule design. To simulate a pathogenic exon, MMP9 exon 2 was placed between GFP exons 1 and 3 on the target molecule, along with corresponding flanking introns: MMP9 intron 1 and MMP9 intron 2. The internal repair template was designed to have GFP exon 2 flanked by two synthetic introns, each with an ms2 hairpin.

Figure 11B:
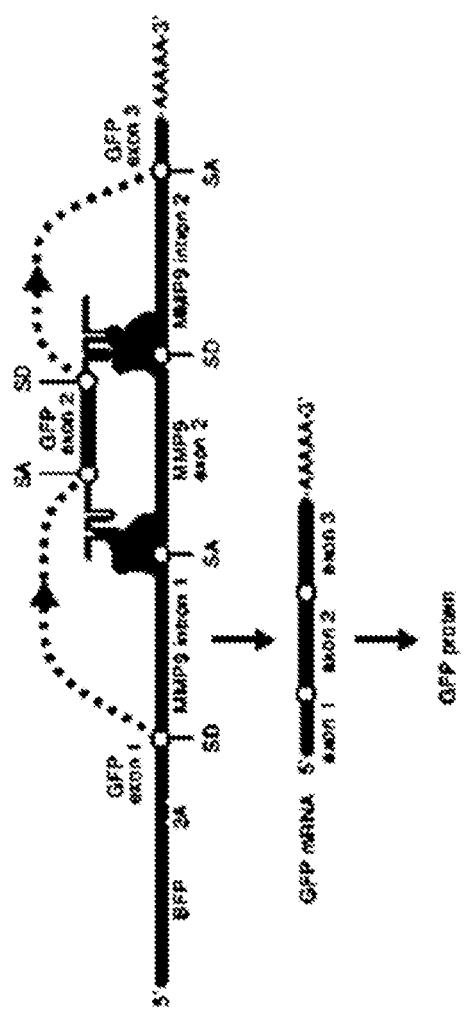
FIG. 11B illustrates monitoring of expression of the target transcript via expression of blue fluorescent protein (BFP), and monitoring internal exon repair via expression of green fluorescent protein (GFP).

FIG. 11B illustrates an assay for monitoring internal exon repair. The target transcript is monitored via expression of blue fluorescent protein (BFP). Cells expressing the target transcript are GFP negative, as the middle exon of GFP (GFP exon 2) is missing from the transcript. Upon internal exon repair, GFP exon 2 from the repair template is trans-spliced in order to create a complete GFP mRNA, and the BFP moiety is lost via the T2A self cleaving peptide. The presence of GFP mRNA leads to translation and expression of GFP protein, which can be measured through flow cytometry.

Figure 11C:
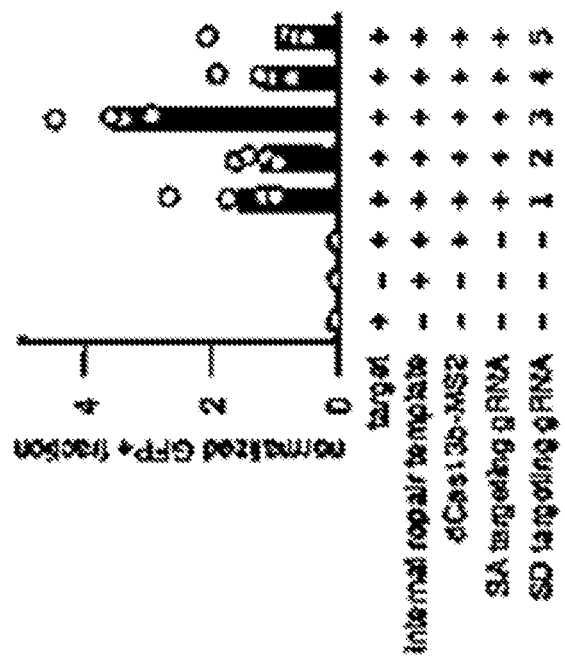
FIG. 11C measures GFP expression following internal exon repair, demonstrating that GFP expression is only possible in the presence of the CRISPR system along with gRNAs targeting splice sites.

FIG. 11C is a readout of GFP expression following internal exon repair. 293FT cells were transfected using lipofectamine 2000 per manufacturer's instructions and cells were transfected in a 96 well format (100 ng per well) with four biological replicates for each condition. Flow cytometry was conducted 48 hours after transfection. Several gRNAs targeting the splice donor (SD) were designed (SD targeting gRNAs 1-5), and delivered in conjunction with a splice acceptor (SA) targeting gRNA. In the absence of gRNAs, no GFP+ cells were detected. However, upon introduction of gRNAs, GFP+ cells were detected and the fraction of GFP+ cells varied depending on the placement of the gRNA relative to the splice donor.

Example 8—Use of Cas13 Orthologs

Figure 12:
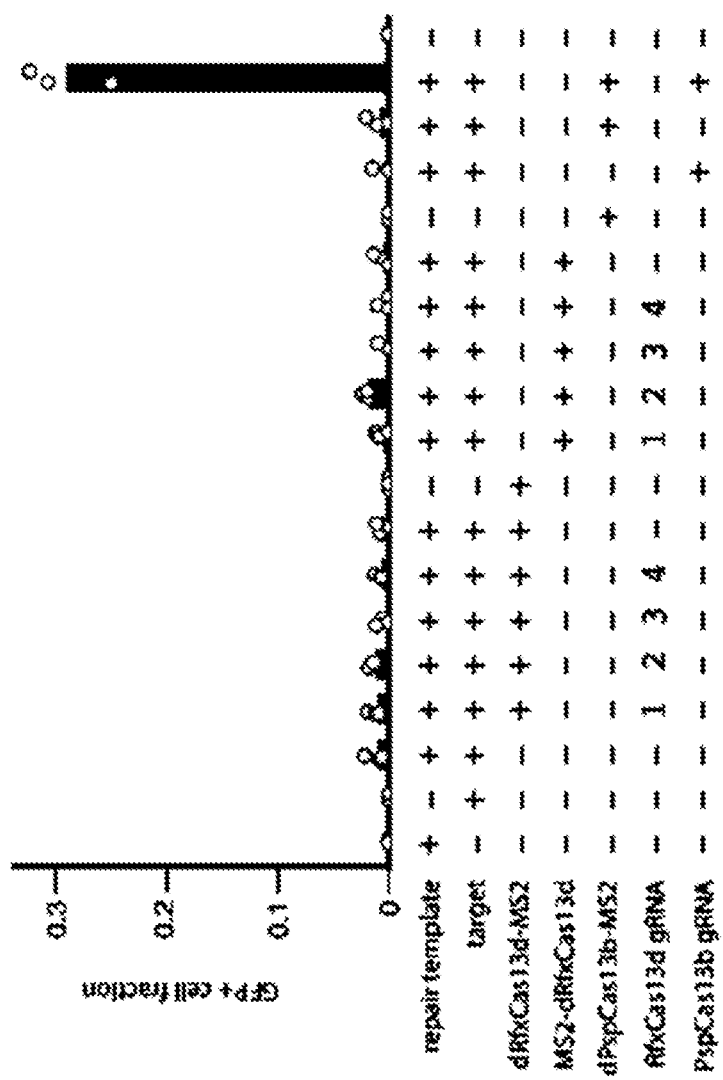
FIG. 12 is fluorescence measurements to illustrate that trans-splicing can be mediated using other Cas13 orthologs, such as Cas13d.

To test whether Cas13d could also lead to CRISPR-mediated trans-splicing, dRfxCas13d was benchmarked against dPspCas13b. Four guides were designed for RfxCas13d, which all targeted the splice acceptor site in the target reporter. MS2 was fused to the N and C-terminus in two different Cas13d architectures. 293FT cells were transfected using lipofectamine 2000 per manufacturer's instructions and cells were transfected in a 96 well format (100 ng per well) with three biological replicates per condition. Flow cytometry was conducted 48 hours after transfection, and cells were gated on BFP and mCherry in order to only consider cells with both target and repair template reporters. BFP+mCherry+ cells were gated on GFP to determine trans-splicing frequency. Mild trans-splicing was observed in the RfxCas13d systems, which were far outperformed by the PspCas13b system (FIG. 12).

Example 9—AAV-Based Delivery of CRISPR Trans-Splicing System

Figure 13:
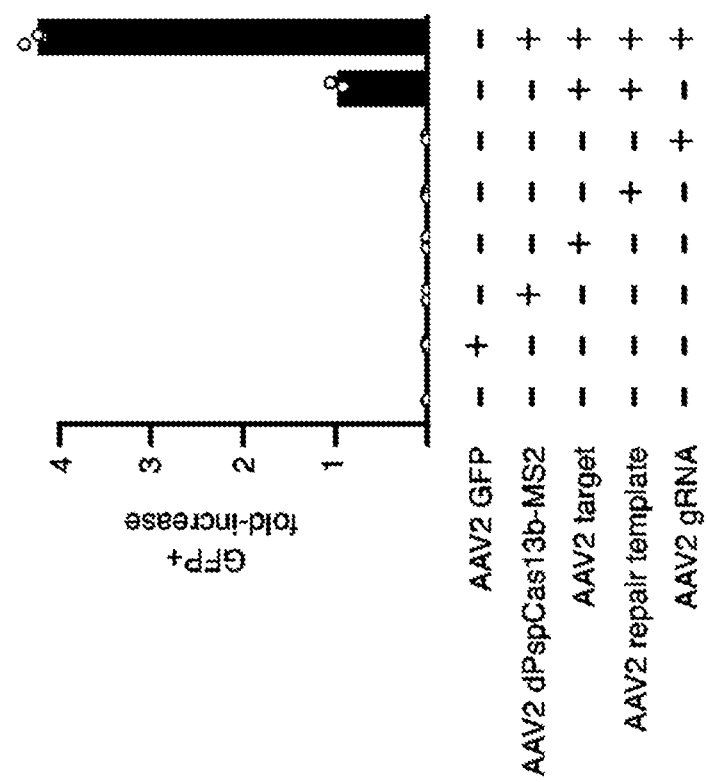
FIG. 13 demonstrates CRISPR-mediated trans-splicing accomplished with a construct delivered with a multi-vector AAV-based approach.

To test whether the CRISPR system could be delivered with a multi-vector AAV-based approach, individual components were cloned into constructs with AAV2 ITRs to enable AAV packaging. AAV2/8 was produced in 293FT cells by PEI co-transfecting each transfer vector with Rep2/Cap8 (pAAV2/8) and AAV helper plasmid (pAdDeltaF6) in a 3:5:6 ratio at 30 ug of DNA per 150 mm dish. Media was changed 24 hours after transfection, and supernatants were harvested 72 hours after transfection. Supernatant was then filtered with a 0.45 um cellulose acetate filter and AAV was concentrated by using a 100 kDa MWCO amicon filter at 4000 rcf for 30 minutes at 4 C. 293FT cells were then transduced in suspension using 3 uL of AAV per well in a 96 well plate with four biological replicates per condition. Flow cytometry was conducted 72 hours after AAV transduction in order to measure CRISPR-mediated trans-splicing. Cells were gated on BFP and mCherry in order to only consider cells with both target and repair template reporters. BFP+ mCherry+ cells were gated on GFP to determine trans-splicing frequency. Delivery of the CRISPR system via a multi-vector AAV approach showed significant increase in trans-sicing as measured by GFP+ fluorescence in flow cytometry (FIG. 13).

The invention claimed is:

1. A system for targeting a nucleic acid for trans-splicing, the system comprising:
   (i) a CRISPR/Cas system comprising a Type VI Cas polypeptide and a nucleic acid guide;
   (ii) a specific RNA-binding polypeptide that associates with the CRISPR/Cas system; and
   (iii) a trans-splicing template comprising a splice donor and/or acceptor and an RNA sequence that binds to the specific RNA-binding polypeptide, thereby targeting the nucleic acid for trans-splicing.

2. The system of claim 1, wherein the nucleic acid guide is an RNA guide.

3. The system of claim 1, wherein the nucleic acid guide is a DNA guide.

4. The system of claim 1, wherein the CRISPR/Cas system comprises one nucleic acid guide.

5. The system of claim 1, wherein the CRISPR/Cas system comprises more than one nucleic acid guide.

6. The system of claim 5, wherein the nucleic acid guides recognize multiple targets.

7. The system of claim 1, wherein the nucleic acid guide targets a splice acceptor (SA) site.

8. The system of claim 1, wherein the nucleic acid guide targets a splice donor (SD) site.

9. The system of claim 1, wherein the nucleic acid guide targets a region near a splice site.

10. The system of claim 9, wherein the nucleic acid guide targets a region within 200 nucleotides of a splice site.

11. The system of claim 5, wherein the more than one nucleic acid guides target one nucleic acid of interest.

12. The system of claim 5, wherein the more than one nucleic acid guides target multiple nucleic acids of interest.

13. The system of claim 1, wherein the Cas polypeptide is selected from the group consisting of Cas13a, Cas13b, and Cas13d.

14. The system of claim 1, wherein the specific RNA-binding polypeptide comprises a viral protein.

15. The system of claim 1, comprising one trans-splicing template.

16. The system of claim 1, wherein the trans-splicing activity is regulated by a small molecule.

17. The system of claim 1, wherein the Cas polypeptide is a nuclease-inactive Cas13 polypeptide.

18. The system of claim 1, comprising one or more polynucleotides encoding the Cas polypeptide, the RNA guide, the specific RNA-binding polypeptide, and/or the trans-splicing template.

19. The system of claim 18, comprising one or more vectors comprising the one or more polynucleotides.

* * * * *

```
SEQUENCE LISTING

<160> NUMBER OF SEQ ID NOS: 101

<210> SEQ ID NO 1
<211> LENGTH: 3282
<212> TYPE: DNA
<213> ORGANISM: Artificial Sequence
<220> FEATURE:
<223> OTHER INFORMATION: dPspCas13b nucleic acid sequence

<400> SEQUENCE: 1
atgaacatcc ccgctctggt ggaaaaccag aagaagtact ttggcaccta cagcgtgatg      60
gccatgctga acgctcagac cgtgctggac cacatccaga aggtggccga tattgagggc     120
gagcagaacg agaacaacga gaatctgtgg tttcaccccg tgatgagcca cctgtacaac     180
gccaagaacg gctacgacaa gcagcccgag aaaaccatgt tcatcatcga gcggctgcag     240
agctacttcc cattcctgaa gatcatggcc gagaaccaga gagagtacag caacggcaag     300
tacaagcaga accgcgtgga agtgaacagc aacgacatct tcgaggtgct gaagcgcgcc     360
ttcggcgtgc tgaagatgta cagggacctg accaacgcat acaagaccta cgaggaaaag     420
ctgaacgacg gctgcgagtt cctgaccagc acagagcaac ctctgagcgg catgatcaac     480
aactactaca cagtggccct gcggaacatg aacgagagat acggctacaa gacagaggac     540
ctggccttca tccaggacaa gcggttcaag ttcgtgaagg acgcctacgg caagaaaaag     600
tcccaagtga ataccggatt cttcctgagc ctgcaggact acaacggcga cacacagaag     660
aagctgcacc tgagcggagt gggaatcgcc ctgctgatct gcctgttcct ggacaagcag     720
tacatcaaca tcttttctgag caggctgccc atcttctcca gctacaatgc cagagcgag     780 gaacggcgga tcatcatcag atccttcggc atcaacagca tcaagctgcc caaggaccgg     840
atccacagcg agaagtccaa caagagcgtg gccatggata tgctcaacga agtgaagcgg     900
tgccccgacg agctgttcac aacactgtct gccgagaagc agtcccggtt cagaatcatc     960
agcgacgacc acaatgaagt gctgatgaag cggagcagcg acagattcgt gcctctgctg    1020
ctgcagtata tcgattacgg caagctgttc gaccacatca ggttccacgt gaacatgggc    1080
aagctgagat acctgctgaa ggccgacaag acctgcatcg acggccagac cagagtcaga    1140
gtgatcgagc agccctgaa cggcttcggc agactggaag aggccgagac aatgcggaag    1200
caagagaacg gcaccttcgg caacagcggc atccggatca gagacttcga gaacatgaag    1260
cgggacgacg ccaatcctgc caactatccc tacatcgtgg acacctacac acactacatc    1320
ctggaaaaca caaggtcga gatgtttatc aacgacaaag aggacagcgc cccactgctg    1380
cccgtgatcg aggatgatag atacgtggtc aagacaatcc ccagctgccg gatgagcacc    1440
ctggaaattc cagccatggc cttccacatg tttctgttcg gcagcaagaa aaccgagaag    1500
ctgatcgtgg acgtgcacaa ccggtacaag agactgttca aggccatgca gaaagaagaa    1560
gtgaccgccg agaatatcgc cagcttcgga atcgccgaga gcgacctgcc tcagaagatc    1620
```

```
ctggatctga tcagcggcaa tgcccacggc aaggatgtgg acgccttcat cagactgacc    1680
gtggacgaca tgctgaccga caccgagcgg agaatcaaga gattcaagga cgaccggaag    1740
tccattcgga gcgccgacaa caagatggga agagaggct tcaagcagat ctccacaggc     1800
aagctggccg acttcctggc caaggacatc gtgctgtttc agcccagcgt gaacgatggc    1860
gagaacaaga tcaccggcct gaactaccgg atcatgcaga gcgccattgc cgtgtacgat    1920
agcggcgacg attacgaggc caagcagcag ttcaagctga tgttcgagaa ggcccggctg    1980
atcggcaagg gcacaacaga gcctcatcca tttctgtaca aggtgttcgc ccgcagcatc    2040
cccgccaatg ccgtcgagtt ctacgagcgc tacctgatcg agcggaagtt ctacctgacc    2100
ggcctgtcca acgagatcaa gaaggcaac agagtggatg tgcccttcat ccggcgggac     2160
cagaacaagt ggaaaacacc cgccatgaag accctgggca gaatctacag cgaggatctg    2220
cccgtggaac tgcccagaca gatgttcgac aatgagatca gtcccacct gaagtccctg     2280 ccacagatgg aaggcatcga cttcaacaat gccaacgtga cctatctgat cgccgagtac    2340
atgaagagag tgctggacga cgacttccag accttctacc agtggaaccg caactaccgg    2400
tacatggaca tgcttaaggg cgagtacgac agaaagggct ccctgcagca ctgcttcacc    2460
agcgtggaag agagagaagg cctctggaaa gagcgggcct ccagaacaga gcggtacaga    2520
aagcaggcca gcaacaagat ccgcagcaac cggcagatga aaacgccag cagcgaagag     2580 atcgagacaa tcctggataa gcggctgagc aacagccgga cgagtacca gaaaagcgag     2640 aaagtgatcc ggcgctacag agtgcaggat gccctgctgt ttctgctggc caaaaagacc    2700
ctgaccgaac tggccgattt cgacggcgag aggttcaaac tgaaagaaat catgcccgac    2760
gccgagaagg gaatcctgag cgagatcatg cccatgagct tcaccttcga gaaggcggc     2820 aagaagtaca ccatcaccag cgagggcatg aagctgaaga actacggcga cttctttgtg    2880
ctggctagcg acaagaggat cggcaacctg ctggaactcg tgggcagcga catcgtgtcc    2940
aaagaggata tcatggaaga gttcaacaaa tacgaccagt gcaggcccga gatcagctcc    3000
atcgtgttca acctggaaaa gtgggccttc gacacatacc ccgagctgtc tgccagagtg    3060
gaccgggaag agaaggtgga cttcaagagc atcctgaaaa tcctgctgaa caacaagaac    3120
atcaacaaag agcagagcga catcctgcgg aagatccgga acgccttcga tgcaaacaat    3180
taccccgaca aggcgtggt ggaaatcaag gccctgcctg agatcgccat gagcatcaag      3240
aaggcctttg gggagtacgc catcatgaag ggaagcctgc ag                        3282
```

<210> SEQ ID NO 2
<211> LENGTH: 1094
<212> TYPE: PRT
<213> ORGANISM: Artificial Sequence
<220> FEATURE:
<223> OTHER INFORMATION: dPspCas13b amino acid sequence

<400> SEQUENCE: 2

Met Asn Ile Pro Ala Leu Val Glu Asn Gln Lys Lys Tyr Phe Gly Thr
1               5                   10                  15

Tyr Ser Val Met Ala Met Leu Asn Ala Gln Thr Val Leu Asp His Ile
            20                  25                  30

Gln Lys Val Ala Asp Ile Glu Gly Glu Gln Asn Glu Asn Asn Glu Asn
        35                  40                  45

Leu Trp Phe His Pro Val Met Ser His Leu Tyr Asn Ala Lys Asn Gly
    50                  55                  60

```
Tyr Asp Lys Gln Pro Glu Lys Thr Met Phe Ile Ile Glu Arg Leu Gln
 65                  70                  75                  80

Ser Tyr Phe Pro Phe Leu Lys Ile Met Ala Glu Asn Gln Arg Glu Tyr
                 85                  90                  95

Ser Asn Gly Lys Tyr Lys Gln Asn Arg Val Glu Val Asn Ser Asn Asp
            100                 105                 110

Ile Phe Glu Val Leu Lys Arg Ala Phe Gly Val Leu Lys Met Tyr Arg
        115                 120                 125

Asp Leu Thr Asn Ala Tyr Lys Thr Tyr Glu Glu Lys Leu Asn Asp Gly
    130                 135                 140

Cys Glu Phe Leu Thr Ser Thr Glu Gln Pro Leu Ser Gly Met Ile Asn
145                 150                 155                 160

Asn Tyr Tyr Thr Val Ala Leu Arg Asn Met Asn Glu Arg Tyr Gly Tyr
            165                 170                 175

Lys Thr Glu Asp Leu Ala Phe Ile Gln Asp Lys Arg Phe Lys Phe Val
            180                 185                 190

Lys Asp Ala Tyr Gly Lys Lys Ser Gln Val Asn Thr Gly Phe Phe
            195                 200                 205

Leu Ser Leu Gln Asp Tyr Asn Gly Asp Thr Gln Lys Lys Leu His Leu
    210                 215                 220

Ser Gly Val Gly Ile Ala Leu Leu Ile Cys Leu Phe Leu Asp Lys Gln
225                 230                 235                 240

Tyr Ile Asn Ile Phe Leu Ser Arg Leu Pro Ile Phe Ser Ser Tyr Asn
                245                 250                 255

Ala Gln Ser Glu Glu Arg Arg Ile Ile Ile Arg Ser Phe Gly Ile Asn
            260                 265                 270

Ser Ile Lys Leu Pro Lys Asp Arg Ile His Ser Glu Lys Ser Asn Lys
        275                 280                 285

Ser Val Ala Met Asp Met Leu Asn Glu Val Lys Arg Cys Pro Asp Glu
    290                 295                 300

Leu Phe Thr Thr Leu Ser Ala Glu Lys Gln Ser Arg Phe Arg Ile Ile
305                 310                 315                 320

Ser Asp Asp His Asn Glu Val Leu Met Lys Arg Ser Ser Asp Arg Phe
                325                 330                 335

Val Pro Leu Leu Leu Gln Tyr Ile Asp Tyr Gly Lys Leu Phe Asp His
            340                 345                 350

Ile Arg Phe His Val Asn Met Gly Lys Leu Arg Tyr Leu Leu Lys Ala
        355                 360                 365

Asp Lys Thr Cys Ile Asp Gly Gln Thr Arg Val Arg Val Ile Glu Gln
    370                 375                 380

Pro Leu Asn Gly Phe Gly Arg Leu Glu Glu Ala Glu Thr Met Arg Lys
385                 390                 395                 400

Gln Glu Asn Gly Thr Phe Gly Asn Ser Gly Ile Arg Ile Arg Asp Phe
                405                 410                 415

Glu Asn Met Lys Arg Asp Asp Ala Asn Pro Ala Asn Tyr Pro Tyr Ile
            420                 425                 430

Val Asp Thr Tyr Thr His Tyr Ile Leu Glu Asn Asn Lys Val Glu Met
        435                 440                 445

Phe Ile Asn Asp Lys Glu Asp Ser Ala Pro Leu Leu Pro Val Ile Glu
    450                 455                 460

Asp Asp Arg Tyr Val Val Lys Thr Ile Pro Ser Cys Arg Met Ser Thr
465                 470                 475                 480

Leu Glu Ile Pro Ala Met Ala Phe His Met Phe Leu Phe Gly Ser Lys
```

```
                485                 490                 495
Lys Thr Glu Lys Leu Ile Val Asp Val His Asn Arg Tyr Lys Arg Leu
                500                 505                 510

Phe Gln Ala Met Gln Lys Glu Glu Val Thr Ala Glu Asn Ile Ala Ser
                515                 520                 525

Phe Gly Ile Ala Glu Ser Asp Leu Pro Gln Lys Ile Leu Asp Leu Ile
                530                 535                 540

Ser Gly Asn Ala His Gly Lys Asp Val Asp Ala Phe Ile Arg Leu Thr
545                 550                 555                 560

Val Asp Asp Met Leu Thr Asp Thr Glu Arg Arg Ile Lys Arg Phe Lys
                565                 570                 575

Asp Asp Arg Lys Ser Ile Arg Ser Ala Asp Asn Lys Met Gly Lys Arg
                580                 585                 590

Gly Phe Lys Gln Ile Ser Thr Gly Lys Leu Ala Asp Phe Leu Ala Lys
                595                 600                 605

Asp Ile Val Leu Phe Gln Pro Ser Val Asn Asp Gly Glu Asn Lys Ile
                610                 615                 620

Thr Gly Leu Asn Tyr Arg Ile Met Gln Ser Ala Ile Ala Val Tyr Asp
625                 630                 635                 640

Ser Gly Asp Asp Tyr Glu Ala Lys Gln Gln Phe Lys Leu Met Phe Glu
                645                 650                 655

Lys Ala Arg Leu Ile Gly Lys Gly Thr Thr Glu Pro His Pro Phe Leu
                660                 665                 670

Tyr Lys Val Phe Ala Arg Ser Ile Pro Ala Asn Ala Val Glu Phe Tyr
                675                 680                 685

Glu Arg Tyr Leu Ile Glu Arg Lys Phe Tyr Leu Thr Gly Leu Ser Asn
                690                 695                 700

Glu Ile Lys Lys Gly Asn Arg Val Asp Val Pro Phe Ile Arg Arg Asp
705                 710                 715                 720

Gln Asn Lys Trp Lys Thr Pro Ala Met Lys Thr Leu Gly Arg Ile Tyr
                725                 730                 735

Ser Glu Asp Leu Pro Val Glu Leu Pro Arg Gln Met Phe Asp Asn Glu
                740                 745                 750

Ile Lys Ser His Leu Lys Ser Leu Pro Gln Met Glu Gly Ile Asp Phe
                755                 760                 765

Asn Asn Ala Asn Val Thr Tyr Leu Ile Ala Glu Tyr Met Lys Arg Val
                770                 775                 780

Leu Asp Asp Asp Phe Gln Thr Phe Tyr Gln Trp Asn Arg Asn Tyr Arg
785                 790                 795                 800

Tyr Met Asp Met Leu Lys Gly Glu Tyr Asp Arg Lys Gly Ser Leu Gln
                805                 810                 815

His Cys Phe Thr Ser Val Glu Glu Arg Glu Gly Leu Trp Lys Glu Arg
                820                 825                 830

Ala Ser Arg Thr Glu Arg Tyr Arg Lys Gln Ala Ser Asn Lys Ile Arg
                835                 840                 845

Ser Asn Arg Gln Met Arg Asn Ala Ser Ser Glu Glu Ile Glu Thr Ile
                850                 855                 860

Leu Asp Lys Arg Leu Ser Asn Ser Arg Asn Glu Tyr Gln Lys Ser Glu
865                 870                 875                 880

Lys Val Ile Arg Arg Tyr Arg Val Gln Asp Ala Leu Leu Phe Leu Leu
                885                 890                 895

Ala Lys Lys Thr Leu Thr Glu Leu Ala Asp Phe Asp Gly Glu Arg Phe
                900                 905                 910
```

```
Lys Leu Lys Glu Ile Met Pro Asp Ala Glu Lys Gly Ile Leu Ser Glu
        915                 920                 925

Ile Met Pro Met Ser Phe Thr Phe Glu Lys Gly Gly Lys Lys Tyr Thr
        930                 935                 940

Ile Thr Ser Glu Gly Met Lys Leu Lys Asn Tyr Gly Asp Phe Phe Val
945                 950                 955                 960

Leu Ala Ser Asp Lys Arg Ile Gly Asn Leu Leu Glu Leu Val Gly Ser
                965                 970                 975

Asp Ile Val Ser Lys Glu Asp Ile Met Glu Glu Phe Asn Lys Tyr Asp
            980                 985                 990

Gln Cys Arg Pro Glu Ile Ser Ser  Ile Val Phe Asn Leu  Glu Lys Trp
        995                 1000                 1005

Ala Phe Asp Thr Tyr Pro Glu  Leu Ser Ala Arg Val  Asp Arg Glu
    1010                1015                 1020

Glu Lys Val Asp Phe Lys Ser  Ile Leu Lys Ile Leu  Leu Asn Asn
    1025                1030                 1035

Lys Asn Ile Asn Lys Glu Gln  Ser Asp Ile Leu Arg  Lys Ile Arg
    1040                1045                 1050

Asn Ala Phe Asp Ala Asn Asn  Tyr Pro Asp Lys Gly  Val Val Glu
    1055                1060                 1065

Ile Lys Ala Leu Pro Glu Ile  Ala Met Ser Ile Lys  Lys Ala Phe
    1070                1075                 1080

Gly Glu Tyr Ala Ile Met Lys  Gly Ser Leu Gln
    1085                1090

<210> SEQ ID NO 3
<211> LENGTH: 3717
<212> TYPE: DNA
<213> ORGANISM: Artificial Sequence
<220> FEATURE:
<223> OTHER INFORMATION: dPspCas13b-SV40NLS-linker-MS2 nucleic acid
      sequence

<400> SEQUENCE: 3
atgaacatcc ccgctctggt ggaaaaccag aagaagtact tggcaccta cagcgtgatg      60 gccatgctga cgctcagac cgtgctggac cacatccaga aggtggccga tattgagggc     120
gagcagaacg agaacaacga gaatctgtgg tttcaccccg tgatgagcca cctgtacaac     180
gccaagaacg gctacgacaa gcagcccgag aaaaccatgt tcatcatcga gcggctgcag     240
agctacttcc cattcctgaa gatcatggcc gagaaccaga gagtacag caacggcaag     300 tacaagcaga accgcgtgga agtgaacagc aacgacatct tcgaggtgct gaagcgcgcc     360
ttcggcgtgc tgaagatgta cagggacctg accaacgcat acaagaccta cgaggaaaag     420
ctgaacgacg gctgcgagtt cctgaccagc acagagcaac tctctgagcg catgatcaac     480
aactactaca cagtggccct gcggaacatg aacgagagat acggctacaa gacagaggac     540
ctggccttca tccaggacaa gcggttcaag ttcgtgaagg acgcctacgg caagaaaaag     600
tcccaagtga ataccggatt cttcctgagc ctgcaggact acaacggcga cacacagaag     660
aagctgcacc tgagcggagt gggaatcgcc ctgctgatct gcctgttcct ggacaagcag     720
tacatcaaca tctttctgag caggctgccc atcttctcca gctacaatgc cagagcgag     780 gaacggcgga tcatcatcag atccttcggc atcaacagca tcaagctgcc caaggaccgg     840
atccacagcg agagtccaa caagagcgtg gccatggata tgctcaacga agtgaagcgg     900
tgccccgacg agctgttcac aacactgtct gccgagaagc agtcccggtt cagaatcatc     960
```

```
agcgacgacc acaatgaagt gctgatgaag cggagcagcg acagattcgt gcctctgctg    1020
ctgcagtata tcgattacgg caagctgttc gaccacatca ggttccacgt gaacatgggc    1080
aagctgagat acctgctgaa ggccgacaag acctgcatcg acggccagac cagagtcaga    1140
gtgatcgagc agcccctgaa cggcttcggc agactggaag aggccgagac aatgcggaag    1200
caagagaacg gcaccttcgg caacagcggc atccggatca gagacttcga gaacatgaag    1260
cgggacgacg ccaatcctgc caactatccc tacatcgtgg acacctacac acactacatc    1320
ctggaaaaca acaaggtcga gatgtttatc aacgacaaag aggacagcgc cccactgctg    1380
cccgtgatcg aggatgatag atacgtggtc aagacaatcc ccagctgccg gatgagcacc    1440
ctggaaattc cagccatggc cttccacatg tttctgttcg gcagcaagaa aaccgagaag    1500
ctgatcgtgg acgtgcacaa ccggtacaag agactgttcc aggccatgca gaaagaagaa    1560
gtgaccgccg agaatatcgc cagcttcgga atcgccgaga gcgacctgcc tcagaagatc    1620
ctggatctga tcagcggcaa tgcccacggc aaggatgtgg acgccttcat cagactgacc    1680
gtggacgaca tgctgaccga caccgagcgg agaatcaaga gattcaagga cgaccggaag    1740
tccattcgga gcgccgacaa caagatggga aagagaggct tcaagcagat ctccacaggc    1800
aagctggccg acttcctggc caaggacatc gtgctgtttc agcccagcgt gaacgatggc    1860
gagaacaaga tcaccggcct gaactaccgg atcatgcaga gcgccattgc cgtgtacgat    1920
agcggcgacg attacgaggc caagcagcag ttcaagctga tgttcgagaa ggcccggctg    1980
atcggcaagg gcacaacaga gcctcatcca tttctgtaca aggtgttcgc ccgcagcatc    2040
cccgccaatg ccgtcgagtt ctacgagcgc tacctgatcg agcggaagtt ctacctgacc    2100
ggcctgtcca acgagatcaa gaaaggcaac agagtggatg tgcccttcat ccggcgggac    2160
cagaacaagt ggaaaacacc cgccatgaag accctgggca gaatctacag cgaggatctg    2220
cccgtggaac tgcccagaca gatgttcgac aatgagatca gtccacctt gaagtccctg    2280 ccacagatgg aaggcatcga cttcaacaat gccaacgtga cctatctgat cgccgagtac    2340
atgaagagag tgctggacga cgacttccag accttctacc agtggaaccg caactaccgg    2400
tacatggaca tgcttaaggg cgagtacgac agaaagggct ccctgcagca ctgcttcacc    2460
agcgtggaag agagagaagg cctctggaaa gagcgggcct ccagaacaga gcggtacaga    2520
aagcaggcca gcaacaagat ccgcagcaac cggcagatga gaaacgccag cagcgaagag    2580
atcgagacaa tcctggataa gcggctgagc aacagccgga acgagtacca gaaaagcgag    2640 aaaagtgatcc ggcgctacag agtgcaggat gccctgctgt ttctgctggc caaaaagacc    2700
ctgaccgaac tggccgattt cgacggcgag aggttcaaac tgaaagaaat catgcccgac    2760
gccgagaagg gaatcctgag cgagatcatg ccccatgagct tcaccttcga gaaggcggc    2820 aagaagtaca ccatcaccag cgagggcatg aagctgaaga actacggcga cttcttgtg    2880 ctggctagcg acaagaggat cggcaacctg ctggaactcg tgggcagcga catcgtgtcc    2940
aaagaggata tcatggaaga gttcaacaaa tacgaccagt gcaggcccga gatcagctcc    3000
atcgtgttca acctggaaaa gtgggccttc gacacatacc ccgagctgtc tgccagagtg    3060
gaccgggaag agaaggtgga cttcaagagc atcctgaaaa tcctgctgaa caacaagaac    3120
atcaacaaag agcagagcga catcctgcgg aagatccgga acgccttcga tgcaaacaat    3180 tacccccgaca aaggcgtggt ggaaatcaag gccctgcctg agatcgccat gagcatcaag    3240
aaggcctttg gggagtacgc catcatgaag ggaagcctgc agccaaagaa gaagcggaag    3300
```

```
gtcggtggat ccggaggagg tggaagcatg gcttcaaact ttactcagtt cgtgctcgtg    3360
gacaatggtg ggacagggga tgtgacagtg gctccttcta atttcgctaa tggggtggca    3420
gagtggatca gctccaactc acggagccag gcctacaagg tgacatgcag cgtcaggcag    3480
tctagtgccc agaagagaaa gtataccatc aaggtggagg tccccaaagt ggctacccag    3540
acagtgggcg gagtcgaact gcctgtcgcc gcttggaggt cctacctgaa catggagctc    3600
actatcccaa ttttcgctac caattctgac tgtgaactca tcgtgaaggc aatgcagggg    3660
ctcctcaaag acggtaatcc tatcccttcc gccatcgccg ctaactcagg tatctac     3717
```

<210> SEQ ID NO 4
<211> LENGTH: 1239
<212> TYPE: PRT
<213> ORGANISM: Artificial Sequence
<220> FEATURE:
<223> OTHER INFORMATION: dPspCas13b-SV40NLS-linker-MS2 amino acid sequence

<400> SEQUENCE: 4

```
Met Asn Ile Pro Ala Leu Val Glu Asn Gln Lys Lys Tyr Phe Gly Thr
1               5                   10                  15

Tyr Ser Val Met Ala Met Leu Asn Ala Gln Thr Val Leu Asp His Ile
            20                  25                  30

Gln Lys Val Ala Asp Ile Glu Gly Glu Gln Asn Glu Asn Asn Glu Asn
        35                  40                  45

Leu Trp Phe His Pro Val Met Ser His Leu Tyr Asn Ala Lys Asn Gly
    50                  55                  60

Tyr Asp Lys Gln Pro Glu Lys Thr Met Phe Ile Ile Glu Arg Leu Gln
65                  70                  75                  80

Ser Tyr Phe Pro Phe Leu Lys Ile Met Ala Glu Asn Gln Arg Glu Tyr
                85                  90                  95

Ser Asn Gly Lys Tyr Lys Gln Asn Arg Val Glu Val Asn Ser Asn Asp
            100                 105                 110

Ile Phe Glu Val Leu Lys Arg Ala Phe Gly Val Leu Lys Met Tyr Arg
        115                 120                 125

Asp Leu Thr Asn Ala Tyr Lys Thr Tyr Glu Glu Lys Leu Asn Asp Gly
    130                 135                 140

Cys Glu Phe Leu Thr Ser Thr Glu Gln Pro Leu Ser Gly Met Ile Asn
145                 150                 155                 160

Asn Tyr Tyr Thr Val Ala Leu Arg Asn Met Asn Glu Arg Tyr Gly Tyr
                165                 170                 175

Lys Thr Glu Asp Leu Ala Phe Ile Gln Asp Lys Arg Phe Lys Phe Val
            180                 185                 190

Lys Asp Ala Tyr Gly Lys Lys Lys Ser Gln Val Asn Thr Gly Phe Phe
        195                 200                 205

Leu Ser Leu Gln Asp Tyr Asn Gly Asp Thr Gln Lys Lys Leu His Leu
    210                 215                 220

Ser Gly Val Gly Ile Ala Leu Leu Ile Cys Leu Phe Leu Asp Lys Gln
225                 230                 235                 240

Tyr Ile Asn Ile Phe Leu Ser Arg Leu Pro Ile Phe Ser Ser Tyr Asn
                245                 250                 255

Ala Gln Ser Glu Glu Arg Arg Ile Ile Ile Arg Ser Phe Gly Ile Asn
            260                 265                 270

Ser Ile Lys Leu Pro Lys Asp Arg Ile His Ser Glu Lys Ser Asn Lys
        275                 280                 285
```

```
Ser Val Ala Met Asp Met Leu Asn Glu Val Lys Arg Cys Pro Asp Glu
    290                 295                 300

Leu Phe Thr Thr Leu Ser Ala Glu Lys Gln Ser Arg Phe Arg Ile Ile
305                 310                 315                 320

Ser Asp Asp His Asn Glu Val Leu Met Lys Arg Ser Ser Asp Arg Phe
                325                 330                 335

Val Pro Leu Leu Leu Gln Tyr Ile Asp Tyr Gly Lys Leu Phe Asp His
                340                 345                 350

Ile Arg Phe His Val Asn Met Gly Lys Leu Arg Tyr Leu Leu Lys Ala
            355                 360                 365

Asp Lys Thr Cys Ile Asp Gly Gln Thr Arg Val Arg Val Ile Glu Gln
    370                 375                 380

Pro Leu Asn Gly Phe Gly Arg Leu Glu Glu Ala Glu Thr Met Arg Lys
385                 390                 395                 400

Gln Glu Asn Gly Thr Phe Gly Asn Ser Gly Ile Arg Ile Arg Asp Phe
                405                 410                 415

Glu Asn Met Lys Arg Asp Asp Ala Asn Pro Ala Asn Tyr Pro Tyr Ile
            420                 425                 430

Val Asp Thr Tyr Thr His Tyr Ile Leu Glu Asn Asn Lys Val Glu Met
    435                 440                 445

Phe Ile Asn Asp Lys Glu Asp Ser Ala Pro Leu Leu Pro Val Ile Glu
450                 455                 460

Asp Asp Arg Tyr Val Val Lys Thr Ile Pro Ser Cys Arg Met Ser Thr
465                 470                 475                 480

Leu Glu Ile Pro Ala Met Ala Phe His Met Phe Leu Phe Gly Ser Lys
                485                 490                 495

Lys Thr Glu Lys Leu Ile Val Asp Val His Asn Arg Tyr Lys Arg Leu
            500                 505                 510

Phe Gln Ala Met Gln Lys Glu Val Thr Ala Glu Asn Ile Ala Ser
    515                 520                 525

Phe Gly Ile Ala Glu Ser Asp Leu Pro Gln Lys Ile Leu Asp Leu Ile
530                 535                 540

Ser Gly Asn Ala His Gly Lys Asp Val Asp Ala Phe Ile Arg Leu Thr
545                 550                 555                 560

Val Asp Asp Met Leu Thr Asp Thr Glu Arg Arg Ile Lys Arg Phe Lys
                565                 570                 575

Asp Asp Arg Lys Ser Ile Arg Ser Ala Asp Asn Lys Met Gly Lys Arg
            580                 585                 590

Gly Phe Lys Gln Ile Ser Thr Gly Lys Leu Ala Asp Phe Leu Ala Lys
    595                 600                 605

Asp Ile Val Leu Phe Gln Pro Ser Val Asn Asp Gly Glu Asn Lys Ile
610                 615                 620

Thr Gly Leu Asn Tyr Arg Ile Met Gln Ser Ala Ile Ala Val Tyr Asp
625                 630                 635                 640

Ser Gly Asp Asp Tyr Glu Ala Lys Gln Gln Phe Lys Leu Met Phe Glu
                645                 650                 655

Lys Ala Arg Leu Ile Gly Lys Gly Thr Thr Glu Pro His Pro Phe Leu
            660                 665                 670

Tyr Lys Val Phe Ala Arg Ser Ile Pro Ala Asn Ala Val Glu Phe Tyr
    675                 680                 685

Glu Arg Tyr Leu Ile Glu Arg Lys Phe Tyr Leu Thr Gly Leu Ser Asn
690                 695                 700

Glu Ile Lys Lys Gly Asn Arg Val Asp Val Pro Phe Ile Arg Arg Asp
```

```
            705                 710                 715                 720
        Gln Asn Lys Trp Lys Thr Pro Ala Met Lys Thr Leu Gly Arg Ile Tyr
                        725                 730                 735
        Ser Glu Asp Leu Pro Val Glu Leu Pro Arg Gln Met Phe Asp Asn Glu
                        740                 745                 750
        Ile Lys Ser His Leu Lys Ser Leu Pro Gln Met Glu Gly Ile Asp Phe
                        755                 760                 765
        Asn Asn Ala Asn Val Thr Tyr Leu Ile Ala Glu Tyr Met Lys Arg Val
                        770                 775                 780
        Leu Asp Asp Asp Phe Gln Thr Phe Tyr Gln Trp Asn Arg Asn Tyr Arg
        785                 790                 795                 800
        Tyr Met Asp Met Leu Lys Gly Glu Tyr Asp Arg Lys Gly Ser Leu Gln
                            805                 810                 815
        His Cys Phe Thr Ser Val Glu Glu Arg Glu Gly Leu Trp Lys Glu Arg
                            820                 825                 830
        Ala Ser Arg Thr Glu Arg Tyr Arg Lys Gln Ala Ser Asn Lys Ile Arg
                            835                 840                 845
        Ser Asn Arg Gln Met Arg Asn Ala Ser Ser Glu Glu Ile Glu Thr Ile
        850                 855                 860
        Leu Asp Lys Arg Leu Ser Asn Ser Arg Asn Glu Tyr Gln Lys Ser Glu
        865                 870                 875                 880
        Lys Val Ile Arg Arg Tyr Arg Val Gln Asp Ala Leu Leu Phe Leu Leu
                            885                 890                 895
        Ala Lys Lys Thr Leu Thr Glu Leu Ala Asp Phe Asp Gly Glu Arg Phe
                            900                 905                 910
        Lys Leu Lys Glu Ile Met Pro Asp Ala Glu Lys Gly Ile Leu Ser Glu
                            915                 920                 925
        Ile Met Pro Met Ser Phe Thr Phe Glu Lys Gly Gly Lys Lys Tyr Thr
                            930                 935                 940
        Ile Thr Ser Glu Gly Met Lys Leu Lys Asn Tyr Gly Asp Phe Phe Val
        945                 950                 955                 960
        Leu Ala Ser Asp Lys Arg Ile Gly Asn Leu Leu Glu Leu Val Gly Ser
                            965                 970                 975
        Asp Ile Val Ser Lys Glu Asp Ile Met Glu Glu Phe Asn Lys Tyr Asp
                            980                 985                 990
        Gln Cys Arg Pro Glu Ile Ser Ser Ile Val Phe Asn Leu Glu Lys Trp
                            995                 1000                1005
        Ala Phe Asp Thr Tyr Pro Glu Leu Ser Ala Arg Val Asp Arg Glu
                1010                1015                1020
        Glu Lys Val Asp Phe Lys Ser Ile Leu Lys Ile Leu Leu Asn Asn
                1025                1030                1035
        Lys Asn Ile Asn Lys Glu Gln Ser Asp Ile Leu Arg Lys Ile Arg
                1040                1045                1050
        Asn Ala Phe Asp Ala Asn Asn Tyr Pro Asp Lys Gly Val Val Glu
                1055                1060                1065
        Ile Lys Ala Leu Pro Glu Ile Ala Met Ser Ile Lys Lys Ala Phe
                1070                1075                1080
        Gly Glu Tyr Ala Ile Met Lys Gly Ser Leu Gln Pro Lys Lys Lys
                1085                1090                1095
        Arg Lys Val Gly Gly Ser Gly Gly Gly Ser Met Ala Ser Asn
                1100                1105                1110
        Phe Thr Gln Phe Val Leu Val Asp Asn Gly Gly Thr Gly Asp Val
                1115                1120                1125
```

```
Thr Val Ala Pro Ser Asn Phe Ala Asn Gly Val Ala Glu Trp Ile
    1130                1135                1140

Ser Ser Asn Ser Arg Ser Gln Ala Tyr Lys Val Thr Cys Ser Val
    1145                1150                1155

Arg Gln Ser Ser Ala Gln Lys Arg Lys Tyr Thr Ile Lys Val Glu
    1160                1165                1170

Val Pro Lys Val Ala Thr Gln Thr Val Gly Gly Val Glu Leu Pro
    1175                1180                1185

Val Ala Ala Trp Arg Ser Tyr Leu Asn Met Glu Leu Thr Ile Pro
    1190                1195                1200

Ile Phe Ala Thr Asn Ser Asp Cys Glu Leu Ile Val Lys Ala Met
    1205                1210                1215

Gln Gly Leu Leu Lys Asp Gly Asn Pro Ile Pro Ser Ala Ile Ala
    1220                1225                1230

Ala Asn Ser Gly Ile Tyr
    1235

<210> SEQ ID NO 5
<211> LENGTH: 390
<212> TYPE: DNA
<213> ORGANISM: Artificial Sequence
<220> FEATURE:
<223> OTHER INFORMATION: MS2 coat protein nucleic acid sequence

<400> SEQUENCE: 5
atggcttcaa actttactca gttcgtgctc gtggacaatg gtgggacagg ggatgtgaca      60
gtggctcctt ctaatttcgc taatggggtg gcagagtgga tcagctccaa ctcacggagc     120
caggcctaca aggtgacatg cagcgtcagg cagtctagtg cccagaagag aaagtatacc     180
atcaaggtgg aggtccccaa agtggctacc cagacagtgg gcggagtcga actgcctgtc     240
gccgcttgga ggtcctacct gaacatggag ctcactatcc cattttttcgc taccaattct     300 gactgtgaac tcatcgtgaa ggcaatgcag gggctcctca agacggtaa  tcctatccct     360 tccgccatcg ccgctaactc aggtatctac                                      390

<210> SEQ ID NO 6
<211> LENGTH: 130
<212> TYPE: PRT
<213> ORGANISM: Artificial Sequence
<220> FEATURE:
<223> OTHER INFORMATION: MS2 coat protein amino acid sequence

<400> SEQUENCE: 6

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110
```

Leu Lys Asp Gly Asn Pro Ile Pro Ser Ala Ile Ala Ala Asn Ser Gly
        115                 120                 125

Ile Tyr
    130

<210> SEQ ID NO 7
<211> LENGTH: 22
<212> TYPE: PRT
<213> ORGANISM: Artificial Sequence
<220> FEATURE:
<223> OTHER INFORMATION: LambdaN amino acid sequence

<400> SEQUENCE: 7

Met Asn Ala Arg Thr Arg Arg Arg Glu Arg Arg Ala Glu Lys Gln Ala
1               5                   10                  15

Gln Trp Lys Ala Ala Asn
            20

<210> SEQ ID NO 8
<211> LENGTH: 133
<212> TYPE: PRT
<213> ORGANISM: Artificial Sequence
<220> FEATURE:
<223> OTHER INFORMATION: QBeta coat protein amino acid seqeunce

<400> SEQUENCE: 8

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Arg Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Gly Thr Ala Asn Gly Ser
65                  70                  75                  80

Gly Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Arg Pro Ala Tyr
    130

<210> SEQ ID NO 9
<211> LENGTH: 123
<212> TYPE: PRT
<213> ORGANISM: Artificial Sequence
<220> FEATURE:
<223> OTHER INFORMATION: PP7 coat protein amino acid sequence

<400> SEQUENCE: 9

Met Ala Ser Lys Thr Ile Val Leu Ser Val Gly Glu Ala Thr Arg Thr
1               5                   10                  15

Leu Thr Glu Ile Gln Ser Thr Ala Asp Arg Gln Ile Phe Glu Glu Lys
            20                  25                  30

Val Gly Pro Leu Val Gly Arg Leu Arg Leu Thr Ala Ser Leu Arg Gln
        35                  40                  45

```
Asn Gly Ala Lys Thr Ala Tyr Arg Val Asn Leu Lys Leu Asp Gln Ala
 50                  55                  60

Asp Val Val Asp Ser Gly Leu Pro Lys Val Arg Tyr Thr Gln Val Trp
 65                  70                  75                  80

Ser His Asp Val Thr Ile Val Ala Asn Ser Thr Glu Ala Ser Arg Lys
                 85                  90                  95

Ser Leu Tyr Asp Leu Thr Lys Ser Leu Val Ala Thr Ser Gln Val Glu
            100                 105                 110

Asp Leu Val Val Asn Leu Val Pro Leu Gly Arg
            115                 120

<210> SEQ ID NO 10
<211> LENGTH: 36
<212> TYPE: DNA
<213> ORGANISM: Artificial Sequence
<220> FEATURE:
<223> OTHER INFORMATION: PspCas13b direct repeat

<400> SEQUENCE: 10
gttgtggaag gtccagtttt gagggggctat tacaac                          36

<210> SEQ ID NO 11
<211> LENGTH: 56
<212> TYPE: DNA
<213> ORGANISM: Artificial Sequence
<220> FEATURE:
<223> OTHER INFORMATION: PspCas13 gRNA
<220> FEATURE:
<221> NAME/KEY: misc_feature
<222> LOCATION: (1)..(20)
<223> OTHER INFORMATION: n is a, c, g, or t

<400> SEQUENCE: 11
nnnnnnnnnn nnnnnnnnnn gttgtggaag gtccagtttt gagggggctat tacaac    56

<210> SEQ ID NO 12
<211> LENGTH: 56
<212> TYPE: DNA
<213> ORGANISM: Artificial Sequence
<220> FEATURE:
<223> OTHER INFORMATION: PspCas13b gRNA

<400> SEQUENCE: 12
tagcggtaca ggtattcctg gttgtggaag gtccagtttt gagggggctat tacaac    56

<210> SEQ ID NO 13
<211> LENGTH: 19
<212> TYPE: DNA
<213> ORGANISM: Artificial Sequence
<220> FEATURE:
<223> OTHER INFORMATION: MS2 hairpin

<400> SEQUENCE: 13
acatgaggat cacccatgt                                              19

<210> SEQ ID NO 14
<211> LENGTH: 17
<212> TYPE: DNA
<213> ORGANISM: Artificial Sequence
<220> FEATURE:
<223> OTHER INFORMATION: boxB hairpin

<400> SEQUENCE: 14
ggccctgaaa aagggcc                                                17
```

```
<210> SEQ ID NO 15
<211> LENGTH: 20
<212> TYPE: DNA
<213> ORGANISM: Artificial Sequence
<220> FEATURE:
<223> OTHER INFORMATION: QBeta hairpin

<400> SEQUENCE: 15
atgcatgtct aagacagcat                                                   20

<210> SEQ ID NO 16
<211> LENGTH: 25
<212> TYPE: DNA
<213> ORGANISM: Artificial Sequence
<220> FEATURE:
<223> OTHER INFORMATION: PP7 hairpin

<400> SEQUENCE: 16
taaggagttt atatggaaac cctta                                             25

<210> SEQ ID NO 17
<211> LENGTH: 4170
<212> TYPE: DNA
<213> ORGANISM: Artificial Sequence
<220> FEATURE:
<223> OTHER INFORMATION: LshCas13a nucleic acid sequence

<400> SEQUENCE: 17
atggggaacc tgttcggaca caagcggtgg tacgaggtgc gagataagaa agacttcaag       60
atcaagcgaa aggtgaaagt caagcggaat atgacgggga caagtacat tctgaacatc      120 aacgaaaaca caacaaaga gaagatcgac aacaacaagt catcagaaa gtacatcaac       180 tacaagaaaa acgataatat tctgaaggag ttcactagga aatttcatgc aggaaatatc      240
ctgttcaaac tgaagggcaa agaagggatc attagaattg agaataacga cgacttcctg      300
gagacagagg aagtggtgct gtatatcgag gcctacggca agagcgagaa gctgaaagca      360
ctggggatca caaagaaaaa gatcattgac gaggccatca ggcagggcat tactaaggac      420
gataaaaaga tcgagatcaa cgacaggag aacgaggaag agatcgaaat tgacatccgg      480
gatgagtaca ctaataagac cctgaacgac tgctccatca ttctgcgcat cattgaaaac      540
gatgaactgg agacaaagaa gagcatctac gagatcttca gaacatcaa tatgagcctg      600 tataagatca tcgagaagat catcgaaaac gagacagaaa aggtgtttga aaatagatac      660
tacgaagagc acctgaggga gaagctgctg aaagacgata gattgacgt gatcctgacc      720 aacttcatgg aaatccggga gaagatcaag tctaatctgg atcctgggg cttcgtgaag      780 ttttacctga cgtcggcgg ggacaaaaag aaagtaaaa ataagaaaat gctggtggaa      840
aagattctga acatcaatgt ggatctgacc gtcgaggaca ttgccgattt cgtgatcaag      900
gagctggaat tttggaacat cacaaagcgc attgagaaag tgaagaaagt caataacgag      960
ttcctggaga agcggagaaa tcggacatac atcaagtcct atgtgctgct ggacaagcac     1020
gaaaagttta aatcgagag agaaaacaag aaggataaga tcgtgaagtt cttgtcgag      1080 aacattaaga caactctat caaggaaaag attgagaaga tcctggctga gttcaagatc     1140
gacgagctga ttaagaaact ggagaaggaa ctgaagaaag ggactgtga taccgagatc     1200 ttcggaatct ttaagaagca ttacaaggtg aacttcgaca gcaagaaatt ttccaagaaa     1260
tctgatgaag agaggagct gtataagatc atctacagat acctgaaggg cagaattgaa     1320
aaaatcctgg tgaacgagca gaaggtcaga ctgaagaaaa tggagaagat cgagatcgaa     1380
```

```
aagattctga atgaaagtat cctgtcagag aaaattctga agagagtgaa acagtataca    1440
ctggagcaca ttatgtacct ggggaagctg aggcataacg acatcgatat gaccacagtg    1500
aatactgacg atttcagccg cctgcacgcc aaggaagagc tggacctgga actgatcacc    1560
ttctttgcca gcacaaatat ggagctgaac aagatctttt cccgagaaaa catcaacaac    1620
gacgagaaca tcgatttctt tggaggcgac cgggagaaga actatgtgct ggataagaaa    1680
atcctgaata gtaagatcaa gatcatccgc gacctggatt tcatcgataa caagaacaac    1740
atcacaaaca acttcattcg aaagtttaca aagatcggca ctaatgaaag gaaccgcatc    1800
ctgcatgcca tttccaaaga gagggacctg caggggactc aggacgatta caacaaagtg    1860
atcaacatca ttcagaatct gaagatctcc gatgaagagg tgagcaaagc tctgaacctg    1920
gacgtggtct ttaaggacaa gaaaacatc atcacaaaga tcaatgacat caagatctct    1980
gaagagaaca caacgatat caagtatctg cccagcttca gcaaagtgct gcccgaaatc    2040
ctgaacctgt accgcaacaa tcccaagaat gagccttttg cacaatcga gactgaaaaa    2100 attgtgctga acgctctgat ctacgtcaat aaggagctgt ataagaaact gatcctggag    2160
gacgatctgg aagagaacga gtccaagaat atcttcctgc aggaactgaa gaaaaccctg    2220
ggcaacattg acgaaatcga tgagaacatc atcgagaact actacaagaa cgcacagatt    2280
tctgccagta aggggaacaa caaggcaatc aagaaatatc agaagaaagt gatcgagtgc    2340
tacattggat atctgcgcaa aaactacgaa gagctgttcg acttttcaga cttcaagatg    2400
aacatccagg aaatcaagaa acagattaag gacatcaacg ataacaagac ttatgagtgg    2460
atcaccgtga aaaccagcga caaaaccatt gtcatcaacg acgatttcga gtacatcatt    2520
tctatctttg cactgctgaa cagtaatgcc gtgattaata agatccgaaa cagattcttc    2580
gccaccagcg tgtggctgaa cacctcagaa taccagaata tcattgacat cctggatgag    2640
attatgcagc tgaatacccct gcggaacgaa tgcatcacag agaactggaa tctgaacctg    2700
gaagagttca ttcagaagat gaaagagatc gaaaaggatt cgacgactt caagatccag    2760 actaagaaag aaatcttcaa caactactac gaggacatca gaacaacat tctgaccgag    2820 tttaaagacg atatcaacgg ctgtgatgtg ctggaaaaga aactggagaa gattgtcatc    2880
ttcgacgatg aaaccaagtt cgagatcgac aagaaatcca acatcctgca ggatgaacag    2940
agaaagctgt ctaacatcaa caagaaggac ctgaagaaaa aggtggatca gtatatcaag    3000
gacaaagatc aggagatcaa gtctaaaatc ctgtgcagga tcattttcaa cagtgacttt    3060
ctgaaaaagt acaagaagga aatcgacaat ctgattgagg atatggagtc tgaaaatgag    3120
aacaagttcc aggagatcta ctatcccaag gaacggaaga acgagctgta tatctacaaa    3180
aagaatctgt tcctgaacat cggaaatcct aactttgaca agatctacgg cctgattagc    3240
aacgacatca agatggccga tgctaaattc ctgtttaata tcgatggaaa gaacatcaga    3300
aagaacaaaa tcagtgagat cgacgctatt ctgaagaatc tgaacgataa actgaacggc    3360
tactcaaagg aatacaagga gaagtacatc aaaaagctga aggagaacga cgatttcttt    3420
gcaaagaaca tccagaataa gaactacaaa tccttcgaaa aggactataa ccgcgtgtct    3480
gagtacaaaa agattcgaga tctggtcgag ttcaactatc tgaacaaaat cgagtcctac    3540
ctgattgaca tcaactggaa gctggctatt cagatggcaa gattcgaaag ggatatgcac    3600
tatatcgtga tggactgag ggagctgggc atcattaagc tgtcaggcta taacaccggg    3660
atcagcaggg catacccaaa gcgcaatgga agcgacggct tttacactac cacagcctac    3720
```

```
tacaagttct tgatgaaga gtcctacaag aagttcgaga agatttgcta cgggtttgga    3780
atcgacctga gcgaaaattc cgagatcaac aagcctgaaa atgagagcat tcggaactat    3840
atctcccatt tctacatcgt gagaaatcca tttgccgact acagtattgc tgagcagatc    3900
gatcgggtga gcaacctgct gtcatatagc acacgctaca acaattcaac ttatgccagc    3960
gtgttcgaag tctttaaaaa ggacgtgaat ctggactacg atgagctgaa aagaaattc    4020 aaactgatcg gcaacaatga tattctggag cgcctgatga agcccaagaa agtgagcgtc    4080
ctggaactgg agtcctacaa cagtgactac attaagaatc tgatcattga actgctgacc    4140
aaaatcgaga atactaacga taccctgtga                                     4170
```

```
<210> SEQ ID NO 18
<211> LENGTH: 1389
<212> TYPE: PRT
<213> ORGANISM: Artificial Sequence
<220> FEATURE:
<223> OTHER INFORMATION: LshCas13a amino acid sequence

<400> SEQUENCE: 18

Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
                20                  25                  30

Gly Asn Lys Tyr Ile Leu Asn Ile Asn Glu Asn Asn Asn Lys Glu Lys
            35                  40                  45

Ile Asp Asn Asn Lys Phe Ile Arg Lys Tyr Ile Asn Tyr Lys Lys Asn
        50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
                85                  90                  95

Asp Asp Phe Leu Glu Thr Glu Glu Val Val Leu Tyr Ile Glu Ala Tyr
                100                 105                 110

Gly Lys Ser Glu Lys Leu Lys Ala Leu Gly Ile Thr Lys Lys Lys Ile
            115                 120                 125

Ile Asp Glu Ala Ile Arg Gln Gly Ile Thr Lys Asp Asp Lys Lys Ile
        130                 135                 140

Glu Ile Lys Arg Gln Glu Asn Glu Glu Ile Glu Ile Asp Ile Arg
145                 150                 155                 160

Asp Glu Tyr Thr Asn Lys Thr Leu Asn Asp Cys Ser Ile Ile Leu Arg
                165                 170                 175

Ile Ile Glu Asn Asp Glu Leu Glu Thr Lys Lys Ser Ile Tyr Glu Ile
                180                 185                 190

Phe Lys Asn Ile Asn Met Ser Leu Tyr Lys Ile Ile Glu Lys Ile Ile
            195                 200                 205

Glu Asn Glu Thr Glu Lys Val Phe Glu Asn Arg Tyr Tyr Glu Glu His
        210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
                245                 250                 255

Gly Phe Val Lys Phe Tyr Leu Asn Val Gly Gly Asp Lys Lys Lys Ser
                260                 265                 270

Lys Asn Lys Lys Met Leu Val Glu Lys Ile Leu Asn Ile Asn Val Asp
            275                 280                 285
```

```
Leu Thr Val Glu Asp Ile Ala Asp Phe Val Ile Lys Glu Leu Glu Phe
        290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
                    325                 330                 335

Leu Asp Lys His Glu Lys Phe Lys Ile Glu Arg Glu Asn Lys Lys Asp
                340                 345                 350

Lys Ile Val Lys Phe Phe Val Glu Asn Ile Lys Asn Ser Ile Lys
            355                 360                 365

Glu Lys Ile Glu Lys Ile Leu Ala Glu Phe Lys Ile Asp Glu Leu Ile
        370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
                    405                 410                 415

Phe Ser Lys Lys Ser Asp Glu Glu Lys Glu Leu Tyr Lys Ile Ile Tyr
                420                 425                 430

Arg Tyr Leu Lys Gly Arg Ile Glu Lys Ile Leu Val Asn Glu Gln Lys
                435                 440                 445

Val Arg Leu Lys Lys Met Glu Lys Ile Glu Ile Glu Lys Ile Leu Asn
450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Asp
                    485                 490                 495

Met Thr Thr Val Asn Thr Asp Asp Phe Ser Arg Leu His Ala Lys Glu
            500                 505                 510

Glu Leu Asp Leu Glu Leu Ile Thr Phe Phe Ala Ser Thr Asn Met Glu
        515                 520                 525

Leu Asn Lys Ile Phe Ser Arg Glu Asn Ile Asn Asn Asp Glu Asn Ile
530                 535                 540

Asp Phe Phe Gly Gly Asp Arg Glu Lys Asn Tyr Val Leu Asp Lys Lys
545                 550                 555                 560

Ile Leu Asn Ser Lys Ile Lys Ile Ile Arg Asp Leu Asp Phe Ile Asp
                565                 570                 575

Asn Lys Asn Asn Ile Thr Asn Asn Phe Ile Arg Lys Phe Thr Lys Ile
                580                 585                 590

Gly Thr Asn Glu Arg Asn Arg Ile Leu His Ala Ile Ser Lys Glu Arg
                595                 600                 605

Asp Leu Gln Gly Thr Gln Asp Asp Tyr Asn Lys Val Ile Asn Ile Ile
610                 615                 620

Gln Asn Leu Lys Ile Ser Asp Glu Glu Val Ser Lys Ala Leu Asn Leu
625                 630                 635                 640

Asp Val Val Phe Lys Asp Lys Lys Asn Ile Ile Thr Lys Ile Asn Asp
                    645                 650                 655

Ile Lys Ile Ser Glu Glu Asn Asn Asn Asp Ile Lys Tyr Leu Pro Ser
                660                 665                 670

Phe Ser Lys Val Leu Pro Glu Ile Leu Asn Leu Tyr Arg Asn Asn Pro
            675                 680                 685

Lys Asn Glu Pro Phe Asp Thr Ile Glu Thr Glu Lys Ile Val Leu Asn
690                 695                 700
```

```
Ala Leu Ile Tyr Val Asn Lys Glu Leu Tyr Lys Lys Leu Ile Leu Glu
705                 710                 715                 720

Asp Asp Leu Glu Glu Asn Glu Ser Lys Asn Ile Phe Leu Gln Glu Leu
            725                 730                 735

Lys Lys Thr Leu Gly Asn Ile Asp Glu Ile Asp Glu Asn Ile Ile Glu
        740                 745                 750

Asn Tyr Tyr Lys Asn Ala Gln Ile Ser Ala Ser Lys Gly Asn Asn Lys
    755                 760                 765

Ala Ile Lys Lys Tyr Gln Lys Val Ile Glu Cys Tyr Ile Gly Tyr
770                 775                 780

Leu Arg Lys Asn Tyr Glu Glu Leu Phe Asp Phe Ser Asp Phe Lys Met
785                 790                 795                 800

Asn Ile Gln Glu Ile Lys Lys Gln Ile Lys Asp Ile Asn Asp Asn Lys
            805                 810                 815

Thr Tyr Glu Trp Ile Thr Val Lys Thr Ser Asp Lys Thr Ile Val Ile
        820                 825                 830

Asn Asp Asp Phe Glu Tyr Ile Ile Ser Ile Phe Ala Leu Leu Asn Ser
            835                 840                 845

Asn Ala Val Ile Asn Lys Ile Arg Asn Arg Phe Phe Ala Thr Ser Val
850                 855                 860

Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
            885                 890                 895

Asn Leu Asn Leu Glu Glu Phe Ile Gln Lys Met Lys Glu Ile Glu Lys
            900                 905                 910

Asp Phe Asp Asp Phe Lys Ile Gln Thr Lys Lys Glu Ile Phe Asn Asn
    915                 920                 925

Tyr Tyr Glu Asp Ile Lys Asn Asn Ile Leu Thr Glu Phe Lys Asp Asp
    930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
            965                 970                 975

Gln Asp Glu Gln Arg Lys Leu Ser Asn Ile Lys Lys Asp Leu Lys
        980                 985                 990

Lys Lys Val Asp Gln Tyr Ile Lys Asp Lys Asp Gln Glu Ile Lys Ser
        995                 1000                1005

Lys Ile Leu Cys Arg Ile Ile Phe Asn Ser Asp Phe Leu Lys Lys
    1010                1015                1020

Tyr Lys Lys Glu Ile Asp Asn Leu Ile Glu Asp Met Glu Ser Glu
    1025                1030                1035

Asn Glu Asn Lys Phe Gln Glu Ile Tyr Tyr Pro Lys Glu Arg Lys
    1040                1045                1050

Asn Glu Leu Tyr Ile Tyr Lys Lys Asn Leu Phe Leu Asn Ile Gly
    1055                1060                1065

Asn Pro Asn Phe Asp Lys Ile Tyr Gly Leu Ile Ser Asn Asp Ile
    1070                1075                1080

Lys Met Ala Asp Ala Lys Phe Leu Phe Asn Ile Asp Gly Lys Asn
    1085                1090                1095

Ile Arg Lys Asn Lys Ile Ser Glu Ile Asp Ala Ile Leu Lys Asn
    1100                1105                1110

Leu Asn Asp Lys Leu Asn Gly Tyr Ser Lys Glu Tyr Lys Glu Lys
```

```
                    1115                 1120                 1125
Tyr Ile Lys Lys Leu Lys Glu Asn Asp Asp Phe Phe Ala Lys Asn
                1130                 1135                 1140
Ile Gln Asn Lys Asn Tyr Lys Ser Phe Glu Lys Asp Tyr Asn Arg
                1145                 1150                 1155
Val Ser Glu Tyr Lys Lys Ile Arg Asp Leu Val Glu Phe Asn Tyr
                1160                 1165                 1170
Leu Asn Lys Ile Glu Ser Tyr Leu Ile Asp Ile Asn Trp Lys Leu
                1175                 1180                 1185
Ala Ile Gln Met Ala Arg Phe Glu Arg Asp Met His Tyr Ile Val
                1190                 1195                 1200
Asn Gly Leu Arg Glu Leu Gly Ile Ile Lys Leu Ser Gly Tyr Asn
                1205                 1210                 1215
Thr Gly Ile Ser Arg Ala Tyr Pro Lys Arg Asn Gly Ser Asp Gly
                1220                 1225                 1230
Phe Tyr Thr Thr Thr Ala Tyr Tyr Lys Phe Phe Asp Glu Glu Ser
                1235                 1240                 1245
Tyr Lys Lys Phe Glu Lys Ile Cys Tyr Gly Phe Gly Ile Asp Leu
                1250                 1255                 1260
Ser Glu Asn Ser Glu Ile Asn Lys Pro Glu Asn Glu Ser Ile Arg
                1265                 1270                 1275
Asn Tyr Ile Ser His Phe Tyr Ile Val Arg Asn Pro Phe Ala Asp
                1280                 1285                 1290
Tyr Ser Ile Ala Glu Gln Ile Asp Arg Val Ser Asn Leu Leu Ser
                1295                 1300                 1305
Tyr Ser Thr Arg Tyr Asn Asn Ser Thr Tyr Ala Ser Val Phe Glu
                1310                 1315                 1320
Val Phe Lys Lys Asp Val Asn Leu Asp Tyr Asp Glu Leu Lys Lys
                1325                 1330                 1335
Lys Phe Lys Leu Ile Gly Asn Asn Asp Ile Leu Glu Arg Leu Met
                1340                 1345                 1350
Lys Pro Lys Lys Val Ser Val Leu Glu Leu Glu Ser Tyr Asn Ser
                1355                 1360                 1365
Asp Tyr Ile Lys Asn Leu Ile Ile Glu Leu Leu Thr Lys Ile Glu
                1370                 1375                 1380
Asn Thr Asn Asp Thr Leu
                1385

<210> SEQ ID NO 19
<211> LENGTH: 28
<212> TYPE: DNA
<213> ORGANISM: Artificial Sequence
<220> FEATURE:
<223> OTHER INFORMATION: LshCas13a direct repeat

<400> SEQUENCE: 19
ccaccccaat atcgaagggg actaaaac                                         28

<210> SEQ ID NO 20
<211> LENGTH: 3456
<212> TYPE: DNA
<213> ORGANISM: Artificial Sequence
<220> FEATURE:
<223> OTHER INFORMATION: LwaCas13a nucleic acid sequence

<400> SEQUENCE: 20
atgaaagtga ccaaggtcga cggcatcagc cacaagaagt acatcgaaga gggcaagctc      60
```

```
gtgaagtcca ccagcgagga aaaccggacc agcgagagac tgagcgagct gctgagcatc    120
cggctggaca tctacatcaa gaaccccgac aacgcctccg aggaagagaa ccggatcaga    180
agagagaacc tgaagaagtt ctttagcaac aaggtgctgc acctgaagga cagcgtgctg    240
tatctgaaga accggaaaga aaagaacgcc gtgcaggaca gaactatag cgaagaggac    300 atcagcgagt acgacctgaa aaacaagaac agcttctccg tgctgaagaa gatcctgctg    360
aacgaggacg tgaactctga ggaactggaa atctttcgga aggacgtgga agccaagctg    420
aacaagatca acagcctgaa gtacagcttc gaagagaaca aggccaacta ccagaagatc    480
aacgagaaca acgtggaaaa agtgggcggc aagagcaagc ggaacatcat ctacgactac    540
tacagagaga gcgccaagcg caacgactac atcaacaacg tgcaggaagc cttcgacaag    600
ctgtataaga aagaggatat cgagaaactg ttttcctga tcgagaacag caagaagcac    660
gagaagtaca agatccgcga gtactatcac aagatcatcg gccggaagaa cgacaaagag    720
aacttcgcca agattatcta cgaagagatc cagaacgtga acaacatcaa agagctgatt    780
gagaagatcc ccgacatgtc tgagctgaag aaaagccagg tgttctacaa gtactacctg    840
gacaaagagg aactgaacga caagaatatt aagtacgcct ctgccactt cgtggaaatc    900 gagatgtccc agctgctgaa aaactacgtg tacaagcggc tgagcaacat cagcaacgat    960
aagatcaagc ggatcttcga gtaccagaat ctgaaaaagc tgatcgaaaa caactgctg   1020 aacaagctgg acacctacgt gcggaactgc ggcaagtaca actactatct gcaagtgggc   1080
gagatcgcca cctccgactt tatcgcccgg aaccggcaga acgaggcctt cctgagaaac   1140
atcatcggcg tgtccagcgt ggcctacttc agcctgagga acatcctgga aaccgagaac   1200
gagaacggta tcaccggccg gatgcggggc aagaccgtga agaacaacaa gggcgaagag   1260
aaatacgtgt ccggcgaggt ggacaagatc tacaatgaga acaagcagaa cgaagtgaaa   1320
gaaaatctga agatgttcta cagctacgac ttcaacatgg acaacaagaa cgagatcgag   1380
gacttcttcg ccaacatcga cgaggccatc agcagcatca gacacggcat cgtgcacttc   1440
aacctggaac tggaaggcaa ggacatcttc gccttcaaga atatcgcccc cagcgagatc   1500
tccaagaaga tgtttcagaa cgaaatcaac gaaaagaagc tgaagctgaa aatcttcaag   1560
cagctgaaca gcgccaacgt gttcaactac tacgagaagg atgtgatcat caagtacctg   1620
aagaatacca gttcaactt cgtgaacaaa acatcccct tcgtgcccag cttcaccaag   1680
ctgtacaaca gattgagga cctgcggaat accctgaagt tttttggag cgtgcccaag   1740 gacaaagaag agaaggacgc ccagatctac ctgctgaaga atatctacta cggcgagttc   1800
ctgaacaagt tcgtgaaaaa ctccaaggtg ttctttaaga tcaccaatga agtgatcaag   1860
attaacaagc agcggaacca gaaaccggc cactacaagt atcagaagtt cgagaacatc   1920 gagaaaccg tgcccgtgga atacctggcc atcatccaga gcagagagat gatcaacaac   1980
caggacaaag aggaaagaa tacctacatc gactttattc agcagatttt cctgaagggc   2040
ttcatcgact acctgaacaa gaacaatctg aagtatatcg agagcaacaa caacaatgac   2100
aacaacgaca tcttctccaa gatcaagatc aaaaaggata caaagagaa gtacgacaag   2160 atcctgaaga actatgagaa gcacaatcgg aacaagaaa tccctcacga gatcaatgag   2220
ttcgtgcgcg agatcaagct ggggaagatt ctgaagtaca ccgagaatct gaacatgttt   2280
tacctgatcc tgaagctgct gaaccacaaa gagctgacca acctgaaggg cagcctggaa   2340
aagtaccagt ccgccaacaa agaagaaacc ttcagcgacg agttggaact gatcaacctg   2400
```

```
ctgaacctgg acaacaacag agtgaccgag gacttcgagc tggaagccaa cgagatcggc    2460
aagttcctgg acttcaacga aaacaaaatc aaggaccgga agagctgaa aaagttcgac     2520 accaacaaga tctatttcga cggcgagaac atcatcaagc accgggcctt ctacaatatc    2580
aagaaatacg gcatgctgaa tctgctggaa aagatcgccg ataaggccaa gtataagatc    2640
agcctgaaag aactgaaaga gtacagcaac aagaagaatg agattgaaaa gaactacacc    2700
atgcagcaga acctgcaccg gaagtacgcc agacccaaga aggacgaaaa gttcaacgac    2760
gaggactaca agagtatga gaaggccatc ggcaacatcc agaagtacac ccacctgaag     2820
aacaaggtgg aattcaatga gctgaacctg ctgcagggcc tgctgctgaa gatcctgcac    2880
cggctcgtgg gctacaccag catctgggag cgggacctga gattccggct gaagggcgag    2940
tttcccgaga accactacat cgaggaaatt ttcaatttcg acaactccaa gaatgtgaag    3000
tacaaaagcg gccagatcgt ggaaaagtat atcaacttct acaagaact gtacaaggac     3060 aatgtggaaa gcggagcat ctactccgac aagaaagtga agaaactgaa gcaggaaaaa    3120
aaggacctgt acatccggaa ctacattgcc cacttcaact acatccccca cgccgagatt    3180
agcctgctgg aagtgctgga aaacctgcgg aagctgctgt cctacgaccg gaagctgaag    3240
aacgccatca tgaagtccat cgtggacatt ctgaaagaat acggcttcgt ggccaccttc    3300
aagatcggcg ctgacaagaa gatcgaaatc cagaccctgg aatcagaaa gatcgtgcac    3360 ctgaagaatc tgaagaaaaa gaaactgatg accgaccgga acagcgagga actgtgcgaa    3420
ctcgtgaaag tcatgttcga gtacaaggcc ctggaa                              3456
```

<210> SEQ ID NO 21
<211> LENGTH: 1152
<212> TYPE: PRT
<213> ORGANISM: Artificial Sequence
<220> FEATURE:
<223> OTHER INFORMATION: LwaCas13 amino acid sequence

<400> SEQUENCE: 21

```
Met Lys Val Thr Lys Val Asp Gly Ile Ser His Lys Lys Tyr Ile Glu
1               5                   10                  15

Glu Gly Lys Leu Val Lys Ser Thr Ser Glu Glu Asn Arg Thr Ser Glu
            20                  25                  30

Arg Leu Ser Glu Leu Leu Ser Ile Arg Leu Asp Ile Tyr Ile Lys Asn
        35                  40                  45

Pro Asp Asn Ala Ser Glu Glu Glu Asn Arg Ile Arg Arg Glu Asn Leu
    50                  55                  60

Lys Lys Phe Phe Ser Asn Lys Val Leu His Leu Lys Asp Ser Val Leu
65                  70                  75                  80

Tyr Leu Lys Asn Arg Lys Glu Lys Asn Ala Val Gln Asp Lys Asn Tyr
                85                  90                  95

Ser Glu Glu Asp Ile Ser Glu Tyr Asp Leu Lys Asn Lys Asn Ser Phe
            100                 105                 110

Ser Val Leu Lys Lys Ile Leu Leu Asn Glu Asp Val Asn Ser Glu Glu
        115                 120                 125

Leu Glu Ile Phe Arg Lys Asp Val Glu Ala Lys Leu Asn Lys Ile Asn
    130                 135                 140

Ser Leu Lys Tyr Ser Phe Glu Glu Asn Lys Ala Asn Tyr Gln Lys Ile
145                 150                 155                 160

Asn Glu Asn Asn Val Glu Lys Val Gly Gly Lys Ser Lys Arg Asn Ile
                165                 170                 175
```

-continued

Ile Tyr Asp Tyr Tyr Arg Glu Ser Ala Lys Arg Asn Asp Tyr Ile Asn
            180                 185                 190

Asn Val Gln Glu Ala Phe Asp Lys Leu Tyr Lys Lys Glu Asp Ile Glu
        195                 200                 205

Lys Leu Phe Phe Leu Ile Glu Asn Ser Lys Lys His Glu Lys Tyr Lys
    210                 215                 220

Ile Arg Glu Tyr Tyr His Lys Ile Ile Gly Arg Lys Asn Asp Lys Glu
225                 230                 235                 240

Asn Phe Ala Lys Ile Ile Tyr Glu Glu Ile Gln Asn Val Asn Asn Ile
                245                 250                 255

Lys Glu Leu Ile Glu Lys Ile Pro Asp Met Ser Glu Leu Lys Lys Ser
            260                 265                 270

Gln Val Phe Tyr Lys Tyr Tyr Leu Asp Lys Glu Glu Leu Asn Asp Lys
        275                 280                 285

Asn Ile Lys Tyr Ala Phe Cys His Phe Val Glu Ile Glu Met Ser Gln
    290                 295                 300

Leu Leu Lys Asn Tyr Val Tyr Lys Arg Leu Ser Asn Ile Ser Asn Asp
305                 310                 315                 320

Lys Ile Lys Arg Ile Phe Glu Tyr Gln Asn Leu Lys Lys Leu Ile Glu
                325                 330                 335

Asn Lys Leu Leu Asn Lys Leu Asp Thr Tyr Val Arg Asn Cys Gly Lys
            340                 345                 350

Tyr Asn Tyr Tyr Leu Gln Val Gly Glu Ile Ala Thr Ser Asp Phe Ile
        355                 360                 365

Ala Arg Asn Arg Gln Asn Glu Ala Phe Leu Arg Asn Ile Ile Gly Val
    370                 375                 380

Ser Ser Val Ala Tyr Phe Ser Leu Arg Asn Ile Leu Glu Thr Glu Asn
385                 390                 395                 400

Glu Asn Gly Ile Thr Gly Arg Met Arg Gly Lys Thr Val Lys Asn Asn
                405                 410                 415

Lys Gly Glu Glu Lys Tyr Val Ser Gly Glu Val Asp Lys Ile Tyr Asn
            420                 425                 430

Glu Asn Lys Gln Asn Glu Val Lys Glu Asn Leu Lys Met Phe Tyr Ser
        435                 440                 445

Tyr Asp Phe Asn Met Asp Asn Lys Asn Glu Ile Glu Asp Phe Phe Ala
    450                 455                 460

Asn Ile Asp Glu Ala Ile Ser Ser Ile Arg His Gly Ile Val His Phe
465                 470                 475                 480

Asn Leu Glu Leu Glu Gly Lys Asp Ile Phe Ala Phe Lys Asn Ile Ala
                485                 490                 495

Pro Ser Glu Ile Ser Lys Lys Met Phe Gln Asn Glu Ile Asn Glu Lys
            500                 505                 510

Lys Leu Lys Leu Lys Ile Phe Lys Gln Leu Asn Ser Ala Asn Val Phe
        515                 520                 525

Asn Tyr Tyr Glu Lys Asp Val Ile Ile Lys Tyr Leu Asn Thr Lys
    530                 535                 540

Phe Asn Phe Val Asn Lys Asn Ile Pro Phe Val Pro Ser Phe Thr Lys
545                 550                 555                 560

Leu Tyr Asn Lys Ile Glu Asp Leu Arg Asn Thr Leu Lys Phe Phe Trp
                565                 570                 575

Ser Val Pro Lys Asp Lys Glu Glu Lys Asp Ala Gln Ile Tyr Leu Leu
            580                 585                 590

Lys Asn Ile Tyr Tyr Gly Glu Phe Leu Asn Lys Phe Val Lys Asn Ser

-continued

```
                595                 600                 605
Lys Val Phe Phe Lys Ile Thr Asn Glu Val Ile Lys Ile Asn Lys Gln
610                 615                 620

Arg Asn Gln Lys Thr Gly His Tyr Lys Tyr Gln Lys Phe Glu Asn Ile
625                 630                 635                 640

Glu Lys Thr Val Pro Val Glu Tyr Leu Ala Ile Ile Gln Ser Arg Glu
                645                 650                 655

Met Ile Asn Asn Gln Asp Lys Glu Lys Asn Thr Tyr Ile Asp Phe
                660                 665                 670

Ile Gln Gln Ile Phe Leu Lys Gly Phe Ile Asp Tyr Leu Asn Lys Asn
                675                 680                 685

Asn Leu Lys Tyr Ile Glu Ser Asn Asn Asn Asp Asn Asn Asp Ile
690                 695                 700

Phe Ser Lys Ile Lys Ile Lys Lys Asp Lys Glu Lys Tyr Asp Lys
705                 710                 715                 720

Ile Leu Lys Asn Tyr Glu Lys His Asn Arg Asn Lys Glu Ile Pro His
                725                 730                 735

Glu Ile Asn Glu Phe Val Arg Glu Ile Lys Leu Gly Lys Ile Leu Lys
                740                 745                 750

Tyr Thr Glu Asn Leu Asn Met Phe Tyr Leu Ile Leu Lys Leu Leu Asn
                755                 760                 765

His Lys Glu Leu Thr Asn Leu Lys Gly Ser Leu Glu Lys Tyr Gln Ser
770                 775                 780

Ala Asn Lys Glu Glu Thr Phe Ser Asp Glu Leu Glu Leu Ile Asn Leu
785                 790                 795                 800

Leu Asn Leu Asp Asn Asn Arg Val Thr Glu Asp Phe Glu Leu Glu Ala
                805                 810                 815

Asn Glu Ile Gly Lys Phe Leu Asp Phe Asn Glu Asn Lys Ile Lys Asp
                820                 825                 830

Arg Lys Glu Leu Lys Lys Phe Asp Thr Asn Lys Ile Tyr Phe Asp Gly
                835                 840                 845

Glu Asn Ile Ile Lys His Arg Ala Phe Tyr Asn Ile Lys Lys Tyr Gly
850                 855                 860

Met Leu Asn Leu Leu Glu Lys Ile Ala Asp Lys Ala Lys Tyr Lys Ile
865                 870                 875                 880

Ser Leu Lys Glu Leu Lys Glu Tyr Ser Asn Lys Lys Asn Glu Ile Glu
                885                 890                 895

Lys Asn Tyr Thr Met Gln Gln Asn Leu His Arg Lys Tyr Ala Arg Pro
                900                 905                 910

Lys Lys Asp Glu Lys Phe Asn Asp Glu Asp Tyr Lys Glu Tyr Glu Lys
                915                 920                 925

Ala Ile Gly Asn Ile Gln Lys Tyr Thr His Leu Lys Asn Lys Val Glu
                930                 935                 940

Phe Asn Glu Leu Asn Leu Leu Gln Gly Leu Leu Leu Lys Ile Leu His
945                 950                 955                 960

Arg Leu Val Gly Tyr Thr Ser Ile Trp Glu Arg Asp Leu Arg Phe Arg
                965                 970                 975

Leu Lys Gly Glu Phe Pro Glu Asn His Tyr Ile Glu Glu Ile Phe Asn
                980                 985                 990

Phe Asp Asn Ser Lys Asn Val Lys  Tyr Lys Ser Gly Gln  Ile Val Glu
             995                 1000                1005

Lys Tyr  Ile Asn Phe Tyr Lys  Glu Leu Tyr Lys Asp  Asn Val Glu
       1010                1015                1020
```

| Lys | Arg | Ser | Ile | Tyr | Ser | Asp | Lys | Lys | Val | Lys | Leu | Lys | Gln |
|---|---|---|---|---|---|---|---|---|---|---|---|---|---|
| 1025 | | | | 1030 | | | | 1035 | | | | | |

| Glu | Lys | Lys | Asp | Leu | Tyr | Ile | Arg | Asn | Tyr | Ile | Ala | His | Phe | Asn |
|---|---|---|---|---|---|---|---|---|---|---|---|---|---|---|
| 1040 | | | | | 1045 | | | | 1050 | | | | | |

| Tyr | Ile | Pro | His | Ala | Glu | Ile | Ser | Leu | Leu | Glu | Val | Leu | Glu | Asn |
|---|---|---|---|---|---|---|---|---|---|---|---|---|---|---|
| 1055 | | | | | 1060 | | | | 1065 | | | | | |

| Leu | Arg | Lys | Leu | Leu | Ser | Tyr | Asp | Arg | Lys | Leu | Lys | Asn | Ala | Ile |
|---|---|---|---|---|---|---|---|---|---|---|---|---|---|---|
| 1070 | | | | | 1075 | | | | 1080 | | | | | |

| Met | Lys | Ser | Ile | Val | Asp | Ile | Leu | Lys | Glu | Tyr | Gly | Phe | Val | Ala |
|---|---|---|---|---|---|---|---|---|---|---|---|---|---|---|
| 1085 | | | | | 1090 | | | | 1095 | | | | | |

| Thr | Phe | Lys | Ile | Gly | Ala | Asp | Lys | Lys | Ile | Glu | Ile | Gln | Thr | Leu |
|---|---|---|---|---|---|---|---|---|---|---|---|---|---|---|
| 1100 | | | | | 1105 | | | | 1110 | | | | | |

| Glu | Ser | Glu | Lys | Ile | Val | His | Leu | Lys | Asn | Leu | Lys | Lys | Lys | Lys |
|---|---|---|---|---|---|---|---|---|---|---|---|---|---|---|
| 1115 | | | | | 1120 | | | | 1125 | | | | | |

| Leu | Met | Thr | Asp | Arg | Asn | Ser | Glu | Glu | Leu | Cys | Glu | Leu | Val | Lys |
|---|---|---|---|---|---|---|---|---|---|---|---|---|---|---|
| 1130 | | | | | 1135 | | | | 1140 | | | | | |

| Val | Met | Phe | Glu | Tyr | Lys | Ala | Leu | Glu |
|---|---|---|---|---|---|---|---|---|
| 1145 | | | | | 1150 | | | |

```
<210> SEQ ID NO 22
<211> LENGTH: 36
<212> TYPE: DNA
<213> ORGANISM: Artificial Sequence
<220> FEATURE:
<223> OTHER INFORMATION: LwaCas13a direct repeat

<400> SEQUENCE: 22
gatttagact accccaaaaa cgaagggac taaaac                              36

<210> SEQ ID NO 23
<211> LENGTH: 3363
<212> TYPE: DNA
<213> ORGANISM: Artificial Sequence
<220> FEATURE:
<223> OTHER INFORMATION: LseCas13a nucleic acid sequence

<400> SEQUENCE: 23
atgtggatca gcattaagac cctgatccac catctgggcg tgctgttctt ttgcgattac    60
atgtataacc ggagagagaa gaaaatcatc gaagtcaaaa caatgaggat cactaaggtg   120
gaggtcgatc ggaagaaagt gctgatcagc cgggacaaga atggcgggaa actggtctat   180
gagaacgaaa tgcaggacaa tacagagcag atcatgcacc ataagaaaag ctcctcctac   240
aaaagcgtgg tcaacaagac tatttgtcgc cctgagcaga agcagatgaa gaaactggtg   300
cacggcctgc tgcaggagaa cagccaggaa aagatcaagg tgagcgatgt cactaagctg   360
aatatctcaa acttcctgaa tcacagattc aagaagagcc tgtactattt cccagagaac   420
agtcccgata gtcagagga atacagaatc gaaattaatc tgtctcagct gctggaggac   480
agtctgaaga acagcagggg aaccttcatc tgctgggagt cctttctaa ggacatggaa    540 ctgtatatta ctgggccga gaactacatc tctagtaaga ctaaactgat taagaaaagt    600
atcaggaaca atcgcatcca gtcaaccgag agtaggtcag gccagctgat ggaccgctat   660
atgaaggata ttctgaacaa gaacaagccc ttcgatatcc agagcgtgtc cgagaaatac   720
cagctggaaa agctgacatc cgccctgaag gctactttta agaagctaa gaaaaacgac    780 aaggagatca attacaagct gaatctacc ctgcagaacc acgagaggca gatcattgag    840
gaactgaaag agaatagcga actgaaccag ttcaatatcg agattcgcaa gcatctggaa    900
```

```
acttacttcc ctattaagaa aaccaacaga aaagtgggag atatcaggaa tctggagatc    960
ggcgaaattc agaagatcgt gaaccaccgc ctgaagaaca agattgtcca gcgaatcctg   1020
caggagggaa agctggcctc ctatgagatc gaatctacag tgaactctaa tagtctgcag   1080
aagatcaaaa ttgaggaagc cttcgctctg aagtttatca acgcttgcct gttcgcatct   1140
aacaatctga ggaatatggt gtaccccgtc tgtaagaaag acattctgat gatcggcgag   1200
ttcaagaaca gcttcaagga gattaagcac aagaagttca tccgccagtg gagccagttc   1260 tttcccagg aaattactgt ggacgatatc gagctggcct cttggggact gcgaggagca   1320
attgccccta tccggaacga gatcattcac ctgaagaaac atagctggaa gaaattcttt   1380
aacaacccaa ctttcaaagt gaagaaatcc aagatcatta tggcaagac caaagacgtg   1440 accagcgagt cctgtataa ggaaaccctg ttcaaggatt acttttattc tgagctggac   1500
agtgtgcccg aactgatcat taacaaaatg gagtcaagca agatcctgga ctactattcc   1560
tctgatcagc tgaaccaggt gttcaccatt cctaattttg agctgtcact gctgacaagc   1620
gccgtgccct tcgctccttc ctttaaaaga gtctatctga agggcttcga ctaccagaac   1680
caggatgagg cacagccaga ctataatctg aagctgaaca tctacaatga aaagccttc   1740 aacagcgaag catttcaggc ccagtactcc ctgtttaaga tggtgtacta tcaggtgttc   1800
ctgccccagt ttaccacaaa caatgatctg ttcaagagtt cagtggactt tatcctgacc   1860
ctgaacaaag agaggaaggg ctatgctaag gcattccagg atatccgcaa aatgaataag   1920
gacgagaaac cttccgaata catgtcttat attcagagtc agctgatgct gtaccagaag   1980
aaacaggagg aaaggagaa aatcaaccac ttcgaaaagt ttattaacca ggtgtttatc   2040
aaagggttca acagctttat tgagaagaat aggctgacct acatctgcca ccctaccaag   2100
aacacagtgc cagagaacga taatatcgaa attccattcc atacagacat ggacgatagc   2160
aatatcgctt tttggctgat gtgcaaactg ctggatgcaa agcagctgtc cgagctgcgg   2220
aacgaaatga tcaagttcag ctgtagcctg cagagtacag aggaaattc aactttacc   2280 aaggcaagag aagtgatcgg cctggccctg ctgaacgggg agaaaggatg taatgactgg   2340
aaggagctgt tcgacgataa agaagcctgg aagaaaaaca tgtcactgta tgtgagcgag   2400
gaactgctgc agtctctgcc ctacacccag gaggatgggc agacacctgt gattaatcgg   2460
agtatcgacc tggtcaagaa atatggaaca gagactatcc tggaaaagct gttcagctcc   2520
tctgacgatt ataaggtgag cgcaaaagat attgccaagc tgcacgagta cgacgtgaca   2580
gaaaagattg ctcagcagga atccctgcat aaacagtgga tcgagaagcc agggctggct   2640
cgggatagcg catggactaa gaaataccag aacgtgatta tgacatctc caactaccag   2700 tgggcaaaga ctaaagtgga gctgaccag gtcagacacc tgcatcagct gaccattgac   2760
ctgctgtccc ggctggccgg atacatgtct atcgctgaca gagatttcca gtttagttca   2820
aactacattc tggagcgcga aaatagcgaa taccgagtga caagctggat tctgctgtcc   2880
gagaacaaga acaagaacaa gtacaacgat tatgaactgt ataacctgaa gaatgcctcc   2940
atcaaagtga gctccaagaa tgatccccag ctgaaagtcg acctgaagca gctgcggctg   3000
accctggagt atctggaact gttcgacaat cgactgaaag agaagcggaa caatatcagt   3060
cactttaact acctgaatgg ccagctgggg aactcaattc tggaactgtt cgacgatgcc   3120
agagatgtgc tgagctatga caggaaactg aagaatgctg tctccaagtc tctgaaagaa   3180
atcctgtcta gtcatggcat ggaggtgacc ttcaagccac tgtaccagac taaccaccat   3240
```

-continued

```
ctgaagattg acaaactgca gcccaagaaa atccaccatc tggggagaa gtctacagtg    3300 tcaagcaacc aggtcagtaa cgaatactgt cagctggtga gaactctgct gaccatgaag    3360
tga                                                                  3363
```

<210> SEQ ID NO 24
<211> LENGTH: 1120
<212> TYPE: PRT
<213> ORGANISM: Artificial Sequence
<220> FEATURE:
<223> OTHER INFORMATION: LseCas13a amino acid sequence

<400> SEQUENCE: 24

```
Met Trp Ile Ser Ile Lys Thr Leu Ile His His Leu Gly Val Leu Phe
1               5                   10                  15

Phe Cys Asp Tyr Met Tyr Asn Arg Arg Glu Lys Lys Ile Ile Glu Val
                20                  25                  30

Lys Thr Met Arg Ile Thr Lys Val Glu Val Asp Arg Lys Lys Val Leu
            35                  40                  45

Ile Ser Arg Asp Lys Asn Gly Gly Lys Leu Val Tyr Glu Asn Glu Met
        50                  55                  60

Gln Asp Asn Thr Glu Gln Ile Met His His Lys Lys Ser Ser Phe Tyr
65                  70                  75                  80

Lys Ser Val Val Asn Lys Thr Ile Cys Arg Pro Glu Gln Lys Gln Met
                85                  90                  95

Lys Lys Leu Val His Gly Leu Leu Gln Glu Asn Ser Gln Glu Lys Ile
            100                 105                 110

Lys Val Ser Asp Val Thr Lys Leu Asn Ile Ser Asn Phe Leu Asn His
        115                 120                 125

Arg Phe Lys Lys Ser Leu Tyr Tyr Phe Pro Glu Asn Ser Pro Asp Lys
    130                 135                 140

Ser Glu Glu Tyr Arg Ile Glu Ile Asn Leu Ser Gln Leu Leu Glu Asp
145                 150                 155                 160

Ser Leu Lys Lys Gln Gln Gly Thr Phe Ile Cys Trp Glu Ser Phe Ser
                165                 170                 175

Lys Asp Met Glu Leu Tyr Ile Asn Trp Ala Glu Asn Tyr Ile Ser Ser
            180                 185                 190

Lys Thr Lys Leu Ile Lys Lys Ser Ile Arg Asn Asn Arg Ile Gln Ser
        195                 200                 205

Thr Glu Ser Arg Ser Gly Gln Leu Met Asp Arg Tyr Met Lys Asp Ile
    210                 215                 220

Leu Asn Lys Asn Lys Pro Phe Asp Ile Gln Ser Val Ser Glu Lys Tyr
225                 230                 235                 240

Gln Leu Glu Lys Leu Thr Ser Ala Leu Lys Ala Thr Phe Lys Glu Ala
                245                 250                 255

Lys Lys Asn Asp Lys Glu Ile Asn Tyr Lys Leu Lys Ser Thr Leu Gln
            260                 265                 270

Asn His Glu Arg Gln Ile Ile Glu Glu Leu Lys Glu Asn Ser Glu Leu
        275                 280                 285

Asn Gln Phe Asn Ile Glu Ile Arg Lys His Leu Glu Thr Tyr Phe Pro
    290                 295                 300

Ile Lys Lys Thr Asn Arg Lys Val Gly Asp Ile Arg Asn Leu Glu Ile
305                 310                 315                 320

Gly Glu Ile Gln Lys Ile Val Asn His Arg Leu Lys Asn Lys Ile Val
                325                 330                 335
```

-continued

Gln Arg Ile Leu Gln Glu Gly Lys Leu Ala Ser Tyr Glu Ile Glu Ser
                340                 345                 350

Thr Val Asn Ser Asn Ser Leu Gln Lys Ile Lys Ile Glu Glu Ala Phe
        355                 360                 365

Ala Leu Lys Phe Ile Asn Ala Cys Leu Phe Ala Ser Asn Asn Leu Arg
        370                 375                 380

Asn Met Val Tyr Pro Val Cys Lys Lys Asp Ile Leu Met Ile Gly Glu
385                 390                 395                 400

Phe Lys Asn Ser Phe Lys Glu Ile Lys His Lys Lys Phe Ile Arg Gln
                405                 410                 415

Trp Ser Gln Phe Phe Ser Gln Glu Ile Thr Val Asp Asp Ile Glu Leu
            420                 425                 430

Ala Ser Trp Gly Leu Arg Gly Ala Ile Ala Pro Ile Arg Asn Glu Ile
        435                 440                 445

Ile His Leu Lys Lys His Ser Trp Lys Lys Phe Phe Asn Asn Pro Thr
        450                 455                 460

Phe Lys Val Lys Ser Lys Ile Ile Asn Gly Lys Thr Lys Asp Val
465                 470                 475                 480

Thr Ser Glu Phe Leu Tyr Lys Glu Thr Leu Phe Lys Asp Tyr Phe Tyr
                485                 490                 495

Ser Glu Leu Asp Ser Val Pro Glu Leu Ile Ile Asn Lys Met Glu Ser
            500                 505                 510

Ser Lys Ile Leu Asp Tyr Tyr Ser Asp Gln Leu Asn Gln Val Phe
        515                 520                 525

Thr Ile Pro Asn Phe Glu Leu Ser Leu Thr Ser Ala Val Pro Phe
        530                 535                 540

Ala Pro Ser Phe Lys Arg Val Tyr Leu Lys Gly Phe Asp Tyr Gln Asn
545                 550                 555                 560

Gln Asp Glu Ala Gln Pro Asp Tyr Asn Leu Lys Leu Asn Ile Tyr Asn
                565                 570                 575

Glu Lys Ala Phe Asn Ser Glu Ala Phe Gln Ala Gln Tyr Ser Leu Phe
            580                 585                 590

Lys Met Val Tyr Tyr Gln Val Phe Leu Pro Gln Phe Thr Thr Asn Asn
        595                 600                 605

Asp Leu Phe Lys Ser Ser Val Asp Phe Ile Leu Thr Leu Asn Lys Glu
        610                 615                 620

Arg Lys Gly Tyr Ala Lys Ala Phe Gln Asp Ile Arg Lys Met Asn Lys
625                 630                 635                 640

Asp Glu Lys Pro Ser Glu Tyr Met Ser Tyr Ile Gln Ser Gln Leu Met
                645                 650                 655

Leu Tyr Gln Lys Lys Gln Glu Glu Lys Glu Lys Ile Asn His Phe Glu
            660                 665                 670

Lys Phe Ile Asn Gln Val Phe Ile Lys Gly Phe Asn Ser Phe Ile Glu
        675                 680                 685

Lys Asn Arg Leu Thr Tyr Ile Cys His Pro Thr Lys Asn Thr Val Pro
        690                 695                 700

Glu Asn Asp Asn Ile Glu Ile Pro Phe His Thr Asp Met Asp Asp Ser
705                 710                 715                 720

Asn Ile Ala Phe Trp Leu Met Cys Lys Leu Leu Asp Ala Lys Gln Leu
                725                 730                 735

Ser Glu Leu Arg Asn Glu Met Ile Lys Phe Ser Cys Ser Leu Gln Ser
            740                 745                 750

Thr Glu Glu Ile Ser Thr Phe Thr Lys Ala Arg Glu Val Ile Gly Leu

```
                755                 760                 765
Ala Leu Leu Asn Gly Glu Lys Gly Cys Asn Asp Trp Lys Glu Leu Phe
770                 775                 780

Asp Asp Lys Glu Ala Trp Lys Lys Asn Met Ser Leu Tyr Val Ser Glu
785                 790                 795                 800

Glu Leu Leu Gln Ser Leu Pro Tyr Thr Gln Glu Asp Gly Gln Thr Pro
                805                 810                 815

Val Ile Asn Arg Ser Ile Asp Leu Val Lys Lys Tyr Gly Thr Glu Thr
                820                 825                 830

Ile Leu Glu Lys Leu Phe Ser Ser Asp Asp Tyr Lys Val Ser Ala
                835                 840                 845

Lys Asp Ile Ala Lys Leu His Glu Tyr Asp Val Thr Glu Lys Ile Ala
850                 855                 860

Gln Gln Glu Ser Leu His Lys Gln Trp Ile Glu Lys Pro Gly Leu Ala
865                 870                 875                 880

Arg Asp Ser Ala Trp Thr Lys Lys Tyr Gln Asn Val Ile Asn Asp Ile
                885                 890                 895

Ser Asn Tyr Gln Trp Ala Lys Thr Lys Val Glu Leu Thr Gln Val Arg
                900                 905                 910

His Leu His Gln Leu Thr Ile Asp Leu Leu Ser Arg Leu Ala Gly Tyr
                915                 920                 925

Met Ser Ile Ala Asp Arg Asp Phe Gln Phe Ser Ser Asn Tyr Ile Leu
930                 935                 940

Glu Arg Glu Asn Ser Glu Tyr Arg Val Thr Ser Trp Ile Leu Leu Ser
945                 950                 955                 960

Glu Asn Lys Asn Lys Asn Lys Tyr Asn Asp Tyr Glu Leu Tyr Asn Leu
                965                 970                 975

Lys Asn Ala Ser Ile Lys Val Ser Lys Asn Asp Pro Gln Leu Lys
                980                 985                 990

Val Asp Leu Lys Gln Leu Arg Leu  Thr Leu Glu Tyr Leu  Glu Leu Phe
                995                 1000                1005

Asp Asn  Arg Leu Lys Glu Lys  Arg Asn Asn Ile Ser  His Phe Asn
   1010                 1015                1020

Tyr Leu  Asn Gly Gln Leu Gly  Asn Ser Ile Leu Glu  Leu Phe Asp
   1025                 1030                1035

Asp Ala  Arg Asp Val Leu Ser  Tyr Asp Arg Lys Leu  Lys Asn Ala
   1040                 1045                1050

Val Ser  Lys Ser Leu Lys Glu  Ile Leu Ser Ser His  Gly Met Glu
   1055                 1060                1065

Val Thr  Phe Lys Pro Leu Tyr  Gln Thr Asn His His  Leu Lys Ile
   1070                 1075                1080

Asp Lys  Leu Gln Pro Lys Lys  Ile His His Leu Gly  Glu Lys Ser
   1085                 1090                1095

Thr Val  Ser Ser Asn Gln Val  Ser Asn Glu Tyr Cys  Gln Leu Val
   1100                 1105                1110

Arg Thr  Leu Leu Thr Met Lys
   1115                 1120

<210> SEQ ID NO 25
<211> LENGTH: 36
<212> TYPE: DNA
<213> ORGANISM: Artificial Sequence
<220> FEATURE:
<223> OTHER INFORMATION: LseCas13a direct repeat
```

<400> SEQUENCE: 25
gtaagagact acctctatat gaaagaggac taaaac                                    36

<210> SEQ ID NO 26
<211> LENGTH: 4023
<212> TYPE: DNA
<213> ORGANISM: Artificial Sequence
<220> FEATURE:
<223> OTHER INFORMATION: LbmCas13a nucleic acid sequence

<400> SEQUENCE: 26

| | | |
|---|---|---|
| atgcagatct ccaaggtgaa ccacaagcac gtggcagtgg gacagaagga cagggagaga | 60 |
| atcaccggct tcatctataa tgacccagtg ggcgatgaga agagcctgga ggacgtggtg | 120 |
| gcaaagaggg ccaacgatac caaggtgctg ttcaacgtgt tcaacacaaa ggacctgtac | 180 |
| gattctcagg agagcgacaa gtccgagaag gataaggaga tcatctccaa gggcgccaag | 240 |
| ttcgtggcca gtctttttaa cagcgccatc acaatcctga agaagcagaa taagatctat | 300 |
| tccaccctga catctcagca ggtcatcaag gagctgaagg acaagttcgg cggcgcccgc | 360 |
| atctacgacg atgacatcga ggaggccctg accgagacac tgaagaagtc ttttagaaag | 420 |
| gagaatgtga gaacagcat caaggtgctg atcgagaatg cagcaggcat ccggagctcc | 480 |
| ctgtccaagg acgaggagga gctgatccag gagtatttcg tgaagcagct ggtggaggag | 540 |
| tacaccaaga caaagctgca agaacgtg gtgaagagca tcaagaatca gaacatggtc | 600 |
| atccagcccg atagcgactc ccaggtgctg tctctgagcg agtcccggag agagaagcag | 660 |
| tctagcgccg tgtcctctga cacctggtg aattgcaagg agaaggacgt gctgaaggcc | 720 |
| ttcctgacag attacgccgt gctggatgag gacgagcgca cagcctgct gtggaagctg | 780 |
| cggaatctgg tgaacctgta cttttatggc tctgagagca tcaggattac tcttatacc | 840 |
| aaggagaaga gcgtgtggaa ggagcacgac gagcagaagg ccaacaagac cctgttcatc | 900 |
| gatgagatct gccacatcac aaagatcggc aagaacggca aggagcagaa ggtgctggac | 960 |
| tatgaggaga ataggagccg ctgtcggaag cagaatatca actactatcg ctccgccctg | 1020 |
| aattacgcca gaacaatac cagcggcatc ttcgagaatg aggattccaa ccactttggg | 1080 |
| attcacctga tcgagaacga ggtggagcgg ctgtataatg gcatcgagaa cggcgaggag | 1140 |
| ttcaagtttg agacaggcta catctctgag aaagtgtgga aggccgtgat caaccacctg | 1200 |
| agcatcaagt acatcgccct gggcaaggcc gtgtataact atgccatgaa ggagctgagc | 1260 |
| tcccccggcg catcgagcc tgcaagatc gatgactcct atatcaacgg catcaccctct | 1320 |
| ttcgactacg agatcatcaa ggccgaggag tccctgcaga gagatatctc tatgaatgtg | 1380 |
| gtgtttgcca caactacct ggcctgcgcc accgtggata cagacaagga tttcctgctg | 1440 |
| tttagcaagg aggacatcag gtcctgcacc aagaaggatg caacctgtg caagaacatc | 1500 |
| atgcagttct ggggcggcta ttccacatgg aagaatttt gtgaggagta cctgaaggat | 1560 |
| gacaaggacg ccctggagct gctgtactcc ctgaagtcta tgctgtattc tatgagaaac | 1620 |
| tctagcttcc acttttctac cgagaatgtg gacaacggca gctgggatac agagctgatc | 1680 |
| ggcaagctgt cgaggagga ttgtaaccgc gccgccgga tcgagaagga aagttctac | 1740 |
| aacaataacc tgcacatgtt ttattcctct agcctgctgg agaaggtgct ggagagactg | 1800 |
| tactcctctc accacgagag ggccagccag gtgccttcct tcaacagagt gtttgtgagg | 1860 |
| aagaatttcc aagctccct gtccgagcag agaatcaccc ccaagtttac agactccaag | 1920 |
| gatgagcaga tctggcagtc tgccgtgtac tatctgtgca aggagatcta ctataacgac | 1980 |

-continued

```
ttcctgcaga gcaaggaggc ctacaagctg tttagggagg gcgtgaagaa tctggacaag      2040
aacgatatca ataaccagaa ggccgccgat agcttcaagc aggccgtggt gtactatggc      2100
aaggccatcg gcaacgccac cctgtcccag gtgtgccagg ccatcatgac agagtataat      2160
aggcagaata cgacggcct gaagaagaag agcgcctacg ccgagaagca gaacagcaac       2220
aagtacaagc actatcctct gttcctgaag caggtgctgc agagcgcctt tgggagtac       2280 ctggatgaga caaggagat ctatggcttc atctctgccc agatccacaa gagcaacgtg       2340
gagatcaagg ccgaggactt tatcgccaat tactctagcc agcagtataa gaagctggtg      2400
gataaggtga agaaaacccc tgagctgcag aagtggtata cactgggccg cctgatcaat     2460
ccacggcagg ccaaccagtt cctgggctcc atcagaaatt acgtgcagtt tgtgaaggac     2520
atccagaggc gcgccaagga gaatggcaac ccaatcagga actactatga ggtgctggag    2580
tccgattcta tcatcaagat cctggagatg tgcaccaagc tgaatggcac cacaagcaac    2640
gacatccacg attacttccg cgacgaggat gagtacgccg agtatatctc ccagttcgtg     2700
aactttggcg acgtgcactc tggcgccgcc ctgaatgcct tttgcaacag cgagtccgag    2760
ggcaagaaga acggcatcta ctatgacggc atcaatccca tcgtgaatcg gaactgggtg    2820
ctgtgcaagc tgtatggctc ccctgatctg atctctaaga tcatcagccg cgtgaatgag    2880
aacatgatcc acgacttcca caagcaggag gatctgatcc gggagtacca gatcaagggc   2940
atctgttcta acaagaagga gcagcaggac ctgcgcacct ttcaggtgct gaagaatcgc     3000
gtggagctgc gggatatcgt ggagtacagc gagatcatca cgagctgta tggccagctg     3060 atcaagtggt gctacctgag agagagggac ctgatgtact ccagctgggg cttcactac     3120 ctgtgcctga ataacgcctc ctctaaggag gccgattata tcaagatcaa tgtggatgac   3180
cggaacatca gcggcgccat cctgtaccag atcgccgcca tgtatatcaa tggcctgccc    3240
gtgtactata agaaggatga catgtacgtg gccctgaagt ccggcaagaa ggcctctgac    3300
gagctgaata gcaacgagca gacctccaag aagatcaact acttcctgaa gtatggcaat   3360
aacatcctgg gcgacaagaa ggatcagctg tacctggccg gcctggagct gttcgagaat   3420
gtggccgagc acgagaacat catcatcttt agaaatgaga tcgaccactt ccactacttt    3480
tatgaccgcg atcggtccat gctggatctg tattctgagg tgtttgaccg cttctttacc   3540
tacgatatga agctgcggaa gaatgtggtg aacatgctgt ataacatcct gctgaccac    3600 aatatcgtga gctccttcgt gtttgagaca ggcgagaaga aggtcggcag gggcgatagc    3660
gaagtgatca agccttccgc caagatcaga ctgagggcca ataacggcgt gtctagcgac    3720
gtgttcacct acaaagtggg cagcaaggat gagctgaaga tcgccacact gccagccaag    3780
aacgaggagt ttctgctgaa tgtgccaga ctgatctact atcccgacat ggaggccgtg    3840
tccgagaaca tggtgaggga gggcgtggtg aaggtggaga agtctaatga taagaaggc    3900 aagatcagca gaggctccaa taccaggtcc tctaaccagt ctaagtacaa caacaagagc    3960
aagaacagaa tgaactactc tatgggcagc atcttcgaga agatggacct gaagtttgat    4020
tga                                                                   4023
```

<210> SEQ ID NO 27
<211> LENGTH: 1340
<212> TYPE: PRT
<213> ORGANISM: Artificial Sequence
<220> FEATURE:
<223> OTHER INFORMATION: LbmCas13a amino acid sequence

```
<400> SEQUENCE: 27

Met Gln Ile Ser Lys Val Asn His Lys His Val Ala Val Gly Gln Lys
1               5                   10                  15

Asp Arg Glu Arg Ile Thr Gly Phe Ile Tyr Asn Asp Pro Val Gly Asp
            20                  25                  30

Glu Lys Ser Leu Glu Asp Val Ala Lys Arg Ala Asn Asp Thr Lys
        35                  40                  45

Val Leu Phe Asn Val Phe Asn Thr Lys Asp Leu Tyr Asp Ser Gln Glu
    50                  55                  60

Ser Asp Lys Ser Glu Lys Asp Lys Glu Ile Ile Ser Lys Gly Ala Lys
65                  70                  75                  80

Phe Val Ala Lys Ser Phe Asn Ser Ala Ile Thr Ile Leu Lys Lys Gln
                85                  90                  95

Asn Lys Ile Tyr Ser Thr Leu Thr Ser Gln Gln Val Ile Lys Glu Leu
            100                 105                 110

Lys Asp Lys Phe Gly Gly Ala Arg Ile Tyr Asp Asp Ile Glu Glu
        115                 120                 125

Ala Leu Thr Glu Thr Leu Lys Lys Ser Phe Arg Lys Glu Asn Val Arg
    130                 135                 140

Asn Ser Ile Lys Val Leu Ile Glu Asn Ala Ala Gly Ile Arg Ser Ser
145                 150                 155                 160

Leu Ser Lys Asp Glu Glu Glu Leu Ile Gln Glu Tyr Phe Val Lys Gln
                165                 170                 175

Leu Val Glu Glu Tyr Thr Lys Thr Lys Leu Gln Lys Asn Val Val Lys
            180                 185                 190

Ser Ile Lys Asn Gln Asn Met Val Ile Gln Pro Asp Ser Asp Ser Gln
        195                 200                 205

Val Leu Ser Leu Ser Glu Ser Arg Arg Glu Lys Gln Ser Ser Ala Val
    210                 215                 220

Ser Ser Asp Thr Leu Val Asn Cys Lys Glu Lys Asp Val Leu Lys Ala
225                 230                 235                 240

Phe Leu Thr Asp Tyr Ala Val Leu Asp Glu Asp Glu Arg Asn Ser Leu
                245                 250                 255

Leu Trp Lys Leu Arg Asn Leu Val Asn Leu Tyr Phe Tyr Gly Ser Glu
            260                 265                 270

Ser Ile Arg Asp Tyr Ser Tyr Thr Lys Glu Lys Ser Val Trp Lys Glu
        275                 280                 285

His Asp Glu Gln Lys Ala Asn Lys Thr Leu Phe Ile Asp Glu Ile Cys
    290                 295                 300

His Ile Thr Lys Ile Gly Lys Asn Gly Lys Glu Gln Lys Val Leu Asp
305                 310                 315                 320

Tyr Glu Glu Asn Arg Ser Arg Cys Arg Lys Gln Asn Ile Asn Tyr Tyr
                325                 330                 335

Arg Ser Ala Leu Asn Tyr Ala Lys Asn Asn Thr Ser Gly Ile Phe Glu
            340                 345                 350

Asn Glu Asp Ser Asn His Phe Trp Ile His Leu Ile Glu Asn Glu Val
        355                 360                 365

Glu Arg Leu Tyr Asn Gly Ile Glu Asn Gly Glu Phe Lys Phe Glu
    370                 375                 380

Thr Gly Tyr Ile Ser Glu Lys Val Trp Lys Ala Val Ile Asn His Leu
385                 390                 395                 400

Ser Ile Lys Tyr Ile Ala Leu Gly Lys Ala Val Tyr Asn Tyr Ala Met
                405                 410                 415
```

```
Lys Glu Leu Ser Ser Pro Gly Asp Ile Glu Pro Gly Lys Ile Asp Asp
                420                 425                 430

Ser Tyr Ile Asn Gly Ile Thr Ser Phe Asp Tyr Glu Ile Ile Lys Ala
            435                 440                 445

Glu Glu Ser Leu Gln Arg Asp Ile Ser Met Asn Val Val Phe Ala Thr
450                 455                 460

Asn Tyr Leu Ala Cys Ala Thr Val Asp Thr Asp Lys Asp Phe Leu Leu
465                 470                 475                 480

Phe Ser Lys Glu Asp Ile Arg Ser Cys Thr Lys Lys Asp Gly Asn Leu
                485                 490                 495

Cys Lys Asn Ile Met Gln Phe Trp Gly Gly Tyr Ser Thr Trp Lys Asn
                500                 505                 510

Phe Cys Glu Glu Tyr Leu Lys Asp Asp Lys Asp Ala Leu Glu Leu Leu
            515                 520                 525

Tyr Ser Leu Lys Ser Met Leu Tyr Ser Met Arg Asn Ser Ser Phe His
530                 535                 540

Phe Ser Thr Glu Asn Val Asp Asn Gly Ser Trp Asp Thr Glu Leu Ile
545                 550                 555                 560

Gly Lys Leu Phe Glu Glu Asp Cys Asn Arg Ala Ala Arg Ile Glu Lys
                565                 570                 575

Glu Lys Phe Tyr Asn Asn Asn Leu His Met Phe Tyr Ser Ser Ser Leu
            580                 585                 590

Leu Glu Lys Val Leu Glu Arg Leu Tyr Ser Ser His His Glu Arg Ala
            595                 600                 605

Ser Gln Val Pro Ser Phe Asn Arg Val Phe Val Arg Lys Asn Phe Pro
610                 615                 620

Ser Ser Leu Ser Glu Gln Arg Ile Thr Pro Lys Phe Thr Asp Ser Lys
625                 630                 635                 640

Asp Glu Gln Ile Trp Gln Ser Ala Val Tyr Tyr Leu Cys Lys Glu Ile
                645                 650                 655

Tyr Tyr Asn Asp Phe Leu Gln Ser Lys Glu Ala Tyr Lys Leu Phe Arg
            660                 665                 670

Glu Gly Val Lys Asn Leu Asp Lys Asn Asp Ile Asn Asn Gln Lys Ala
            675                 680                 685

Ala Asp Ser Phe Lys Gln Ala Val Val Tyr Tyr Gly Lys Ala Ile Gly
690                 695                 700

Asn Ala Thr Leu Ser Gln Val Cys Gln Ala Ile Met Thr Glu Tyr Asn
705                 710                 715                 720

Arg Gln Asn Asn Asp Gly Leu Lys Lys Lys Ser Ala Tyr Ala Glu Lys
                725                 730                 735

Gln Asn Ser Asn Lys Tyr Lys His Tyr Pro Leu Phe Leu Lys Gln Val
            740                 745                 750

Leu Gln Ser Ala Phe Trp Glu Tyr Leu Asp Glu Asn Lys Glu Ile Tyr
            755                 760                 765

Gly Phe Ile Ser Ala Gln Ile His Lys Ser Asn Val Glu Ile Lys Ala
            770                 775                 780

Glu Asp Phe Ile Ala Asn Tyr Ser Ser Gln Gln Tyr Lys Lys Leu Val
785                 790                 795                 800

Asp Lys Val Lys Lys Thr Pro Glu Leu Gln Lys Trp Tyr Thr Leu Gly
                805                 810                 815

Arg Leu Ile Asn Pro Arg Gln Ala Asn Gln Phe Leu Gly Ser Ile Arg
            820                 825                 830
```

```
Asn Tyr Val Gln Phe Val Lys Asp Ile Gln Arg Arg Ala Lys Glu Asn
        835                 840                 845

Gly Asn Pro Ile Arg Asn Tyr Tyr Glu Val Leu Glu Ser Asp Ser Ile
850                 855                 860

Ile Lys Ile Leu Glu Met Cys Thr Lys Leu Asn Gly Thr Thr Ser Asn
865                 870                 875                 880

Asp Ile His Asp Tyr Phe Arg Asp Glu Asp Glu Tyr Ala Glu Tyr Ile
            885                 890                 895

Ser Gln Phe Val Asn Phe Gly Asp Val His Ser Gly Ala Ala Leu Asn
                900                 905                 910

Ala Phe Cys Asn Ser Glu Ser Glu Gly Lys Lys Asn Gly Ile Tyr Tyr
            915                 920                 925

Asp Gly Ile Asn Pro Ile Val Asn Arg Asn Trp Val Leu Cys Lys Leu
        930                 935                 940

Tyr Gly Ser Pro Asp Leu Ile Ser Lys Ile Ile Ser Arg Val Asn Glu
945                 950                 955                 960

Asn Met Ile His Asp Phe His Lys Gln Glu Asp Leu Ile Arg Glu Tyr
            965                 970                 975

Gln Ile Lys Gly Ile Cys Ser Asn Lys Lys Glu Gln Gln Asp Leu Arg
        980                 985                 990

Thr Phe Gln Val Leu Lys Asn Arg  Val Glu Leu Arg Asp  Ile Val Glu
        995                 1000                1005

Tyr Ser  Glu Ile Ile Asn Glu  Leu Tyr Gly Gln Leu  Ile Lys Trp
    1010                1015                1020

Cys Tyr  Leu Arg Glu Arg Asp  Leu Met Tyr Phe Gln  Leu Gly Phe
    1025                1030                1035

His Tyr  Leu Cys Leu Asn Asn  Ala Ser Ser Lys Glu  Ala Asp Tyr
    1040                1045                1050

Ile Lys  Ile Asn Val Asp Asp  Arg Asn Ile Ser Gly  Ala Ile Leu
    1055                1060                1065

Tyr Gln  Ile Ala Ala Met Tyr  Ile Asn Gly Leu Pro  Val Tyr Tyr
    1070                1075                1080

Lys Lys  Asp Asp Met Tyr Val  Ala Leu Lys Ser Gly  Lys Lys Ala
    1085                1090                1095

Ser Asp  Glu Leu Asn Ser Asn  Glu Gln Thr Ser Lys  Lys Ile Asn
    1100                1105                1110

Tyr Phe  Leu Lys Tyr Gly Asn  Asn Ile Leu Gly Asp  Lys Lys Asp
    1115                1120                1125

Gln Leu  Tyr Leu Ala Gly Leu  Glu Leu Phe Glu Asn  Val Ala Glu
    1130                1135                1140

His Glu  Asn Ile Ile Ile Phe  Arg Asn Glu Ile Asp  His Phe His
    1145                1150                1155

Tyr Phe  Tyr Asp Arg Asp Arg  Ser Met Leu Asp Leu  Tyr Ser Glu
    1160                1165                1170

Val Phe  Asp Arg Phe Phe Thr  Tyr Asp Met Lys Leu  Arg Lys Asn
    1175                1180                1185

Val Val  Asn Met Leu Tyr Asn  Ile Leu Leu Asp His  Asn Ile Val
    1190                1195                1200

Ser Ser  Phe Val Phe Glu Thr  Gly Glu Lys Lys Val  Gly Arg Gly
    1205                1210                1215

Asp Ser  Glu Val Ile Lys Pro  Ser Ala Lys Ile Arg  Leu Arg Ala
    1220                1225                1230

Asn Asn  Gly Val Ser Ser Asp  Val Phe Tyr Lys  Val Gly Ser
```

```
          1235                1240                1245
Lys Asp Glu Leu Lys Ile Ala Thr Leu Pro Ala Lys Asn Glu Glu
      1250                1255                1260

Phe Leu Leu Asn Val Ala Arg Leu Ile Tyr Tyr Pro Asp Met Glu
      1265                1270                1275

Ala Val Ser Glu Asn Met Val Arg Glu Gly Val Val Lys Val Glu
      1280                1285                1290

Lys Ser Asn Asp Lys Lys Gly Lys Ile Ser Arg Gly Ser Asn Thr
      1295                1300                1305

Arg Ser Ser Asn Gln Ser Lys Tyr Asn Asn Lys Ser Lys Asn Arg
      1310                1315                1320

Met Asn Tyr Ser Met Gly Ser Ile Phe Glu Lys Met Asp Leu Lys
      1325                1330                1335

Phe Asp
      1340

<210> SEQ ID NO 28
<211> LENGTH: 35
<212> TYPE: DNA
<213> ORGANISM: Artificial Sequence
<220> FEATURE:
<223> OTHER INFORMATION: LbmCas13a direct repeat

<400> SEQUENCE: 28
gtattgagaa aagccagata tagttggcaa tagac                              35

<210> SEQ ID NO 29
<211> LENGTH: 4314
<212> TYPE: DNA
<213> ORGANISM: Artificial Sequence
<220> FEATURE:
<223> OTHER INFORMATION: LbnCas13a nucleic acid sequence

<400> SEQUENCE: 29
atgaagatca gcaaggtgcg ggaggagaac agaggcgcca agctgaccgt gaatgccaag     60
acagccgtgg tgtctgagaa ccggagccag gagggcatcc tgtataatga cccaagcagg    120
tacggcaagt cccgcaagaa cgacgaggat agggaccgct atatcgagag cagactgaag    180
agctccggca agctgtaccg gatctttaac gaggataaga ataagcgcga gacagacgag    240
ctgcagtggt tcctgtccga gatcgtgaag aagatcaacc ggagaaatgg cctggtgctg    300
tccgacatgc tgtctgtgga cgatagagcc ttcgagaagg cctttgagaa gtacgccgag    360
ctgtcttata ccaacaggcg caataaggtg tccggctctc cgccttcga gacatgcgga    420 gtggatgcag caacagcaga gcggctgaag ggaatcatct ccgagacaaa cttcatcaac    480
agaatcaaga caacatcga caacaaggtg tctgaggaca tcatcgatcg gatcatcgcc    540
aagtacctga agaagagcct gtgccgggag agagtgaaga gaggcctgaa gaagctgctg    600
atgaatgcct tgatctgcc atactctgat cccgacatcg atgtgcagag ggacttcatc    660
gattatgtgc tggaggactt ttaccacgtg cgggccaaga gccaggtgag cagatccatc    720
aagaacatga atatgcccgt gcagcctgag ggcgacggca gttcgccat caccgtgagc    780 aagggcggca cagagtctgg caacaagcgc agcgccgaga aggaggcctt caagaagttt    840
ctgagcgatt acgcctccct ggacgagagg gtgcgcgacg atatgctgcg gagaatgagg    900
cgcctggtgg tgctgtactt ttatggctcc gacgattcta agctgagcga tgtgaacgag    960
aagttcgacg tgtgggagga ccacgcagcc cggagagtgg acaatagga gttcatcaag    1020
```

```
ctgccactgg agaacaagct ggccaatggc aagaccgaca aggatgccga gcggatcaga    1080
aagaacacag tgaaggagct gtatagaaac cagaatatcg gctgctacag caggccgtg     1140 aaggccgtgg aggaggacaa caatggccgg tactttgacg ataagatgct gaacatgttc    1200
tttatccaca gaatcgagta tggcgtggag aagatctacg ccaatctgaa gcaggtgacc    1260
gagttcaagg cccgcacagg ctacctgagc gagaagatct ggaaggatct gatcaactac    1320
atctctatca gtatatcgc catgggcaag gccgtgtata actatgccat ggatgagctg    1380
aatgcctccg acaagaagga gatcgagctg ggcaagatct ccgaggagta tctgtctggc    1440
atctctagct tcgactacga gctgatcaag gccgaggaga tgctgcagag ggagacagcc    1500
gtgtacgtgg cctttgccgc aaggcacctg tcctctcaga cagtggagct ggattccgag    1560
aactctgact cctgctgct gaagcctaag ggcaccatgg acaagaacga taagaataag    1620
ctggcctcca acaatatcct gaattttctg aaggataagg agacactgcg ggacacaatc    1680
ctgcagtatt tcggcggcca ctctctgtgg acagatttcc catttgacaa gtacctggcc    1740
ggcggcaagg acgatgtgga ttttctgacc gacctgaagg atgtgatcta tagcatgcgg    1800
aacgactcct tccactacgc cacagagaac cacaacaatg caagtggaa taaggagctg    1860 atctccgcca tgtttgagca cgagacagag agaatgacag tggtcatgaa ggacaagttc    1920
tattctaaca atctgcccat gttttacaag aacgacgatc tgaagaagct gctgatcgac    1980
ctgtataagc acaatgtgga gagagcctct caggtgccca gcttcaacaa ggtgtttgtg    2040
cgcaagaatt ccctgcccct ggtgcgggac aaggataacc tgggcatcga gctggatctg    2100
aaggccgacg ccgataaggg cgagaatgag ctgaagttct acaacgccct gtactacatg    2160
ttcaaggaga tctactacaa cgccttcctg aacgacaaga atgtgaggga gcggttcatc    2220
accaaggcca caaggtggc cgacaactat gataggaata aggagcgcaa cctgaaggat    2280
aggatcaaga gcgccggctc cgacgagaag aagaagctgc gcgagcagct gcagaattac    2340
atcgccgaga acgatttcgg ccagaggatc aagaatatcg tgcaggtgaa ccctgactat    2400
accctggccc agatctgcca gctgatcatg acagagtaca accagcagaa caatggctgt    2460
atgcagaaga gagcgccgc ccggaaggat atcaataagg actcctacca gcactataag    2520
atgctgctgc tggtgaacct gagaaaggcc ttcctggagt ttatcaagga gaattatgcc    2580
tttgtgctga gcccctacaa gcacgacctg tgcgataagg ccgacttcgt gcctgatttt    2640
gccaagtacg tgaagcccta cgccggcctg atcagcaggg tggcaggcag ctccgagctg    2700
cagaagtggt atatcgtgtc ccgctttctg tctcctgccc aggccaacca catgctgggc    2760
ttcctgcact cctacaagca gtacgtgtgg gacatctaca ggcgcgcctc tgagacaggc    2820
accgagatca atcacagcat cgccgaggat aagatcgccg cgtggacat caccgacgtg    2880 gatgccgtga tcgatctgag cgtgaagctg tgcggcacaa tctctagcga gatctccgac    2940
tacttcaagg acgatgaggt gtacgccgag tatatctcct cttacctgga ttttgagtat    3000
gacggcggca actacaagga tagcctgaat aggttctgta actccgatgc cgtgaatgac    3060
cagaaggtgg ccctgtacta tgacggcgag caccctaagc tgaaccgcaa tatcatcctg    3120
agcaagctgt acgcgagcg gagatttctg gagaagatca ccgatcgggt gagccggagc    3180
gacatcgtgg agtactataa gctgaagaag gagacaagcc agtaccagac aaagggcatc    3240
ttcgatagcg aggacgagca gaagaacatc aagaagtttc aggagatgaa gaatatcgtg    3300
gagttcagag atctgatgga ctatagcgag atcgccgatg agctgcaggg ccagctgatc    3360
aactggatct acctgcggga gcgggaccg atgaatttcc agctgggcta ccactatgcc    3420
```

```
tgcctgaaca atgattccaa caagcaggcc acctatgtga cactggacta ccagggcaag    3480
aagaatcgga agatcaacgg cgccatcctg tatcagatct gtgccatgta tcaatggc     3540 ctgcctctgt actatgtgga caaggatagc tccgagtgga ccgtgtctga cggcaaggag    3600
agcacaggcg ccaagatcgg cgagttctac agatatgcca agtcctttga gaacacctct    3660
gattgctacg ccagcggcct ggagatcttt gagaatatca gcgagcacga caacatcaca    3720
gagctgagga attatatcga gcactttcgc tactacagca gcttcgaccg gagcttcctg    3780
ggcatctact ctgaggtgtt cgatcggttc tttacctacg acctgaagta tagaaagaac    3840
gtgccaacaa tcctgtataa catcctgctg cagcacttcg tgaacgtgag gttcgagttc    3900
gtgagcggca agaagatgat cggcatcgat aagaaggacc gcaagatcgc caaggagaag    3960
gagtgtgccc ggatcaccat cagagagaag aacggcgtgt atagcgagca gtttacctac    4020
aagctgaaga atggcacagt gtatgtggat gccagggaca agagataccct gcagtccatc    4080 atcaggctgc tgttctatcc agagaaggtg aacatggatg agatgatcga ggtgaaggag    4140
aagaagaagc cctccgacaa caataccggc aagggctact ctaagaggga tcgccagcag    4200
gaccgcaagg agtacgataa gtataaggag aagaagaaga aggagggcaa tttcctgagc    4260
ggcatgggcg gcaacatcaa ttgggacgag atcaatgccc agctgaagaa ctga         4314
```

<210> SEQ ID NO 30
<211> LENGTH: 1437
<212> TYPE: PRT
<213> ORGANISM: Artificial Sequence
<220> FEATURE:
<223> OTHER INFORMATION: LbnCas13a amino acid sequence

<400> SEQUENCE: 30

```
Met Lys Ile Ser Lys Val Arg Glu Glu Asn Arg Gly Ala Lys Leu Thr
1               5                   10                  15

Val Asn Ala Lys Thr Ala Val Val Ser Glu Asn Arg Ser Gln Glu Gly
            20                  25                  30

Ile Leu Tyr Asn Asp Pro Ser Arg Tyr Gly Lys Ser Arg Lys Asn Asp
        35                  40                  45

Glu Asp Arg Asp Arg Tyr Ile Glu Ser Arg Leu Lys Ser Ser Gly Lys
    50                  55                  60

Leu Tyr Arg Ile Phe Asn Glu Asp Lys Asn Lys Arg Glu Thr Asp Glu
65                  70                  75                  80

Leu Gln Trp Phe Leu Ser Glu Ile Val Lys Lys Ile Asn Arg Arg Asn
                85                  90                  95

Gly Leu Val Leu Ser Asp Met Leu Ser Val Asp Asp Arg Ala Phe Glu
            100                 105                 110

Lys Ala Phe Glu Lys Tyr Ala Glu Leu Ser Tyr Thr Asn Arg Arg Asn
        115                 120                 125

Lys Val Ser Gly Ser Pro Ala Phe Glu Thr Cys Gly Val Asp Ala Ala
    130                 135                 140

Thr Ala Glu Arg Leu Lys Gly Ile Ile Ser Glu Thr Asn Phe Ile Asn
145                 150                 155                 160

Arg Ile Lys Asn Asn Ile Asp Asn Lys Val Ser Glu Asp Ile Ile Asp
                165                 170                 175

Arg Ile Ile Ala Lys Tyr Leu Lys Lys Ser Leu Cys Arg Glu Arg Val
            180                 185                 190

Lys Arg Gly Leu Lys Lys Leu Leu Met Asn Ala Phe Asp Leu Pro Tyr
        195                 200                 205
```

```
Ser Asp Pro Asp Ile Asp Val Gln Arg Asp Phe Ile Asp Tyr Val Leu
    210                 215                 220

Glu Asp Phe Tyr His Val Arg Ala Lys Ser Gln Val Ser Arg Ser Ile
225                 230                 235                 240

Lys Asn Met Asn Met Pro Val Gln Pro Glu Gly Asp Gly Lys Phe Ala
                245                 250                 255

Ile Thr Val Ser Lys Gly Gly Thr Glu Ser Gly Asn Lys Arg Ser Ala
                260                 265                 270

Glu Lys Glu Ala Phe Lys Lys Phe Leu Ser Asp Tyr Ala Ser Leu Asp
            275                 280                 285

Glu Arg Val Arg Asp Asp Met Leu Arg Arg Met Arg Arg Leu Val Val
        290                 295                 300

Leu Tyr Phe Tyr Gly Ser Asp Asp Ser Lys Leu Ser Asp Val Asn Glu
305                 310                 315                 320

Lys Phe Asp Val Trp Glu Asp His Ala Ala Arg Arg Val Asp Asn Arg
                325                 330                 335

Glu Phe Ile Lys Leu Pro Leu Glu Asn Lys Leu Ala Asn Gly Lys Thr
                340                 345                 350

Asp Lys Asp Ala Glu Arg Ile Arg Lys Asn Thr Val Lys Glu Leu Tyr
            355                 360                 365

Arg Asn Gln Asn Ile Gly Cys Tyr Arg Gln Ala Val Lys Ala Val Glu
370                 375                 380

Glu Asp Asn Asn Gly Arg Tyr Phe Asp Asp Lys Met Leu Asn Met Phe
385                 390                 395                 400

Phe Ile His Arg Ile Glu Tyr Gly Val Glu Lys Ile Tyr Ala Asn Leu
                405                 410                 415

Lys Gln Val Thr Glu Phe Lys Ala Arg Thr Gly Tyr Leu Ser Glu Lys
            420                 425                 430

Ile Trp Lys Asp Leu Ile Asn Tyr Ile Ser Ile Lys Tyr Ile Ala Met
            435                 440                 445

Gly Lys Ala Val Tyr Asn Tyr Ala Met Asp Glu Leu Asn Ala Ser Asp
        450                 455                 460

Lys Lys Glu Ile Glu Leu Gly Lys Ile Ser Glu Glu Tyr Leu Ser Gly
465                 470                 475                 480

Ile Ser Ser Phe Asp Tyr Glu Leu Ile Lys Ala Glu Glu Met Leu Gln
                485                 490                 495

Arg Glu Thr Ala Val Tyr Val Ala Phe Ala Ala Arg His Leu Ser Ser
            500                 505                 510

Gln Thr Val Glu Leu Asp Ser Glu Asn Ser Asp Phe Leu Leu Leu Lys
        515                 520                 525

Pro Lys Gly Thr Met Asp Lys Asn Asp Lys Asn Lys Leu Ala Ser Asn
530                 535                 540

Asn Ile Leu Asn Phe Leu Lys Asp Lys Glu Thr Leu Arg Asp Thr Ile
545                 550                 555                 560

Leu Gln Tyr Phe Gly Gly His Ser Leu Trp Thr Asp Phe Pro Phe Asp
                565                 570                 575

Lys Tyr Leu Ala Gly Gly Lys Asp Asp Val Asp Phe Leu Thr Asp Leu
            580                 585                 590

Lys Asp Val Ile Tyr Ser Met Arg Asn Asp Ser Phe His Tyr Ala Thr
        595                 600                 605

Glu Asn His Asn Asn Gly Lys Trp Asn Lys Glu Leu Ile Ser Ala Met
610                 615                 620
```

```
Phe Glu His Glu Thr Glu Arg Met Thr Val Val Met Lys Asp Lys Phe
625                 630                 635                 640

Tyr Ser Asn Asn Leu Pro Met Phe Tyr Lys Asn Asp Leu Lys Lys
        645                 650                 655

Leu Leu Ile Asp Leu Tyr Lys Asp Asn Val Glu Arg Ala Ser Gln Val
            660                 665                 670

Pro Ser Phe Asn Lys Val Phe Arg Lys Asn Phe Pro Ala Leu Val
        675                 680                 685

Arg Asp Lys Asp Asn Leu Gly Ile Glu Leu Asp Leu Lys Ala Asp Ala
690                 695                 700

Asp Lys Gly Glu Asn Glu Leu Lys Phe Tyr Asn Ala Leu Tyr Tyr Met
705                 710                 715                 720

Phe Lys Glu Ile Tyr Tyr Asn Ala Phe Leu Asn Asp Lys Asn Val Arg
            725                 730                 735

Glu Arg Phe Ile Thr Lys Ala Thr Lys Val Ala Asp Asn Tyr Asp Arg
            740                 745                 750

Asn Lys Glu Arg Asn Leu Lys Asp Arg Ile Lys Ser Ala Gly Ser Asp
        755                 760                 765

Glu Lys Lys Lys Leu Arg Glu Gln Leu Gln Asn Tyr Ile Ala Glu Asn
770                 775                 780

Asp Phe Gly Gln Arg Ile Lys Asn Ile Val Gln Val Asn Pro Asp Tyr
785                 790                 795                 800

Thr Leu Ala Gln Ile Cys Gln Leu Ile Met Thr Glu Tyr Asn Gln Gln
                805                 810                 815

Asn Asn Gly Cys Met Gln Lys Lys Ser Ala Ala Arg Lys Asp Ile Asn
            820                 825                 830

Lys Asp Ser Tyr Gln His Tyr Lys Met Leu Leu Leu Val Asn Leu Arg
835                 840                 845

Lys Ala Phe Leu Glu Phe Ile Lys Glu Asn Tyr Ala Phe Val Leu Lys
850                 855                 860

Pro Tyr Lys His Asp Leu Cys Asp Lys Ala Asp Phe Val Pro Asp Phe
865                 870                 875                 880

Ala Lys Tyr Val Lys Pro Tyr Ala Gly Leu Ile Ser Arg Val Ala Gly
                885                 890                 895

Ser Ser Glu Leu Gln Lys Trp Tyr Ile Val Ser Arg Phe Leu Ser Pro
            900                 905                 910

Ala Gln Ala Asn His Met Leu Gly Phe Leu His Ser Tyr Lys Gln Tyr
        915                 920                 925

Val Trp Asp Ile Tyr Arg Arg Ala Ser Glu Thr Gly Thr Glu Ile Asn
930                 935                 940

His Ser Ile Ala Glu Asp Lys Ile Ala Gly Val Asp Ile Thr Asp Val
945                 950                 955                 960

Asp Ala Val Ile Asp Leu Ser Val Lys Leu Cys Gly Thr Ile Ser Ser
                965                 970                 975

Glu Ile Ser Asp Tyr Phe Lys Asp Glu Val Tyr Ala Glu Tyr Ile
            980                 985                 990

Ser Ser Tyr Leu Asp Phe Glu Tyr Asp Gly Gly Asn Tyr Lys Asp Ser
        995                 1000                1005

Leu Asn Arg Phe Cys Asn Ser Asp Ala Val Asn Asp Gln Lys Val
        1010                1015                1020

Ala Leu Tyr Tyr Asp Gly Glu His Pro Lys Leu Asn Arg Asn Ile
        1025                1030                1035

Ile Leu Ser Lys Leu Tyr Gly Glu Arg Arg Phe Leu Glu Lys Ile
```

```
            1040                1045                1050
Thr Asp Arg Val Ser Arg Ser Asp Ile Val Glu Tyr Tyr Lys Leu
    1055                1060                1065
Lys Lys Glu Thr Ser Gln Tyr Gln Thr Lys Gly Ile Phe Asp Ser
    1070                1075                1080
Glu Asp Glu Gln Lys Asn Ile Lys Lys Phe Gln Glu Met Lys Asn
    1085                1090                1095
Ile Val Glu Phe Arg Asp Leu Met Asp Tyr Ser Glu Ile Ala Asp
    1100                1105                1110
Glu Leu Gln Gly Gln Leu Ile Asn Trp Ile Tyr Leu Arg Glu Arg
    1115                1120                1125
Asp Leu Met Asn Phe Gln Leu Gly Tyr His Tyr Ala Cys Leu Asn
    1130                1135                1140
Asn Asp Ser Asn Lys Gln Ala Thr Tyr Val Thr Leu Asp Tyr Gln
    1145                1150                1155
Gly Lys Lys Asn Arg Lys Ile Asn Gly Ala Ile Leu Tyr Gln Ile
    1160                1165                1170
Cys Ala Met Tyr Ile Asn Gly Leu Pro Leu Tyr Tyr Val Asp Lys
    1175                1180                1185
Asp Ser Ser Glu Trp Thr Val Ser Asp Gly Lys Glu Ser Thr Gly
    1190                1195                1200
Ala Lys Ile Gly Glu Phe Tyr Arg Tyr Ala Lys Ser Phe Glu Asn
    1205                1210                1215
Thr Ser Asp Cys Tyr Ala Ser Gly Leu Glu Ile Phe Glu Asn Ile
    1220                1225                1230
Ser Glu His Asp Asn Ile Thr Glu Leu Arg Asn Tyr Ile Glu His
    1235                1240                1245
Phe Arg Tyr Tyr Ser Ser Phe Asp Arg Ser Phe Leu Gly Ile Tyr
    1250                1255                1260
Ser Glu Val Phe Asp Arg Phe Phe Thr Tyr Asp Leu Lys Tyr Arg
    1265                1270                1275
Lys Asn Val Pro Thr Ile Leu Tyr Asn Ile Leu Leu Gln His Phe
    1280                1285                1290
Val Asn Val Arg Phe Glu Phe Val Ser Gly Lys Lys Met Ile Gly
    1295                1300                1305
Ile Asp Lys Lys Asp Arg Lys Ile Ala Lys Glu Lys Glu Cys Ala
    1310                1315                1320
Arg Ile Thr Ile Arg Glu Lys Asn Gly Val Tyr Ser Glu Gln Phe
    1325                1330                1335
Thr Tyr Lys Leu Lys Asn Gly Thr Val Tyr Val Asp Ala Arg Asp
    1340                1345                1350
Lys Arg Tyr Leu Gln Ser Ile Ile Arg Leu Leu Phe Tyr Pro Glu
    1355                1360                1365
Lys Val Asn Met Asp Glu Met Ile Glu Val Lys Glu Lys Lys Lys
    1370                1375                1380
Pro Ser Asp Asn Asn Thr Gly Lys Gly Tyr Ser Lys Arg Asp Arg
    1385                1390                1395
Gln Gln Asp Arg Lys Glu Tyr Asp Lys Tyr Lys Glu Lys Lys Lys
    1400                1405                1410
Lys Glu Gly Asn Phe Leu Ser Gly Met Gly Gly Asn Ile Asn Trp
    1415                1420                1425
Asp Glu Ile Asn Ala Gln Leu Lys Asn
    1430                1435
```

<210> SEQ ID NO 31
<211> LENGTH: 35
<212> TYPE: DNA
<213> ORGANISM: Artificial Sequence
<220> FEATURE:
<223> OTHER INFORMATION: LbnCas13a direct repeat

<400> SEQUENCE: 31
gttgatgaga agagcccaag atagagggca ataac                          35

<210> SEQ ID NO 32
<211> LENGTH: 4158
<212> TYPE: DNA
<213> ORGANISM: Artificial Sequence
<220> FEATURE:
<223> OTHER INFORMATION: CamCas13a nucleic acid sequence

<400> SEQUENCE: 32
atgaagttct ctaaggtgga ccacacccgg agcgccgtgg gcatccagaa ggccaccgac     60
tctgtgcacg gcatgctgta taccgacccc aagaagcagg aagtgaatga tctggacaag    120
aggtttgatc agctgaacgt gaaggccaag cgcctgtata cgtgttcaa tcagtccaag     180 gccgaggagg acgatgacga gaagcggttt ggcaaggtgg tgaagaagct gaacagagag    240
ctgaaggacc tgctgttcca ccgggaggtg agcagataca actccatcgg caatgccaag    300
tataactact atggcatcaa gtccaaccct gaggagatcg tgtctaatct gggcatggtg    360
gagagcctga aggagagcg ggaccccag aaagtgatca gcaagctgct gctgtactat     420
ctgagaaagg gcctgaagcc tggcaccgac ggcctgagga tgatcctgga ggcctcctgc    480
ggcctgcgca gctgtctgg cgatgagaag gagctgaagg tgttcctgca gaccctggat    540
gaggactttg agaagaaaac cttcaagaag aacctgatcc ggtctatcga gaaccagaat    600
atggccgtgc agccaagcaa cgagggcgac cccatcatcg catcaccca gggccggttt    660 aatagccaga gaacgagga gaagtccgcc atcgagagaa tgatgtctat gtacgccgat    720
ctgaacgagg accacaggga ggatgtgctg cgcaagctgc ggagactgaa tgtgctgtat    780
ttcaacgtgg acaccgagaa aaccgaggag cccacctgc ctggagaggt ggatacaaat    840
ccagtgtttg aagtgtggca cgaccacgag aagggcaagg agaacgatag acagtttgcc    900
accttcgcca agatcctgac cgaggacagg agacacgca agaaggagaa gctggccgtg    960
aaggaggccc tgaatgacct gaagagcgcc atcagggatc acaacatcat ggcctaccgc   1020
tgttccatca ggtgaccga gcaggataag acggcctgt tctttgagga ccagcggatc   1080
aatagattct ggattcacca catcgagtct gccgtggaga aatcctggc cagcatcaac   1140 cccgagaagc tgtataagct gcgcatcggc tatctgggcg agaaagtgtg gaaggatctg   1200
ctgaattacc tgagcatcaa gtatatcgcc gtgggcaagg ccgtgttcca ctttgccatg   1260
gaggacctgg gcaagaccgg ccaggatatc gagctgggca agctgagcaa ctccgtgtct   1320
ggcggcctga ccagcttcga ctacgagcag atccgggccg atgagacact gcagagacag   1380
ctgtccgtgg aggtggcctt tgccgccaac aatctgttca gggcagtggt gggacagacc   1440
ggcaagaaga tcgagcagag caagtccgag agaatgagg aggactttct gctgtggaag   1500
gccgagaaga tcgccgagtc catcaagaag gagggcgagg caacacact gaagtctatc   1560 ctgcagttct ttggcggcgc cagctcctgg gatctgaatc acttctgcgc agcctacggc   1620
aacgagtcta gcgccctggg ctatgagaca aagtttgccg atgacctgag gaaggccatc   1680

```
tactccctgc gcaatgagac attccacttt accacactga acaagggctc ttttgactgg    1740
aatgccaagc tgatcggcga tatgttcagc cacgaggcag caaccggcat cgcagtggag    1800
aggacacgct tttacagcaa caatctgcct atgttctatc gggagtccga cctgaagaga    1860
atcatggatc acctgtataa cacctatcac cctcgcgcca gccaggtgcc atctttcaac    1920
agcgtgtttg tgaggaagaa ttttcgcctg ttcctgtcca cacccctgaa caccaataca    1980
tctttcgaca cagaggtgta ccagaagtgg gagtccggcg tgtactatct gtttaaggag    2040
atctactaca actctttcct gccaagcggc gacgcccacc acctgttctt tgagggcctg    2100
aggcgcatca ggaaggaggc cgataatctg cccatcgtgg gcaaggaggc caagaagcgc    2160
aacgccgtgc aggactttgg ccggagatgc gatgagctga agaacctgtc tctgagcgcc    2220
atctgtcaga tgatcatgac cgagtacaat gagcagaaca atggcaacag gaaggtgaag    2280
agcacacggg aggacaagag aaagcccgat atcttccagc actacaagat gctgctgctg    2340
cgcacactgc aggaggcctt tgccatctat atcaggcgcg aggagttcaa gtttatcttc    2400
gacctgccca agacactgta cgtgatgaag cccgtggagg agtttctgcc taactggaag    2460
tccggcatgt tcgactctct ggtggagcgg gtgaagcagt cccctgatct gcagagatgg    2520
tatgtgctgt gcaagttcct gaatggccgg ctgctgaacc agctgagcgg cgtgatcaga    2580
tcctacatcc agtttgcagg cgacatccag cggagagcaa aggcaaacca aatcggctg    2640 tatatggata tacccagag agtggagtac tattctaacg tgctggaggt ggtggacttc    2700
tgcatcaagg gcacatccag gttctctaac gtgttcagcg attacttccg cgatgaggac    2760
gcctacgccg attatctgga caactatctg cagtttaagg acgagaagat cgccgaggtg    2820
agcagcttcg ccgccctgaa aaccttctgt aacgaggagg aggtgaaggc cggcatctac    2880
atggacggca gaatcctgt gatgcagagg aacatcgtga tggccaagct gttcggccct    2940
gatgaggtgc tgaagaatgt ggtgccaaag gtgacacggg aggagatcga ggagtactat    3000
cagctggaga agcagatcgc cccatacaga cagaacggct attgtaagtc cgaggaggac    3060
cagaagaagc tgctgaggtt ccagcgcatc aagaatcgcg tggagtttca gaccatcaca    3120
gagttctctg agatcatcaa cgagctgctg ggccagctga tctcctggtc ttttctgcgg    3180
gagagagatc tgctgtactt tcagctgggc ttccactatc tgtgcctgca caatgacacc    3240
gagaagcctg ccgagtacaa ggagatcagc cgggaggatg gcacagtgat cagaaacgcc    3300
atcctgcacc aggtggcagc aatgtacgtg ggaggcctgc cagtgtatac cctggccgac    3360
aagaagctgg ccgccttcga aagggagag gcagactgta agctgagcat ctccaaggat    3420
acagccggcg ccggcaagaa gatcaaggat tctttcggt actccaagta tgtgctgatc    3480
aaggacagaa tgctgaccga tcagaaccag aagtacacaa tctatctggc cggcctggag    3540
ctgttcgaga ataccgatga gcacgacaac atcacagacg tgcggaagta cgtggatcac    3600
tttaagtact atgccacctc tgacgagaat gccatgagca cctggatct gtattccgag    3660 atccacgaca gattctttac atacgatatg aagtaccaga gaacgtggc caatatgctg    3720 gagaacatcc tgctgaggca cttcgtgctg atccgccccg agttctttac cggcagcaag    3780
aaggtcggcg agggcaagaa gatcacatgc aaggccaggg cccagatcga gatcgccgag    3840
aatggcatgc gctccgagga ctttacctac aagctgagcg atggcaagaa gaatatctcc    3900
acatgtatga tcgccgccag ggaccagaag tatctgaaca ccgtggcccg cctgctgtac    3960
tatccacacg aggccaagaa gagcatcgtg gacacgggg agaagaagaa caacaagaaa    4020
accaatagag gcgatggcac attcaacaag cagaagggca ccgccaggaa ggagaaggac    4080
```

```
aatggccccc gcgagtttaa cgataccggc ttctccaata caccatttgc cggcttcgat    4140
ccctttagaa actcttga                                                  4158
```

<210> SEQ ID NO 33
<211> LENGTH: 1385
<212> TYPE: PRT
<213> ORGANISM: Artificial Sequence
<220> FEATURE:
<223> OTHER INFORMATION: CamCas13a amino acid sequence

<400> SEQUENCE: 33

```
Met Lys Phe Ser Lys Val Asp His Thr Arg Ser Ala Val Gly Ile Gln
1               5                   10                  15

Lys Ala Thr Asp Ser Val His Gly Met Leu Tyr Thr Asp Pro Lys Lys
            20                  25                  30

Gln Glu Val Asn Asp Leu Asp Lys Arg Phe Asp Gln Leu Asn Val Lys
        35                  40                  45

Ala Lys Arg Leu Tyr Asn Val Phe Asn Gln Ser Lys Ala Glu Glu Asp
    50                  55                  60

Asp Asp Glu Lys Arg Phe Gly Lys Val Val Lys Lys Leu Asn Arg Glu
65                  70                  75                  80

Leu Lys Asp Leu Leu Phe His Arg Glu Val Ser Arg Tyr Asn Ser Ile
                85                  90                  95

Gly Asn Ala Lys Tyr Asn Tyr Tyr Gly Ile Lys Ser Asn Pro Glu Glu
            100                 105                 110

Ile Val Ser Asn Leu Gly Met Val Glu Ser Leu Lys Gly Glu Arg Asp
        115                 120                 125

Pro Gln Lys Val Ile Ser Lys Leu Leu Leu Tyr Tyr Leu Arg Lys Gly
    130                 135                 140

Leu Lys Pro Gly Thr Asp Gly Leu Arg Met Ile Leu Glu Ala Ser Cys
145                 150                 155                 160

Gly Leu Arg Lys Leu Ser Gly Asp Glu Lys Glu Leu Lys Val Phe Leu
                165                 170                 175

Gln Thr Leu Asp Glu Asp Phe Glu Lys Lys Thr Phe Lys Lys Asn Leu
            180                 185                 190

Ile Arg Ser Ile Glu Asn Gln Asn Met Ala Val Gln Pro Ser Asn Glu
        195                 200                 205

Gly Asp Pro Ile Ile Gly Ile Thr Gln Gly Arg Phe Asn Ser Gln Lys
    210                 215                 220

Asn Glu Glu Lys Ser Ala Ile Glu Arg Met Met Ser Met Tyr Ala Asp
225                 230                 235                 240

Leu Asn Glu Asp His Arg Glu Asp Val Leu Arg Lys Leu Arg Arg Leu
                245                 250                 255

Asn Val Leu Tyr Phe Asn Val Asp Thr Glu Lys Thr Glu Glu Pro Thr
            260                 265                 270

Leu Pro Gly Glu Val Asp Thr Asn Pro Val Phe Glu Val Trp His Asp
        275                 280                 285

His Glu Lys Gly Lys Glu Asn Asp Arg Gln Phe Ala Thr Phe Ala Lys
    290                 295                 300

Ile Leu Thr Glu Asp Arg Glu Thr Arg Lys Lys Glu Lys Leu Ala Val
305                 310                 315                 320

Lys Glu Ala Leu Asn Asp Leu Lys Ser Ala Ile Arg Asp His Asn Ile
                325                 330                 335

Met Ala Tyr Arg Cys Ser Ile Lys Val Thr Glu Gln Asp Lys Asp Gly
```

```
                340             345             350
Leu Phe Phe Glu Asp Gln Arg Ile Asn Arg Phe Trp Ile His His Ile
        355                 360                 365
Glu Ser Ala Val Glu Arg Ile Leu Ala Ser Ile Asn Pro Glu Lys Leu
        370                 375                 380
Tyr Lys Leu Arg Ile Gly Tyr Leu Gly Glu Lys Val Trp Lys Asp Leu
385                 390                 395                 400
Leu Asn Tyr Leu Ser Ile Lys Tyr Ile Ala Val Gly Lys Ala Val Phe
                405                 410                 415
His Phe Ala Met Glu Asp Leu Gly Lys Thr Gly Gln Asp Ile Glu Leu
                420                 425                 430
Gly Lys Leu Ser Asn Ser Val Ser Gly Gly Leu Thr Ser Phe Asp Tyr
        435                 440                 445
Glu Gln Ile Arg Ala Asp Glu Thr Leu Gln Arg Gln Leu Ser Val Glu
        450                 455                 460
Val Ala Phe Ala Ala Asn Asn Leu Phe Arg Ala Val Val Gly Gln Thr
465                 470                 475                 480
Gly Lys Lys Ile Glu Gln Ser Lys Ser Glu Glu Asn Glu Glu Asp Phe
                485                 490                 495
Leu Leu Trp Lys Ala Glu Lys Ile Ala Glu Ser Ile Lys Lys Glu Gly
        500                 505                 510
Glu Gly Asn Thr Leu Lys Ser Ile Leu Gln Phe Phe Gly Gly Ala Ser
        515                 520                 525
Ser Trp Asp Leu Asn His Phe Cys Ala Ala Tyr Gly Asn Glu Ser Ser
        530                 535                 540
Ala Leu Gly Tyr Glu Thr Lys Phe Ala Asp Asp Leu Arg Lys Ala Ile
545                 550                 555                 560
Tyr Ser Leu Arg Asn Glu Thr Phe His Phe Thr Thr Leu Asn Lys Gly
                565                 570                 575
Ser Phe Asp Trp Asn Ala Lys Leu Ile Gly Asp Met Phe Ser His Glu
                580                 585                 590
Ala Ala Thr Gly Ile Ala Val Glu Arg Thr Arg Phe Tyr Ser Asn Asn
                595                 600                 605
Leu Pro Met Phe Tyr Arg Glu Ser Asp Leu Lys Arg Ile Met Asp His
        610                 615                 620
Leu Tyr Asn Thr Tyr His Pro Arg Ala Ser Gln Val Pro Ser Phe Asn
625                 630                 635                 640
Ser Val Phe Val Arg Lys Asn Phe Arg Leu Phe Leu Ser Asn Thr Leu
                645                 650                 655
Asn Thr Asn Thr Ser Phe Asp Thr Glu Val Tyr Gln Lys Trp Glu Ser
                660                 665                 670
Gly Val Tyr Tyr Leu Phe Lys Glu Ile Tyr Tyr Asn Ser Phe Leu Pro
                675                 680                 685
Ser Gly Asp Ala His His Leu Phe Phe Glu Gly Leu Arg Arg Ile Arg
        690                 695                 700
Lys Glu Ala Asp Asn Leu Pro Ile Val Gly Lys Ala Lys Lys Arg
705                 710                 715                 720
Asn Ala Val Gln Asp Phe Gly Arg Arg Cys Asp Glu Leu Lys Asn Leu
                725                 730                 735
Ser Leu Ser Ala Ile Cys Gln Met Ile Met Thr Glu Tyr Asn Glu Gln
                740                 745                 750
Asn Asn Gly Asn Arg Lys Val Lys Ser Thr Arg Glu Asp Lys Arg Lys
        755                 760                 765
```

-continued

Pro Asp Ile Phe Gln His Tyr Lys Met Leu Leu Arg Thr Leu Gln
    770             775             780

Glu Ala Phe Ala Ile Tyr Ile Arg Arg Glu Glu Phe Lys Phe Ile Phe
785             790             795             800

Asp Leu Pro Lys Thr Leu Tyr Val Met Lys Pro Val Glu Glu Phe Leu
                805             810             815

Pro Asn Trp Lys Ser Gly Met Phe Asp Ser Leu Val Glu Arg Val Lys
            820             825             830

Gln Ser Pro Asp Leu Gln Arg Trp Tyr Val Leu Cys Lys Phe Leu Asn
        835             840             845

Gly Arg Leu Leu Asn Gln Leu Ser Gly Val Ile Arg Ser Tyr Ile Gln
    850             855             860

Phe Ala Gly Asp Ile Gln Arg Arg Ala Lys Ala Asn His Asn Arg Leu
865             870             875             880

Tyr Met Asp Asn Thr Gln Arg Val Glu Tyr Tyr Ser Asn Val Leu Glu
                885             890             895

Val Val Asp Phe Cys Ile Lys Gly Thr Ser Arg Phe Ser Asn Val Phe
            900             905             910

Ser Asp Tyr Phe Arg Asp Glu Asp Ala Tyr Ala Asp Tyr Leu Asp Asn
        915             920             925

Tyr Leu Gln Phe Lys Asp Glu Lys Ile Ala Glu Val Ser Ser Phe Ala
    930             935             940

Ala Leu Lys Thr Phe Cys Asn Glu Glu Glu Val Lys Ala Gly Ile Tyr
945             950             955             960

Met Asp Gly Glu Asn Pro Val Met Gln Arg Asn Ile Val Met Ala Lys
                965             970             975

Leu Phe Gly Pro Asp Glu Val Leu Lys Asn Val Val Pro Lys Val Thr
            980             985             990

Arg Glu Glu Ile Glu Glu Tyr Tyr Gln Leu Glu Lys Gln Ile Ala Pro
        995             1000            1005

Tyr Arg Gln Asn Gly Tyr Cys Lys Ser Glu Glu Asp Gln Lys Lys
    1010            1015            1020

Leu Leu Arg Phe Gln Arg Ile Lys Asn Arg Val Glu Phe Gln Thr
    1025            1030            1035

Ile Thr Glu Phe Ser Glu Ile Ile Asn Glu Leu Leu Gly Gln Leu
    1040            1045            1050

Ile Ser Trp Ser Phe Leu Arg Glu Arg Asp Leu Leu Tyr Phe Gln
    1055            1060            1065

Leu Gly Phe His Tyr Leu Cys Leu His Asn Asp Thr Glu Lys Pro
    1070            1075            1080

Ala Glu Tyr Lys Glu Ile Ser Arg Glu Asp Gly Thr Val Ile Arg
    1085            1090            1095

Asn Ala Ile Leu His Gln Val Ala Ala Met Tyr Val Gly Gly Leu
    1100            1105            1110

Pro Val Tyr Thr Leu Ala Asp Lys Lys Leu Ala Ala Phe Glu Lys
    1115            1120            1125

Gly Glu Ala Asp Cys Lys Leu Ser Ile Ser Lys Asp Thr Ala Gly
    1130            1135            1140

Ala Gly Lys Lys Ile Lys Asp Phe Phe Arg Tyr Ser Lys Tyr Val
    1145            1150            1155

Leu Ile Lys Asp Arg Met Leu Thr Asp Gln Asn Gln Lys Tyr Thr
    1160            1165            1170

```
Ile Tyr Leu Ala Gly Leu Glu Leu Phe Glu Asn Thr Asp Glu His
1175                1180                1185

Asp Asn Ile Thr Asp Val Arg Lys Tyr Val Asp His Phe Lys Tyr
1190                1195                1200

Tyr Ala Thr Ser Asp Glu Asn Ala Met Ser Ile Leu Asp Leu Tyr
1205                1210                1215

Ser Glu Ile His Asp Arg Phe Phe Thr Tyr Asp Met Lys Tyr Gln
1220                1225                1230

Lys Asn Val Ala Asn Met Leu Glu Asn Ile Leu Leu Arg His Phe
1235                1240                1245

Val Leu Ile Arg Pro Glu Phe Phe Thr Gly Ser Lys Lys Val Gly
1250                1255                1260

Glu Gly Lys Lys Ile Thr Cys Lys Ala Arg Ala Gln Ile Glu Ile
1265                1270                1275

Ala Glu Asn Gly Met Arg Ser Glu Asp Phe Thr Tyr Lys Leu Ser
1280                1285                1290

Asp Gly Lys Lys Asn Ile Ser Thr Cys Met Ile Ala Ala Arg Asp
1295                1300                1305

Gln Lys Tyr Leu Asn Thr Val Ala Arg Leu Leu Tyr Tyr Pro His
1310                1315                1320

Glu Ala Lys Lys Ser Ile Val Asp Thr Arg Glu Lys Lys Asn Asn
1325                1330                1335

Lys Lys Thr Asn Arg Gly Asp Gly Thr Phe Asn Lys Gln Lys Gly
1340                1345                1350

Thr Ala Arg Lys Glu Lys Asp Asn Gly Pro Arg Glu Phe Asn Asp
1355                1360                1365

Thr Gly Phe Ser Asn Thr Pro Phe Ala Gly Phe Asp Pro Phe Arg
1370                1375                1380

Asn Ser
1385

<210> SEQ ID NO 34
<211> LENGTH: 35
<212> TYPE: DNA
<213> ORGANISM: Artificial Sequence
<220> FEATURE:
<223> OTHER INFORMATION: CamCas13a direct repeat

<400> SEQUENCE: 34
gtctattgcc ctctatatcg ggctgttctc caaac                              35

<210> SEQ ID NO 35
<211> LENGTH: 3354
<212> TYPE: DNA
<213> ORGANISM: Artificial Sequence
<220> FEATURE:
<223> OTHER INFORMATION: CgaCas13a nucleic acid sequence

<400> SEQUENCE: 35
atgcggatca caaaggtgaa gatcaagctg gacaacaagc tgtaccaggt gaccatgcag      60
aaggaggaga gtatggcac actgaagctg aatgaggaga gcaggaagtc caccgccgag     120
atcctgcgcc tgaagaaggc cagcttcaac aagtcttttc acagcaagac catcaattcc    180
cagaaggaga acaagaatgc cacaatcaag aagaacggcg actacatcag ccagatcttc    240
gagaagctgg tgggcgtgga taccaacaag aatatcagga gcccaagat gtccctgaca     300 gacctgaagg atctgcctaa gaaggacctg gccctgttca tcaagcgcaa gtttaagaac    360
```

```
gacgatatcg tggagatcaa gaatctggat ctgatctccc tgttttataa tgccctgcag    420
aaggtgccag gcgagcactt caccgacgag tcttgggccg attttttgcca ggagatgatg    480
ccctaccggg agtataagaa caagttcatc gagagaaaga tcatcctgct ggccaactcc    540
atcgagcaga ataagggctt ctctatcaat cccgagacat tcagcaagcg aaagagagtg    600
ctgcaccagt gggcaatcga ggtgcaggag agggggcgact tttccatcct ggatgagaag    660
ctgtctaagc tggccgagat ctacaacttc aagaagatgt gcaagagagt gcaggacgag    720
ctgaacgatc tggagaagag catgaagaag ggcaagaatc tgagaaggaa gaaggaggcc    780
tataagaagc agaagaactt taagatcaag accatctgga aggactaccc atataagaca    840
cacatcggcc tgatcgagaa gatcaaggag aatgaggagc tgaaccagtt caatatcgag    900
atcggcaagt acttcgagca ctattttcca atcaagaagg agagatgcac cgaggatgag    960
ccctactatc tgaacagcga gacaatcgcc accacagtga actaccagct gaagaatgcc   1020
ctgatctcct acctgatgca gatcggcaag tataagcagt ttggcctgga aatcaggtg    1080
ctggactcca agaagctgca ggagatcggc atctatgagg gcttccagac caagtttatg   1140
gatgcctgcg tgttcgccac aagctccctg aagaacatca tcgagcctat gcggagcggc   1200
gacatcctgg gcaagagaga gtttaaggag gccatcgcca catctagctt cgtgaattac   1260
caccacttct ttccctattt ccctttttgag ctgaagggca tgaaggatag ggagtccgag   1320
ctgatcccat ttggcgagca gaccgaggcc aagcagatgc agaacatctg ggcccctgagg   1380
ggctctgtgc agcagatccg caatgagatc ttccacagct ttgacaagaa ccagaagttc   1440
aatctgcccc agctggacaa gagcaacttc gagtttgatg cctccgagaa cagcaccggc   1500
aagtctcaga gctacatcga gacagattat aagttcctgt ttgaggccga gaagaaccag   1560
ctggagcagt tctttatcga gcgcatcaag tcctctggcg ccctggagta ctatcccctg   1620
aagtccctgg agaagctgtt cgccaagaag gagatgaagt ttagcctggg ctcccaggtg   1680
gtggccttcg cccctagcta caagaagctg gtgaagaagg ccactcccta tcagaccgcc   1740
acagagggca ccgccaacta cctgggcctg tcctactata ataggtatga gctgaaggag   1800
gagtcttttc aggcccagta ctatctgctg aagctgatct accagtacgt gttcctgcct   1860
aactttttccc agggcaattc tccagccttc cgcgagacag tgaaggccat cctgcggatc   1920
aacaaggacg aggccagaaa gaagatgaag aagaataaga agttcctgag gaagtacgcc   1980
tttgagcagg tgcgcgagat ggagttcaag agagacacccg accagtacat gagctatctg   2040
cagtccgaga tgagggagga aaggtgcgc aaggccgaga gaacgataaa gggcttcgag   2100
aagaacatca ccatgaattt tgagaagctg ctgatgcaga tcttcgtgaa gggcttcgac   2160
gtgttcctga ccacatttgc cggcaaggag ctgctgctga gctccgagga aaagtgatc   2220
aaggagacag agatctccct gtctaagaag atcaacgagc gggagaaaac cctgaaggcc   2280
agcatccagg tggagcacca gctggtggcc accaattctg ccatcagcta ctggctgttc   2340
tgcaagctgc tggactcccg gcacctgaac gagctgagaa atgagatgat caagttcaag   2400
cagagccgga tcaagttcaa ccacacacag cacgccgagc tgatccagaa tctgctgcct   2460
atcgtggagc tgaccatcct gtctaacgac tacgatgaga agaacgactc ccagaatgtg   2520
gacgtgagcg cctattttga ggataagagc ctgtacgaga cagcccctta tgtgcagacc   2580
gacgatagga cacgcgtgtc tttcaggcca atcctgaagc tggagaagta ccacacaaag   2640
agcctgatcg aggccctgct gaaggacaac ccacagtttc gcgtggccgc caccgatatc   2700
caggagtgga tgcacaagag ggaggagatc ggcgagctgg tggagaagcg caagaatctg   2760
```

-continued

```
cacaccgagt gggcagaggg acagcagaca ctgggagcag agaagcggga ggagtacaga    2820
gactattgta agaagatcga tcggttcaac tggaaggcca ataaggtgac cctgacatac    2880
ctgtctcagc tgcactatct gatcacagac ctgctgggca gaatggtggg cttcagcgcc    2940
ctgtttgaga gggatctggt gtacttcagc cgctccttt ctgagctggg cggcgagaca     3000
taccacatca gcgattataa gaacctgtcc ggcgtgctgc ggctgaatgc cgaggtgaag    3060
cccatcaaga tcaagaacat caaagtgatc gacaacgagg agaatcctta caagggcaat    3120
gagccagagg tgaagccctt cctggatcgg ctgcacgcct atctggagaa cgtgatcggc    3180
atcaaggccg tgcacggcaa gatcagaaat cagacagccc acctgtccgt gctgcagctg    3240
gagctgtcta tgatcgagag catgaacaat ctgcgggacc tgatggccta cgatagaaag    3300
ctgaagaacg ccgtgaccaa gtctatgatc aagatcctgg acaagcacgg ctga          3354
```

<210> SEQ ID NO 36
<211> LENGTH: 1117
<212> TYPE: PRT
<213> ORGANISM: Artificial Sequence
<220> FEATURE:
<223> OTHER INFORMATION: CgaCas13a amino acid sequence

<400> SEQUENCE: 36

```
Met Arg Ile Thr Lys Val Lys Ile Lys Leu Asp Asn Lys Leu Tyr Gln
1               5                   10                  15

Val Thr Met Gln Lys Glu Glu Lys Tyr Gly Thr Leu Lys Leu Asn Glu
            20                  25                  30

Glu Ser Arg Lys Ser Thr Ala Glu Ile Leu Arg Leu Lys Lys Ala Ser
        35                  40                  45

Phe Asn Lys Ser Phe His Ser Lys Thr Ile Asn Ser Gln Lys Glu Asn
    50                  55                  60

Lys Asn Ala Thr Ile Lys Lys Asn Gly Asp Tyr Ile Ser Gln Ile Phe
65                  70                  75                  80

Glu Lys Leu Val Gly Val Asp Thr Asn Lys Asn Ile Arg Lys Pro Lys
                85                  90                  95

Met Ser Leu Thr Asp Leu Lys Asp Leu Pro Lys Lys Asp Leu Ala Leu
            100                 105                 110

Phe Ile Lys Arg Lys Phe Lys Asn Asp Asp Ile Val Glu Ile Lys Asn
        115                 120                 125

Leu Asp Leu Ile Ser Leu Phe Tyr Asn Ala Leu Gln Lys Val Pro Gly
    130                 135                 140

Glu His Phe Thr Asp Glu Ser Trp Ala Asp Phe Cys Gln Glu Met Met
145                 150                 155                 160

Pro Tyr Arg Glu Tyr Lys Asn Lys Phe Ile Glu Arg Lys Ile Ile Leu
                165                 170                 175

Leu Ala Asn Ser Ile Glu Gln Asn Lys Gly Phe Ser Ile Asn Pro Glu
            180                 185                 190

Thr Phe Ser Lys Arg Lys Arg Val Leu His Gln Trp Ala Ile Glu Val
        195                 200                 205

Gln Glu Arg Gly Asp Phe Ser Ile Leu Asp Glu Lys Leu Ser Lys Leu
    210                 215                 220

Ala Glu Ile Tyr Asn Phe Lys Lys Met Cys Lys Arg Val Gln Asp Glu
225                 230                 235                 240

Leu Asn Asp Leu Glu Lys Ser Met Lys Lys Gly Lys Asn Pro Glu Lys
                245                 250                 255
```

-continued

```
Glu Lys Glu Ala Tyr Lys Lys Gln Lys Asn Phe Lys Ile Lys Thr Ile
            260                 265                 270

Trp Lys Asp Tyr Pro Tyr Lys Thr His Ile Gly Leu Ile Glu Lys Ile
        275                 280                 285

Lys Glu Asn Glu Glu Leu Asn Gln Phe Asn Ile Glu Ile Gly Lys Tyr
    290                 295                 300

Phe Glu His Tyr Phe Pro Ile Lys Lys Glu Arg Cys Thr Glu Asp Glu
305                 310                 315                 320

Pro Tyr Tyr Leu Asn Ser Glu Thr Ile Ala Thr Thr Val Asn Tyr Gln
                325                 330                 335

Leu Lys Asn Ala Leu Ile Ser Tyr Leu Met Gln Ile Gly Lys Tyr Lys
            340                 345                 350

Gln Phe Gly Leu Glu Asn Gln Val Leu Asp Ser Lys Lys Leu Gln Glu
        355                 360                 365

Ile Gly Ile Tyr Glu Gly Phe Gln Thr Lys Phe Met Asp Ala Cys Val
    370                 375                 380

Phe Ala Thr Ser Ser Leu Lys Asn Ile Ile Glu Pro Met Arg Ser Gly
385                 390                 395                 400

Asp Ile Leu Gly Lys Arg Glu Phe Lys Glu Ala Ile Ala Thr Ser Ser
                405                 410                 415

Phe Val Asn Tyr His His Phe Pro Tyr Phe Pro Phe Glu Leu Lys
            420                 425                 430

Gly Met Lys Asp Arg Glu Ser Glu Leu Ile Pro Phe Gly Glu Gln Thr
        435                 440                 445

Glu Ala Lys Gln Met Gln Asn Ile Trp Ala Leu Arg Gly Ser Val Gln
    450                 455                 460

Gln Ile Arg Asn Glu Ile Phe His Ser Phe Asp Lys Asn Gln Lys Phe
465                 470                 475                 480

Asn Leu Pro Gln Leu Asp Lys Ser Asn Phe Glu Phe Asp Ala Ser Glu
                485                 490                 495

Asn Ser Thr Gly Lys Ser Gln Ser Tyr Ile Glu Thr Asp Tyr Lys Phe
            500                 505                 510

Leu Phe Glu Ala Glu Lys Asn Gln Leu Glu Gln Phe Phe Ile Glu Arg
        515                 520                 525

Ile Lys Ser Ser Gly Ala Leu Glu Tyr Tyr Pro Leu Lys Ser Leu Glu
    530                 535                 540

Lys Leu Phe Ala Lys Lys Glu Met Lys Phe Ser Leu Gly Ser Gln Val
545                 550                 555                 560

Val Ala Phe Ala Pro Ser Tyr Lys Lys Leu Val Lys Lys Gly His Ser
                565                 570                 575

Tyr Gln Thr Ala Thr Glu Gly Thr Ala Asn Tyr Leu Gly Leu Ser Tyr
            580                 585                 590

Tyr Asn Arg Tyr Glu Leu Lys Glu Glu Ser Phe Gln Ala Gln Tyr Tyr
        595                 600                 605

Leu Leu Lys Leu Ile Tyr Gln Tyr Val Phe Leu Pro Asn Phe Ser Gln
    610                 615                 620

Gly Asn Ser Pro Ala Phe Arg Glu Thr Val Lys Ala Ile Leu Arg Ile
625                 630                 635                 640

Asn Lys Asp Glu Ala Arg Lys Lys Met Lys Lys Asn Lys Lys Phe Leu
                645                 650                 655

Arg Lys Tyr Ala Phe Glu Gln Val Arg Glu Met Glu Phe Lys Glu Thr
            660                 665                 670

Pro Asp Gln Tyr Met Ser Tyr Leu Gln Ser Glu Met Arg Glu Glu Lys
```

-continued

```
            675                 680                 685
Val Arg Lys Ala Glu Lys Asn Asp Lys Gly Phe Glu Lys Asn Ile Thr
690                     695                 700
Met Asn Phe Glu Lys Leu Leu Met Gln Ile Phe Val Lys Gly Phe Asp
705                 710                 715                 720
Val Phe Leu Thr Thr Phe Ala Gly Lys Glu Leu Leu Ser Ser Glu
                    725                 730                 735
Glu Lys Val Ile Lys Glu Thr Glu Ile Ser Leu Ser Lys Ile Asn
                740                 745                 750
Glu Arg Glu Lys Thr Leu Lys Ala Ser Ile Gln Val Glu His Gln Leu
                755                 760                 765
Val Ala Thr Asn Ser Ala Ile Ser Tyr Trp Leu Phe Cys Lys Leu Leu
770                 775                 780
Asp Ser Arg His Leu Asn Glu Leu Arg Asn Glu Met Ile Lys Phe Lys
785                 790                 795                 800
Gln Ser Arg Ile Lys Phe Asn His Thr Gln His Ala Glu Leu Ile Gln
                805                 810                 815
Asn Leu Leu Pro Ile Val Glu Leu Thr Ile Leu Ser Asn Asp Tyr Asp
                820                 825                 830
Glu Lys Asn Asp Ser Gln Asn Val Asp Val Ser Ala Tyr Phe Glu Asp
                835                 840                 845
Lys Ser Leu Tyr Glu Thr Ala Pro Tyr Val Gln Thr Asp Asp Arg Thr
850                 855                 860
Arg Val Ser Phe Arg Pro Ile Leu Lys Leu Glu Lys Tyr His Thr Lys
865                 870                 875                 880
Ser Leu Ile Glu Ala Leu Leu Lys Asp Asn Pro Gln Phe Arg Val Ala
                885                 890                 895
Ala Thr Asp Ile Gln Glu Trp Met His Lys Arg Glu Glu Ile Gly Glu
                900                 905                 910
Leu Val Glu Lys Arg Lys Asn Leu His Thr Glu Trp Ala Glu Gly Gln
                915                 920                 925
Gln Thr Leu Gly Ala Glu Lys Arg Glu Glu Tyr Arg Asp Tyr Cys Lys
                930                 935                 940
Lys Ile Asp Arg Phe Asn Trp Lys Ala Asn Lys Val Thr Leu Thr Tyr
945                 950                 955                 960
Leu Ser Gln Leu His Tyr Leu Ile Thr Asp Leu Leu Gly Arg Met Val
                965                 970                 975
Gly Phe Ser Ala Leu Phe Glu Arg Asp Leu Val Tyr Phe Ser Arg Ser
                980                 985                 990
Phe Ser Glu Leu Gly Gly Glu Thr Tyr His Ile Ser Asp Tyr Lys Asn
                995                 1000                1005
Leu Ser Gly Val Leu Arg Leu Asn Ala Glu Val Lys Pro Ile Lys
    1010                1015                1020
Ile Lys Asn Ile Lys Val Ile Asp Asn Glu Glu Asn Pro Tyr Lys
    1025                1030                1035
Gly Asn Glu Pro Glu Val Lys Pro Phe Leu Asp Arg Leu His Ala
    1040                1045                1050
Tyr Leu Glu Asn Val Ile Gly Ile Lys Ala Val His Gly Lys Ile
    1055                1060                1065
Arg Asn Gln Thr Ala His Leu Ser Val Leu Gln Leu Glu Leu Ser
    1070                1075                1080
Met Ile Glu Ser Met Asn Asn Leu Arg Asp Leu Met Ala Tyr Asp
    1085                1090                1095
```

-continued

```
Arg Lys  Leu Lys Asn Ala Val  Thr Lys Ser Met Ile  Lys Ile Leu
    1100              1105                 1110
Asp Lys  His Gly
    1115

<210> SEQ ID NO 37
<211> LENGTH: 36
<212> TYPE: DNA
<213> ORGANISM: Artificial Sequence
<220> FEATURE:
<223> OTHER INFORMATION: CgaCas13a direct repeat

<400> SEQUENCE: 37
attaaagact acctctaaat gtaagaggac tataac                           36

<210> SEQ ID NO 38
<211> LENGTH: 3669
<212> TYPE: DNA
<213> ORGANISM: Artificial Sequence
<220> FEATURE:
<223> OTHER INFORMATION: Cga2Cas13a nucleic acid sequence

<400> SEQUENCE: 38
atgatcctga agctgaagat cgacgagaac cacaagaatt tcgagatcga gagcctgatc    60
ccaaaggaga tcatccacct gaaggataag gccatcaaga ccaaccaggt gtccgaggag   120
tactgccagc tggtgctggc cctgctgacc acaaaccccg gcaatcagct gaacatgagg   180
atgacaaagg tgaagatcaa cggcagcccc gtgagcatga atcgcagcaa gctgaacggc   240
cacctggtgt ggaatggcac cacaaatacc gtgaacatcc tgacaaagaa ggagcagagc   300
ttcgccgcct cctttctgaa caagaccctg gtgaaggccg accaggtgaa gggctacaag   360
gtgctggccg agaatatctt catcatcttt gagcagctgg agaagtccaa ctctgagaag   420
cccagcgtgt acctgaacaa tatccggaga ctgaaggagg ccggcctgaa gcggttcttt   480
aagagcaagt accacgagga gatcaagtat acctctgaga agaatcagag cgtgccaaca   540
aagctgaatc tgatccccct gttctttaac gccgtggaca gaatccagga ggacaagttc   600
gatgagaaga actggtccta ctttttgcaag gagatgtctc cctacctgga ttataagaag   660
agctatctga ataggaagaa ggagatcctg gccaattcta tccagcagaa caggggcttc   720
agcatgccaa ccgcagagga gcctaacctg ctgtctaagc ggaagcagct gttccagcag   780
tgggccatga agtttcagga gagccctctg atccagcaga caattttgc cgtggagcag   840 ttcaataagg agtttgccaa taagatcaac gagctggccg ccgtgtataa cgtggacgag   900
ctgtgcaccg ccatcacaga gaagctgatg aacttcgaca aggataagtc aataagacc   960 agaaactttg atcaagaa gctgtggaag cagcaccctc acaacaagga taaggccctg  1020
atcaagctgt caatcagga gggcaacgag gccctgaatc agtttaacat cgagctgggc  1080
aagtacttcg agcactattt tcctaagaca ggcaagaagg agagcgccga gtcctactat  1140
ctgaatccac agaccatcat caagacagtg ggctaccagc tgaggaacgc cttcgtgcag  1200
tatctgctgc aagtgggcaa gctgcaccag tacaacaagg gcgtgctgga cagccagacc  1260
ctgcaggaga tcggcatgta tgagggcttc agacaaagt ttatggatgc ctgcgtgttc  1320
gccagctcct ctctgcggaa tatcatccag gccaccacaa acgaggacat cctgaccaga  1380
gagaagttta agaaggagct ggagaagaac gtggagctga gcacgacct gttctttaag  1440 accgagatcg tggaggagcg cgatgagaat cctgccaaga gatcgccat gacaccaaac  1500
```

```
gagctggacc tgtgggcaat caggggagcc gtgcagaggg tgcgcaatca gatcttccac    1560
cagcagatca ataagagaca cgagcccaac cagctgaagg tcggctcctt tgagaatggc    1620
gatctgggca acgtgtctta ccagaaaacc atctatcaga agctgttcga cgccgagatc    1680
aaggatatcg agatctactt tgccgagaag atcaagagct ccggcgccct ggagcagtat    1740
tccatgaagg acctggagaa gctgttcagc aacaaggagc tgacactgtc cctgggagga    1800
caggtggtgg ccttcgcccc ttcttacaag aagctgtata agcagggcta ctttttatcag    1860 aatgagaaaa ccatcgagct ggagcagttt acagactacg atttctctaa tgacgtgttc    1920
aaggccaact actatctgat caagctgatc taccactacg tgttcctgcc acagtttagc    1980
caggccaaca ataagctgtt caaggacacc gtgcactacg tgatccagca gaataaggag    2040
ctgaacacca cagagaagga taagaagaac aataagaaga tcagaaagta tgcctttgag    2100
caggtgaagc tgatgaagaa cgagtcccca gagaagtaca tgcagtatct gcagagggag    2160
atgcaggagg agcgcaccat caaggaggcc aagaaaacca acgaggagaa gcccaactac    2220
aatttcgaga agctgctgat ccagatcttt atcaagggct tcgacacctt tctgaggaat    2280
ttcgatctga acctgaatcc tgccgaggag ctggtgggca cagtgaagga aaggccgag     2340 ggcctgcgga agagaaagga gcgcatcgcc aagatcctga cgtggacga gcagatcaag    2400 accggcgatg aggagatcgc cttctggatc tttgcaaagc tgctggacgc aaggcacctg    2460
agcgagctga gaaacgagat gatcaagttt agcagtcta gcgtgaagaa gggcctgatc    2520
aagaatggcg atctgatcga gcagatgcag ccaatcctgg agctgtgcat cctgagcaac    2580
gacagcgagt ccatggagaa ggagtccttc gataagatcg aggtgtttct ggagaaggtg    2640
gagctggcca agaatgagcc atacatgcag gaggacaagc tgaccccgt gaagttcagg     2700 tttatgaagc agctggagaa gtatcagaca cgcaatttca tcgagaacct ggtcatcgag    2760
aatccagagt ttaaggtgtc cgagaagatc gtgctgaact ggcacgagga aaggagaag    2820 atcgccgacc tggtggataa gcggaccaag ctgcacgagg agtgggcctc caaggccaga    2880
gagatcgagg agtacaatga aagatcaag aagaacaagt ctaagaagct ggacaagccc    2940
gccgagttcg ccaagtttgc cgagtataag atcatctgtg aggccatcga acttcaat     3000 aggctggatc acaaggtgcg cctgacatac ctgaagaacc tgcactatct gatgatcgac    3060
ctgatgggca gatggtggg cttctccgtg ctgtttgagc gggatttcgt gtatatgggc    3120
agatcttata gcgccctgaa gaagcagtct atctacctga atgactatga taccttcgcc    3180
aacatccgcg actgggaggt gaacgagaat aagcacctgt ttggcacatc ctctagcgat    3240
ctgaccttcc aggagacagc cgagtttaag aatctgaaga agcccatgga gaaccagctg    3300
aaggccctgc tgggcgtgac caaccacagc ttcgagatcc ggaacaatat cgcccacctg    3360
cacgtgctga aaatgatgg caagggcgag ggcgtgtctc tgctgagctg catgaacgac    3420
ctgaggaagc tgatgtccta cgatcgcaag ctgaagaatg ccgtgacaaa ggccatcatc    3480
aagatcctgg acaagcacgg catgatcctg aagctgacca caatgatca cacaaagccc    3540 ttcgagattg agagcctgaa gcctaagaag atcatccacc tggagaagtc caaccactct    3600
ttccctatgg accaggtgtc ccaggagtac tgtgatctgg tgaagaagat gctggtgttt    3660
accaattga                                                            3669
```

<210> SEQ ID NO 39
<211> LENGTH: 1222
<212> TYPE: PRT
<213> ORGANISM: Artificial Sequence
<220> FEATURE:
<223> OTHER INFORMATION: Cga2Cas13a amino acid sequence

<400> SEQUENCE: 39

Met Ile Leu Lys Leu Lys Ile Asp Glu Asn His Lys Asn Phe Glu Ile
1               5                   10                  15

Glu Ser Leu Ile Pro Lys Glu Ile Ile His Leu Lys Asp Lys Ala Ile
            20                  25                  30

Lys Thr Asn Gln Val Ser Glu Glu Tyr Cys Gln Leu Val Leu Ala Leu
        35                  40                  45

Leu Thr Thr Asn Pro Gly Asn Gln Leu Asn Met Arg Met Thr Lys Val
    50                  55                  60

Lys Ile Asn Gly Ser Pro Val Ser Met Asn Arg Ser Lys Leu Asn Gly
65                  70                  75                  80

His Leu Val Trp Asn Gly Thr Thr Asn Thr Val Asn Ile Leu Thr Lys
                85                  90                  95

Lys Glu Gln Ser Phe Ala Ala Ser Phe Leu Asn Lys Thr Leu Val Lys
            100                 105                 110

Ala Asp Gln Val Lys Gly Tyr Lys Val Leu Ala Glu Asn Ile Phe Ile
        115                 120                 125

Ile Phe Glu Gln Leu Glu Lys Ser Asn Ser Glu Lys Pro Ser Val Tyr
    130                 135                 140

Leu Asn Asn Ile Arg Arg Leu Lys Glu Ala Gly Leu Lys Arg Phe Phe
145                 150                 155                 160

Lys Ser Lys Tyr His Glu Glu Ile Lys Tyr Thr Ser Glu Lys Asn Gln
                165                 170                 175

Ser Val Pro Thr Lys Leu Asn Leu Ile Pro Leu Phe Phe Asn Ala Val
            180                 185                 190

Asp Arg Ile Gln Glu Asp Lys Phe Asp Glu Lys Asn Trp Ser Tyr Phe
        195                 200                 205

Cys Lys Glu Met Ser Pro Tyr Leu Asp Tyr Lys Lys Ser Tyr Leu Asn
    210                 215                 220

Arg Lys Lys Glu Ile Leu Ala Asn Ser Ile Gln Gln Asn Arg Gly Phe
225                 230                 235                 240

Ser Met Pro Thr Ala Glu Glu Pro Asn Leu Leu Ser Lys Arg Lys Gln
                245                 250                 255

Leu Phe Gln Gln Trp Ala Met Lys Phe Gln Glu Ser Pro Leu Ile Gln
            260                 265                 270

Gln Asn Asn Phe Ala Val Glu Gln Phe Asn Lys Glu Phe Ala Asn Lys
        275                 280                 285

Ile Asn Glu Leu Ala Ala Val Tyr Asn Val Asp Glu Leu Cys Thr Ala
    290                 295                 300

Ile Thr Glu Lys Leu Met Asn Phe Asp Lys Asp Lys Ser Asn Lys Thr
305                 310                 315                 320

Arg Asn Phe Glu Ile Lys Lys Leu Trp Lys Gln His Pro His Asn Lys
                325                 330                 335

Asp Lys Ala Leu Ile Lys Leu Phe Asn Gln Glu Gly Asn Glu Ala Leu
            340                 345                 350

Asn Gln Phe Asn Ile Glu Leu Gly Lys Tyr Phe Glu His Tyr Phe Pro
        355                 360                 365

Lys Thr Gly Lys Lys Glu Ser Ala Glu Ser Tyr Tyr Leu Asn Pro Gln
    370                 375                 380

Thr Ile Ile Lys Thr Val Gly Tyr Gln Leu Arg Asn Ala Phe Val Gln
385                 390                 395                 400

```
Tyr Leu Leu Gln Val Gly Lys Leu His Gln Tyr Asn Lys Gly Val Leu
            405                 410                 415

Asp Ser Gln Thr Leu Gln Glu Ile Gly Met Tyr Glu Gly Phe Gln Thr
        420                 425                 430

Lys Phe Met Asp Ala Cys Val Phe Ala Ser Ser Leu Arg Asn Ile
    435                 440                 445

Ile Gln Ala Thr Thr Asn Glu Asp Ile Leu Thr Arg Glu Lys Phe Lys
    450                 455                 460

Lys Glu Leu Glu Lys Asn Val Glu Leu Lys His Asp Leu Phe Phe Lys
465                 470                 475                 480

Thr Glu Ile Val Glu Glu Arg Asp Glu Asn Pro Ala Lys Lys Ile Ala
            485                 490                 495

Met Thr Pro Asn Glu Leu Asp Leu Trp Ala Ile Arg Gly Ala Val Gln
            500                 505                 510

Arg Val Arg Asn Gln Ile Phe His Gln Ile Asn Lys Arg His Glu
515                 520                 525

Pro Asn Gln Leu Lys Val Gly Ser Phe Glu Asn Gly Asp Leu Gly Asn
    530                 535                 540

Val Ser Tyr Gln Lys Thr Ile Tyr Gln Lys Leu Phe Asp Ala Glu Ile
545                 550                 555                 560

Lys Asp Ile Glu Ile Tyr Phe Ala Glu Lys Ile Lys Ser Ser Gly Ala
            565                 570                 575

Leu Glu Gln Tyr Ser Met Lys Asp Leu Glu Lys Leu Phe Ser Asn Lys
            580                 585                 590

Glu Leu Thr Leu Ser Leu Gly Gly Gln Val Val Ala Phe Ala Pro Ser
            595                 600                 605

Tyr Lys Lys Leu Tyr Lys Gln Gly Tyr Phe Tyr Gln Asn Glu Lys Thr
            610                 615                 620

Ile Glu Leu Glu Gln Phe Thr Asp Tyr Asp Phe Ser Asn Asp Val Phe
625                 630                 635                 640

Lys Ala Asn Tyr Tyr Leu Ile Lys Leu Ile Tyr His Tyr Val Phe Leu
            645                 650                 655

Pro Gln Phe Ser Gln Ala Asn Asn Lys Leu Phe Lys Asp Thr Val His
            660                 665                 670

Tyr Val Ile Gln Gln Asn Lys Glu Leu Asn Thr Thr Glu Lys Asp Lys
            675                 680                 685

Lys Asn Asn Lys Lys Ile Arg Lys Tyr Ala Phe Glu Gln Val Lys Leu
            690                 695                 700

Met Lys Asn Glu Ser Pro Glu Lys Tyr Met Gln Tyr Leu Gln Arg Glu
705                 710                 715                 720

Met Gln Glu Glu Arg Thr Ile Lys Glu Ala Lys Lys Thr Asn Glu Glu
            725                 730                 735

Lys Pro Asn Tyr Asn Phe Glu Lys Leu Leu Ile Gln Ile Phe Ile Lys
            740                 745                 750

Gly Phe Asp Thr Phe Leu Arg Asn Phe Asp Leu Asn Leu Asn Pro Ala
            755                 760                 765

Glu Glu Leu Val Gly Thr Val Lys Glu Lys Ala Glu Gly Leu Arg Lys
    770                 775                 780

Arg Lys Glu Arg Ile Ala Lys Ile Leu Asn Val Asp Glu Gln Ile Lys
785                 790                 795                 800

Thr Gly Asp Glu Glu Ile Ala Phe Trp Ile Phe Ala Lys Leu Leu Asp
            805                 810                 815
```

```
Ala Arg His Leu Ser Glu Leu Arg Asn Glu Met Ile Lys Phe Lys Gln
            820                 825                 830

Ser Ser Val Lys Lys Gly Leu Ile Lys Asn Gly Asp Leu Ile Glu Gln
            835                 840                 845

Met Gln Pro Ile Leu Glu Leu Cys Ile Leu Ser Asn Asp Ser Glu Ser
850                 855                 860

Met Glu Lys Glu Ser Phe Asp Lys Ile Glu Val Phe Leu Glu Lys Val
865                 870                 875                 880

Glu Leu Ala Lys Asn Glu Pro Tyr Met Gln Asp Lys Leu Thr Pro
                885                 890                 895

Val Lys Phe Arg Phe Met Lys Gln Leu Glu Lys Tyr Gln Thr Arg Asn
            900                 905                 910

Phe Ile Glu Asn Leu Val Ile Glu Asn Pro Glu Phe Lys Val Ser Glu
            915                 920                 925

Lys Ile Val Leu Asn Trp His Glu Lys Glu Lys Ile Ala Asp Leu
            930                 935                 940

Val Asp Lys Arg Thr Lys Leu His Glu Glu Trp Ala Ser Lys Ala Arg
945                 950                 955                 960

Glu Ile Glu Glu Tyr Asn Glu Lys Ile Lys Asn Lys Ser Lys Lys
                965                 970                 975

Leu Asp Lys Pro Ala Glu Phe Ala Lys Phe Ala Glu Tyr Lys Ile Ile
            980                 985                 990

Cys Glu Ala Ile Glu Asn Phe Asn Arg Leu Asp His Lys Val Arg Leu
            995                1000                1005

Thr Tyr Leu Lys Asn Leu His Tyr Leu Met Ile Asp Leu Met Gly
    1010                1015                1020

Arg Met Val Gly Phe Ser Val Leu Phe Glu Arg Asp Phe Val Tyr
    1025                1030                1035

Met Gly Arg Ser Tyr Ser Ala Leu Lys Lys Gln Ser Ile Tyr Leu
    1040                1045                1050

Asn Asp Tyr Asp Thr Phe Ala Asn Ile Arg Asp Trp Glu Val Asn
    1055                1060                1065

Glu Asn Lys His Leu Phe Gly Thr Ser Ser Ser Asp Leu Thr Phe
    1070                1075                1080

Gln Glu Thr Ala Glu Phe Lys Asn Leu Lys Lys Pro Met Glu Asn
    1085                1090                1095

Gln Leu Lys Ala Leu Leu Gly Val Thr Asn His Ser Phe Glu Ile
    1100                1105                1110

Arg Asn Asn Ile Ala His Leu His Val Leu Arg Asn Asp Gly Lys
    1115                1120                1125

Gly Glu Gly Val Ser Leu Leu Ser Cys Met Asn Asp Leu Arg Lys
    1130                1135                1140

Leu Met Ser Tyr Asp Arg Lys Leu Lys Asn Ala Val Thr Lys Ala
    1145                1150                1155

Ile Ile Lys Ile Leu Asp Lys His Gly Met Ile Leu Lys Leu Thr
    1160                1165                1170

Asn Asn Asp His Thr Lys Pro Phe Glu Ile Glu Ser Leu Lys Pro
    1175                1180                1185

Lys Lys Ile Ile His Leu Glu Lys Ser Asn His Ser Phe Pro Met
    1190                1195                1200

Asp Gln Val Ser Gln Glu Tyr Cys Asp Leu Val Lys Lys Met Leu
    1205                1210                1215

Val Phe Thr Asn
```

<210> SEQ ID NO 40
<211> LENGTH: 36
<212> TYPE: DNA
<213> ORGANISM: Artificial Sequence
<220> FEATURE:
<223> OTHER INFORMATION: Cga2Cas13a direct repeat

<400> SEQUENCE: 40
aatataaact acctctaaat gtaagaggac tataac                                 36

<210> SEQ ID NO 41
<211> LENGTH: 3465
<212> TYPE: DNA
<213> ORGANISM: Artificial Sequence
<220> FEATURE:
<223> OTHER INFORMATION: PprCas13a nucleic acid sequence

<400> SEQUENCE: 41

```
atgcgggtgt ccaaggtgaa ggtgaaggac ggcggcaagg ataagatggt gctggtgcac        60
agaaagacca caggcgcaca gctggtgtac tctggacagc ccgtgtctaa tgagacaagc       120
aacatcctgc ctgagaagaa gaggcagtcc tttgacctgt ctaccctgaa caagacaatc       180
atcaagttcg acacagccaa gaagcagaag ctgaatgtgg atcagtacaa gatcgtggag       240
aagatcttta gtatcctaa gcaggagctg ccaaagcaga tcaaggccga ggagatcctg       300
ccatttctga atcacaagtt ccaggagccc gtgaagtact ggaagaacgg caaggaggag       360
tccttcaatc tgaccctgct gatcgtggag gccgtgcagg cacaggacaa cgcaagctg       420 cagccctact atgattggaa aacctggtat atccagacaa gagcgacct gctgaagaag       480 tccatcgaga caataggat cgatctgaca gagaacctgt ctaagcgcaa gaaggccctg       540
ctggcctggg agacagagtt cacagccagc ggctccatcg acctgaccca ctaccacaag       600
gtgtatatga cagacgtgct gtgcaagatg ctgcaggatg tgaagccact gaccgacgat       660
aagggcaaga tcaacacaaa tgcctaccac cggggcctga gaaggccct gcagaatcac       720 cagcctgcca tctttggcac ccgggaggtg ccaaacgagg ccaatagagc cgataaccag       780
ctgtccatct accacctgga ggtggtgaag tacctggagc actatttccc catcaagacc       840
tctaagcgga gaaacacagc cgacgatatc gcccactatc tgaaggccca gaccctgaaa       900
accacaatcg agaagcagct ggtgaacgcc atcagagcca atatcatcca gcagggcaag       960
accaaccacc acgagctgaa ggccgacacc caagcaatg atctgatccg gatcaagaca      1020
aacgaggcct ttgtgctgaa tctgaccggc acatgtgcct tcgccgccaa caatatcaga      1080
aatatggtgg acaacgagca gaccaatgat atcctgggca agggcgactt catcaagtct      1140
ctgctgaagg acaacacaaa tagccagctg tactccttct ttttcggcga gggcctgagc      1200
accaataagg ccgagaagga cacacagctg tggggcatca ggggagccgt gcagcagatc      1260
cgcaacaatg tgaaccacta taagaaggat gccctgaaaa ccgtgttcaa catctccaat      1320
ttcgagaacc ccaccatcac agaccctaag cagcagacca actacgccga tacaatctat      1380
aaggccaggt ttatcaatga gctggagaag atccctgagg ccttcgccca gcagctgaaa      1440
accggcggag ccgtgtctta ctatacaatc gagaatctga gagcctgct gaccacattt      1500 cagttctctc tgtgccgcag caccatccca tttgccccg gcttcaagaa ggtgtttaac      1560
ggcggcatca attaccagaa cgccaagcag gacgagagct ctctacgagct gatgctggag      1620 cagtatctga ggaaggagaa ctttgccgag gagtcctaca tgcccgcta tttcatgctg      1680
```

```
aagctgatct ataacaatct gttcctgcca ggctttacca cagatcggaa ggcctttgcc    1740
gacagcgtgg gcttcgtgca gatgcagaac aagaagcagg ccgagaaagt gaatccaagg    1800
aagaaggagg cctacgcctt tgaggccgtg cgccccatga ccgcagcaga ctccatcgcc    1860
gattacatgg cctatgtgca gtctgagctg atgcaggagc agaacaagaa ggaggagaag    1920
gtggccgagg agacaaggat caattttgag aagttcgtgc tgcaggtgtt catcaagggc    1980
tttgactcct tcctgcgcgc caaggagttt gatttcgtgc agatgccaca gcctcagctg    2040
accgcaacag cctctaacca gcagaaggcc gacaagctga atcagctgga ggccagcatc    2100
accgccgatt gcaagctgac accccagtac gccaaggccg acgatgccac ccacatcgcc    2160
ttctacgtgt tctgcaagct gctggacgcc gcccacctga gcaatctgcg aacgagctg    2220
atcaagttca gagagtccgt gaacgagttt aagttccacc acctgctgga gatcatcgag    2280
atctgcctgc tgagcgccga cgtggtgccc accgactaca gagatctgta tagctccgag    2340
gcagattgtc tggcaaggct gcgcccttt atcgagcagg gcgccgatat cacaaactgg    2400
tccgacctgt tcgtgcagtc cgataagcac tctcctgtga tccacgccaa tatcgagctg    2460
tctgtgaagt acggcaccac aaagctgctg gagcagatca tcaacaagga cacccagttt    2520
aagaccacag aggccaactt caccgcctgg aatacagccc agaagagcat cgagcagctg    2580
atcaagcaga gggaggatca ccacgagcag tgggtgaagg ccaagaacgc cgacgataag    2640
gagaagcagg agcggaagag agagaagtcc aatttcgccc agaagtttat cgagaagcac    2700
ggcgacgatt atctggacat ctgcgattac atcaatacct ataactggct ggacaacaag    2760
atgcacttcg tgcacctgaa tcgcctgcac ggcctgacaa tcgagctgct gggaaggatg    2820
gcaggattcg tggccctgtt tgacagagat ttccagtttt tcgacgagca gcagatcgcc    2880
gatgagttta agctgcacgg cttcgtgaac ctgcactcca tcgacaagaa gctgaatgag    2940
gtgcccacca agaagatcaa ggagatctac gatatccgga acaagatcat ccagatcaac    3000
ggcaataaga tcaacgagtc tgtgcgggcc aatctgatcc agtttatctc tagcaagaga    3060
aactactata caatgccctt cctgcacgtg agcaatgacg agatcaagga gaagcagatg    3120
tacgatatca gaaaccacat cgcccacttt aattatctga ccaaggacgc cgccgatttc    3180
agcctgatcg acctgatcaa cgagctgagg gagctgctgc actacgatcg caagctgaag    3240
aatgccgtgt ccaaggcctt tatcgacctg ttcgataagc acggcatgat cctgaagctg    3300
aagctgaacg ccgaccacaa gctgaaggtg gagtctctgg agcctaagaa gatctaccac    3360
ctgggctcct ctgccaagga taagccagag taccagtatt gtaccaacca ggtcatgatg    3420
gcctattgca atatgtgccg gagcctgctg gagatgaaga agtga                     3465
```

<210> SEQ ID NO 42
<211> LENGTH: 1154
<212> TYPE: PRT
<213> ORGANISM: Artificial Sequence
<220> FEATURE:
<223> OTHER INFORMATION: PprCas13a amino acid sequence

<400> SEQUENCE: 42

```
Met Arg Val Ser Lys Val Lys Val Lys Asp Gly Gly Lys Asp Lys Met
1               5                   10                  15

Val Leu Val His Arg Lys Thr Thr Gly Ala Gln Leu Val Tyr Ser Gly
            20                  25                  30

Gln Pro Val Ser Asn Glu Thr Ser Asn Ile Leu Pro Glu Lys Lys Arg
        35                  40                  45
```

```
Gln Ser Phe Asp Leu Ser Thr Leu Asn Lys Thr Ile Ile Lys Phe Asp
    50                  55                  60

Thr Ala Lys Lys Gln Lys Leu Asn Val Asp Gln Tyr Lys Ile Val Glu
65                  70                  75                  80

Lys Ile Phe Lys Tyr Pro Lys Gln Glu Leu Pro Lys Gln Ile Lys Ala
                85                  90                  95

Glu Glu Ile Leu Pro Phe Leu Asn His Lys Phe Gln Glu Pro Val Lys
            100                 105                 110

Tyr Trp Lys Asn Gly Lys Glu Ser Phe Asn Leu Thr Leu Leu Ile
        115                 120                 125

Val Glu Ala Val Gln Ala Gln Asp Lys Arg Lys Leu Gln Pro Tyr Tyr
    130                 135                 140

Asp Trp Lys Thr Trp Tyr Ile Gln Thr Lys Ser Asp Leu Leu Lys Lys
145                 150                 155                 160

Ser Ile Glu Asn Asn Arg Ile Asp Leu Thr Glu Asn Leu Ser Lys Arg
                165                 170                 175

Lys Lys Ala Leu Leu Ala Trp Glu Thr Glu Phe Thr Ala Ser Gly Ser
            180                 185                 190

Ile Asp Leu Thr His Tyr His Lys Val Tyr Met Thr Asp Val Leu Cys
        195                 200                 205

Lys Met Leu Gln Asp Val Lys Pro Leu Thr Asp Asp Lys Gly Lys Ile
    210                 215                 220

Asn Thr Asn Ala Tyr His Arg Gly Leu Lys Lys Ala Leu Gln Asn His
225                 230                 235                 240

Gln Pro Ala Ile Phe Gly Thr Arg Glu Val Pro Asn Glu Ala Asn Arg
                245                 250                 255

Ala Asp Asn Gln Leu Ser Ile Tyr His Leu Glu Val Val Lys Tyr Leu
            260                 265                 270

Glu His Tyr Phe Pro Ile Lys Thr Ser Lys Arg Arg Asn Thr Ala Asp
        275                 280                 285

Asp Ile Ala His Tyr Leu Lys Ala Gln Thr Leu Lys Thr Thr Ile Glu
    290                 295                 300

Lys Gln Leu Val Asn Ala Ile Arg Ala Asn Ile Gln Gln Gly Lys
305                 310                 315                 320

Thr Asn His His Glu Leu Lys Ala Asp Thr Thr Ser Asn Asp Leu Ile
                325                 330                 335

Arg Ile Lys Thr Asn Glu Ala Phe Val Leu Asn Leu Thr Gly Thr Cys
            340                 345                 350

Ala Phe Ala Ala Asn Asn Ile Arg Asn Met Val Asp Asn Glu Gln Thr
        355                 360                 365

Asn Asp Ile Leu Gly Lys Gly Asp Phe Ile Lys Ser Leu Leu Lys Asp
    370                 375                 380

Asn Thr Asn Ser Gln Leu Tyr Ser Phe Phe Gly Glu Gly Leu Ser
385                 390                 395                 400

Thr Asn Lys Ala Glu Lys Glu Thr Gln Leu Trp Gly Ile Arg Gly Ala
                405                 410                 415

Val Gln Gln Ile Arg Asn Asn Val Asn His Tyr Lys Lys Asp Ala Leu
            420                 425                 430

Lys Thr Val Phe Asn Ile Ser Asn Phe Glu Asn Pro Thr Ile Thr Asp
        435                 440                 445

Pro Lys Gln Gln Thr Asn Tyr Ala Asp Thr Ile Tyr Lys Ala Arg Phe
    450                 455                 460
```

```
Ile Asn Glu Leu Glu Lys Ile Pro Glu Ala Phe Ala Gln Gln Leu Lys
465                 470                 475                 480

Thr Gly Gly Ala Val Ser Tyr Tyr Thr Ile Glu Asn Leu Lys Ser Leu
                485                 490                 495

Leu Thr Thr Phe Gln Phe Ser Leu Cys Arg Ser Thr Ile Pro Phe Ala
            500                 505                 510

Pro Gly Phe Lys Lys Val Phe Asn Gly Gly Ile Asn Tyr Gln Asn Ala
        515                 520                 525

Lys Gln Asp Glu Ser Phe Tyr Glu Leu Met Leu Gln Tyr Leu Arg
    530                 535                 540

Lys Glu Asn Phe Ala Glu Glu Ser Tyr Asn Ala Arg Tyr Phe Met Leu
545                 550                 555                 560

Lys Leu Ile Tyr Asn Asn Leu Phe Leu Pro Gly Phe Thr Thr Asp Arg
                565                 570                 575

Lys Ala Phe Ala Asp Ser Val Gly Phe Val Gln Met Gln Asn Lys Lys
            580                 585                 590

Gln Ala Glu Lys Val Asn Pro Arg Lys Lys Glu Ala Tyr Ala Phe Glu
        595                 600                 605

Ala Val Arg Pro Met Thr Ala Ala Asp Ser Ile Ala Asp Tyr Met Ala
        610                 615                 620

Tyr Val Gln Ser Glu Leu Met Gln Glu Gln Asn Lys Lys Glu Glu Lys
625                 630                 635                 640

Val Ala Glu Glu Thr Arg Ile Asn Phe Glu Lys Phe Val Leu Gln Val
                645                 650                 655

Phe Ile Lys Gly Phe Asp Ser Phe Leu Arg Ala Lys Glu Phe Asp Phe
                660                 665                 670

Val Gln Met Pro Gln Pro Gln Leu Thr Ala Thr Ala Ser Asn Gln Gln
            675                 680                 685

Lys Ala Asp Lys Leu Asn Gln Leu Glu Ala Ser Ile Thr Ala Asp Cys
    690                 695                 700

Lys Leu Thr Pro Gln Tyr Ala Lys Ala Asp Asp Ala Thr His Ile Ala
705                 710                 715                 720

Phe Tyr Val Phe Cys Lys Leu Leu Asp Ala Ala His Leu Ser Asn Leu
                725                 730                 735

Arg Asn Glu Leu Ile Lys Phe Arg Glu Ser Val Asn Glu Phe Lys Phe
            740                 745                 750

His His Leu Leu Glu Ile Ile Glu Ile Cys Leu Leu Ser Ala Asp Val
        755                 760                 765

Val Pro Thr Asp Tyr Arg Asp Leu Tyr Ser Ser Glu Ala Asp Cys Leu
        770                 775                 780

Ala Arg Leu Arg Pro Phe Ile Glu Gln Gly Ala Asp Ile Thr Asn Trp
785                 790                 795                 800

Ser Asp Leu Phe Val Gln Ser Asp Lys His Ser Pro Val Ile His Ala
                805                 810                 815

Asn Ile Glu Leu Ser Val Lys Tyr Gly Thr Thr Lys Leu Leu Glu Gln
            820                 825                 830

Ile Ile Asn Lys Asp Thr Gln Phe Lys Thr Thr Glu Ala Asn Phe Thr
        835                 840                 845

Ala Trp Asn Thr Ala Gln Lys Ser Ile Glu Gln Leu Ile Lys Gln Arg
        850                 855                 860

Glu Asp His His Glu Gln Trp Val Lys Ala Lys Asn Ala Asp Asp Lys
865                 870                 875                 880

Glu Lys Gln Glu Arg Lys Arg Glu Lys Ser Asn Phe Ala Gln Lys Phe
```

-continued

```
                    885                 890                 895
Ile Glu Lys His Gly Asp Asp Tyr Leu Asp Ile Cys Asp Tyr Ile Asn
                900                 905                 910

Thr Tyr Asn Trp Leu Asp Asn Lys Met His Phe Val His Leu Asn Arg
            915                 920                 925

Leu His Gly Leu Thr Ile Glu Leu Leu Gly Arg Met Ala Gly Phe Val
        930                 935                 940

Ala Leu Phe Asp Arg Asp Phe Gln Phe Phe Asp Glu Gln Gln Ile Ala
945                 950                 955                 960

Asp Glu Phe Lys Leu His Gly Phe Val Asn Leu His Ser Ile Asp Lys
                965                 970                 975

Lys Leu Asn Glu Val Pro Thr Lys Lys Ile Lys Glu Ile Tyr Asp Ile
            980                 985                 990

Arg Asn Lys Ile Ile Gln Ile Asn Gly Asn Lys Ile Asn Glu Ser Val
        995                 1000                1005

Arg Ala Asn Leu Ile Gln Phe Ile Ser Ser Lys Arg Asn Tyr Tyr
    1010                1015                1020

Asn Asn Ala Phe Leu His Val Ser Asn Asp Glu Ile Lys Glu Lys
    1025                1030                1035

Gln Met Tyr Asp Ile Arg Asn His Ile Ala His Phe Asn Tyr Leu
    1040                1045                1050

Thr Lys Asp Ala Ala Asp Phe Ser Leu Ile Asp Leu Ile Asn Glu
    1055                1060                1065

Leu Arg Glu Leu Leu His Tyr Asp Arg Lys Leu Lys Asn Ala Val
    1070                1075                1080

Ser Lys Ala Phe Ile Asp Leu Phe Asp Lys His Gly Met Ile Leu
    1085                1090                1095

Lys Leu Lys Leu Asn Ala Asp His Lys Leu Lys Val Glu Ser Leu
    1100                1105                1110

Glu Pro Lys Lys Ile Tyr His Leu Gly Ser Ser Ala Lys Asp Lys
    1115                1120                1125

Pro Glu Tyr Gln Tyr Cys Thr Asn Gln Val Met Met Ala Tyr Cys
    1130                1135                1140

Asn Met Cys Arg Ser Leu Leu Glu Met Lys Lys
    1145                1150
```

<210> SEQ ID NO 43
<211> LENGTH: 36
<212> TYPE: DNA
<213> ORGANISM: Artificial Sequence
<220> FEATURE:
<223> OTHER INFORMATION: PprCas13a direct repeat

<400> SEQUENCE: 43
cttgtggatt atcccaaaat tgaagggaac tacaac            36

<210> SEQ ID NO 44
<211> LENGTH: 2913
<212> TYPE: DNA
<213> ORGANISM: Artificial Sequence
<220> FEATURE:
<223> OTHER INFORMATION: LweCas13a nucleic acid sequence

<400> SEQUENCE: 44
atgctggccc tgctgcacca ggaggtgcct tcccagaagc tgcacaacct gaagagcctg      60
aataccgagt ccctgacaaa gctgtttaag ccaaagttcc agaacatgat cagctatcca      120

| | |
|---|---|
| ccttccaagg gagcagagca cgtgcagttc tgcctgaccg acatcgccgt gcccgcaatc | 180 |
| agggacctgg atgagatcaa gcctgactgg ggcatcttct tgagaagct gaagccatac | 240 |
| acagattggg ccgagtctta catccactat aagcagacca caatccagaa gagcatcgag | 300 |
| cagaacaaga tccagagccc agactcccca aggaagctgg tgctgcagaa gtatgtgacc | 360 |
| gcctttctga atggagagcc actgggcctg gacctggtgg ccaagaagta caagctggcc | 420 |
| gatctggccg agtccttcaa ggtggtggac ctgaacgagg ataagtctgc caattataag | 480 |
| atcaaggcct gtctgcagca gcaccagcgg aacatcctgg acgagctgaa ggaggacccc | 540 |
| gagctgaatc agtacggcat cgaggtgaag aagtacatcc agcggtattt cccaatcaag | 600 |
| agggcaccaa accgcagcaa gcacgccaga gccgactttc tgaagaagga gctgatcgag | 660 |
| tccaccgtgg agcagcagtt caagaatgcc gtgtaccact atgtgctgga gcagggcaag | 720 |
| atggaggcct acgagctgac cgatcccaag acaaaggacc tgcaggatat cagatctggc | 780 |
| gaggccttca gctttaagtt catcaacgcc tgcgcctttg ccagcaacaa tctgaagatg | 840 |
| atcctgaatc ctgagtgtga aaggacatc ctgggcaagg cgatttcaa gaagaacctg | 900 |
| ccaaattcta ccacacagag cgacgtggtg aagaagatga ccccttctt ttccgacgag | 960 |
| atccagaacg tgaatttcga tgaggccatc tgggccatcc ggggctctat ccagcagatc | 1020 |
| agaaacgagg tgtatcactg caagaagcac tcttggaaga gcatcctgaa gatcaagggc | 1080 |
| tttgagttcg agccaaacaa tatgaagtac accgactccg atatgcagaa gctgatggac | 1140 |
| aaggatatcg ccaagatccc cgactttatc gaggagaagc tgaagagctc cggcatcatc | 1200 |
| aggttctact cccacgataa gctgcagtct atctgggaga tgaagcaggg ctttagcctg | 1260 |
| ctgaccacaa cgccccttt tgtgccatcc ttcaagaggg tgtacgccaa gggccacgac | 1320 |
| tatcagacaa gcaagaatcg ctactatgac ctgggcctga ccacattcga tatcctggag | 1380 |
| tacggagagg aggacttccg ggcacgctat ttcctgacca agctggtgta ctatcagcag | 1440 |
| tttatgcctt ggttcacagc cgacaacaat gcctttcgcg atgccgccaa cttcgtgctg | 1500 |
| aggctgaaca agaatcgcca gcaggacgcc aaggccttta tcaatatccg ggaggtggag | 1560 |
| gagggcgaga tgcctagaga ttacatgggc tatgtgcagg ccagatcgc catccacgag | 1620 |
| gactccaccg aggatacacc aaaccacttt gagaagttca tctctcaggt gtttatcaag | 1680 |
| ggcttcgact cccacatgcg gtctgccgat ctgaagttca tcaagaaccc cagaaatcag | 1740 |
| ggcctggagc agagcgagat cgaggagatg tcctttgaca tcaaggtgga gcctagcttc | 1800 |
| ctgaagaaca aggacgatta tatcgccttt tggaccttct gcaagatgct ggacgcaagg | 1860 |
| cacctgtccg agctgagaaa tgagatgatc aagtacgatg ccacctgac aggcgagcag | 1920 |
| gagatcatcg gcctggccct gctgggagtg gactctaggg agaacgattg gaagcagttc | 1980 |
| ttttctagcg agcgcgagta cgagaagatc atgaagggct atgtgggcga ggagctgtac | 2040 |
| cagcgggagc cttatagaca gagcgacggc aagacccaa tcctgttcag ggagtggag | 2100 |
| caggcaagga agtacggcac cgagacagtg atccagcggc tgtttgatgc ctctcctgag | 2160 |
| ttcaaggtga gcaagtgtaa catcacagag tgggagagac agaaggagac aatcgaggag | 2220 |
| acaatcgagc ggagaaagga gctgcacaac gagtgggaga gaatcccaa gaagcctcag | 2280 |
| aacaatgcct tctttaagga gtacaaggag tgctgtgacg ccatcgatgc ctataactgg | 2340 |
| cacaagaata gaccacact ggtgtacgtg aatgagctgc accacctgct gatcgagatc | 2400 |
| ctgggcaggt acgtgggcta tgtggccatc gccgaccgcg attttcagtg catggccaac | 2460 |
| cagtatttca gcactctgg catcaccgag agggtggagt actgggcga caatcgcctg | 2520 |

-continued

```
aagagcatca agaagctgga tacatttctg aagaaggagg gcctgttcgt gtccgagaag    2580
aacgccagga atcacatcgc ccacctgaac tacctgtccc tgaagtctga gtgtaccctg    2640
ctgtatctgt ccgagcggct gagagagatc tttaagtacg acaggaagct gaagaatgcc    2700
gtgtccaagt ctctgatcga catcctggat cgccacggca tgtctgtggt gttcgccaac    2760
ctgaaggaga ataagcaccg gctggtcatc aagagcctgg agccaaagaa gctgagacac    2820
ctgggcgaga agaagatcga taacggctac atcgagacaa atcaggtgag cgaggagtat    2880
tgtggcatcg tgaagagact gctggagatc tga                                 2913
```

<210> SEQ ID NO 45
<211> LENGTH: 970
<212> TYPE: PRT
<213> ORGANISM: Artificial Sequence
<220> FEATURE:
<223> OTHER INFORMATION: LweCas13a amino acid sequence

<400> SEQUENCE: 45

```
Met Leu Ala Leu Leu His Gln Glu Val Pro Ser Gln Lys Leu His Asn
1               5                   10                  15

Leu Lys Ser Leu Asn Thr Glu Ser Leu Thr Lys Leu Phe Lys Pro Lys
            20                  25                  30

Phe Gln Asn Met Ile Ser Tyr Pro Pro Ser Lys Gly Ala Glu His Val
        35                  40                  45

Gln Phe Cys Leu Thr Asp Ile Ala Val Pro Ala Ile Arg Asp Leu Asp
    50                  55                  60

Glu Ile Lys Pro Asp Trp Gly Ile Phe Phe Glu Lys Leu Lys Pro Tyr
65                  70                  75                  80

Thr Asp Trp Ala Glu Ser Tyr Ile His Tyr Lys Gln Thr Thr Ile Gln
                85                  90                  95

Lys Ser Ile Glu Gln Asn Lys Ile Gln Ser Pro Asp Ser Pro Arg Lys
            100                 105                 110

Leu Val Leu Gln Lys Tyr Val Thr Ala Phe Leu Asn Gly Glu Pro Leu
        115                 120                 125

Gly Leu Asp Leu Val Ala Lys Lys Tyr Lys Leu Ala Asp Leu Ala Glu
    130                 135                 140

Ser Phe Lys Val Val Asp Leu Asn Glu Asp Lys Ser Ala Asn Tyr Lys
145                 150                 155                 160

Ile Lys Ala Cys Leu Gln Gln His Gln Arg Asn Ile Leu Asp Glu Leu
                165                 170                 175

Lys Glu Asp Pro Glu Leu Asn Gln Tyr Gly Ile Glu Val Lys Lys Tyr
            180                 185                 190

Ile Gln Arg Tyr Phe Pro Ile Lys Arg Ala Pro Asn Arg Ser Lys His
        195                 200                 205

Ala Arg Ala Asp Phe Leu Lys Lys Glu Leu Ile Glu Ser Thr Val Glu
    210                 215                 220

Gln Gln Phe Lys Asn Ala Val Tyr His Tyr Val Leu Glu Gln Gly Lys
225                 230                 235                 240

Met Glu Ala Tyr Glu Leu Thr Asp Pro Lys Thr Lys Asp Leu Gln Asp
                245                 250                 255

Ile Arg Ser Gly Glu Ala Phe Ser Phe Lys Phe Ile Asn Ala Cys Ala
            260                 265                 270

Phe Ala Ser Asn Asn Leu Lys Met Ile Leu Asn Pro Glu Cys Glu Lys
        275                 280                 285
```

```
Asp Ile Leu Gly Lys Gly Asp Phe Lys Lys Asn Leu Pro Asn Ser Thr
    290                 295                 300

Thr Gln Ser Asp Val Val Lys Lys Met Ile Pro Phe Phe Ser Asp Glu
305                 310                 315                 320

Ile Gln Asn Val Asn Phe Asp Glu Ala Ile Trp Ala Ile Arg Gly Ser
                325                 330                 335

Ile Gln Gln Ile Arg Asn Glu Val Tyr His Cys Lys Lys His Ser Trp
            340                 345                 350

Lys Ser Ile Leu Lys Ile Lys Gly Phe Glu Phe Glu Pro Asn Asn Met
        355                 360                 365

Lys Tyr Thr Asp Ser Asp Met Gln Lys Leu Met Asp Lys Asp Ile Ala
370                 375                 380

Lys Ile Pro Asp Phe Ile Glu Glu Lys Leu Lys Ser Ser Gly Ile Ile
385                 390                 395                 400

Arg Phe Tyr Ser His Asp Lys Leu Gln Ser Ile Trp Glu Met Lys Gln
                405                 410                 415

Gly Phe Ser Leu Leu Thr Thr Asn Ala Pro Phe Val Pro Ser Phe Lys
            420                 425                 430

Arg Val Tyr Ala Lys Gly His Asp Tyr Gln Thr Ser Lys Asn Arg Tyr
        435                 440                 445

Tyr Asp Leu Gly Leu Thr Thr Phe Asp Ile Leu Glu Tyr Gly Glu Glu
    450                 455                 460

Asp Phe Arg Ala Arg Tyr Phe Leu Thr Lys Leu Val Tyr Gln Gln
465                 470                 475                 480

Phe Met Pro Trp Phe Thr Ala Asp Asn Asn Ala Phe Arg Asp Ala Ala
                485                 490                 495

Asn Phe Val Leu Arg Leu Asn Lys Asn Arg Gln Gln Asp Ala Lys Ala
            500                 505                 510

Phe Ile Asn Ile Arg Glu Val Glu Glu Gly Glu Met Pro Arg Asp Tyr
        515                 520                 525

Met Gly Tyr Val Gln Gly Gln Ile Ala Ile His Glu Asp Ser Thr Glu
530                 535                 540

Asp Thr Pro Asn His Phe Glu Lys Phe Ile Ser Gln Val Phe Ile Lys
545                 550                 555                 560

Gly Phe Asp Ser His Met Arg Ser Ala Asp Leu Lys Phe Ile Lys Asn
                565                 570                 575

Pro Arg Asn Gln Gly Leu Glu Gln Ser Glu Ile Glu Met Ser Phe
            580                 585                 590

Asp Ile Lys Val Glu Pro Ser Phe Leu Lys Asn Lys Asp Asp Tyr Ile
        595                 600                 605

Ala Phe Trp Thr Phe Cys Lys Met Leu Asp Ala Arg His Leu Ser Glu
610                 615                 620

Leu Arg Asn Glu Met Ile Lys Tyr Asp Gly His Leu Thr Gly Glu Gln
625                 630                 635                 640

Glu Ile Ile Gly Leu Ala Leu Leu Gly Val Asp Ser Arg Glu Asn Asp
                645                 650                 655

Trp Lys Gln Phe Phe Ser Ser Glu Arg Glu Tyr Glu Lys Ile Met Lys
            660                 665                 670

Gly Tyr Val Gly Glu Glu Leu Tyr Gln Arg Glu Pro Tyr Arg Gln Ser
        675                 680                 685

Asp Gly Lys Thr Pro Ile Leu Phe Arg Gly Val Glu Gln Ala Arg Lys
690                 695                 700

Tyr Gly Thr Glu Thr Val Ile Gln Arg Leu Phe Asp Ala Ser Pro Glu
```

```
                705                 710                 715                 720
            Phe Lys Val Ser Lys Cys Asn Ile Thr Glu Trp Glu Arg Gln Lys Glu
                            725                 730                 735

Thr Ile Glu Glu Thr Ile Glu Arg Arg Lys Glu Leu His Asn Glu Trp
                        740                 745                 750

Glu Lys Asn Pro Lys Pro Gln Asn Asn Ala Phe Phe Lys Glu Tyr
                        755                 760                 765

Lys Glu Cys Cys Asp Ala Ile Asp Ala Tyr Asn Trp His Lys Asn Lys
                770                 775                 780

Thr Thr Leu Val Tyr Val Asn Glu Leu His His Leu Leu Ile Glu Ile
            785                 790                 795                 800

Leu Gly Arg Tyr Val Gly Tyr Val Ala Ile Ala Asp Arg Asp Phe Gln
                            805                 810                 815

Cys Met Ala Asn Gln Tyr Phe Lys His Ser Gly Ile Thr Glu Arg Val
                        820                 825                 830

Glu Tyr Trp Gly Asp Asn Arg Leu Lys Ser Ile Lys Lys Leu Asp Thr
                        835                 840                 845

Phe Leu Lys Lys Glu Gly Leu Phe Val Ser Glu Lys Asn Ala Arg Asn
                850                 855                 860

His Ile Ala His Leu Asn Tyr Leu Ser Leu Lys Ser Glu Cys Thr Leu
            865                 870                 875                 880

Leu Tyr Leu Ser Glu Arg Leu Arg Glu Ile Phe Lys Tyr Asp Arg Lys
                            885                 890                 895

Leu Lys Asn Ala Val Ser Lys Ser Leu Ile Asp Ile Leu Asp Arg His
                        900                 905                 910

Gly Met Ser Val Val Phe Ala Asn Leu Lys Glu Asn Lys His Arg Leu
                        915                 920                 925

Val Ile Lys Ser Leu Glu Pro Lys Lys Leu Arg His Leu Gly Glu Lys
                930                 935                 940

Lys Ile Asp Asn Gly Tyr Ile Glu Thr Asn Gln Val Ser Glu Glu Tyr
            945                 950                 955                 960

Cys Gly Ile Val Lys Arg Leu Leu Glu Ile
                            965                 970

<210> SEQ ID NO 46
<211> LENGTH: 36
<212> TYPE: DNA
<213> ORGANISM: Artificial Sequence
<220> FEATURE:
<223> OTHER INFORMATION: LweCas13a direct repeat

<400> SEQUENCE: 46
gatttagagt acctcaaaat agaagaggtc taaaac                                  36

<210> SEQ ID NO 47
<211> LENGTH: 3156
<212> TYPE: DNA
<213> ORGANISM: Artificial Sequence
<220> FEATURE:
<223> OTHER INFORMATION: LbfCas13a nucleic acid sequence

<400> SEQUENCE: 47
atgaagatca ccaagatgcg ggtggacggc agaaccatcg tgatggagcg acatccaag         60 gagggccagc tgggctatga gggcatcgac ggcaacaaga ccacagagat catctttgat       120
aagaagaagg agagcttcta caagtccatc ctgaacaaga ccgtgagaaa gcctgatgag       180
aaggagaaga atcggagaaa gcaggccatc aacaaggcca tcaataagga gatcacagag       240
```

```
ctgatgctgg ccgtgctgca ccaggaggtg cctagccaga agctgcacaa cctgaagagc    300
ctgaataccg agtccctgac aaagctgttt aagccaaagt tccagaatat gatctcttat    360
ccacctagca agggagcaga gcacgtgcag ttctgcctga ccgacatcgc cgtgcccgca    420
atccgggacc tggatgagat caagcctgac tggggcatct tctttgagaa gctgaagcca    480
tacacagatt gggccgagtc ctacatccac tataagcaga ccacaatcca gaagtctatc    540
gagcagaaca agatccagag cccagactcc cccagaaagc tggtgctgca agtatgtg     600 accgcctttc tgaatggaga gccactgggc ctggacctgg tggccaagaa gtacaagctg    660
gccgatctgg ccgagtcttt caagctggtg gacctgaacg aggataagag cgccaattat    720
aagatcaagg cctgtctgca gcagcaccag cggaacatcc tggacgagct gaaggaggac    780
cccgagctga atcagtacgg catcgaggtg aagaagtaca tccagaggta tttcccaatc    840
aagagggccc ccaaccgctc taagcacgcc agagccgact ttctgaagaa ggagctgatc    900
gagagcaccg tggagcagca gttcaagaat gccgtgtacc actatgtgct ggagcagggc    960
aagatggagg cctacgagct gaccgatccc aagacaaagg acctgcagga tatcaggtct   1020
ggcgaggcct tcagctttaa gttcatcaac gcctgcgcct ttgcctccaa caatctgaag   1080
atgatcctga accctgagtg tgagaaggac atcctgggca agggcaattt caagaagaac   1140
ctgccaaatt ccaccacacg ctctgatgtg gtgaagaaga tgatcccctt ctttagcgac   1200
gagctgcaga acgtgaattt cgatgaggcc atctgggcca tccggggctc catccagcag   1260
atcagaaatg aggtgtatca ctgcaagaag cactcttgga agagcatcct gaagatcaag   1320
ggctttgagt tcgagccaaa caatatgaag tacgccgaca gcgatatgca gaagctgatg   1380
gacaaggata tcgccaagat ccccgagttt atcgaggaga gctgaagag ctccggcgtg   1440 gtgcggttct acagacacga cgagctgcag agcatctggg agatgaagca gggcttttcc   1500
ctgctgacca caaacgcccc ttttgtgccc agcttcaagc gggtgtacgc caagggccac   1560
gactatcaga cctccaagaa cagatactat aatctggacc tgaccacatt cgatatcctg   1620
gagtacggcg aggaggattt tcgggccaga tatttcctga ccaagctggt gtactatcag   1680
cagtttatgc cctggttcac agccgacaac aatgccttta gggatgccgc caacttcgtg   1740
ctgaggctga acaagaatcg ccagcaggac gccaaggcct ttatcaatat ccgggaggtg   1800
gaggagggcg agatgcctag agattacatg ggctatgtgc agggcagat cgccatccac   1860 gaggacagca tcgaggatac cccaaaccac tttgagaagt tcatctccca ggtgtttatc   1920
aagggcttcg acaggcacat cgcgctctgcc aatctgaagt tcatcaagaa cccccgcaat   1980
cagggcctgg agcagtccga gatcgaggag atgtcttttg atatcaaggt ggagccttct   2040
ttcctgaaga acaaggacga ttatatcgcc ttttggatct tctgcaagat gctggacgca   2100
aggcacctga gcgagctgag aaatgagatg atcaagtacg atggccacct gaccggcgag   2160
caggagatca tcggcctgrc cctgctggga gtggactccc gggagaacga ttggaagcag   2220
ttcttttcta gcgagagaga gtacgagaag atcatgaagg gctatgtggt ggaggagctg   2280
taccagcggg agccttatag acagtctgac ggcaagacac caatcctgtt caggggagtg   2340
gagcaggcaa ggaagtacgg caccgagaca gtgatccaga gctgtttga tgccaacccc   2400 gagttcaagg tgagcaagtg taatctggcc gagtgggagc gccagaagga gacaatcgag   2460
gagacaatca gaggcgcaa ggagctgcac aacgagtggg ccaagaatcc caagaagcct   2520
cagaacaatg ccttctttaa ggagtacaag gagtgctgtg acgccatcga tgcctataac   2580
```

-continued

```
tggcacaaga ataagaccac actggcctac gtgaacgagc tgcaccacct gctgatcgag      2640
atcctgggca ggtacgtggg ctatgtggcc atcgccgacc gcgattttca gtgcatggcc      2700
aaccagtatt tcaagcactc cggcatcacc gagagggtgg agtactgggg cgacaatcgc      2760
ctgaagtcta tcaagaagct ggatacattt ctgaagaagg agggcctgtt cgtgagcgag      2820
aagaacgccc ggaatcacat cgcccacctg aactacctgt ccctgaagtc tgagtgtacc      2880
ctgctgtatc tgtccgagag gctgcgcgag atctttaagt acgaccggaa gctgaagaat      2940
gccgtgtcca agtctctgat cgacatcctg gatagacacg gcatgtccgt ggtgttcgcc      3000
aacctgaagg agaataagca ccggctggtc atcaagagcc tggagcctaa gaagctgcgc      3060
cacctgggcg gcaagaagat cgatggcggc tacatcgaga caaaccaggt gagcgaggag      3120
tattgtggca tcgtgaagag actgctggag atgtga                                3156
```

<210> SEQ ID NO 48
<211> LENGTH: 1050
<212> TYPE: PRT
<213> ORGANISM: Artificial Sequence
<220> FEATURE:
<223> OTHER INFORMATION: LbfCas13a amino acid sequence

<400> SEQUENCE: 48

```
Met Lys Ile Thr Lys Met Arg Val Asp Gly Arg Thr Ile Val Met Glu
1               5                   10                  15

Arg Thr Ser Lys Glu Gly Gln Leu Gly Tyr Glu Gly Ile Asp Gly Asn
            20                  25                  30

Lys Thr Thr Glu Ile Ile Phe Asp Lys Lys Glu Ser Phe Tyr Lys
        35                  40                  45

Ser Ile Leu Asn Lys Thr Val Arg Lys Pro Asp Glu Lys Glu Lys Asn
    50                  55                  60

Arg Arg Lys Gln Ala Ile Asn Lys Ala Ile Asn Lys Glu Ile Thr Glu
65                  70                  75                  80

Leu Met Leu Ala Val Leu His Gln Glu Val Pro Ser Gln Lys Leu His
                85                  90                  95

Asn Leu Lys Ser Leu Asn Thr Glu Ser Leu Thr Lys Leu Phe Lys Pro
            100                 105                 110

Lys Phe Gln Asn Met Ile Ser Tyr Pro Pro Ser Lys Gly Ala Glu His
        115                 120                 125

Val Gln Phe Cys Leu Thr Asp Ile Ala Val Pro Ala Ile Arg Asp Leu
    130                 135                 140

Asp Glu Ile Lys Pro Asp Trp Gly Ile Phe Phe Glu Lys Leu Lys Pro
145                 150                 155                 160

Tyr Thr Asp Trp Ala Glu Ser Tyr Ile His Tyr Lys Gln Thr Thr Ile
                165                 170                 175

Gln Lys Ser Ile Glu Gln Asn Lys Ile Gln Ser Pro Asp Ser Pro Arg
            180                 185                 190

Lys Leu Val Leu Gln Lys Tyr Val Thr Ala Phe Leu Asn Gly Glu Pro
        195                 200                 205

Leu Gly Leu Asp Leu Val Ala Lys Lys Tyr Lys Leu Ala Asp Leu Ala
    210                 215                 220

Glu Ser Phe Lys Leu Val Asp Leu Asn Glu Asp Lys Ser Ala Asn Tyr
225                 230                 235                 240

Lys Ile Lys Ala Cys Leu Gln Gln His Gln Arg Asn Ile Leu Asp Glu
                245                 250                 255

Leu Lys Glu Asp Pro Glu Leu Asn Gln Tyr Gly Ile Glu Val Lys Lys
```

```
                260                 265                 270
Tyr Ile Gln Arg Tyr Phe Pro Ile Lys Arg Ala Pro Asn Arg Ser Lys
            275                 280                 285

His Ala Arg Ala Asp Phe Leu Lys Lys Glu Leu Ile Glu Ser Thr Val
        290                 295                 300

Glu Gln Gln Phe Lys Asn Ala Val Tyr His Tyr Val Leu Glu Gln Gly
305                 310                 315                 320

Lys Met Glu Ala Tyr Glu Leu Thr Asp Pro Lys Thr Lys Asp Leu Gln
                325                 330                 335

Asp Ile Arg Ser Gly Glu Ala Phe Ser Phe Lys Phe Ile Asn Ala Cys
            340                 345                 350

Ala Phe Ala Ser Asn Asn Leu Lys Met Ile Leu Asn Pro Glu Cys Glu
        355                 360                 365

Lys Asp Ile Leu Gly Lys Gly Asn Phe Lys Lys Asn Leu Pro Asn Ser
    370                 375                 380

Thr Thr Arg Ser Asp Val Val Lys Lys Met Ile Pro Phe Phe Ser Asp
385                 390                 395                 400

Glu Leu Gln Asn Val Asn Phe Asp Glu Ala Ile Trp Ala Ile Arg Gly
                405                 410                 415

Ser Ile Gln Gln Ile Arg Asn Glu Val Tyr His Cys Lys Lys His Ser
            420                 425                 430

Trp Lys Ser Ile Leu Lys Ile Lys Gly Phe Glu Phe Glu Pro Asn Asn
        435                 440                 445

Met Lys Tyr Ala Asp Ser Asp Met Gln Lys Leu Met Asp Lys Asp Ile
    450                 455                 460

Ala Lys Ile Pro Glu Phe Ile Glu Lys Leu Lys Ser Ser Gly Val
465                 470                 475                 480

Val Arg Phe Tyr Arg His Asp Glu Leu Gln Ser Ile Trp Glu Met Lys
                485                 490                 495

Gln Gly Phe Ser Leu Leu Thr Thr Asn Ala Pro Phe Val Pro Ser Phe
            500                 505                 510

Lys Arg Val Tyr Ala Lys Gly His Asp Tyr Gln Thr Ser Lys Asn Arg
        515                 520                 525

Tyr Tyr Asn Leu Asp Leu Thr Thr Phe Asp Ile Leu Glu Tyr Gly Glu
    530                 535                 540

Glu Asp Phe Arg Ala Arg Tyr Phe Leu Thr Lys Leu Val Tyr Tyr Gln
545                 550                 555                 560

Gln Phe Met Pro Trp Phe Thr Ala Asp Asn Asn Ala Phe Arg Asp Ala
                565                 570                 575

Ala Asn Phe Val Leu Arg Leu Asn Lys Asn Arg Gln Gln Asp Ala Lys
            580                 585                 590

Ala Phe Ile Asn Ile Arg Glu Val Glu Glu Gly Glu Met Pro Arg Asp
        595                 600                 605

Tyr Met Gly Tyr Val Gln Gly Gln Ile Ala Ile His Glu Asp Ser Ile
    610                 615                 620

Glu Asp Thr Pro Asn His Phe Glu Lys Phe Ile Ser Gln Val Phe Ile
625                 630                 635                 640

Lys Gly Phe Asp Arg His Met Arg Ser Ala Asn Leu Lys Phe Ile Lys
                645                 650                 655

Asn Pro Arg Asn Gln Gly Leu Glu Gln Ser Glu Ile Glu Glu Met Ser
            660                 665                 670

Phe Asp Ile Lys Val Glu Pro Ser Phe Leu Lys Asn Lys Asp Asp Tyr
        675                 680                 685
```

Ile Ala Phe Trp Ile Phe Cys Lys Met Leu Asp Ala Arg His Leu Ser
690                 695                 700

Glu Leu Arg Asn Glu Met Ile Lys Tyr Asp Gly His Leu Thr Gly Glu
705                 710                 715                 720

Gln Glu Ile Ile Gly Leu Leu Gly Val Asp Ser Arg Glu Asn Asp
        725                 730                 735

Trp Lys Gln Phe Phe Ser Ser Glu Arg Glu Tyr Glu Lys Ile Met Lys
                740                 745                 750

Gly Tyr Val Val Glu Glu Leu Tyr Gln Arg Glu Pro Tyr Arg Gln Ser
        755                 760                 765

Asp Gly Lys Thr Pro Ile Leu Phe Arg Gly Val Glu Gln Ala Arg Lys
770                 775                 780

Tyr Gly Thr Glu Thr Val Ile Gln Arg Leu Phe Asp Ala Asn Pro Glu
785                 790                 795                 800

Phe Lys Val Ser Lys Cys Asn Leu Ala Glu Trp Glu Arg Gln Lys Glu
                805                 810                 815

Thr Ile Glu Glu Thr Ile Lys Arg Arg Lys Glu Leu His Asn Glu Trp
                820                 825                 830

Ala Lys Asn Pro Lys Lys Pro Gln Asn Asn Ala Phe Phe Lys Glu Tyr
            835                 840                 845

Lys Glu Cys Cys Asp Ala Ile Asp Ala Tyr Asn Trp His Lys Asn Lys
850                 855                 860

Thr Thr Leu Ala Tyr Val Asn Glu Leu His His Leu Leu Ile Glu Ile
865                 870                 875                 880

Leu Gly Arg Tyr Val Gly Tyr Val Ala Ile Ala Asp Arg Asp Phe Gln
                885                 890                 895

Cys Met Ala Asn Gln Tyr Phe Lys His Ser Gly Ile Thr Glu Arg Val
            900                 905                 910

Glu Tyr Trp Gly Asp Asn Arg Leu Lys Ser Ile Lys Lys Leu Asp Thr
            915                 920                 925

Phe Leu Lys Lys Glu Gly Leu Phe Val Ser Glu Lys Asn Ala Arg Asn
930                 935                 940

His Ile Ala His Leu Asn Tyr Leu Ser Leu Lys Ser Glu Cys Thr Leu
945                 950                 955                 960

Leu Tyr Leu Ser Glu Arg Leu Arg Glu Ile Phe Lys Tyr Asp Arg Lys
                965                 970                 975

Leu Lys Asn Ala Val Ser Lys Ser Leu Ile Asp Ile Leu Asp Arg His
            980                 985                 990

Gly Met Ser Val Val Phe Ala Asn Leu Lys Glu Asn Lys His Arg Leu
            995                 1000                1005

Val Ile Lys Ser Leu Glu Pro Lys Lys Leu Arg His Leu Gly Gly
    1010                1015                1020

Lys Lys Ile Asp Gly Gly Tyr Ile Glu Thr Asn Gln Val Ser Glu
    1025                1030                1035

Glu Tyr Cys Gly Ile Val Lys Arg Leu Leu Glu Met
    1040                1045                1050

<210> SEQ ID NO 49
<211> LENGTH: 36
<212> TYPE: DNA
<213> ORGANISM: Artificial Sequence
<220> FEATURE:
<223> OTHER INFORMATION: LbfCas13a direct repeat

<400> SEQUENCE: 49
gatttagagt acctcaaaac aaaagaggac taaaac        36

<210> SEQ ID NO 50
<211> LENGTH: 3459
<212> TYPE: DNA
<213> ORGANISM: Artificial Sequence
<220> FEATURE:
<223> OTHER INFORMATION: Lwa2Cas13a nucleic acid sequence

<400> SEQUENCE: 50

```
atgaaggtga ccaaggtgga cggcatcagc cacaagaagt acatcgagga gggcaagctg      60
gtgaagtcca cctctgagga gaaccggaca tctgagagac tgagcgagct gctgtccatc     120
aggctggaca tctacatcaa gaaccccgat aatgcctccg aggaggagaa ccgcatccgg     180
agagagaatc tgaagaagtt cttttctaac aaggtgctgc acctgaagga cagcgtgctg     240
tacctgaaga acaggaagga gaagaatgcc gtgcaggata agaattattc cgaggaggac     300
atctctgagt acgatctgaa gaacaagaat agcttctccg tgctgaagaa gatcctgctg     360
aacgaggacg tgaatagcga ggagctggag atcttcagga aggatgtgga ggccaagctg     420
aacaagatca attctctgaa gtatagcttt gaggagaaca aggccaatta ccagaagatc     480
aacgagaaca atgtggagaa gtgggcggc aagagcaagc gcaacatcat ctatgactac     540
tatcgggagt ccgccaagag aaatgattac atcaacaatg tgcaggaggc cttcgacaag     600
ctgtataaga aggaggatat cgagaagctg ttctttctga tcgagaactc caagaagcac     660
gagaagtaca gatccggga gtactatcac aagatcatcg gcagaaagaa cgacaaggag     720
aatttcgcca agatcatcta tgaggagatc cagaacgtga acaatatcaa ggagctgatc     780
gagaagatcc ctgatatgag cgagctgaag aagtcccagg tgttttacaa gtactatctg     840
gacaaggagg agctgaacga taagaatatc aagtatgcct ctgccacttt gtggagatc      900
gagatgagcc agctgctgaa gaactacgtg tataagcggc tgtctaacat cagcaatgac     960
aagatcaaga gaatcttcga gtaccagaat ctgaagaagc tgatcgagaa caagctgctg    1020
aataagctgg acacctatgt gcgcaactgt ggcaagtaca attactatct gcaagtgggc    1080
gagatcgcca catccgattt catcgccagg aaccgccaga tgaggccttt ctgcggaaac    1140
atcatcggcg tgagctccgt ggcctacttt tctctgagaa atatcctgga cacagagaac    1200
gagaatgaca tcacaggccg gatgagaggc aagaccgtga agaacaataa gggcgaggag    1260
aagtacgtga gcggcgaggt ggataagatc tacaacgaga taagcagaa cgaggtgaag    1320
gagaatctga agatgttcta cagctatgac tttaacatgg ataacaagaa tgagatcgag    1380
gacttctttg ccaatatcga tgaggccatc tctagcatcc ggcacggcat cgtgcacttc    1440
aacctggagc tggagggcaa ggacatcttc gcctttaaga tatcgcccc atccgagatc    1500
tctaagaaga tgtttcagaa cgagatcaat gagaagaagc tgaagctgaa gatcttcaag    1560
cagctgaact ccgccaacgt gttcaactac tatgagaagg acgtgatcat caagtacctg    1620
aagaacacca gttcaatttt gtgaacaag aatatcccct tcgtgccttc ctttacaaag    1680
ctgtataaca agatcgagga tctgagaaat accctgaagt tcttttggtc tgtgccaaag    1740
gacaaggagg agaaggatgc ccagatctac ctgctgaaga acatctacta tggcgagttc    1800
ctgaacaagt ttgtgaagaa cagcaaggtg ttcttaaga tcacaaatga agtgatcaag    1860
atcaacaagc agcggaatca gaaaaccggc cactacaagt atcagaagtt cgagaacatc    1920
gagaaaaccg tgcccgtgga gtacctggcc atcatccaga gcagagagat gatcaacaat    1980
```

```
caggacaagg aggagaagaa cacctatatc gatttcatcc agcagatctt cctgaagggc    2040
tttatcgact atctgaataa gaacaatctg aagtacatcg agtccaacaa caacaacgac    2100
aacaacgata tcttttctaa gatcaagatc aagaaggaca caaggagaa gtatgataag     2160 atcctgaaga attacgagaa gcacaacagg aataaggaga tcccccacga gatcaacgag    2220
ttcgtgcgcg agatcaagct gggcaagatc ctgaagtata cagagaacct gaatatgttt    2280
tacctgatcc tgaagctgct gaaccacaag gagctgacca atctgaaggg ctctctggag    2340
aagtaccaga gcgccaacaa ggaggagaca ttcagcgatg agctggagct gatcaatctg    2400
ctgaacctgg acaacaatcg ggtgaccgag gattttgagc tggaggccaa cgagatcggc    2460
aagttcctgg actttaacga gaataagatc aaggatagga aggagctgaa gaagttcgac    2520
acaaacaaga tctactttga tggcgagaat atcatcaagc accgcgcctt ctataacatc    2580
aagaagtacg gcatgctgaa tctgctggag aagatcgccg acaaggccaa gtataagatc    2640
agcctgaagg agctgaagga gtactccaat aagaagaacg agatcgagaa gaactatacc    2700
atgcagcaga atctgcacag gaagtacgcc cgccctaaga aggatgagaa gttcaacgac    2760
gaggattaca aggagtatga aaggccatc ggcaacatcc agaagtacac ccacctgaag    2820
aataaggtgg agtttaatga gctgaacctg ctgcagggcc tgctgctgaa gatcctgcac    2880
aggctggtgg gctatacatc catctgggag cgcgacctga ggttccgcct gaagggcgag    2940
tttccagaga accactacat cgaggagatc ttcaatttcg ataactccaa gaatgtgaag    3000
tacaagtctg gccagatcgt ggagaagtac atcaacttct ataaggagct gtataaggac    3060
aatgtggaga gcggagcat ctactccgat aagaaggtga agaagctgaa gcaggagaag    3120
aaggacctgt atatcagaaa ctacatcgcc cactttaatt atatccctca cgccgagatc    3180
agcctgctgg aggtgctgga gaacctgagg aagctgctgt cttacgaccg caagctgaag    3240
aatgccatca tgaagagcat cgtggatatc ctgaaggagt atggcttcgt ggccaccttc    3300
aagatcggcg ccgacaagaa gatcgagatc agacccctgg agagcgagaa gatcgtgcac    3360
ctgaagaacc tgaagaagaa gaagctgatg acagatcgga cagcgagga gctgtgcgag    3420 ctggtgaaag tgatgttcga gtacaaggcc ctggagtga                          3459
```

<210> SEQ ID NO 51
<211> LENGTH: 1152
<212> TYPE: PRT
<213> ORGANISM: Artificial Sequence
<220> FEATURE:
<223> OTHER INFORMATION: Lwa2Cas13a amino acid sequence

<400> SEQUENCE: 51

```
Met Lys Val Thr Lys Val Asp Gly Ile Ser His Lys Lys Tyr Ile Glu
1               5                   10                  15

Glu Gly Lys Leu Val Lys Ser Thr Ser Glu Glu Asn Arg Thr Ser Glu
            20                  25                  30

Arg Leu Ser Glu Leu Leu Ser Ile Arg Leu Asp Ile Tyr Ile Lys Asn
        35                  40                  45

Pro Asp Asn Ala Ser Glu Glu Asn Arg Ile Arg Arg Glu Asn Leu
    50                  55                  60

Lys Lys Phe Phe Ser Asn Lys Val Leu His Leu Lys Asp Ser Val Leu
65                  70                  75                  80

Tyr Leu Lys Asn Arg Lys Glu Lys Asn Ala Val Gln Asp Lys Asn Tyr
                85                  90                  95

Ser Glu Glu Asp Ile Ser Glu Tyr Asp Leu Lys Asn Lys Asn Ser Phe
```

-continued

```
            100                 105                 110
Ser Val Leu Lys Lys Ile Leu Leu Asn Glu Asp Val Asn Ser Glu Glu
            115                 120                 125

Leu Glu Ile Phe Arg Lys Asp Val Glu Ala Lys Leu Asn Lys Ile Asn
            130                 135             140

Ser Leu Lys Tyr Ser Phe Glu Glu Asn Lys Ala Asn Tyr Gln Lys Ile
145                 150                 155                 160

Asn Glu Asn Asn Val Glu Lys Val Gly Gly Lys Ser Lys Arg Asn Ile
                165                 170                 175

Ile Tyr Asp Tyr Tyr Arg Glu Ser Ala Lys Arg Asn Asp Tyr Ile Asn
                180                 185                 190

Asn Val Gln Glu Ala Phe Asp Lys Leu Tyr Lys Lys Glu Asp Ile Glu
            195                 200                 205

Lys Leu Phe Phe Leu Ile Glu Asn Ser Lys Lys His Glu Lys Tyr Lys
            210                 215                 220

Ile Arg Glu Tyr Tyr His Lys Ile Ile Gly Arg Lys Asn Asp Lys Glu
225                 230                 235                 240

Asn Phe Ala Lys Ile Ile Tyr Glu Glu Ile Gln Asn Val Asn Asn Ile
                245                 250                 255

Lys Glu Leu Ile Glu Lys Ile Pro Asp Met Ser Glu Leu Lys Lys Ser
            260                 265                 270

Gln Val Phe Tyr Lys Tyr Tyr Leu Asp Lys Glu Glu Leu Asn Asp Lys
            275                 280                 285

Asn Ile Lys Tyr Ala Phe Cys His Phe Val Glu Ile Glu Met Ser Gln
            290                 295                 300

Leu Leu Lys Asn Tyr Val Tyr Lys Arg Leu Ser Asn Ile Ser Asn Asp
305                 310                 315                 320

Lys Ile Lys Arg Ile Phe Glu Tyr Gln Asn Leu Lys Lys Leu Ile Glu
                325                 330                 335

Asn Lys Leu Leu Asn Lys Leu Asp Thr Tyr Val Arg Asn Cys Gly Lys
            340                 345                 350

Tyr Asn Tyr Tyr Leu Gln Val Gly Glu Ile Ala Thr Ser Asp Phe Ile
            355                 360                 365

Ala Arg Asn Arg Gln Asn Glu Ala Phe Leu Arg Asn Ile Ile Gly Val
            370                 375             380

Ser Ser Val Ala Tyr Phe Ser Leu Arg Asn Ile Leu Glu Thr Glu Asn
385                 390                 395                 400

Glu Asn Asp Ile Thr Gly Arg Met Arg Gly Lys Thr Val Lys Asn Asn
                405                 410                 415

Lys Gly Glu Glu Lys Tyr Val Ser Gly Glu Val Asp Lys Ile Tyr Asn
                420                 425                 430

Glu Asn Lys Gln Asn Glu Val Lys Glu Asn Leu Lys Met Phe Tyr Ser
            435                 440                 445

Tyr Asp Phe Asn Met Asp Asn Lys Asn Glu Ile Glu Asp Phe Phe Ala
            450                 455             460

Asn Ile Asp Glu Ala Ile Ser Ser Ile Arg His Gly Ile Val His Phe
465                 470                 475                 480

Asn Leu Glu Leu Glu Gly Lys Asp Ile Phe Ala Phe Lys Asn Ile Ala
                485                 490                 495

Pro Ser Glu Ile Ser Lys Lys Met Phe Gln Asn Glu Ile Asn Glu Lys
            500                 505                 510

Lys Leu Lys Leu Lys Ile Phe Lys Gln Leu Asn Ser Ala Asn Val Phe
            515                 520                 525
```

```
Asn Tyr Tyr Glu Lys Asp Val Ile Ile Lys Tyr Leu Lys Asn Thr Lys
            530                 535                 540

Phe Asn Phe Val Asn Lys Asn Ile Pro Phe Val Pro Ser Phe Thr Lys
545                 550                 555                 560

Leu Tyr Asn Lys Ile Glu Asp Leu Arg Asn Thr Leu Lys Phe Phe Trp
                565                 570                 575

Ser Val Pro Lys Asp Lys Glu Lys Asp Ala Gln Ile Tyr Leu Leu
            580                 585                 590

Lys Asn Ile Tyr Tyr Gly Glu Phe Leu Asn Lys Phe Val Lys Asn Ser
                595                 600                 605

Lys Val Phe Phe Lys Ile Thr Asn Glu Val Ile Lys Ile Asn Lys Gln
            610                 615                 620

Arg Asn Gln Lys Thr Gly His Tyr Lys Tyr Gln Lys Phe Glu Asn Ile
625                 630                 635                 640

Glu Lys Thr Val Pro Val Glu Tyr Leu Ala Ile Ile Gln Ser Arg Glu
                645                 650                 655

Met Ile Asn Asn Gln Asp Lys Glu Glu Lys Asn Thr Tyr Ile Asp Phe
                660                 665                 670

Ile Gln Gln Ile Phe Leu Lys Gly Phe Ile Asp Tyr Leu Asn Lys Asn
            675                 680                 685

Asn Leu Lys Tyr Ile Glu Ser Asn Asn Asn Asp Asn Asn Asp Ile
            690                 695                 700

Phe Ser Lys Ile Lys Ile Lys Lys Asp Asn Lys Glu Lys Tyr Asp Lys
705                 710                 715                 720

Ile Leu Lys Asn Tyr Glu Lys His Asn Arg Asn Lys Glu Ile Pro His
                725                 730                 735

Glu Ile Asn Glu Phe Val Arg Glu Ile Lys Leu Gly Lys Ile Leu Lys
            740                 745                 750

Tyr Thr Glu Asn Leu Asn Met Phe Tyr Leu Ile Leu Lys Leu Leu Asn
                755                 760                 765

His Lys Glu Leu Thr Asn Leu Lys Gly Ser Leu Glu Lys Tyr Gln Ser
            770                 775                 780

Ala Asn Lys Glu Glu Thr Phe Ser Asp Glu Leu Glu Leu Ile Asn Leu
785                 790                 795                 800

Leu Asn Leu Asp Asn Asn Arg Val Thr Glu Asp Phe Glu Leu Glu Ala
                805                 810                 815

Asn Glu Ile Gly Lys Phe Leu Asp Phe Asn Glu Asn Lys Ile Lys Asp
            820                 825                 830

Arg Lys Glu Leu Lys Lys Phe Asp Thr Asn Lys Ile Tyr Phe Asp Gly
            835                 840                 845

Glu Asn Ile Ile Lys His Arg Ala Phe Tyr Asn Ile Lys Lys Tyr Gly
850                 855                 860

Met Leu Asn Leu Leu Glu Lys Ile Ala Asp Lys Ala Lys Tyr Lys Ile
865                 870                 875                 880

Ser Leu Lys Glu Leu Lys Glu Tyr Ser Asn Lys Lys Asn Glu Ile Glu
            885                 890                 895

Lys Asn Tyr Thr Met Gln Gln Asn Leu His Arg Lys Tyr Ala Arg Pro
            900                 905                 910

Lys Lys Asp Glu Lys Phe Asn Asp Glu Asp Tyr Lys Glu Tyr Glu Lys
            915                 920                 925

Ala Ile Gly Asn Ile Gln Lys Tyr Thr His Leu Lys Asn Lys Val Glu
930                 935                 940
```

| | | | | | | | | | | | | |
|---|---|---|---|---|---|---|---|---|---|---|---|---|
|Phe|Asn|Glu|Leu|Asn|Leu|Leu|Gln|Gly|Leu|Leu|Lys|Ile|Leu|His|
|945| | | | |950| | | | |955| | | |960|

| | | | | | | | | | | | |
|---|---|---|---|---|---|---|---|---|---|---|---|
|Arg|Leu|Val|Gly|Tyr|Thr|Ser|Ile|Trp|Glu|Arg|Asp|Leu|Arg|Phe|Arg|
| | | | |965| | | | |970| | | | |975| |

Leu Lys Gly Glu Phe Pro Glu Asn His Tyr Ile Glu Glu Ile Phe Asn
            980                 985                 990

Phe Asp Asn Ser Lys Asn Val Lys  Tyr Lys Ser Gly Gln  Ile Val Glu
        995                1000                 1005

Lys Tyr  Ile Asn Phe Tyr Lys  Glu Leu Tyr Lys Asp  Asn Val Glu
    1010                 1015                 1020

Lys Arg  Ser Ile Tyr Ser Asp  Lys Lys Val Lys Lys  Leu Lys Gln
    1025                 1030                 1035

Glu Lys  Lys Asp Leu Tyr Ile  Arg Asn Tyr Ile Ala  His Phe Asn
    1040                 1045                 1050

Tyr Ile  Pro His Ala Glu Ile  Ser Leu Leu Glu Val  Leu Glu Asn
    1055                 1060                 1065

Leu Arg  Lys Leu Leu Ser Tyr  Asp Arg Lys Leu Lys  Asn Ala Ile
    1070                 1075                 1080

Met Lys  Ser Ile Val Asp Ile  Leu Lys Glu Tyr Gly  Phe Val Ala
    1085                 1090                 1095

Thr Phe  Lys Ile Gly Ala Asp  Lys Lys Ile Glu Ile  Gln Thr Leu
    1100                 1105                 1110

Glu Ser  Glu Lys Ile Val His  Leu Lys Asn Leu Lys  Lys Lys Lys
    1115                 1120                 1125

Leu Met  Thr Asp Arg Asn Ser  Glu Glu Leu Cys Glu  Leu Val Lys
    1130                 1135                 1140

Val Met  Phe Glu Tyr Lys Ala  Leu Glu
    1145                 1150

<210> SEQ ID NO 52
<211> LENGTH: 36
<212> TYPE: DNA
<213> ORGANISM: Artificial Sequence
<220> FEATURE:
<223> OTHER INFORMATION: Lwa2Cas13a direct repeat

<400> SEQUENCE: 52
gatatagata accccaaaaa cgaagggatc taaaac                              36

<210> SEQ ID NO 53
<211> LENGTH: 3858
<212> TYPE: DNA
<213> ORGANISM: Artificial Sequence
<220> FEATURE:
<223> OTHER INFORMATION: RcsCas13a nucleic acid sequence

<400> SEQUENCE: 53
atgcagattg aaaagtgca gggaaggact attagcgagt ttggggaccc cgcaggagga      60
ctgaagagaa agattagcac cgatggaaag aatcgcaagg aactgccagc acacctgtca    120
agtgatccaa aggccctgat tggacagtgg atctcaggga tcgacaaaat ctaccggaag    180
cccgatagta ggaaatccga tgcaaagca atccactccc caaccctag caaaatgcag      240 tttgacgcaa gggatgacct gggagaggca ttctggaaac tggtgtcaga agctggcctg    300
gctcaggata gtgactatga tcagtttaag cggcgactgc atccatacgg agacaaattt    360
cagcctgctg atagcggagc aaaactgaag ttcgaagccg accccactga gcctcaggcc    420
ttccacggca ggtggtatgg agcaatgtcc aagcgcggga tgacgcaaa ggagctggca    480

```
gtcgctctgt acgaacatct gcacgtcgat gagaaaagaa tcgatggcca gcctaagcgg      540
aatcctaaga ctgataaatt cgctccaggg ctggtggtgg cccgcgctct ggggattgag      600
tcaagcgtgc tgccaagagg aatggctaga ctggctagga attggggcga agaggaaatc      660
cagacttact ttgtcgtgga tgtggccgca tcagtgaagg aggtggctaa agctgctgtg      720
agcgcagcac aggctttcga tccacctcgc caggtcagcg ggagaagtct gagtcccaaa      780
gtggggttcg cactggcaga gcatctggaa agggtgacag gctccaagag gtgctcattc      840
gatcccgcag ccggcccttc tgtcctggca ctgcacgacg aagtgaagaa aacttataaa      900
agactgtgcg cccggggaaa gaatgcagcc agagcttttc cagccgacaa gaccgaactg      960
ctggctctga tgagacatac ccatgagaac agagtccgga atcagatggt cagaatggga     1020
agggtgtcag ataccgagg ccagcaggcc ggggatctgg ctcagtccca ctattggaca     1080
agtgccggcc agacagaaat caaagaaagc gagatctttg tcaggctgtg ggtgggagct     1140
tttgcactgg ctgggcgcag catgaaagca tggattgacc caatgggaa gatcgtgaac     1200 actgagaaga atgatagaga tctgactgcc gccgtcaaca tcagacaggt aatctccaac     1260
aaggagatgt cgctgaggc aatggctcgg cgcggaatct atttcggcga gacaccagag     1320
ctggatagac tgggggcaga gggaaatgaa ggcttcgtgt tcgctctgct gcgatacctg     1380
agagggtgta gaaaccagac ttttcatctg ggggctcggg caggatttct gaaggaaatc     1440
cgcaaggagc tggaaaagac acggtggggc aaggcaaaag aagccgagca tgtggtcctg     1500
accgacaaga cagtggcagc cattagcaga atcattgaca atgacgccaa agccctgggc     1560
gcccggctgc tggcagacct gagcggagct tttgtggcac actatgcaag caaagaacac     1620
ttcagcacac tgtattccga gatcgtcaaa gcagtgaaag acgctcctga agtgtcatcc     1680
gggctgcctc ggctgaagct gctgctgaaa cgggcagacg gagtcagggg atacgtgcat     1740
ggactgcggg ataccgaaa acatgctttc gccactaagc tgccacctcc tccagctcca     1800
cgggaactgg acgaccctgc aacaaaggcc aggtatatcg ctctgctgcg gctgtatgat     1860
ggcccatttc gggcctacgc aagtggaatc actggaactg ccctggcagg acctgctgcc     1920
agagctaaag aggcagctac tgcactggcc cagtccgtga atgtcactaa agcatattcc     1980
gatgtgatgg agggacgcac ctcacgactg aggccaccta atgatggcga aaccctgagg     2040
gaatacctga gtgcactgac tggcgagact gccacagagt ccgggtgca gattggctat     2100 gagtccgact cagagaatgc tagaaagcag gccgagttta tcgagaacta taggcgagat     2160
atgctggcct tcatgttcga ggattacatt cgagcaaagg ggttcgactg gattctgaag     2220
attgaacctg ggccacagc aatgaccaga gcccctgtgc tgccagagcc aatcgataca     2280
cgaggccagt atgaacactg gcaggccgca ctgtacctgg tcatgcactt cgtcccagct     2340
agtgatgtga gcaacctgct gcaccagctg agaaagtggg aagcactgca gggcaaatac     2400
gagctggtcc aggatgggga cgccacagac caggcagatg cccggaggga ggccctggat     2460
ctggtgaaaa ggttccgcga tgtgctggtc ctgtttctga aaacagggga agccagattt     2520
gaaggccgcg ccgctccatt tgatctgaag cctttccggg cactgtttgc taatccagct     2580
actttcgatc ggctgtttat ggccacacca accactgcta ggcccgctga agatgacccc     2640
gagggcgacg gagcctccga accagagctg cgggtcgcca ggacactgcg cgggctgcgc     2700
cagattgcac gatataacca catggcagtg ctgagcgatc tgttcgctaa acataaagtg     2760
cgggatgagg aagtcgcacg cctggccgag attgaggacg aaactcagga aaaatctcag     2820
```

```
attgtcgccg cacaggaact gaggacagat ctgcacgata aagtcatgaa atgccaccct    2880
aaaaccatca gccccgagga gcggcagagt tacgccgccg caatcaaaac cattgaggag    2940
cacaggttcc tggtgggcag agtgtacctg ggggatcacc tgcggctgca tcgcctgatg    3000
atggatgtca tcggccgcct gattgattac gctggcgctt atgagcgcga tactggcact    3060
ttcctgatca acgccagcaa acagctgggg gctggcgctg attgggcagt gaccattgca    3120
ggcgccgcta ataccgacgc acgcacccag acccggaaag acctggcaca tttcaacgtg    3180
ctggatagag ccgacggaac ccccgacctg acagctctgg tgaacagggc aagagaaatg    3240
atggcctacg atcgcaaacg caaaaacgca gtcccacgga gtatcctgga tatgctggct    3300
cggctggggc tgacactgaa gtggcagatg aaggaccacc tgctgcagga cgctacaatc    3360
acccaggctg caatcaaaca cctggataaa gtgcggctga ccgtgggggg ccccgccgcc    3420
gtcaccgaag cacgcttctc acaggactac ctgcagatgg tcgctgcagt gttcaatggg    3480
agcgtgcaga accctaaacc acggcgccgg gatgatgggg acgcctggca caagccaccc    3540
aagcctgcaa ctgctcagtc tcagcctgat cagaaacctc ccaacaaagc accttctgca    3600
gggtccaggc tgccaccccc acaggtcggg gaggtctacg aaggagtcgt ggtcaaagtc    3660
attgataccg gctcactggg ctttctggcc gtggaggggg tggctggcaa tattggcctg    3720
catatctccc gcctgcgacg aatcagagag gacgccatca ttgtcgggcg gagatacaga    3780
ttcagggtcg aaatctatgt ccccccccaag agcaacactt ccaaactgaa cgccgctgac    3840
ctggtgcgaa ttgactga                                                 3858
```

<210> SEQ ID NO 54
<211> LENGTH: 1285
<212> TYPE: PRT
<213> ORGANISM: Artificial Sequence
<220> FEATURE:
<223> OTHER INFORMATION: RcsCas13a amino acid sequence

<400> SEQUENCE: 54

```
Met Gln Ile Gly Lys Val Gln Gly Arg Thr Ile Ser Glu Phe Gly Asp
1               5                   10                  15

Pro Ala Gly Gly Leu Lys Arg Lys Ile Ser Thr Asp Gly Lys Asn Arg
            20                  25                  30

Lys Glu Leu Pro Ala His Leu Ser Ser Asp Pro Lys Ala Leu Ile Gly
        35                  40                  45

Gln Trp Ile Ser Gly Ile Asp Lys Ile Tyr Arg Lys Pro Asp Ser Arg
    50                  55                  60

Lys Ser Asp Gly Lys Ala Ile His Ser Pro Thr Pro Ser Lys Met Gln
65                  70                  75                  80

Phe Asp Ala Arg Asp Asp Leu Gly Glu Ala Phe Trp Lys Leu Val Ser
                85                  90                  95

Glu Ala Gly Leu Ala Gln Asp Ser Asp Tyr Asp Gln Phe Lys Arg Arg
            100                 105                 110

Leu His Pro Tyr Gly Asp Lys Phe Gln Pro Ala Asp Ser Gly Ala Lys
        115                 120                 125

Leu Lys Phe Glu Ala Asp Pro Pro Glu Pro Gln Ala Phe His Gly Arg
    130                 135                 140

Trp Tyr Gly Ala Met Ser Lys Arg Gly Asn Asp Ala Lys Glu Leu Ala
145                 150                 155                 160

Val Ala Leu Tyr Glu His Leu Val Asp Glu Lys Arg Ile Asp Gly
                165                 170                 175
```

```
Gln Pro Lys Arg Asn Pro Lys Thr Asp Lys Phe Ala Pro Gly Leu Val
            180                 185                 190

Val Ala Arg Ala Leu Gly Ile Glu Ser Ser Val Leu Pro Arg Gly Met
        195                 200                 205

Ala Arg Leu Ala Arg Asn Trp Gly Glu Glu Ile Gln Thr Tyr Phe
    210                 215                 220

Val Val Asp Val Ala Ala Ser Val Lys Glu Val Ala Lys Ala Ala Val
225                 230                 235                 240

Ser Ala Ala Gln Ala Phe Asp Pro Arg Gln Val Ser Gly Arg Ser
                245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
            275                 280                 285

Leu Ala Leu His Asp Glu Val Lys Lys Thr Tyr Lys Arg Leu Cys Ala
        290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
        355                 360                 365

Glu Ser Glu Ile Phe Val Arg Leu Trp Val Gly Ala Phe Ala Leu Ala
    370                 375                 380

Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
                405                 410                 415

Val Ile Ser Asn Lys Glu Met Val Ala Glu Ala Met Ala Arg Arg Gly
            420                 425                 430

Ile Tyr Phe Gly Glu Thr Pro Glu Leu Asp Arg Leu Gly Ala Glu Gly
        435                 440                 445

Asn Glu Gly Phe Val Phe Ala Leu Leu Arg Tyr Leu Arg Gly Cys Arg
450                 455                 460

Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
                485                 490                 495

His Val Val Leu Thr Asp Lys Thr Val Ala Ala Ile Arg Ala Ile Ile
            500                 505                 510

Asp Asn Asp Ala Lys Ala Leu Gly Ala Arg Leu Leu Ala Asp Leu Ser
        515                 520                 525

Gly Ala Phe Val Ala His Tyr Ala Ser Lys His Phe Ser Thr Leu
    530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Lys Arg Ala Asp Gly Val Arg
                565                 570                 575

Gly Tyr Val His Gly Leu Arg Asp Thr Arg Lys His Ala Phe Ala Thr
            580                 585                 590

Lys Leu Pro Pro Pro Pro Ala Pro Arg Glu Leu Asp Asp Pro Ala Thr
```

```
                595                 600                 605
    Lys Ala Arg Tyr Ile Ala Leu Leu Arg Leu Tyr Asp Gly Pro Phe Arg
    610                 615                 620

Ala Tyr Ala Ser Gly Ile Thr Gly Thr Ala Leu Ala Gly Pro Ala Ala
    625                 630                 635                 640

Arg Ala Lys Glu Ala Ala Thr Ala Leu Ala Gln Ser Val Asn Val Thr
                    645                 650                 655

Lys Ala Tyr Ser Asp Val Met Glu Gly Arg Thr Ser Arg Leu Arg Pro
                    660                 665                 670

Pro Asn Asp Gly Glu Thr Leu Arg Glu Tyr Leu Ser Ala Leu Thr Gly
                    675                 680                 685

Glu Thr Ala Thr Glu Phe Arg Val Gln Ile Gly Tyr Glu Ser Asp Ser
    690                 695                 700

Glu Asn Ala Arg Lys Gln Ala Glu Phe Ile Glu Asn Tyr Arg Arg Asp
    705                 710                 715                 720

Met Leu Ala Phe Met Phe Glu Asp Tyr Ile Arg Ala Lys Gly Phe Asp
                    725                 730                 735

Trp Ile Leu Lys Ile Glu Pro Gly Ala Thr Ala Met Thr Arg Ala Pro
                    740                 745                 750

Val Leu Pro Glu Pro Ile Asp Thr Arg Gly Gln Tyr Glu His Trp Gln
                    755                 760                 765

Ala Ala Leu Tyr Leu Val Met His Phe Val Pro Ala Ser Asp Val Ser
                    770                 775                 780

Asn Leu Leu His Gln Leu Arg Lys Trp Glu Ala Leu Gln Gly Lys Tyr
    785                 790                 795                 800

Glu Leu Val Gln Asp Gly Asp Ala Thr Asp Gln Ala Asp Ala Arg Arg
                    805                 810                 815

Glu Ala Leu Asp Leu Val Lys Arg Phe Arg Asp Val Leu Val Leu Phe
                    820                 825                 830

Leu Lys Thr Gly Glu Ala Arg Phe Glu Gly Arg Ala Ala Pro Phe Asp
                    835                 840                 845

Leu Lys Pro Phe Arg Ala Leu Phe Ala Asn Pro Ala Thr Phe Asp Arg
                    850                 855                 860

Leu Phe Met Ala Thr Pro Thr Thr Ala Arg Pro Ala Glu Asp Asp Pro
    865                 870                 875                 880

Glu Gly Asp Gly Ala Ser Glu Pro Glu Leu Arg Val Ala Arg Thr Leu
                    885                 890                 895

Arg Gly Leu Arg Gln Ile Ala Arg Tyr Asn His Met Ala Val Leu Ser
                    900                 905                 910

Asp Leu Phe Ala Lys His Lys Val Arg Asp Glu Glu Val Ala Arg Leu
                    915                 920                 925

Ala Glu Ile Glu Asp Glu Thr Gln Glu Lys Ser Gln Ile Val Ala Ala
                    930                 935                 940

Gln Glu Leu Arg Thr Asp Leu His Asp Lys Val Met Lys Cys His Pro
    945                 950                 955                 960

Lys Thr Ile Ser Pro Glu Glu Arg Gln Ser Tyr Ala Ala Ala Ile Lys
                    965                 970                 975

Thr Ile Glu Glu His Arg Phe Leu Val Gly Arg Val Tyr Leu Gly Asp
                    980                 985                 990

His Leu Arg Leu His Arg Leu Met  Met Asp Val Ile Gly  Arg Leu Ile
                    995                 1000                1005

Asp Tyr  Ala Gly Ala Tyr Glu  Arg Asp Thr Gly Thr  Phe Leu Ile
            1010                1015                1020
```

```
Asn Ala Ser Lys Gln Leu Gly Ala Gly Ala Asp Trp Ala Val Thr
    1025                1030                1035

Ile Ala Gly Ala Ala Asn Thr Asp Ala Arg Thr Gln Thr Arg Lys
    1040                1045                1050

Asp Leu Ala His Phe Asn Val Leu Asp Arg Ala Asp Gly Thr Pro
    1055                1060                1065

Asp Leu Thr Ala Leu Val Asn Arg Ala Arg Glu Met Met Ala Tyr
    1070                1075                1080

Asp Arg Lys Arg Lys Asn Ala Val Pro Arg Ser Ile Leu Asp Met
    1085                1090                1095

Leu Ala Arg Leu Gly Leu Thr Leu Lys Trp Gln Met Lys Asp His
    1100                1105                1110

Leu Leu Gln Asp Ala Thr Ile Thr Gln Ala Ala Ile Lys His Leu
    1115                1120                1125

Asp Lys Val Arg Leu Thr Val Gly Gly Pro Ala Ala Val Thr Glu
    1130                1135                1140

Ala Arg Phe Ser Gln Asp Tyr Leu Gln Met Val Ala Ala Val Phe
    1145                1150                1155

Asn Gly Ser Val Gln Asn Pro Lys Pro Arg Arg Arg Asp Asp Gly
    1160                1165                1170

Asp Ala Trp His Lys Pro Pro Lys Pro Ala Thr Ala Gln Ser Gln
    1175                1180                1185

Pro Asp Gln Lys Pro Pro Asn Lys Ala Pro Ser Ala Gly Ser Arg
    1190                1195                1200

Leu Pro Pro Pro Gln Val Gly Glu Val Tyr Glu Gly Val Val Val
    1205                1210                1215

Lys Val Ile Asp Thr Gly Ser Leu Gly Phe Leu Ala Val Glu Gly
    1220                1225                1230

Val Ala Gly Asn Ile Gly Leu His Ile Ser Arg Leu Arg Arg Ile
    1235                1240                1245

Arg Glu Asp Ala Ile Ile Val Gly Arg Arg Tyr Arg Phe Arg Val
    1250                1255                1260

Glu Ile Tyr Val Pro Pro Lys Ser Asn Thr Ser Lys Leu Asn Ala
    1265                1270                1275

Ala Asp Leu Val Arg Ile Asp
    1280                1285

<210> SEQ ID NO 55
<211> LENGTH: 36
<212> TYPE: DNA
<213> ORGANISM: Artificial Sequence
<220> FEATURE:
<223> OTHER INFORMATION: RcsCas13a direct repeat

<400> SEQUENCE: 55
gcctcacatc accgccaaga cgacggcgga ctgaac                      36

<210> SEQ ID NO 56
<211> LENGTH: 3858
<212> TYPE: DNA
<213> ORGANISM: Artificial Sequence
<220> FEATURE:
<223> OTHER INFORMATION: RcrCas13a nucleic acid sequence

<400> SEQUENCE: 56
atgcagattg ggaaagtcca gggcagaacc attagcgagt ttggcgaccc cgcaggaggg    60
```

-continued

```
ctgaaaagga agattagcac cgacggaaag aaccggaaag aactgcccgc ccatctgtca    120
agcgatccaa aggctctgat cggccagtgg attagcggca ttgataagat ctacaggaag    180
cctgattcaa gaaagagcga tggaaaagcc atccatagcc caactccaag caagatgcag    240
tttgatgcca gggacgacct gggggaagca ttctggaaac tggtgtcaga ggctgggctg    300
gctcaggaca gcgattacga tcagtttaaa aggcggctgc atccctatgg ggataagttt    360
cagcccgccg atagcggcgc taaactgaaa ttcgaagctg atcctccaga gccccaggct    420
tttcacggcc gctggtatgg ggcaatgagc aaaagaggaa cgacgctaa agaactggca    480 gcagcactgt atgaacatct gcatgtcgat gaaaaacgaa ttgatggcca gccaaaaagg    540
aacccaaaga cagataaatt cgcaccaggg ctggtcgtgg ccagggcact ggggatcgag    600
agctctgtgc tgccacgggg gatggcaaga ctggcacgga attgggggga agaggaaatc    660
cagacatact tcgtggtcga cgtggcagca agcgtgaagg aagtggcaaa ggcagccgtg    720
agcgccgcac aggccttcga cccacctcgg caggtgtccg gcaggtcact gagcccaaag    780
gtcgggtttg ccctggctga acatctggag cgggtcacag gctccaaaag gtgcagcttc    840
gatcctgcag ctgggccaag cgtcctggcc ctgcacgacg aagtcaagaa aacctataaa    900
cggctgtgcg cccggggaaa gaacgccgca agagcctttc cagcagacaa aacagaactg    960
ctggccctga tgcggcatac ccacgagaac cgggtgagga atcagatggt cagaatgggg   1020
cgggtgagtg agtataggg gcagcaggca ggggacctgg cacagagcca ctactggaca    1080
agcgcaggac agaccgaaat caaggagtca gagattttg tccgcctgtg ggtcggggct   1140
ttcgcactgg ccgggaggtc aatgaaagcc tggattgatc ccatgggaaa gatcgtcaac   1200
actgaaaaga cgatcgcga cctgaccgct gcagtcaaca ttcggcaggt catcagcaac   1260
aaggagatgt ggccgaagc tatggcacga cgggggatct actttggaga aaccccagag   1320
ctggataggc tgggagcaga aggcaatgag ggcttcgtct ttgcactgct gagatacctg   1380
agagggtgca ggaatcagac cttcacctg ggggccaggg cagggttcct gaaagagatt   1440
agaaaagaac tggaaaaaac ccggtggggg aaggccaagg aggcagagca cgtggtcctg   1500
accgataaaa ctgtcgctgc catcagagcc atcatcgaca acgatgccaa ggcactgggg   1560
gcccggctgc tggcagacct gtcaggggct tttgtcgctc actatgccag taaagaacac   1620
tttagcaccc tgtactcaga aattgtcaag gctgtgaagg acgcaccaga ggtgtcatcc   1680
gggctgcccc ggctgaagct gctgctgaag agggcagacg gagtcagagg ctatgtccat   1740
gggctgaggg atacaaggaa acacgccttt gctactaaac tgccaccacc tccagcacca   1800
agggaactgg atgacccagc caccaaagcc agatacatcg cactgctgag actgtacgat   1860
ggaccattca gggcttatgc atccggcatt actgggacag ctctggccgg gccagctgca   1920
cgagccaagg aggccgcaac cgctctggca cagtccgtga atgtcacaaa agcatacagc   1980
gatgtgatgg agggcaggtc aagcagactg aggccaccca acgatgggga aacactgaga   2040
gaatacctga gcgcactgac aggagaaaca gcaacagaat tcgggtcca gattggctat   2100 gaaagcgact cagagaatgc tcggaagcag gccgagttca ttgagaacta tagacgggat   2160
atgctggctt ttatgtttga ggactacatc cgggctaagg ggttcgactg gattctgaaa   2220
atcgagcccg gagcaactgc aatgacacgg gcacctgtgc tgcccgagcc aattgacacc   2280 cggggggcagt acgaacactg gcaggcagca ctgtatctgg taatgcattt cgtgcccgca   2340
tcagatgtca gcaacctgct gcatcagctg aggaagtggg aggccctgca ggggaaatat   2400
gaactggtgc aggatggcga cgcaacagat caggcagacg cacgacgaga ggccctggat   2460
```

```
ctggtcaagc gatttcgcga tgtcctggtg ctgttcctga aacaggaga ggcccggttc    2520 gagggacggg cagctccatt cgacctgaaa cccttccgag cactgttcgc aaatccagca    2580
actttcgatc ggctgtttat ggctacacct accacagcaa ggccagcaga ggatgatccc    2640
gagggggacg gcgcatcaga accagagctg agggtggccc ggactctgag agggctgcgg    2700
cagattgcca ggtataatca catggcagtc ctgagcgatc tgtttgcaaa gcacaaagtc    2760
cgagatgagg aagtcgcaag gctggcagaa attgaagatg agactcagga gaaatcacag    2820
atcgtcgctg cacaggaact gagaaccgac ctgcatgaca aagtcatgaa gtgtcatccc    2880
aaaaccatct ctcctgaaga aagacagtcc tacgccgcag ctattaagac catcgaagag    2940
cataggtttc tggtggggag ggtctatctg ggagatcatc tgcggctgca cagactgatg    3000
atggatgtga ttggacggct gatcgattac gctggagcct acgagaggga tactgggaca    3060
tttctgatca atgcctcaaa gcagctgggg gccggcgcag actgggcagt gacaattgcc    3120
ggggcagcaa acactggcgc caggactcag actcggaagg acctggccca ctttaacgtg    3180
ctggataggg ccgacgggac acctgacctg accgccctgg tgaatcgagc aagagaaatg    3240
atggcatacg atcggaaaag aaaaaacgca gtcccaagat caattctgga tatgctggcc    3300
aggctgggac tgactctgaa atggcagatg aaggatcacc tgctgcagga tgcaactatt    3360
acccaggctg caattaagca tctggacaaa gtgcggctga cagtgggcgg gcctgcagct    3420
gtgactgagg cacgattctc ccaggactac ctgcagatgg tggccgcagt gtttaacggg    3480
tctgtccaga atccaaagcc aaggaggagg acgacggcg acgcatggca taaaccacct    3540
aagccagcaa ctgcacagtc ccagcccgac cagaagccac ccaacaaagc acctagcgca    3600
gggtcacggc tgcccccacc acaggtcggg gaagtctatg aagggtggt ggtgaaagtg    3660 atcgataccg ggtcactggg attcctggca gtcgaagggg tcgcagggaa tatcggcctg    3720
catattagta ggctgaggag aatcagagaa gatgctatta tcgtgggcag agatacagg    3780 ttttgggtcg agatctacgt gcccccccaag tctaataccct ccaaactgaa cgctgctgac    3840
ctggtgcgaa ttgactga                                                    3858
```

<210> SEQ ID NO 57
<211> LENGTH: 1285
<212> TYPE: PRT
<213> ORGANISM: Artificial Sequence
<220> FEATURE:
<223> OTHER INFORMATION: RcrCas13a amino acid sequence

<400> SEQUENCE: 57

```
Met Gln Ile Gly Lys Val Gln Gly Arg Thr Ile Ser Glu Phe Gly Asp
1               5                   10                  15

Pro Ala Gly Gly Leu Lys Arg Lys Ile Ser Thr Asp Gly Lys Asn Arg
            20                  25                  30

Lys Glu Leu Pro Ala His Leu Ser Ser Asp Pro Lys Ala Leu Ile Gly
        35                  40                  45

Gln Trp Ile Ser Gly Ile Asp Lys Ile Tyr Arg Lys Pro Asp Ser Arg
    50                  55                  60

Lys Ser Asp Gly Lys Ala Ile His Ser Pro Thr Pro Ser Lys Met Gln
65                  70                  75                  80

Phe Asp Ala Arg Asp Asp Leu Gly Glu Ala Phe Trp Lys Leu Val Ser
                85                  90                  95

Glu Ala Gly Leu Ala Gln Asp Ser Asp Tyr Asp Gln Phe Lys Arg Arg
            100                 105                 110
```

```
Leu His Pro Tyr Gly Asp Lys Phe Gln Pro Ala Asp Ser Gly Ala Lys
            115                 120                 125

Leu Lys Phe Glu Ala Asp Pro Pro Glu Pro Gln Ala Phe His Gly Arg
        130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
                165                 170                 175

Gln Pro Lys Arg Asn Pro Lys Thr Asp Lys Phe Ala Pro Gly Leu Val
            180                 185                 190

Val Ala Arg Ala Leu Gly Ile Glu Ser Ser Val Leu Pro Arg Gly Met
        195                 200                 205

Ala Arg Leu Ala Arg Asn Trp Gly Glu Glu Ile Gln Thr Tyr Phe
210                 215                 220

Val Val Asp Val Ala Ala Ser Val Lys Glu Val Ala Lys Ala Ala Val
225                 230                 235                 240

Ser Ala Ala Gln Ala Phe Asp Pro Arg Gln Val Ser Gly Arg Ser
                245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
        275                 280                 285

Leu Ala Leu His Asp Glu Val Lys Lys Thr Tyr Lys Arg Leu Cys Ala
        290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
        355                 360                 365

Glu Ser Glu Ile Phe Val Arg Leu Trp Val Gly Ala Phe Ala Leu Ala
        370                 375                 380

Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
                405                 410                 415

Val Ile Ser Asn Lys Glu Met Val Glu Ala Met Ala Arg Arg Gly
            420                 425                 430

Ile Tyr Phe Gly Glu Thr Pro Glu Leu Asp Arg Leu Gly Ala Glu Gly
        435                 440                 445

Asn Glu Gly Phe Val Phe Ala Leu Leu Arg Tyr Leu Arg Gly Cys Arg
450                 455                 460

Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
                485                 490                 495

His Val Val Leu Thr Asp Lys Thr Val Ala Ala Ile Arg Ala Ile Ile
            500                 505                 510

Asp Asn Asp Ala Lys Ala Leu Gly Ala Arg Leu Leu Ala Asp Leu Ser
        515                 520                 525
```

```
Gly Ala Phe Val Ala His Tyr Ala Ser Lys Glu His Phe Ser Thr Leu
530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Lys Arg Ala Asp Gly Val Arg
                565                 570                 575

Gly Tyr Val His Gly Leu Arg Asp Thr Arg Lys His Ala Phe Ala Thr
                580                 585                 590

Lys Leu Pro Pro Pro Ala Pro Arg Glu Leu Asp Asp Pro Ala Thr
                595                 600                 605

Lys Ala Arg Tyr Ile Ala Leu Leu Arg Leu Tyr Asp Gly Pro Phe Arg
610                 615                 620

Ala Tyr Ala Ser Gly Ile Thr Gly Thr Ala Leu Ala Gly Pro Ala Ala
625                 630                 635                 640

Arg Ala Lys Glu Ala Ala Thr Ala Leu Ala Gln Ser Val Asn Val Thr
                645                 650                 655

Lys Ala Tyr Ser Asp Val Met Glu Gly Arg Ser Ser Arg Leu Arg Pro
                660                 665                 670

Pro Asn Asp Gly Glu Thr Leu Arg Glu Tyr Leu Ser Ala Leu Thr Gly
                675                 680                 685

Glu Thr Ala Thr Glu Phe Arg Val Gln Ile Gly Tyr Glu Ser Asp Ser
690                 695                 700

Glu Asn Ala Arg Lys Gln Ala Glu Phe Ile Glu Asn Tyr Arg Arg Asp
705                 710                 715                 720

Met Leu Ala Phe Met Phe Glu Asp Tyr Ile Arg Ala Lys Gly Phe Asp
                725                 730                 735

Trp Ile Leu Lys Ile Glu Pro Gly Ala Thr Ala Met Thr Arg Ala Pro
                740                 745                 750

Val Leu Pro Glu Pro Ile Asp Thr Arg Gly Gln Tyr Glu His Trp Gln
                755                 760                 765

Ala Ala Leu Tyr Leu Val Met His Phe Val Pro Ala Ser Asp Val Ser
770                 775                 780

Asn Leu Leu His Gln Leu Arg Lys Trp Glu Ala Leu Gln Gly Lys Tyr
785                 790                 795                 800

Glu Leu Val Gln Asp Gly Asp Ala Thr Asp Gln Ala Asp Ala Arg Arg
                805                 810                 815

Glu Ala Leu Asp Leu Val Lys Arg Phe Arg Asp Val Leu Val Leu Phe
                820                 825                 830

Leu Lys Thr Gly Glu Ala Arg Phe Glu Gly Arg Ala Ala Pro Phe Asp
                835                 840                 845

Leu Lys Pro Phe Arg Ala Leu Phe Ala Asn Pro Ala Thr Phe Asp Arg
850                 855                 860

Leu Phe Met Ala Thr Pro Thr Thr Ala Arg Pro Ala Glu Asp Asp Pro
865                 870                 875                 880

Glu Gly Asp Gly Ala Ser Glu Pro Glu Leu Arg Val Ala Arg Thr Leu
                885                 890                 895

Arg Gly Leu Arg Gln Ile Ala Arg Tyr Asn His Met Ala Val Leu Ser
                900                 905                 910

Asp Leu Phe Ala Lys His Lys Val Arg Asp Glu Val Ala Arg Leu
                915                 920                 925

Ala Glu Ile Glu Asp Glu Thr Gln Glu Lys Ser Gln Ile Val Ala Ala
930                 935                 940

Gln Glu Leu Arg Thr Asp Leu His Asp Lys Val Met Lys Cys His Pro
```

| | | | | | 945 | | | 950 | | | 955 | | | 960 |

Lys Thr Ile Ser Pro Glu Glu Arg Gln Ser Tyr Ala Ala Ile Lys
                         965                   970                    975

Thr Ile Glu Glu His Arg Phe Leu Val Gly Arg Val Tyr Leu Gly Asp
                  980                 985                   990

His Leu Arg Leu His Arg Leu Met Met Asp Val Ile Gly Arg Leu Ile
               995                1000               1005

Asp Tyr Ala Gly Ala Tyr Glu Arg Asp Thr Gly Thr Phe Leu Ile
     1010                 1015                 1020

Asn Ala Ser Lys Gln Leu Gly Ala Gly Ala Asp Trp Ala Val Thr
     1025                 1030                 1035

Ile Ala Gly Ala Ala Asn Thr Gly Ala Arg Thr Gln Thr Arg Lys
     1040                 1045                 1050

Asp Leu Ala His Phe Asn Val Leu Asp Arg Ala Asp Gly Thr Pro
     1055                 1060                 1065

Asp Leu Thr Ala Leu Val Asn Arg Ala Arg Glu Met Met Ala Tyr
     1070                 1075                 1080

Asp Arg Lys Arg Lys Asn Ala Val Pro Arg Ser Ile Leu Asp Met
     1085                 1090                 1095

Leu Ala Arg Leu Gly Leu Thr Leu Lys Trp Gln Met Lys Asp His
     1100                 1105                 1110

Leu Leu Gln Asp Ala Thr Ile Thr Gln Ala Ala Ile Lys His Leu
     1115                 1120                 1125

Asp Lys Val Arg Leu Thr Val Gly Gly Pro Ala Ala Val Thr Glu
     1130                 1135                 1140

Ala Arg Phe Ser Gln Asp Tyr Leu Gln Met Val Ala Ala Val Phe
     1145                 1150                 1155

Asn Gly Ser Val Gln Asn Pro Lys Pro Arg Arg Arg Asp Asp Gly
     1160                 1165                 1170

Asp Ala Trp His Lys Pro Pro Lys Pro Ala Thr Ala Gln Ser Gln
     1175                 1180                 1185

Pro Asp Gln Lys Pro Pro Asn Lys Ala Pro Ser Ala Gly Ser Arg
     1190                 1195                 1200

Leu Pro Pro Pro Gln Val Gly Glu Val Tyr Glu Gly Val Val Val
     1205                 1210                 1215

Lys Val Ile Asp Thr Gly Ser Leu Gly Phe Leu Ala Val Glu Gly
     1220                 1225                 1230

Val Ala Gly Asn Ile Gly Leu His Ile Ser Arg Leu Arg Arg Ile
     1235                 1240                 1245

Arg Glu Asp Ala Ile Ile Val Gly Arg Arg Tyr Arg Phe Trp Val
     1250                 1255                 1260

Glu Ile Tyr Val Pro Pro Lys Ser Asn Thr Ser Lys Leu Asn Ala
     1265                 1270                 1275

Ala Asp Leu Val Arg Ile Asp
     1280                 1285

<210> SEQ ID NO 58
<211> LENGTH: 36
<212> TYPE: DNA
<213> ORGANISM: Artificial Sequence
<220> FEATURE:
<223> OTHER INFORMATION: RcrCas13a direct repeat

<400> SEQUENCE: 58
gcctcacatc accgccaaga cgacggcgga ctgaac                                         36

<210> SEQ ID NO 59
<211> LENGTH: 3858
<212> TYPE: DNA
<213> ORGANISM: Artificial Sequence
<220> FEATURE:
<223> OTHER INFORMATION: RcdCas13a nucleic acid sequence

<400> SEQUENCE: 59

```
atgcagatcg gcaaagtgca gggaaggact attagcgagt tcggggaccc agcaggagga    60
ctgaagagga agatttctac tgacggaaag aaccggaaag aactgccagc tcacctgtca   120
agcgatccaa aggctctgat tggccagtgg attagtggca ttgacaagat ctaccggaaa   180
ccagatagca gaaaatcaga cggcaaggct atccacagtc ctacaccaag caaaatgcag   240
ttcgacgccc gggatgatct gggggaagca ttctggaaac tggtgagtga agcagggctg   300
gcacaggact cagattatga tcagtttaag cgcaggctgc accttatggg gacaagttt    360
cagcccgctg acagcggcgc aaaactgaag ttcgaggccg atccccctga gccacaggct   420
ttccacggac gctggtatgg ggccatgtca agagggggga acgacgcaaa ggaactggca   480
gctgcactgt atgagcatct gcatgtggac gaaaaaagga ttgatggcca gccaaagagg   540
aacccaaaga ctgataaatt tgcccccggg ctggtggtcg caagggcact ggggatcgag   600
agctcagtgc tgccaagggg gatggccagg ctggccagga ctggggagag ggaggaaatt   660
cagacttatt tcgtcgtgga cgtggcagcc tcagtgaagg aagtggccaa ggctgccgtg   720
tccgctgctc aggcatttga cccacctcga caggtgtcag acggagcct  gtctccaaag   780
gtcgggtttg ccctggcaga gcacctggaa agggtcaccg gaagcaaaag atgcagcttt   840
gatccagcag ctgggccaag tgtcctggca ctgcacgacg aggtgaaaaa gacctataag   900
cgactgtgcg ccagagggaa aaatgccgca agagcttttc agcagacaa  gacagagctg   960
ctggcactga tgagacacac acacgaaaat agggtgcgca accagatggt caggatgggg  1020
agggtcagcg agtatcgggg gacagcaggc ggggatctgg ctcagagcca ttattggact  1080
agcgcagggc agaccgagat taaggagagc gaaatcttcg tgcggctgtg ggtcggggca  1140
tttgccctgg caggccgatc catgaaggcc tggatcgacc ctatggggaa gatcgtgaac  1200
actgagaaga cgaccgggga cctgactgca gcagtgaaca tcaggcaggt catcagcaat  1260
aaggaaatgg tcgccgaggc aatggctaga aggggaatct acttcgggga gactccagag  1320
ctggaccgac tgggggcaga aggaaacgag gggttcgtgt tcgctctgct gcgatacctg  1380
agggggctgta gaaatcagac atttcatctg ggggcaagag ctggctttct gaaagagatt  1440
cggaaagagc tggaaaagac ccggtggggg aaggccaaag aggcagagca tgtggtcctg  1500
acagacaaaa ctgtggcagc tatccgagct atcatcgaca atgatgccaa agcactgggg  1560
gccagactgc tggcagatct gtccggcgcc tttgtcgccc actacgcaag caaggagcac  1620
ttttctacac tgtattctga tcgtcaag gctgtgaagg atgcacctga agtcagttca  1680
ggactgccca ggctgaagct gctgctgaaa agggccgatg gggtgcgcgg gtatgtccac  1740
gggctgaggg atacaagaaa acatgccttc gcaacaaagc tgccacccc  acctgccccca  1800
agagagctgac gatcccgc aaccaaggcc aggtacatcg ccctgctgcg cctgtatgac  1860
ggcccattca gagcttacgc atccgggatt acagggactg cactggctgg cccagcagct  1920
agggccaaag aggcagcaac agctctggct cagtccgtga atgtcactaa ggcctactct  1980
gacgtgatgg aaggacggtc atcacggctg aggcctccca atgacggaga gactctgaga  2040
```

```
gaatacctgt ctgcactgac tggggaaact gcaacagagt tcgggtcca gatcggatac    2100 gaaagcgaca gcgaaaacgc aagaaaacag gctgagttta ttgagaatta ccggagagat   2160
atgctggctt ttatgttcga ggattatatc agagccaagg ggttcgattg gattctgaaa   2220
attgagcccg ggcaacagc catgactagg gcaccagtgc tgcccgaacc tatcgataca    2280
cgagggcagt acgagcattg gcaggctgca ctgtatctgg tcatgcattt cgtgccagcc   2340
tcagacgtgt ctaacctgct gcaccagctg cggaaatggg aagccctgca ggggaagtac   2400
gagctggtcc aggacgggga cgccacagac caggccgacg cccggcggga agctctggac   2460
ctggtcaagc ggttccgaga tgtcctggtg ctgttcctga aaactggcga ggcacgcttc   2520
gagggaaggg ctgctccttt tgacctgaag ccattccgag ctctgtttgc caccccgca    2580 acattcgatc gcctgtttat ggcaacacct accacagctc gaccagccga ggatgatcca   2640 gaggggacg gggcatccga gcctgaactg cgggtcgcaa ggacactgcg ggggctgcgg    2700
cagatcgcac ggtacaatca catggcagtc ctgtcagacc tgttcgccaa acataaggtg   2760
cgcgatgaag aggtggcaag gctggccgag attgaggatg aaacccagga agtcacag    2820 atcgtcgccg cacaggagct gcggaccgac ctgcacgaca aggtcatgaa gtgccaccct   2880
aagacaatta gccccgagga gcgccagagc tacgcagcag ccatcaaaac tatcgaagag   2940
catagatttc tggtggggag ggtctatctg ggggatcatc tgcgactgca ccggctgatg   3000
atggacgtga tcgccgcct gattgactat gctggagcct atgaaagaga tactggcaca   3060
ttcctgatca atgcaagcaa acagctgggg gccggcgcag actgggcagt gacaatcgcc   3120
ggggccgcca atacagatgc tagaactcag acacggaagg atctggctca cttcaacgtg   3180
ctggatcggg ctgatgggac ccccgacctg actgcactgg tgaatcgcgc acgggaaatg   3240
atggcctacg atcggaagag aaaaaatgcc gtcccaagga gcattctgga tatgctggca   3300
cggctgggac tgaccctgaa gtggcagatg aaggatcacc tgctgcagga tgcaaccatt   3360
acccaggcag ctatcaagca cctggacaag gtgagactga ccgtgggcgg accagcagca   3420
gtcacagaag ctcggttctc tcaggactac ctgcagatgg tggctgcagt gtttaacgga   3480
tcagtgcaga accccaagcc acggcgcagg gacgacggag atgcttggca taaacctcct   3540
aagccagcca ccgcccagag ccagccagat cagaaacctc caacaaagc accttccgca    3600 gggtcccggc tgccccctcc acaggtggga gaggtctacg aaggcgtggt cgtcaaagtc   3660
attgatactg atctctgggg gttcctggct gtcgaaggcg tcgctggaaa tattggcctg   3720
cacatctccc gactgaggcg gattcgggag gatgctatca ttgtcggacg aaggtatagg   3780
ttccgggtgg aaatctacgt gcctccaaag agcaacactt ccaaactgaa cgctgccgac   3840
ctggtgcgga ttgattga                                                3858
```

<210> SEQ ID NO 60
<211> LENGTH: 1285
<212> TYPE: PRT
<213> ORGANISM: Artificial Sequence
<220> FEATURE:
<223> OTHER INFORMATION: RcdCas13a amino acid sequence

<400> SEQUENCE: 60

Met Gln Ile Gly Lys Val Gln Gly Arg Thr Ile Ser Glu Phe Gly Asp
1               5                   10                  15

Pro Ala Gly Gly Leu Lys Arg Lys Ile Ser Thr Asp Gly Lys Asn Arg
            20                  25                  30

Lys Glu Leu Pro Ala His Leu Ser Ser Asp Pro Lys Ala Leu Ile Gly

```
            35                  40                  45
Gln Trp Ile Ser Gly Ile Asp Lys Ile Tyr Arg Lys Pro Asp Ser Arg
 50                  55                  60

Lys Ser Asp Gly Lys Ala Ile His Ser Pro Thr Pro Ser Lys Met Gln
 65                  70                  75                  80

Phe Asp Ala Arg Asp Asp Leu Gly Glu Ala Phe Trp Lys Leu Val Ser
                     85                  90                  95

Glu Ala Gly Leu Ala Gln Asp Ser Asp Tyr Asp Gln Phe Lys Arg Arg
                100                 105                 110

Leu His Pro Tyr Gly Asp Lys Phe Gln Pro Ala Asp Ser Gly Ala Lys
                115                 120                 125

Leu Lys Phe Glu Ala Asp Pro Glu Pro Gln Ala Phe His Gly Arg
130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
                165                 170                 175

Gln Pro Lys Arg Asn Pro Lys Thr Asp Lys Phe Ala Pro Gly Leu Val
                180                 185                 190

Val Ala Arg Ala Leu Gly Ile Glu Ser Ser Val Leu Pro Arg Gly Met
                195                 200                 205

Ala Arg Leu Ala Arg Asn Trp Gly Glu Glu Ile Gln Thr Tyr Phe
210                 215                 220

Val Val Asp Val Ala Ala Ser Val Lys Glu Val Ala Lys Ala Ala Val
225                 230                 235                 240

Ser Ala Ala Gln Ala Phe Asp Pro Arg Gln Val Ser Gly Arg Ser
                245                 250                 255

Leu Ser Pro Lys Val Gly Phe Ala Leu Ala Glu His Leu Glu Arg Val
                260                 265                 270

Thr Gly Ser Lys Arg Cys Ser Phe Asp Pro Ala Ala Gly Pro Ser Val
                275                 280                 285

Leu Ala Leu His Asp Glu Val Lys Lys Thr Tyr Lys Arg Leu Cys Ala
                290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
                340                 345                 350

Leu Ala Gln Ser His Tyr Trp Thr Ser Ala Gly Gln Thr Glu Ile Lys
                355                 360                 365

Glu Ser Glu Ile Phe Val Arg Leu Trp Val Gly Ala Phe Ala Leu Ala
                370                 375                 380

Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
                405                 410                 415

Val Ile Ser Asn Lys Glu Met Val Ala Glu Ala Met Ala Arg Arg Gly
                420                 425                 430

Ile Tyr Phe Gly Glu Thr Pro Glu Leu Asp Arg Leu Gly Ala Glu Gly
                435                 440                 445

Asn Glu Gly Phe Val Phe Ala Leu Leu Arg Tyr Leu Arg Gly Cys Arg
                450                 455                 460
```

-continued

```
Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
                485                 490                 495

His Val Val Leu Thr Asp Lys Thr Val Ala Ala Ile Arg Ala Ile Ile
            500                 505                 510

Asp Asn Asp Ala Lys Ala Leu Gly Ala Arg Leu Leu Ala Asp Leu Ser
        515                 520                 525

Gly Ala Phe Val Ala His Tyr Ala Ser Lys Glu His Phe Ser Thr Leu
    530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Lys Arg Ala Asp Gly Val Arg
                565                 570                 575

Gly Tyr Val His Gly Leu Arg Asp Thr Arg Lys His Ala Phe Ala Thr
            580                 585                 590

Lys Leu Pro Pro Pro Ala Pro Arg Glu Leu Asp Asp Pro Ala Thr
        595                 600                 605

Lys Ala Arg Tyr Ile Ala Leu Leu Arg Leu Tyr Asp Gly Pro Phe Arg
610                 615                 620

Ala Tyr Ala Ser Gly Ile Thr Gly Thr Ala Leu Ala Gly Pro Ala Ala
625                 630                 635                 640

Arg Ala Lys Glu Ala Ala Thr Ala Leu Ala Gln Ser Val Asn Val Thr
                645                 650                 655

Lys Ala Tyr Ser Asp Val Met Glu Gly Arg Ser Ser Arg Leu Arg Pro
                660                 665                 670

Pro Asn Asp Gly Glu Thr Leu Arg Glu Tyr Leu Ser Ala Leu Thr Gly
            675                 680                 685

Glu Thr Ala Thr Glu Phe Arg Val Gln Ile Gly Tyr Glu Ser Asp Ser
    690                 695                 700

Glu Asn Ala Arg Lys Gln Ala Glu Phe Ile Glu Asn Tyr Arg Arg Asp
705                 710                 715                 720

Met Leu Ala Phe Met Phe Glu Asp Tyr Ile Arg Ala Lys Gly Phe Asp
                725                 730                 735

Trp Ile Leu Lys Ile Glu Pro Gly Ala Thr Ala Met Thr Arg Ala Pro
            740                 745                 750

Val Leu Pro Glu Pro Ile Asp Thr Arg Gly Gln Tyr Glu His Trp Gln
        755                 760                 765

Ala Ala Leu Tyr Leu Val Met His Phe Val Pro Ala Ser Asp Val Ser
    770                 775                 780

Asn Leu Leu His Gln Leu Arg Lys Trp Glu Ala Leu Gln Gly Lys Tyr
785                 790                 795                 800

Glu Leu Val Gln Asp Gly Asp Ala Thr Asp Gln Ala Asp Ala Arg Arg
                805                 810                 815

Glu Ala Leu Asp Leu Val Lys Arg Phe Arg Asp Val Leu Val Leu Phe
                820                 825                 830

Leu Lys Thr Gly Glu Ala Arg Phe Glu Gly Arg Ala Ala Pro Phe Asp
            835                 840                 845

Leu Lys Pro Phe Arg Ala Leu Phe Ala Asn Pro Ala Thr Phe Asp Arg
        850                 855                 860

Leu Phe Met Ala Thr Pro Thr Thr Ala Arg Pro Ala Glu Asp Asp Pro
865                 870                 875                 880
```

```
Glu Gly Asp Gly Ala Ser Glu Pro Glu Leu Arg Val Ala Arg Thr Leu
                885                 890                 895

Arg Gly Leu Arg Gln Ile Ala Arg Tyr Asn His Met Ala Val Leu Ser
        900                 905                 910

Asp Leu Phe Ala Lys His Lys Val Arg Asp Glu Glu Val Ala Arg Leu
        915                 920                 925

Ala Glu Ile Glu Asp Glu Thr Gln Glu Lys Ser Gln Ile Val Ala Ala
930                 935                 940

Gln Glu Leu Arg Thr Asp Leu His Asp Lys Val Met Lys Cys His Pro
945                 950                 955                 960

Lys Thr Ile Ser Pro Glu Glu Arg Gln Ser Tyr Ala Ala Ala Ile Lys
                965                 970                 975

Thr Ile Glu Glu His Arg Phe Leu Val Gly Arg Val Tyr Leu Gly Asp
                980                 985                 990

His Leu Arg Leu His Arg Leu Met Met Asp Val Ile Gly Arg Leu Ile
                995                 1000                1005

Asp Tyr Ala Gly Ala Tyr Glu Arg Asp Thr Gly Thr Phe Leu Ile
        1010                1015                1020

Asn Ala Ser Lys Gln Leu Gly Ala Gly Ala Asp Trp Ala Val Thr
        1025                1030                1035

Ile Ala Gly Ala Ala Asn Thr Asp Ala Arg Thr Gln Thr Arg Lys
        1040                1045                1050

Asp Leu Ala His Phe Asn Val Leu Asp Arg Ala Asp Gly Thr Pro
        1055                1060                1065

Asp Leu Thr Ala Leu Val Asn Arg Ala Arg Glu Met Met Ala Tyr
        1070                1075                1080

Asp Arg Lys Arg Lys Asn Ala Val Pro Arg Ser Ile Leu Asp Met
        1085                1090                1095

Leu Ala Arg Leu Gly Leu Thr Leu Lys Trp Gln Met Lys Asp His
        1100                1105                1110

Leu Leu Gln Asp Ala Thr Ile Thr Gln Ala Ala Ile Lys His Leu
        1115                1120                1125

Asp Lys Val Arg Leu Thr Val Gly Gly Pro Ala Ala Val Thr Glu
        1130                1135                1140

Ala Arg Phe Ser Gln Asp Tyr Leu Gln Met Val Ala Ala Val Phe
        1145                1150                1155

Asn Gly Ser Val Gln Asn Pro Lys Pro Arg Arg Arg Asp Asp Gly
        1160                1165                1170

Asp Ala Trp His Lys Pro Pro Lys Pro Ala Thr Ala Gln Ser Gln
        1175                1180                1185

Pro Asp Gln Lys Pro Pro Asn Lys Ala Pro Ser Ala Gly Ser Arg
        1190                1195                1200

Leu Pro Pro Pro Gln Val Gly Glu Val Tyr Glu Gly Val Val Val
        1205                1210                1215

Lys Val Ile Asp Thr Gly Ser Leu Gly Phe Leu Ala Val Glu Gly
        1220                1225                1230

Val Ala Gly Asn Ile Gly Leu His Ile Ser Arg Leu Arg Arg Ile
        1235                1240                1245

Arg Glu Asp Ala Ile Ile Val Gly Arg Arg Tyr Arg Phe Arg Val
        1250                1255                1260

Glu Ile Tyr Val Pro Pro Lys Ser Asn Thr Ser Lys Leu Asn Ala
        1265                1270                1275

Ala Asp Leu Val Arg Ile Asp
```

<210> SEQ ID NO 61
<211> LENGTH: 36
<212> TYPE: DNA
<213> ORGANISM: Artificial Sequence
<220> FEATURE:
<223> OTHER INFORMATION: RcdCas13a direct repeat

<400> SEQUENCE: 61
gcctcacatc accgccaaga cgacggcgga ctgaac        36

<210> SEQ ID NO 62
<211> LENGTH: 3537
<212> TYPE: DNA
<213> ORGANISM: Artificial Sequence
<220> FEATURE:
<223> OTHER INFORMATION: PguCas13b nucleic acid sequence

<400> SEQUENCE: 62

| | | |
|---|---|---|
| atgacagagc agagcgagag gccctacaac ggcacctact acaccctgga agataagcac | 60 |
| ttctgggccg cctttctgaa cctggccaga cacaacgcct acatcaccct gacacacatc | 120 |
| gaccggcagc tggcctacag caaggccgac atcaccaacg accaggacgt gctgagcttc | 180 |
| aaggccctgt ggaagaactt cgacaacgac ctggaaagaa agagccggct gcggagcctg | 240 |
| atcctgaagc acttcagctt tctggaaggc ccgcttacg gcaagaagct gttcgagtct | 300 |
| aagagcagcg gcaacaagag cagcaagaac aaagagctga ccaagaaaga gaaagaggaa | 360 |
| ctgcaggcca cgctctgag cctggacaac ctgaagtcta tcctgttcga cttcctgcag | 420 |
| aagctgaagg acttccggaa ctactacagc cactaccggc acagcggaag cagcgagctg | 480 |
| cctctgttcg acggcaacat gctgcagcgg ctgtacaacg tgttcgacgt gtccgtgcag | 540 |
| cgcgtgaaga tcgaccacga gcacaacgat gaggtggacc tcactacca cttcaaccac | 600 |
| ctcgtgcgga agggcaagaa ggacagatac ggccacaacg acaacccag cttcaagcac | 660 |
| cacttcgtgg acggcgaagg catggttaca gaagccggcc tgctgttctt cgtgtccctg | 720 |
| ttcctggaaa agcgggacgc catctggatg cagaagaaga tccggggctt caaaggcggc | 780 |
| accgagacat accagcagat gaccaacgag gtgttctgcc ggtccagaat cagcctgcct | 840 |
| aagctgaagc tggaaagcct gcggatggac gactggatgc tgctggacat gctgaacgaa | 900 |
| ctcgtgcggt gccccaagcc tctgtacgac agactgagag aggacgaccg ggcctgcttt | 960 |
| agagtgcccg tggatatcct gcctgacgag gacgatacag atggcggcgg agaggacccc | 1020 |
| ttcaagaata ccctcgtccg gcaccaggac agattccctt acttcgccct gcggtacttc | 1080 |
| gacctgaaga aggtgttcac cagcctgcgg ttccacatcg atctgggcac ctaccactt | 1140 |
| gccatctaca gaagatgat cggcgagcag cccgaggaca gacacctgac cagaaacctg | 1200 |
| tacggcttcg gccggatcca ggacttcgcc gaagaacaca gacccgagga atggaagcgg | 1260 |
| ctcgtcagag atctggacta cttcgagaca ggcgacaagc cctacatcag ccagacaagc | 1320 |
| ccacactacc acatcgagaa gggaaagatc ggcctgagat tcatgcccga gggccagcat | 1380 |
| ctttggccct ctccagaagt gggcaccacc agaaccggca gatctaagta cgcccaggac | 1440 |
| aagagactga ccgccgaggc ctttctgtct gtgcacgagc tgatgcctat gatgttctac | 1500 |
| tacttcctgc tgcgcgagaa gtacagcgag gaagtgtctg ccgagagagt gcagggcaga | 1560 |
| atcaagcgcg tgatcgagga tgtgtacgcc gtgtacgatg cctttgccag ggacgagatc | 1620 |
| aacacccggg atgagctgga tgcctgcctg gccgataagg gcatcagaag aggccatctg | 1680 |

```
cctcgccaga tgatcgccat cctgagccaa gagcacaagg acatggaaga gaagattcgg    1740
aagaaactgc aagagatgat ggccgacacc gaccaccggc tggatatgct ggatagacag    1800
accgaccgga agatcagaat cggccggaag aatgccggac tgcctaagag cggagtgatc    1860
gccgattggc tcgtgcggga catgatgaga tttcagcccg tggccaagga cgccagcgga    1920
aagcctctga caactccaa ggccaacagc accgagtacc ggatgctgca gagagccctg    1980
gctctgtttg gaggcgagaa agagaggctg accccatact tccggcagat gaatctgacc    2040
ggcggaaaca accctcatcc ttttctgcac gaaactcgct gggagagcca caccaacatc    2100
ctgtcctttt accggtccta cctgagagcc cgcaaggcct cctcgaaag gatcggcaga    2160 tccgacagag tggaaaaccg gccatttctg ctgctgaaag agcccaagac cgacagacag    2220
acactggtgg ctggatggaa gggcgagttc catctgccaa gaggcatctt cacagaggcc    2280
gtgcgggatt gcctgatcga gatgggacac gatgaagtgg ccagctacaa agaagtggga    2340
ttcatggcca aggccgtgcc actgtacttt gagagagcct gcgaggacag ggtgcagccc    2400
ttttacgaca gccccttcaa cgtgggcaac agcctgaagc ctaagaaggg cagattcctg    2460
agcaaagagg aacgggccga agagtgggag cggggcaaag agagattccg ggatctcgaa    2520
gcctggtcct atagcgccgc cagaagaatc gaggacgcct ttgccggcat cgagtatgct    2580
agccccggaa acaagaagaa aatcgagcag ctcctgcggg acctgagcct gtgggaagcc    2640
tttgagagca agctgaaagt gcgggccgac cggatcaatc tggccaagct gaagaaagaa    2700
atcctggaag cccaagaaca cccctaccac gacttcaaga gctggcagaa gttcgagcgc    2760
gagctgcggc tggtcaagaa ccaggatatc atcacctgga tgatgtgccg cgacctgatg    2820
gaagaaaaca aggtggaagg cctggacacc ggcacactgt acctgaagga catcagaccc    2880
aacgtgcaag agcagggcag cctgaacgtg ctgaacagag tgaagcccat gagactgccc    2940
gtggtggtgt acagagccga tagcagaggc cacgtgcaca agaagaagc ccctctggcc    3000 accgtgtaca tcgaggaaag agacaccaag ctgctgaagc agggcaactt caagtccttc    3060
gtgaaggaca ggcggctgaa cggcctgttc tccttcgttg atactggcgg actggccatg    3120
gaacagtacc ccatctccaa gctgagagtg gaatacgagc tggccaagta ccagaccgcc    3180
agagtgtgtg tgttcgagct gacccctgaga ctggaagagt ccctgctgac ccggtatcct    3240
catctgcccg acgagagctt cagagagatg ctggaatctt ggagcgaccc tctgctggcc    3300 aaaatggcctg aactgcacgg aaaagtgcgg ctgctgatcg ccgtgcggaa tgcctttagc    3360
cacaatcagt accctatgta cgacgaggcc gtgttcagct ccatccggaa gtacgatcct    3420
agcagccccg acgccatcga agagagaatg ggcctgaata tcgcccaccg cctgtctgag    3480
gaagtgaagc aggccaaaga aaccgtggaa cggatcattc aggccggatc ccttcaa     3537
```

<210> SEQ ID NO 63
<211> LENGTH: 1179
<212> TYPE: PRT
<213> ORGANISM: Artificial Sequence
<220> FEATURE:
<223> OTHER INFORMATION: PguCas13b amino acid sequence

<400> SEQUENCE: 63

Met Thr Glu Gln Ser Glu Arg Pro Tyr Asn Gly Thr Tyr Tyr Thr Leu
1               5                   10                  15

Glu Asp Lys His Phe Trp Ala Ala Phe Leu Asn Leu Ala Arg His Asn
            20                  25                  30

-continued

Ala Tyr Ile Thr Leu Thr His Ile Asp Arg Gln Leu Ala Tyr Ser Lys
            35                  40                  45

Ala Asp Ile Thr Asn Asp Gln Asp Val Leu Ser Phe Lys Ala Leu Trp
 50                  55                  60

Lys Asn Phe Asp Asn Asp Leu Glu Arg Lys Ser Arg Leu Arg Ser Leu
 65                  70                  75                  80

Ile Leu Lys His Phe Ser Phe Leu Glu Gly Ala Ala Tyr Gly Lys Lys
                    85                  90                  95

Leu Phe Glu Ser Lys Ser Ser Gly Asn Lys Ser Lys Asn Lys Glu
                100                 105                 110

Leu Thr Lys Lys Glu Lys Glu Leu Gln Ala Asn Ala Leu Ser Leu
                115                 120                 125

Asp Asn Leu Lys Ser Ile Leu Phe Asp Phe Leu Gln Lys Leu Lys Asp
        130                 135                 140

Phe Arg Asn Tyr Tyr Ser His Tyr Arg His Ser Gly Ser Ser Glu Leu
145                 150                 155                 160

Pro Leu Phe Asp Gly Asn Met Leu Gln Arg Leu Tyr Asn Val Phe Asp
                165                 170                 175

Val Ser Val Gln Arg Val Lys Ile Asp His Glu His Asn Asp Glu Val
                180                 185                 190

Asp Pro His Tyr His Phe Asn His Leu Val Arg Lys Gly Lys Lys Asp
        195                 200                 205

Arg Tyr Gly His Asn Asp Asn Pro Ser Phe Lys His Phe Val Asp
210                 215                 220

Gly Glu Gly Met Val Thr Glu Ala Gly Leu Leu Phe Phe Val Ser Leu
225                 230                 235                 240

Phe Leu Glu Lys Arg Asp Ala Ile Trp Met Gln Lys Lys Ile Arg Gly
                245                 250                 255

Phe Lys Gly Gly Thr Glu Thr Tyr Gln Gln Met Thr Asn Glu Val Phe
                260                 265                 270

Cys Arg Ser Arg Ile Ser Leu Pro Lys Leu Lys Leu Glu Ser Leu Arg
        275                 280                 285

Met Asp Asp Trp Met Leu Leu Asp Met Leu Asn Glu Leu Val Arg Cys
        290                 295                 300

Pro Lys Pro Leu Tyr Asp Arg Leu Arg Glu Asp Asp Arg Ala Cys Phe
305                 310                 315                 320

Arg Val Pro Val Asp Ile Leu Pro Asp Glu Asp Thr Asp Gly Gly
                325                 330                 335

Gly Glu Asp Pro Phe Lys Asn Thr Leu Val Arg His Gln Asp Arg Phe
                340                 345                 350

Pro Tyr Phe Ala Leu Arg Tyr Phe Asp Leu Lys Lys Val Phe Thr Ser
                355                 360                 365

Leu Arg Phe His Ile Asp Leu Gly Thr Tyr His Phe Ala Ile Tyr Lys
        370                 375                 380

Lys Met Ile Gly Glu Gln Pro Glu Asp Arg His Leu Thr Arg Asn Leu
385                 390                 395                 400

Tyr Gly Phe Gly Arg Ile Gln Asp Phe Ala Glu Glu His Arg Pro Glu
                405                 410                 415

Glu Trp Lys Arg Leu Val Arg Asp Leu Asp Tyr Phe Glu Thr Gly Asp
                420                 425                 430

Lys Pro Tyr Ile Ser Gln Thr Ser Pro His Tyr His Ile Glu Lys Gly
        435                 440                 445

Lys Ile Gly Leu Arg Phe Met Pro Glu Gly Gln His Leu Trp Pro Ser

```
            450              455              460
Pro Glu Val Gly Thr Thr Arg Thr Gly Arg Ser Lys Tyr Ala Gln Asp
465                  470                  475                  480

Lys Arg Leu Thr Ala Glu Ala Phe Leu Ser Val His Glu Leu Met Pro
                485                  490                  495

Met Met Phe Tyr Tyr Phe Leu Leu Arg Glu Lys Tyr Ser Glu Glu Val
            500                  505                  510

Ser Ala Glu Arg Val Gln Gly Arg Ile Lys Arg Val Ile Glu Asp Val
        515                  520                  525

Tyr Ala Val Tyr Asp Ala Phe Ala Arg Asp Glu Ile Asn Thr Arg Asp
    530                  535                  540

Glu Leu Asp Ala Cys Leu Ala Asp Lys Gly Ile Arg Arg Gly His Leu
545                  550                  555                  560

Pro Arg Gln Met Ile Ala Ile Leu Ser Gln Glu His Lys Asp Met Glu
                565                  570                  575

Glu Lys Ile Arg Lys Lys Leu Gln Glu Met Met Ala Asp Thr Asp His
            580                  585                  590

Arg Leu Asp Met Leu Asp Arg Gln Thr Asp Arg Lys Ile Arg Ile Gly
        595                  600                  605

Arg Lys Asn Ala Gly Leu Pro Lys Ser Gly Val Ile Ala Asp Trp Leu
    610                  615                  620

Val Arg Asp Met Met Arg Phe Gln Pro Val Ala Lys Asp Ala Ser Gly
625                  630                  635                  640

Lys Pro Leu Asn Asn Ser Lys Ala Asn Ser Thr Glu Tyr Arg Met Leu
                645                  650                  655

Gln Arg Ala Leu Ala Leu Phe Gly Gly Glu Lys Glu Arg Leu Thr Pro
            660                  665                  670

Tyr Phe Arg Gln Met Asn Leu Thr Gly Gly Asn Pro His Pro Phe
        675                  680                  685

Leu His Glu Thr Arg Trp Glu Ser His Thr Asn Ile Leu Ser Phe Tyr
    690                  695                  700

Arg Ser Tyr Leu Arg Ala Arg Lys Ala Phe Leu Glu Arg Ile Gly Arg
705                  710                  715                  720

Ser Asp Arg Val Glu Asn Arg Pro Phe Leu Leu Lys Glu Pro Lys
                725                  730                  735

Thr Asp Arg Gln Thr Leu Val Ala Gly Trp Lys Gly Glu Phe His Leu
            740                  745                  750

Pro Arg Gly Ile Phe Thr Glu Ala Val Arg Asp Cys Leu Ile Glu Met
        755                  760                  765

Gly His Asp Glu Val Ala Ser Tyr Lys Glu Val Gly Phe Met Ala Lys
    770                  775                  780

Ala Val Pro Leu Tyr Phe Glu Arg Ala Cys Glu Asp Arg Val Gln Pro
785                  790                  795                  800

Phe Tyr Asp Ser Pro Phe Asn Val Gly Asn Ser Leu Lys Pro Lys Lys
                805                  810                  815

Gly Arg Phe Leu Ser Lys Glu Glu Arg Ala Glu Glu Trp Glu Arg Gly
            820                  825                  830

Lys Glu Arg Phe Arg Asp Leu Glu Ala Trp Ser Tyr Ser Ala Ala Arg
        835                  840                  845

Arg Ile Glu Asp Ala Phe Ala Gly Ile Glu Tyr Ala Ser Pro Gly Asn
    850                  855                  860

Lys Lys Lys Ile Glu Gln Leu Leu Arg Asp Leu Ser Leu Trp Glu Ala
865                  870                  875                  880
```

```
Phe Glu Ser Lys Leu Lys Val Arg Ala Asp Arg Ile Asn Leu Ala Lys
            885                 890                 895

Leu Lys Lys Glu Ile Leu Glu Ala Gln Glu His Pro Tyr His Asp Phe
        900                 905                 910

Lys Ser Trp Gln Lys Phe Glu Arg Glu Leu Arg Leu Val Lys Asn Gln
    915                 920                 925

Asp Ile Ile Thr Trp Met Met Cys Arg Asp Leu Met Glu Glu Asn Lys
930                 935                 940

Val Glu Gly Leu Asp Thr Gly Thr Leu Tyr Leu Lys Asp Ile Arg Pro
945                 950                 955                 960

Asn Val Gln Glu Gln Gly Ser Leu Asn Val Leu Asn Arg Val Lys Pro
                965                 970                 975

Met Arg Leu Pro Val Val Val Tyr Arg Ala Asp Ser Arg Gly His Val
            980                 985                 990

His Lys Glu Glu Ala Pro Leu Ala Thr Val Tyr Ile Glu Glu Arg Asp
        995                1000               1005

Thr Lys Leu Leu Lys Gln Gly Asn Phe Lys Ser Phe Val Lys Asp
    1010               1015               1020

Arg Arg Leu Asn Gly Leu Phe Ser Phe Val Asp Thr Gly Gly Leu
    1025               1030               1035

Ala Met Glu Gln Tyr Pro Ile Ser Lys Leu Arg Val Glu Tyr Glu
    1040               1045               1050

Leu Ala Lys Tyr Gln Thr Ala Arg Val Cys Val Phe Glu Leu Thr
    1055               1060               1065

Leu Arg Leu Glu Glu Ser Leu Leu Thr Arg Tyr Pro His Leu Pro
    1070               1075               1080

Asp Glu Ser Phe Arg Glu Met Leu Glu Ser Trp Ser Asp Pro Leu
    1085               1090               1095

Leu Ala Lys Trp Pro Glu Leu His Gly Lys Val Arg Leu Leu Ile
    1100               1105               1110

Ala Val Arg Asn Ala Phe Ser His Asn Gln Tyr Pro Met Tyr Asp
    1115               1120               1125

Glu Ala Val Phe Ser Ser Ile Arg Lys Tyr Asp Pro Ser Ser Pro
    1130               1135               1140

Asp Ala Ile Glu Glu Arg Met Gly Leu Asn Ile Ala His Arg Leu
    1145               1150               1155

Ser Glu Glu Val Lys Gln Ala Lys Glu Thr Val Glu Arg Ile Ile
    1160               1165               1170

Gln Ala Gly Ser Leu Gln
    1175

<210> SEQ ID NO 64
<211> LENGTH: 36
<212> TYPE: DNA
<213> ORGANISM: Artificial Sequence
<220> FEATURE:
<223> OTHER INFORMATION: PguCas13b direct repeat

<400> SEQUENCE: 64
gttggatcta ccctctattt gaagggtaca cacaac                            36

<210> SEQ ID NO 65
<211> LENGTH: 2943
<212> TYPE: DNA
<213> ORGANISM: Artificial Sequence
<220> FEATURE:
```

<223> OTHER INFORMATION: RfxCas13d-SV40NLS nucleic acid sequence

<400> SEQUENCE: 65

```
atgagcccca agaagaagag aaaggtggag gccagcatcg aaaaaaaaaa gtccttcgcc     60
aagggcatgg gcgtgaagtc cacactcgtg tccggctcca aagtgtacat gacaaccttc    120
gccgaaggca gcgacgccag gctggaaaag atcgtggagg gcgacagcat caggagcgtg    180
aatgagggcg aggccttcag cgctgaaatg gccgataaaa acgccggcta taagatcggc    240
aacgccaaat tcagccatcc taagggctac gccgtggtgg ctaacaaccc tctgtataca    300
ggacccgtcc agcaggatat gctcggcctg aaggaaactc tggaaaagag gtacttcggc    360
gagagcgctg atggcaatga caatatttgt atccaggtga tccataacat cctggacatt    420
gaaaaaatcc tcgccgaata cattaccaac gccgcctacg ccgtcaacaa tatctccggc    480
ctggataagg acattattgg attcggcaag ttctccacag tgtatacctc gacgaattc     540
aaagaccccg agcaccatag gccgctttc aacaataacg ataagctcat caacgccatc    600
aaggcccagt atgacgagtt cgacaacttc ctcgataacc ccagactcgg ctatttcggc    660
caggcctttt tcagcaagga gggcagaaat tacatcatca attacggcaa cgaatgctat    720
gacattctgg ccctcctgag cggactggcg cactgggtgg tcgctaacaa cgaagaagag    780
tccaggatct ccaggacctg gctctacaac ctcgataaga acctcgacaa cgaatacatc    840
tccaccctca actacctcta cgacaggatc accaatgagc tgaccaactc cttctccaag    900
aactccgccg ccaacgtgaa ctatattgcc gaaactctgg aatcaacccc tgccgaattc    960
gccgaacaat atttcagatt cagcattatg aagagcaga aaaacctcgg attcaatatc   1020
accaagctca gggaagtgat gctggacagg aaggatatgt ccgagatcag gaaaaatcat   1080
aaggtgttcg actccatcag gaccaaggtc tacaccatga tggactttgt gatttatagg   1140
tattacatcg aagaggatgc caaggtggct gccgccaata agtccctccc cgataatgag   1200
aagtccctga gcgagaagga tatctttgtg attaacctga gggctccctt caacgacgac   1260
cagaaggatg ccctctacta cgatgaagct aatagaattt ggagaaagct cgaaaatatc   1320
atgcacaaca tcaaggaatt tagggaaaac aagacaagag agtataagaa gaaggacgcc   1380
cctagactgc ccagaatcct gcccgctggc cgtgatgttt ccgccttcag caaactcatg   1440
tatgccctga ccatgttcct ggatggcaag gagatcaacg acctcctgac caccctgatt   1500
aataaattcg ataacatcca gagcttcctg aaggtgatgc ctctcatcgg agtcaacgct   1560
aagttcgtgg aggaatacgc cttttttcaaa gactccgcca agatcgccga tgagctgagg   1620
ctgatcaagt ccttcgctag aatgggagaa cctattgccg atgccaggag ggccatgtat   1680
atcgacgcca tccgtatttt aggaaccaac ctgtcctatg atgagctcaa ggccctcgcc   1740
gacaccttt ccctggacga gaacggaaac aagctcaaga aggcaagca cggcatgaga   1800
aatttcatta ttaataacgt gatcagcaat aaaaggttcc actacctgat cagatacggt   1860
gatcctgccc cctccatga tcgccaaa acgaggccc tggtgaagtt cgtgctcggc   1920
aggatcgctg acatccagaa aaaacagggc cagaacggca agaaccagat cgacaggtac   1980
tacgaaactt gtatcggaaa ggataagggc aagagcgtga cgaaaaggt ggacgctctc   2040
acaaagatca tcaccggaat gaactacgac caattcgaca agaaaaggag cgtcattgag   2100
gacaccggca gggaaaacgc cgagagggag aagtttaaaa agatcatcag cctgtacctc   2160
accgtgatct accacatcct caagaatatt gtcaatatca cgccaggta cgtcatcgga   2220
ttccattgcg tcgagcgtga tgctcaactg tacaaggaga aaggctacga catcaatctc   2280
```

-continued

```
aagaaactgg aagagaaggg attcagctcc gtcaccaagc tctgcgctgg cattgatgaa    2340
actgcccccg ataagagaaa ggacgtggaa aaggagatgg ctgaaagagc caaggagagc    2400
attgacagcc tcgagagcgc caaccccaag ctgtatgcca attacatcaa atacagcgac    2460
gagaagaaag ccgaggagtt caccaggcag attaacaggg agaaggccaa aaccgccctg    2520
aacgcctacc tgaggaacac caagtggaat gtgatcatca gggaggacct cctgagaatt    2580
gacaacaaga catgtaccct gttcgcaaac aaggccgtcg ccctggaagt ggccaggtat    2640
gtccacgcct atatcaacga cattgccgag gtcaattcct acttccaact gtaccattac    2700
atcatgcaga gaattatcat gaatgagagg tacgagaaaa gcagcggaaa ggtgtccgag    2760
tacttcgacg ctgtgaatga cgagaagaag tacaacgata ggctcctgaa actgctgtgt    2820
gtgcctttcg gctactgtat ccccaggttt aagaacctga gcatcgaggc cctgttcgat    2880
aggaacgagg ccgccaagtt cgacaaggag aaaaagaagg tgtccggcaa ttccggatcc    2940
gga                                                                 2943
```

<210> SEQ ID NO 66
<211> LENGTH: 981
<212> TYPE: PRT
<213> ORGANISM: Artificial Sequence
<220> FEATURE:
<223> OTHER INFORMATION: RfxCas13d-SV40NLS amino acid sequence

<400> SEQUENCE: 66

```
Met Ser Pro Lys Lys Arg Lys Val Glu Ala Ser Ile Glu Lys Lys
1               5                   10                  15

Lys Ser Phe Ala Lys Gly Met Gly Val Lys Ser Thr Leu Val Ser Gly
            20                  25                  30

Ser Lys Val Tyr Met Thr Thr Phe Ala Glu Gly Ser Asp Ala Arg Leu
        35                  40                  45

Glu Lys Ile Val Glu Gly Asp Ser Ile Arg Ser Val Asn Glu Gly Glu
    50                  55                  60

Ala Phe Ser Ala Glu Met Ala Asp Lys Asn Ala Gly Tyr Lys Ile Gly
65                  70                  75                  80

Asn Ala Lys Phe Ser His Pro Lys Gly Tyr Ala Val Val Ala Asn Asn
                85                  90                  95

Pro Leu Tyr Thr Gly Pro Val Gln Gln Asp Met Leu Gly Leu Lys Glu
            100                 105                 110

Thr Leu Glu Lys Arg Tyr Phe Gly Glu Ser Ala Asp Gly Asn Asp Asn
        115                 120                 125

Ile Cys Ile Gln Val Ile His Asn Ile Leu Asp Ile Glu Lys Ile Leu
    130                 135                 140

Ala Glu Tyr Ile Thr Asn Ala Ala Tyr Ala Val Asn Asn Ile Ser Gly
145                 150                 155                 160

Leu Asp Lys Asp Ile Ile Gly Phe Gly Lys Phe Ser Thr Val Tyr Thr
                165                 170                 175

Tyr Asp Glu Phe Lys Asp Pro Glu His His Arg Ala Ala Phe Asn Asn
            180                 185                 190

Asn Asp Lys Leu Ile Asn Ala Ile Lys Ala Gln Tyr Asp Glu Phe Asp
        195                 200                 205

Asn Phe Leu Asp Asn Pro Arg Leu Gly Tyr Phe Gly Gln Ala Phe Phe
    210                 215                 220

Ser Lys Glu Gly Arg Asn Tyr Ile Ile Asn Tyr Gly Asn Glu Cys Tyr
225                 230                 235                 240
```

```
Asp Ile Leu Ala Leu Leu Ser Gly Leu Ala His Trp Val Val Ala Asn
                245                 250                 255

Asn Glu Glu Glu Ser Arg Ile Ser Arg Thr Trp Leu Tyr Asn Leu Asp
            260                 265                 270

Lys Asn Leu Asp Asn Glu Tyr Ile Ser Thr Leu Asn Tyr Leu Tyr Asp
        275                 280                 285

Arg Ile Thr Asn Glu Leu Thr Asn Ser Phe Ser Lys Asn Ser Ala Ala
    290                 295                 300

Asn Val Asn Tyr Ile Ala Glu Thr Leu Gly Ile Asn Pro Ala Glu Phe
305                 310                 315                 320

Ala Glu Gln Tyr Phe Arg Phe Ser Ile Met Lys Glu Gln Lys Asn Leu
                325                 330                 335

Gly Phe Asn Ile Thr Lys Leu Arg Glu Val Met Leu Asp Arg Lys Asp
            340                 345                 350

Met Ser Glu Ile Arg Lys Asn His Lys Val Phe Asp Ser Ile Arg Thr
        355                 360                 365

Lys Val Tyr Thr Met Met Asp Phe Val Ile Tyr Arg Tyr Tyr Ile Glu
    370                 375                 380

Glu Asp Ala Lys Val Ala Ala Asn Lys Ser Leu Pro Asp Asn Glu
385                 390                 395                 400

Lys Ser Leu Ser Glu Lys Asp Ile Phe Val Ile Asn Leu Arg Gly Ser
                405                 410                 415

Phe Asn Asp Asp Gln Lys Asp Ala Leu Tyr Tyr Asp Glu Ala Asn Arg
            420                 425                 430

Ile Trp Arg Lys Leu Glu Asn Ile Met His Asn Ile Lys Glu Phe Arg
        435                 440                 445

Gly Asn Lys Thr Arg Glu Tyr Lys Lys Lys Asp Ala Pro Arg Leu Pro
    450                 455                 460

Arg Ile Leu Pro Ala Gly Arg Asp Val Ser Ala Phe Ser Lys Leu Met
465                 470                 475                 480

Tyr Ala Leu Thr Met Phe Leu Asp Gly Lys Glu Ile Asn Asp Leu Leu
                485                 490                 495

Thr Thr Leu Ile Asn Lys Phe Asp Asn Ile Gln Ser Phe Leu Lys Val
            500                 505                 510

Met Pro Leu Ile Gly Val Asn Ala Lys Phe Val Glu Glu Tyr Ala Phe
        515                 520                 525

Phe Lys Asp Ser Ala Lys Ile Ala Asp Glu Leu Arg Leu Ile Lys Ser
    530                 535                 540

Phe Ala Arg Met Gly Glu Pro Ile Ala Asp Ala Arg Arg Ala Met Tyr
545                 550                 555                 560

Ile Asp Ala Ile Arg Ile Leu Gly Thr Asn Leu Ser Tyr Asp Glu Leu
                565                 570                 575

Lys Ala Leu Ala Asp Thr Phe Ser Leu Asp Glu Asn Gly Asn Lys Leu
            580                 585                 590

Lys Lys Gly Lys His Gly Met Arg Asn Phe Ile Ile Asn Asn Val Ile
        595                 600                 605

Ser Asn Lys Arg Phe His Tyr Leu Ile Arg Tyr Gly Asp Pro Ala His
    610                 615                 620

Leu His Glu Ile Ala Lys Asn Glu Ala Val Val Lys Phe Val Leu Gly
625                 630                 635                 640

Arg Ile Ala Asp Ile Gln Lys Lys Gln Gly Gln Asn Gly Lys Asn Gln
                645                 650                 655
```

```
Ile Asp Arg Tyr Tyr Glu Thr Cys Ile Gly Lys Asp Lys Gly Lys Ser
            660                 665                 670

Val Ser Glu Lys Val Asp Ala Leu Thr Lys Ile Ile Thr Gly Met Asn
        675                 680                 685

Tyr Asp Gln Phe Asp Lys Lys Arg Ser Val Ile Glu Asp Thr Gly Arg
    690                 695                 700

Glu Asn Ala Glu Arg Glu Lys Phe Lys Lys Ile Ile Ser Leu Tyr Leu
705                 710                 715                 720

Thr Val Ile Tyr His Ile Leu Lys Asn Ile Val Asn Ile Asn Ala Arg
                725                 730                 735

Tyr Val Ile Gly Phe His Cys Val Glu Arg Asp Ala Gln Leu Tyr Lys
            740                 745                 750

Glu Lys Gly Tyr Asp Ile Asn Leu Lys Lys Leu Glu Glu Lys Gly Phe
        755                 760                 765

Ser Ser Val Thr Lys Leu Cys Ala Gly Ile Asp Glu Thr Ala Pro Asp
    770                 775                 780

Lys Arg Lys Asp Val Glu Lys Glu Met Ala Glu Arg Ala Lys Glu Ser
785                 790                 795                 800

Ile Asp Ser Leu Glu Ser Ala Asn Pro Lys Leu Tyr Ala Asn Tyr Ile
                805                 810                 815

Lys Tyr Ser Asp Glu Lys Lys Ala Glu Glu Phe Thr Arg Gln Ile Asn
            820                 825                 830

Arg Glu Lys Ala Lys Thr Ala Leu Asn Ala Tyr Leu Arg Asn Thr Lys
        835                 840                 845

Trp Asn Val Ile Ile Arg Glu Asp Leu Leu Arg Ile Asp Asn Lys Thr
    850                 855                 860

Cys Thr Leu Phe Ala Asn Lys Ala Val Ala Leu Glu Val Ala Arg Tyr
865                 870                 875                 880

Val His Ala Tyr Ile Asn Asp Ile Ala Glu Val Asn Ser Tyr Phe Gln
                885                 890                 895

Leu Tyr His Tyr Ile Met Gln Arg Ile Ile Met Asn Glu Arg Tyr Glu
            900                 905                 910

Lys Ser Ser Gly Lys Val Ser Glu Tyr Phe Asp Ala Val Asn Asp Glu
        915                 920                 925

Lys Lys Tyr Asn Asp Arg Leu Leu Lys Leu Leu Cys Val Pro Phe Gly
    930                 935                 940

Tyr Cys Ile Pro Arg Phe Lys Asn Leu Ser Ile Glu Ala Leu Phe Asp
945                 950                 955                 960

Arg Asn Glu Ala Ala Lys Phe Asp Lys Glu Lys Lys Val Ser Gly
                965                 970                 975

Asn Ser Gly Ser Gly
            980

<210> SEQ ID NO 67
<211> LENGTH: 30
<212> TYPE: DNA
<213> ORGANISM: Artificial Sequence
<220> FEATURE:
<223> OTHER INFORMATION: RfxCas13d direct repeat

<400> SEQUENCE: 67
aacccctacc aactggtcgg ggtttgaaac                                    30

<210> SEQ ID NO 68
<211> LENGTH: 24
<212> TYPE: DNA
```

```
<213> ORGANISM: Artificial Sequence
<220> FEATURE:
<223> OTHER INFORMATION: SV40 Nuclear Localization Signaling nucleic
      acid sequence

<400> SEQUENCE: 68
ccaaagaaga agcggaaggt cggt                                              24

<210> SEQ ID NO 69
<211> LENGTH: 7
<212> TYPE: PRT
<213> ORGANISM: Artificial Sequence
<220> FEATURE:
<223> OTHER INFORMATION: SV40 Nuclear Localization Signaling amino acid
      sequence

<400> SEQUENCE: 69

Pro Lys Lys Lys Arg Lys Val
1               5

<210> SEQ ID NO 70
<211> LENGTH: 1479
<212> TYPE: DNA
<213> ORGANISM: Artificial Sequence
<220> FEATURE:
<223> OTHER INFORMATION: CMV-BD-2xms2-PPT-exon-bGHpA repair template

<400> SEQUENCE: 70
tagttattaa tagtaatcaa ttacggggtc attagttcat agcccatata tggagttccg        60
cgttacataa cttacggtaa atggcccgcc tggctgaccg cccaacgacc cccgcccatt       120
gacgtcaata atgacgtatg ttcccatagt aacgccaata gggactttcc attgacgtca       180
atgggtggag tatttacggt aaactgccca cttggcagta catcaagtgt atcatatgcc       240
aagtacgccc cctattgacg tcaatgacgg taaatggccc gcctggcatt atgcccagta       300
catgacctta tgggactttc ctacttggca gtacatctac gtattagtca tcgctattac       360
catggtgatg cggttttggc agtacatcaa tgggcgtgga tagcggtttg actcacgggg       420
atttccaagt ctccacccca ttgacgtcaa tgggagtttg ttttggcacc aaaatcaacg       480
ggactttcca aaatgtcgta caactccgcc ccattgacg caaatgggcg gtaggcgtgt       540
acggtgggag gtctatataa gcagagctgg tttagtgaac cgtcggatct tccatttcgg       600
gtgtcgtgac gtacgaatac gatctagacc ctgcatcctc tctgggacac tcaacaccct       660
cacggacagc ccgaattcga cccaagctga cgggagcaca tgaggatcac ccatgtgcca       720
cgagcgacat gaggatcacc catgtcgctt tcactagtct gtggtgtgat atccatggcg       780
gcctacttat cctgtccctt ttttttccac aggagcgcac catcttcttc aaggacgacg       840
gcaactacaa gacccgcgcc gaggtgaagt tcgaggcga caccctggtg aaccgcatcg       900
agctgaaggg catcgacttc aaggaggacg gcaacatcct ggggcacaag ctggagtaca       960
actacaacag ccacaacgtc tatatcatgg ccgacaagca agaacggc atcaaggtga       1020 acttcaagat ccgccacaac atcgaggacg gcagcgtgca gctcgccgac cactaccagc       1080
agaacacccc catcggcgac ggccccgtgc tgctgcccga caaccactac ctgagcaccc       1140
agtccgccct gagcaaagac cccaacgaga agcgcgatca catggtcctg ctggagttcg       1200
tgaccgccgc cgggatcact ctcggcatgg acgagctgta caagtaacta gagctcgctg       1260
atcagcctcg actgtgcctt ctagttgcca gccatctgtt gtttgcccct ccccgtgcc       1320 ttccttgacc ctggaaggtg ccactcccac tgtcctttcc taataaaatg aggaaattgc       1380
```

| | | |
|---|---|---|
| atcgcattgt ctgagtaggt gtcattctat tctggggggt ggggtggggc aggacagcaa | 1440 | |
| gggggaggat tgggaagaga atagcaggca tgctgggga | 1479 | |

<210> SEQ ID NO 71
<211> LENGTH: 3357
<212> TYPE: DNA
<213> ORGANISM: Artificial Sequence
<220> FEATURE:
<223> OTHER INFORMATION: PinCas13b nucleic acid sequence

<400> SEQUENCE: 71

| | |
|---|---|
| atgaccgagc agaacgagaa gccctacaac ggcacctact acaccctgga agataagcac | 60 |
| ttctgggccg cctttctgaa cctggccaga cacaacgcct acatcacact ggcccacatc | 120 |
| gacagacagc tggcctacag caaggccgac atcaccaacg acgaggacat cctgttcttc | 180 |
| aaaggccagt ggaagaacct ggacaacgac ctggaacgga aggccagact gagaagcctg | 240 |
| atcctgaagc acttcagctt tctggaaggc gccgcttacg gcaagaagct gtttgagtct | 300 |
| cagagcagcg gcaacaagag cagcaagaag aaagagctgt ccaagaaaga gaaagaggaa | 360 |
| ctgcaggcca acgctctgag cctggacaat ctgaagtcta tcctgttcga cttcctgcag | 420 |
| aagctgaagg acttccggaa ctactacagc cactacagac accccgagag cagcgagctg | 480 |
| cctctgttcg atggcaacat gctgcagcgg ctgtacaacg tgttcgacgt gtccgtgcag | 540 |
| cgcgtgaaga gagatcacga gcacaacgac aaggtggacc tcaccggca cttcaatcac | 600 |
| ctcgtgcgga agggcaagaa ggataagtac ggcaacaacg ataacccgtt cttcaagcac | 660 |
| cacttcgtgg accgcgaggg cacagtgaca gaagccggac tgctgttctt cgtgtccctg | 720 |
| ttcctggaaa gcggggacgc catctggatg cagaagaaga tccggggctt taaaggcggc | 780 |
| accgaggcct accagcagat gaccaatgag gtgttctgcc gcagccggat cagcctgcct | 840 |
| aagctgaagc tggaaagcct gagaaccgac gactggatgc tgctggacat gctgaacgaa | 900 |
| ctcgtgcggt gccacaagag cctgtacgat agactgagag aagaggaccg ggccagattc | 960 |
| agagtgcccg tggatatcct gagcgacgag gatgataccg acggcaccga agaggatccc | 1020 |
| ttcaagaaca ctctcgtgcg gcaccaggac agattcccct acttcgccct gcggtacttc | 1080 |
| gacctgaaga aggtgttcac cagcctgcgg ttccacatcg atctgggcac ctaccacttc | 1140 |
| gccatctaca gaagaacat cggcgagcag cccgaggaca dacacctgac cagaaacctg | 1200 |
| tacggcttcg gccggatcca ggacttcgcc gaagaacaca gacccgagga atggaagcgg | 1260 |
| ctcgtcagag atctggacta cttcgagaca ggcgacaagc cttacatcac ccagaccaca | 1320 |
| cctcactacc acatcgagaa gggaaagatc ggcctgagat tcgtgcccga gggacagcat | 1380 |
| cttttggccct ctccagaagt gggcgccacc agaacaggca gatctaagta cgcccaggac | 1440 |
| aagagactga ccgccgaggc ctttctgtct gtgcacgagc tgatgcctat gatgttctac | 1500 |
| tacttcctgc tgcgcgagaa gtacagcgag gaagtgtctg ccgagaaggt gcagggcaga | 1560 |
| atcaagcgcg tgatcgagga tgtgtacgcc gtgtacgatg ccttcgccag ggacgagatc | 1620 |
| aacaccagag atgagctgga tgcctgcctg gccgacaagg gcattagaag aggccatctg | 1680 |
| ccaagacaga tgatcgccat cctgagccaa gagcacaagg acatggaaga gaaagtgcgg | 1740 |
| aagaaactgc aagagatgat tgccgacacc gaccaccggc tggatatgct ggatagacag | 1800 |
| accgaccgga agatcagaat cggccggaaa aatgccggcc tgccaaagtc tggcgtggtg | 1860 |
| gctgattggc tcgtgcggga catgatgaga ttccagcctg tggccaagga caccagcggc | 1920 |
| aagcctctga acaactccaa ggccaacagc accgagtacc ggatgctgca gagagccctg | 1980 |

```
gctctgtttg gaggcgagaa agagaggctg accccatact tccggcagat gaatctgacc    2040
ggcggaaaca accctcatcc ttttctgcac gaaactcgct gggagagcca caccaatatc    2100
ctgtccttct accggtccta cctggaagcc cggaaggctt tcctgcagtc catcggcaga    2160
tccgacagag tggaaaacca ccggtttctg ctgctgaaag agcccaagac cgacaggcag    2220
actctggtgg ctggatggaa gggcgagttc catctgccta gaggcatctt tacagaggcc    2280
gtgcgcgact gcctgatcga gatgggctat gatgaagtgg gcagctacaa gaagtggga    2340 ttcatggcca aggccgtgcc tctgtacttt gagagagcca gcaaggaccg ggtgcagccc    2400
ttctacgact accccttcaa cgtgggcaac agcctgaagc ctaagaaggg cagattcctg    2460
tccaaagaga gcgggccga agagtgggag agcggcaaag agagattccg gctggccaag    2520
ctgaagaaag aaatcctcga agccaaagag caccccctacc acgacttcaa gagctggcag    2580
aagttcgagc gcgagctgag actggtcaag aaccaggaca tcatcacctg gatgatgtgc    2640
cgggacctga tggaagaaaa caaagtggaa ggcctggata caggcaccct gtacctgaag    2700
gacatcagga ccgacgtgca agagcagggc agcctgaacg tgctgaacag agtgaagccc    2760
atgagactgc ccgtggtggt gtacagagcc gatagcagag ccacgtgca caaagaacag    2820 gcccctctgg ccaccgtgta catcgaggaa agagacacca agctgctgaa gcagggcaac    2880
ttcaagtcct tcgtgaagga cagacggctg aatggcctgt tcagcttcgt ggatactggc    2940
gccctggcca tggaacagta cccatctct aaactgcgcg tggaatacga gctggccaaa    3000
taccagaccg ccagagtgtg cgccttcgag cagacactgg aactggaaga gagcctgctg    3060
acccggtatc ctcatctgcc cgacaagaac tttcggaaga tgctcgaatc ttggagcgac    3120
cctctgctgg ataagtggcc tgacctgcac ggaaatgtgc ggctgctgat cgccgtgcgg    3180
aatgccttta gccacaatca gtaccctatg tacgacgaga cactgtttag ctccatccgg    3240
aagtacgacc ctagcagccc tgacgccatt gaggaacgga tgggcctgaa tatcgcccac    3300
agactgtctg aggaagtgaa gcaggccaaa gaaatggtgg aacggatcat tcaggcc     3357
```

<210> SEQ ID NO 72
<211> LENGTH: 1119
<212> TYPE: PRT
<213> ORGANISM: Artificial Sequence
<220> FEATURE:
<223> OTHER INFORMATION: PinCas13b amino acid sequence

<400> SEQUENCE: 72

```
Met Thr Glu Gln Asn Glu Lys Pro Tyr Asn Gly Thr Tyr Tyr Thr Leu
1               5                   10                  15

Glu Asp Lys His Phe Trp Ala Ala Phe Leu Asn Leu Ala Arg His Asn
            20                  25                  30

Ala Tyr Ile Thr Leu Ala His Ile Asp Arg Gln Leu Ala Tyr Ser Lys
        35                  40                  45

Ala Asp Ile Thr Asn Asp Glu Asp Ile Leu Phe Phe Lys Gly Gln Trp
    50                  55                  60

Lys Asn Leu Asp Asn Asp Leu Glu Arg Lys Ala Arg Leu Arg Ser Leu
65                  70                  75                  80

Ile Leu Lys His Phe Ser Phe Leu Glu Gly Ala Ala Tyr Gly Lys Lys
                85                  90                  95

Leu Phe Glu Ser Gln Ser Ser Gly Asn Lys Ser Ser Lys Lys Lys Glu
            100                 105                 110

Leu Ser Lys Lys Glu Lys Glu Glu Leu Gln Ala Asn Ala Leu Ser Leu
```

```
            115                 120                 125
Asp Asn Leu Lys Ser Ile Leu Phe Asp Phe Leu Gln Lys Leu Lys Asp
        130                 135                 140
Phe Arg Asn Tyr Tyr Ser His Tyr Arg His Pro Glu Ser Ser Glu Leu
145                 150                 155                 160
Pro Leu Phe Asp Gly Asn Met Leu Gln Arg Leu Tyr Asn Val Phe Asp
                165                 170                 175
Val Ser Val Gln Arg Val Lys Arg Asp His Glu His Asn Asp Lys Val
                180                 185                 190
Asp Pro His Arg His Phe Asn His Leu Val Arg Lys Gly Lys Lys Asp
                195                 200                 205
Lys Tyr Gly Asn Asn Asp Asn Pro Phe Phe Lys His His Phe Val Asp
        210                 215                 220
Arg Glu Gly Thr Val Thr Glu Ala Gly Leu Leu Phe Phe Val Ser Leu
225                 230                 235                 240
Phe Leu Glu Lys Arg Asp Ala Ile Trp Met Gln Lys Lys Ile Arg Gly
                245                 250                 255
Phe Lys Gly Gly Thr Glu Ala Tyr Gln Gln Met Thr Asn Glu Val Phe
                260                 265                 270
Cys Arg Ser Arg Ile Ser Leu Pro Lys Leu Lys Leu Glu Ser Leu Arg
        275                 280                 285
Thr Asp Asp Trp Met Leu Leu Asp Met Leu Asn Glu Leu Val Arg Cys
        290                 295                 300
His Lys Ser Leu Tyr Asp Arg Leu Arg Glu Glu Asp Arg Ala Arg Phe
305                 310                 315                 320
Arg Val Pro Val Asp Ile Leu Ser Asp Glu Asp Thr Asp Gly Thr
                325                 330                 335
Glu Glu Asp Pro Phe Lys Asn Thr Leu Val Arg His Gln Asp Arg Phe
                340                 345                 350
Pro Tyr Phe Ala Leu Arg Tyr Phe Asp Leu Lys Lys Val Phe Thr Ser
        355                 360                 365
Leu Arg Phe His Ile Asp Leu Gly Thr Tyr His Phe Ala Ile Tyr Lys
        370                 375                 380
Lys Asn Ile Gly Glu Gln Pro Glu Asp Arg His Leu Thr Arg Asn Leu
385                 390                 395                 400
Tyr Gly Phe Gly Arg Ile Gln Asp Phe Ala Glu Glu His Arg Pro Glu
                405                 410                 415
Glu Trp Lys Arg Leu Val Arg Asp Leu Asp Tyr Phe Glu Thr Gly Asp
                420                 425                 430
Lys Pro Tyr Ile Thr Gln Thr Thr Pro His Tyr His Ile Glu Lys Gly
        435                 440                 445
Lys Ile Gly Leu Arg Phe Val Pro Glu Gly Gln His Leu Trp Pro Ser
        450                 455                 460
Pro Glu Val Gly Ala Thr Arg Thr Gly Arg Ser Lys Tyr Ala Gln Asp
465                 470                 475                 480
Lys Arg Leu Thr Ala Glu Ala Phe Leu Ser Val His Glu Leu Met Pro
                485                 490                 495
Met Met Phe Tyr Tyr Phe Leu Leu Arg Glu Lys Tyr Ser Glu Val
                500                 505                 510
Ser Ala Glu Lys Val Gln Gly Arg Ile Lys Arg Val Ile Glu Asp Val
        515                 520                 525
Tyr Ala Val Tyr Asp Ala Phe Ala Arg Asp Glu Ile Asn Thr Arg Asp
        530                 535                 540
```

```
Glu Leu Asp Ala Cys Leu Ala Asp Lys Gly Ile Arg Arg Gly His Leu
545                 550                 555                 560

Pro Arg Gln Met Ile Ala Ile Leu Ser Gln Glu His Lys Asp Met Glu
                565                 570                 575

Glu Lys Val Arg Lys Lys Leu Gln Glu Met Ile Ala Asp Thr Asp His
            580                 585                 590

Arg Leu Asp Met Leu Asp Arg Gln Thr Asp Arg Lys Ile Arg Ile Gly
                595                 600                 605

Arg Lys Asn Ala Gly Leu Pro Lys Ser Gly Val Val Ala Asp Trp Leu
        610                 615                 620

Val Arg Asp Met Met Arg Phe Gln Pro Val Ala Lys Thr Ser Gly
625                 630                 635                 640

Lys Pro Leu Asn Asn Ser Lys Ala Asn Ser Thr Glu Tyr Arg Met Leu
                645                 650                 655

Gln Arg Ala Leu Ala Leu Phe Gly Gly Glu Lys Glu Arg Leu Thr Pro
            660                 665                 670

Tyr Phe Arg Gln Met Asn Leu Thr Gly Gly Asn Asn Pro His Pro Phe
        675                 680                 685

Leu His Glu Thr Arg Trp Glu Ser His Thr Asn Ile Leu Ser Phe Tyr
    690                 695                 700

Arg Ser Tyr Leu Glu Ala Arg Lys Ala Phe Leu Gln Ser Ile Gly Arg
705                 710                 715                 720

Ser Asp Arg Val Glu Asn His Arg Phe Leu Leu Leu Lys Glu Pro Lys
                725                 730                 735

Thr Asp Arg Gln Thr Leu Val Ala Gly Trp Lys Gly Glu Phe His Leu
            740                 745                 750

Pro Arg Gly Ile Phe Thr Glu Ala Val Arg Asp Cys Leu Ile Glu Met
        755                 760                 765

Gly Tyr Asp Glu Val Gly Ser Tyr Lys Glu Val Gly Phe Met Ala Lys
    770                 775                 780

Ala Val Pro Leu Tyr Phe Glu Arg Ala Ser Lys Asp Arg Val Gln Pro
785                 790                 795                 800

Phe Tyr Asp Tyr Pro Phe Asn Val Gly Asn Ser Leu Lys Pro Lys Lys
                805                 810                 815

Gly Arg Phe Leu Ser Lys Glu Lys Arg Ala Glu Glu Trp Glu Ser Gly
            820                 825                 830

Lys Glu Arg Phe Arg Leu Ala Lys Leu Lys Lys Glu Ile Leu Glu Ala
        835                 840                 845

Lys Glu His Pro Tyr His Asp Phe Lys Ser Trp Gln Lys Phe Glu Arg
    850                 855                 860

Glu Leu Arg Leu Val Lys Asn Gln Asp Ile Ile Thr Trp Met Met Cys
865                 870                 875                 880

Arg Asp Leu Met Glu Glu Asn Lys Val Glu Gly Leu Asp Thr Gly Thr
                885                 890                 895

Leu Tyr Leu Lys Asp Ile Arg Thr Asp Val Gln Glu Gln Gly Ser Leu
            900                 905                 910

Asn Val Leu Asn Arg Val Lys Pro Met Arg Leu Pro Val Val Val Tyr
        915                 920                 925

Arg Ala Asp Ser Arg Gly His Val His Lys Glu Gln Ala Pro Leu Ala
    930                 935                 940

Thr Val Tyr Ile Glu Glu Arg Asp Thr Lys Leu Leu Lys Gln Gly Asn
945                 950                 955                 960
```

```
Phe Lys Ser Phe Val Lys Asp Arg Arg Leu Asn Gly Leu Phe Ser Phe
                965                 970                 975

Val Asp Thr Gly Ala Leu Ala Met Glu Gln Tyr Pro Ile Ser Lys Leu
            980                 985                 990

Arg Val Glu Tyr Glu Leu Ala Lys Tyr Gln Thr Ala Arg Val Cys Ala
        995                 1000                1005

Phe Glu Gln Thr Leu Glu Leu Glu Ser Leu Leu Thr Arg Tyr
    1010                1015                1020

Pro His Leu Pro Asp Lys Asn Phe Arg Lys Met Leu Glu Ser Trp
    1025                1030                1035

Ser Asp Pro Leu Leu Asp Lys Trp Pro Asp Leu His Gly Asn Val
    1040                1045                1050

Arg Leu Leu Ile Ala Val Arg Asn Ala Phe Ser His Asn Gln Tyr
    1055                1060                1065

Pro Met Tyr Asp Glu Thr Leu Phe Ser Ser Ile Arg Lys Tyr Asp
    1070                1075                1080

Pro Ser Ser Pro Asp Ala Ile Glu Glu Arg Met Gly Leu Asn Ile
    1085                1090                1095

Ala His Arg Leu Ser Glu Glu Val Lys Gln Ala Lys Glu Met Val
    1100                1105                1110

Glu Arg Ile Ile Gln Ala
    1115

<210> SEQ ID NO 73
<211> LENGTH: 36
<212> TYPE: DNA
<213> ORGANISM: Artificial Sequence
<220> FEATURE:
<223> OTHER INFORMATION: PinCas13b direct repeat

<400> SEQUENCE: 73
gttgcatctg cctgctgttt gcaaggtaaa aacaac                              36

<210> SEQ ID NO 74
<211> LENGTH: 3579
<212> TYPE: DNA
<213> ORGANISM: Artificial Sequence
<220> FEATURE:
<223> OTHER INFORMATION: BzoCas13b nucleic acid sequence

<400> SEQUENCE: 74
atggagaata ccgactccgt gttccgggag ctgggcaaga gactgaaggg caaggagtac    60
acatctgaga acttctttga cgccatcttt aaggagaata tctctctggt ggagtacgag   120
cggtatgtga agctgctgag cgattatttc cccatggccc ggctgctgga caagaaggag   180
gtgcctatca aggagagaaa ggagaacttc aagaagaact tcaagggcat catcaaggcc   240
gtgcgggatc tgagaaactt ttacacccac aaggagcacg gcgaggtgga gatcacagac   300
gagatcttcg cgtgctgga tgagatgctg aagtccaccg tgctgacagt gaagaagaag   360
aaggtgaaaa ccgacaagac aaaggagatc ctgaagaagt ctatcgagaa gcagctggat   420
atcctgtgcc agaagaagct ggagtacctg agggacaccg cccgcaagat cgaggagaag   480
cggagaaacc agagggagag gggagagaag gagctggtgg cacctttaa gtattctgat   540 aagcgggacg acctgatcgc cgccatctac aatgacgcct tcgacgtgta tatcgacaag   600
aagaaggatt ccctgaagga gagctccaag gccaagtaca cacacaaagtc tgaccctcag   660 caggaggagg gcgatctgaa gatcccaatc agcaagaatg gcgtggtgtt cctgctgtcc   720
```

```
ctgtttctga ccaagcagga gatccacgcc ttcaagagca agatcgccgg ctttaaggcc    780
acagtgatcg acgaggccac cgtgtccgag gccacagtgt ctcacggcaa gaacagcatc    840
tgtttcatgg ccacccacga gatctttagc cacctggcct acaagaagct gaagaggaag    900
gtgcgcacag ccgagatcaa ctacggcgag gccgagaatg ccgagcagct gtccgtgtat    960
gccaaggaga cactgatgat gcagatgctg gacgagctgt ctaaggtgcc tgatgtggtg   1020
taccagaacc tgagcgagga cgtgcagaaa accttcatcg aggactggaa tgagtatctg   1080
aaggagaaca atggcgacgt gggcacaatg gaggaggagc aggtcatcca cccagtgatc   1140
cggaagagat acgaggataa gttcaactat tttgccatca ggttcctgga cgagttcgcc   1200
cagtttccta ccctgcgctt tcaggtgcac ctgggcaact acctgcacga ttcccggcca   1260
aaggagaatc tgatctctga caggcgcatc aaggagaaga tcacagtgtt tggcagactg   1320
tccgagctgg agcacaagaa ggccctgttc atcaagaaca ccgagacaaa tgaggatagg   1380
gagcactact gggagatctt ccccaaccct aattatgact ttccaaagga gaacatctcc   1440
gtgaatgaca aggattttcc catcgccggc tctatcctgg atcgcgagaa gcagcctgtg   1500
gccggcaaga tcggcatcaa ggtgaagctg ctgaaccagc agtacgtgtc tgaggtggac   1560
aaggccgtga aggcccacca gctgaagcag cggaaggcct ctaagcccag catccagaat   1620
atcatcgagg agatcgtgcc catcaacgag agcaatccta aggaggcaat cgtgttcgga   1680
ggacagccta ccgcctacct gtctatgaac gatatccaca gcatcctgta tgagttcttt   1740
gacaagtggg agaagaagaa ggagaagctg gagaagaagg gcgagaagga gctgagaaag   1800
gagatcggca aggagctgga gaagaagatc gtgggcaaga tccaggccca gatccagcag   1860
atcatcgaca aggataccaa cgccaagatc ctgaagccct accaggacgg caatagcaca   1920
gccatcgata aggagaagct gatcaaggac ctgaagcagg agcagaacat cctgcagaag   1980
ctgaaggatg agcagaccgt gagggagaag gagtacaatg acttcatcgc ctatcaggat   2040
aagaaccgcg agatcaataa ggtgagggat cgcaaccaca gcagtacct gaaggacaat   2100 ctgaagagga gtatcctga ggccccagcc aggaaggagg tgctgtacta cgcgagaag   2160 ggcaaggtgg ccgtgtggct ggccaacgat atcaagcggt tcatgcctac cgactttaag   2220
aatgagtgga agggcgagca gcactcccta ctgcagaagt ctctggccta ctatgagcag   2280
tgcaaggagg agctgaagaa cctgctgcca gagaaggtgt ccagcacct gcccttaag   2340 ctgggcggct acttccagca gaagtacctg tatcagtttt acaccctgcta tctggacaag   2400 aggctggagt atatcagcgg cctggtgcag caggccgaga acttcaagtc cgagaataag   2460
gtgtttaaga aggtggagaa cgagtgtttc aagtttctga agaagcagaa ttacacacac   2520
aaggagctgg atgcccgggt gcagtccatc ctgggctatc aatcttcct ggagagaggc   2580 tttatggacg agaagcccac catcatcaag ggcaagacat caagggcaa cgaggccctg   2640 ttcgccgatt ggtttcgcta ctataaggag taccagaact tccagacctt ttacgacaca   2700
gagaattatc cactggtgga gctggagaag aagcaggccg atcggaagag aaagaccaag   2760
atctatcagc agaagaagaa tgacgtgttt acactgctga tggccaagca catcttcaag   2820
agcgtgttca gcaggacag catcgatcag ttctcctgg aggacctgta ccagagccgg   2880
gaggagagac tgggaaacca ggagagggca aggcagaccg cgagaggaa cacaaattat   2940 atctggaata agaccgtgga cctgaagctg tgcgatggca agatcacagt ggagaacgtg   3000
aagctgaaga atgtgggcga tttcatcaag tacgagtatg accagcgggt gcaggccttt   3060
ctgaagtacg aggagaacat cgagtggcag gccttcctga tcaaggagag caaggaggag   3120
```

-continued

```
gagaattacc cctatgtggt ggagagagag atcgagcagt acgagaaggt gcggagagag    3180
gagctgctga aggaggtgca cctgatcgag gagtatatcc tggagaaggt gaaggataaa    3240
gaaatcctga agaagggcga caaccagaac ttcaagtact atatcctgaa cggcctgctg    3300
aagcagctga agaatgagga tgtggagtcc tacaaggtgt tcaacctgaa taccgagcca    3360
gaggatgtga acatcaatca gctgaagcag gaggccaccg acctggagca gaaggccttc    3420
gtgctgacat atatccggaa caagtttgcc cacaatcagc tgcccaagaa ggagttctgg    3480
gactactgtc aggagaagta tggcaagatc gagaaggaga aaacctacgc cgagtatttc    3540
gccgaggtgt ttaagaagga gaaggaggcc ctgatcaag                           3579
```

```
<210> SEQ ID NO 75
<211> LENGTH: 1193
<212> TYPE: PRT
<213> ORGANISM: Artificial Sequence
<220> FEATURE:
<223> OTHER INFORMATION: BzoCas13b amino acid sequence

<400> SEQUENCE: 75
```

Met Glu Asn Thr Asp Ser Val Phe Arg Glu Leu Gly Lys Arg Leu Lys
1               5                   10                  15

Gly Lys Glu Tyr Thr Ser Glu Asn Phe Phe Asp Ala Ile Phe Lys Glu
            20                  25                  30

Asn Ile Ser Leu Val Glu Tyr Glu Arg Tyr Val Lys Leu Leu Ser Asp
        35                  40                  45

Tyr Phe Pro Met Ala Arg Leu Leu Asp Lys Lys Glu Val Pro Ile Lys
    50                  55                  60

Glu Arg Lys Glu Asn Phe Lys Lys Asn Phe Lys Gly Ile Ile Lys Ala
65                  70                  75                  80

Val Arg Asp Leu Arg Asn Phe Tyr Thr His Lys Glu His Gly Glu Val
                85                  90                  95

Glu Ile Thr Asp Glu Ile Phe Gly Val Leu Asp Glu Met Leu Lys Ser
            100                 105                 110

Thr Val Leu Thr Val Lys Lys Lys Val Lys Thr Asp Lys Thr Lys
        115                 120                 125

Glu Ile Leu Lys Lys Ser Ile Glu Lys Gln Leu Asp Ile Leu Cys Gln
    130                 135                 140

Lys Lys Leu Glu Tyr Leu Arg Asp Thr Ala Arg Lys Ile Glu Glu Lys
145                 150                 155                 160

Arg Arg Asn Gln Arg Glu Arg Gly Glu Lys Glu Leu Val Ala Pro Phe
                165                 170                 175

Lys Tyr Ser Asp Lys Arg Asp Asp Leu Ile Ala Ala Ile Tyr Asn Asp
            180                 185                 190

Ala Phe Asp Val Tyr Ile Asp Lys Lys Lys Asp Ser Leu Lys Glu Ser
        195                 200                 205

Ser Lys Ala Lys Tyr Asn Thr Lys Ser Asp Pro Gln Gln Glu Glu Gly
    210                 215                 220

Asp Leu Lys Ile Pro Ile Ser Lys Asn Gly Val Val Phe Leu Leu Ser
225                 230                 235                 240

Leu Phe Leu Thr Lys Gln Glu Ile His Ala Phe Lys Ser Lys Ile Ala
                245                 250                 255

Gly Phe Lys Ala Thr Val Ile Asp Glu Ala Thr Val Ser Glu Ala Thr
            260                 265                 270

Val Ser His Gly Lys Asn Ser Ile Cys Phe Met Ala Thr His Glu Ile

-continued

```
              275                 280                 285
Phe Ser His Leu Ala Tyr Lys Lys Leu Lys Arg Lys Val Arg Thr Ala
290                 295                 300
Glu Ile Asn Tyr Gly Glu Ala Glu Asn Ala Glu Gln Leu Ser Val Tyr
305                 310                 315                 320
Ala Lys Glu Thr Leu Met Met Gln Met Leu Asp Glu Leu Ser Lys Val
            325                 330                 335
Pro Asp Val Val Tyr Gln Asn Leu Ser Glu Asp Val Gln Lys Thr Phe
                340                 345                 350
Ile Glu Asp Trp Asn Glu Tyr Leu Lys Glu Asn Asn Gly Asp Val Gly
            355                 360                 365
Thr Met Glu Glu Gln Val Ile His Pro Val Ile Arg Lys Arg Tyr
    370                 375                 380
Glu Asp Lys Phe Asn Tyr Phe Ala Ile Arg Phe Leu Asp Glu Phe Ala
385                 390                 395                 400
Gln Phe Pro Thr Leu Arg Phe Gln Val His Leu Gly Asn Tyr Leu His
                405                 410                 415
Asp Ser Arg Pro Lys Glu Asn Leu Ile Ser Asp Arg Ile Lys Glu
                420                 425                 430
Lys Ile Thr Val Phe Gly Arg Leu Ser Glu Leu Glu His Lys Lys Ala
        435                 440                 445
Leu Phe Ile Lys Asn Thr Glu Thr Asn Glu Asp Arg Glu His Tyr Trp
    450                 455                 460
Glu Ile Phe Pro Asn Pro Asn Tyr Asp Phe Pro Lys Glu Asn Ile Ser
465                 470                 475                 480
Val Asn Asp Lys Asp Phe Pro Ile Ala Gly Ser Ile Leu Asp Arg Glu
                485                 490                 495
Lys Gln Pro Val Ala Gly Lys Ile Gly Ile Lys Val Lys Leu Leu Asn
                500                 505                 510
Gln Gln Tyr Val Ser Glu Val Asp Lys Ala Val Lys Ala His Gln Leu
        515                 520                 525
Lys Gln Arg Lys Ala Ser Lys Pro Ser Ile Gln Asn Ile Ile Glu Glu
    530                 535                 540
Ile Val Pro Ile Asn Glu Ser Asn Pro Lys Glu Ala Ile Val Phe Gly
545                 550                 555                 560
Gly Gln Pro Thr Ala Tyr Leu Ser Met Asn Asp Ile His Ser Ile Leu
                565                 570                 575
Tyr Glu Phe Phe Asp Lys Trp Glu Lys Lys Glu Lys Leu Glu Lys
            580                 585                 590
Lys Gly Glu Lys Glu Leu Arg Lys Glu Ile Gly Lys Glu Leu Glu Lys
    595                 600                 605
Lys Ile Val Gly Lys Ile Gln Ala Gln Ile Gln Ile Ile Asp Lys
    610                 615                 620
Asp Thr Asn Ala Lys Ile Leu Lys Pro Tyr Gln Asp Gly Asn Ser Thr
625                 630                 635                 640
Ala Ile Asp Lys Glu Lys Leu Ile Lys Asp Leu Lys Gln Glu Gln Asn
                645                 650                 655
Ile Leu Gln Lys Leu Lys Asp Glu Gln Thr Val Arg Glu Lys Glu Tyr
                660                 665                 670
Asn Asp Phe Ile Ala Tyr Gln Asp Lys Asn Arg Glu Ile Asn Lys Val
            675                 680                 685
Arg Asp Arg Asn His Lys Gln Tyr Leu Lys Asp Asn Leu Lys Arg Lys
    690                 695                 700
```

-continued

Tyr Pro Glu Ala Pro Ala Arg Lys Glu Val Leu Tyr Arg Glu Lys
705                 710                 715                 720

Gly Lys Val Ala Val Trp Leu Ala Asn Asp Ile Lys Arg Phe Met Pro
            725                 730                 735

Thr Asp Phe Lys Asn Glu Trp Lys Gly Glu Gln His Ser Leu Leu Gln
        740                 745                 750

Lys Ser Leu Ala Tyr Tyr Glu Gln Cys Lys Glu Glu Leu Lys Asn Leu
    755                 760                 765

Leu Pro Glu Lys Val Phe Gln His Leu Pro Phe Lys Leu Gly Gly Tyr
770                 775                 780

Phe Gln Gln Lys Tyr Leu Tyr Gln Phe Tyr Thr Cys Tyr Leu Asp Lys
785                 790                 795                 800

Arg Leu Glu Tyr Ile Ser Gly Leu Val Gln Gln Ala Glu Asn Phe Lys
                805                 810                 815

Ser Glu Asn Lys Val Phe Lys Lys Val Glu Asn Glu Cys Phe Lys Phe
            820                 825                 830

Leu Lys Lys Gln Asn Tyr Thr His Lys Glu Leu Asp Ala Arg Val Gln
        835                 840                 845

Ser Ile Leu Gly Tyr Pro Ile Phe Leu Glu Arg Gly Phe Met Asp Glu
    850                 855                 860

Lys Pro Thr Ile Ile Lys Gly Lys Thr Phe Lys Gly Asn Glu Ala Leu
865                 870                 875                 880

Phe Ala Asp Trp Phe Arg Tyr Tyr Lys Glu Tyr Gln Asn Phe Gln Thr
                885                 890                 895

Phe Tyr Asp Thr Glu Asn Tyr Pro Leu Val Glu Leu Glu Lys Lys Gln
            900                 905                 910

Ala Asp Arg Lys Arg Lys Thr Lys Ile Tyr Gln Gln Lys Lys Asn Asp
        915                 920                 925

Val Phe Thr Leu Leu Met Ala Lys His Ile Phe Lys Ser Val Phe Lys
930                 935                 940

Gln Asp Ser Ile Asp Gln Phe Ser Leu Glu Asp Leu Tyr Gln Ser Arg
945                 950                 955                 960

Glu Glu Arg Leu Gly Asn Gln Glu Arg Ala Arg Gln Thr Gly Glu Arg
                965                 970                 975

Asn Thr Asn Tyr Ile Trp Asn Lys Thr Val Asp Leu Lys Leu Cys Asp
            980                 985                 990

Gly Lys Ile Thr Val Glu Asn Val Lys Leu Lys Asn Val Gly Asp Phe
        995                 1000                1005

Ile Lys Tyr Glu Tyr Asp Gln Arg Val Gln Ala Phe Leu Lys Tyr
    1010                1015                1020

Glu Glu Asn Ile Glu Trp Gln Ala Phe Leu Ile Lys Glu Ser Lys
    1025                1030                1035

Glu Glu Glu Asn Tyr Pro Tyr Val Val Glu Arg Glu Ile Glu Gln
    1040                1045                1050

Tyr Glu Lys Val Arg Arg Glu Glu Leu Leu Lys Glu Val His Leu
    1055                1060                1065

Ile Glu Glu Tyr Ile Leu Glu Lys Val Lys Asp Lys Glu Ile Leu
    1070                1075                1080

Lys Lys Gly Asp Asn Gln Asn Phe Lys Tyr Tyr Ile Leu Asn Gly
    1085                1090                1095

Leu Leu Lys Gln Leu Lys Asn Glu Asp Val Glu Ser Tyr Lys Val
    1100                1105                1110

```
Phe Asn Leu Asn Thr Glu Pro Glu Asp Val Asn Ile Asn Gln Leu
    1115                1120                1125

Lys Gln Glu Ala Thr Asp Leu Glu Gln Lys Ala Phe Val Leu Thr
    1130                1135                1140

Tyr Ile Arg Asn Lys Phe Ala His Asn Gln Leu Pro Lys Lys Glu
    1145                1150                1155

Phe Trp Asp Tyr Cys Gln Glu Lys Tyr Gly Lys Ile Glu Lys Glu
    1160                1165                1170

Lys Thr Tyr Ala Glu Tyr Phe Ala Glu Val Phe Lys Lys Glu Lys
    1175                1180                1185

Glu Ala Leu Ile Lys
    1190

<210> SEQ ID NO 76
<211> LENGTH: 36
<212> TYPE: DNA
<213> ORGANISM: Artificial Sequence
<220> FEATURE:
<223> OTHER INFORMATION: BzoCas13b direct repeat

<400> SEQUENCE: 76
gttggaactg ctctcatttt ggagggtaat cacaac                                36

<210> SEQ ID NO 77
<211> LENGTH: 3381
<212> TYPE: DNA
<213> ORGANISM: Artificial Sequence
<220> FEATURE:
<223> OTHER INFORMATION: PbuCas13b nucleic acid sequence

<400> SEQUENCE: 77
atgcagaagc aggacaagct gttcgtggat aggaagaaga acgccatctt cgcctttccc        60
aagtacatca ccatcatgga gaataaggag aagcccgagc ctatctacta tgagctgaca       120
gacaagcact tctgggccgc ctttctgaac ctggcccgcc acaacgtgta ccacaatc         180 aaccacatca atcggagact ggagatcgcc gagctgaagg acgatggcta tgatgggc        240 atcaagggca gctggaacga gcaggccaag aagctggaca gaaaggtgcg gctgagagat      300
ctgatcatga agcacttccc ttttctggag gccgccgcct acgagatgac caatagcaag      360
tccccaaaca ataaggagca gagggagaag gagcagtctg aggccctgag cctgaacaat      420
ctgaagaacg tgctgttcat ctttctggag aagctgcagg tgctgcgcaa ttactatagc      480
cactacaagt attctgagga gagcccaaag cccatcttcg agacatccct gctgaagaac      540
atgtataagg tgtttgacgc caatgtgagg ctggtgaagc gcgattatat gcaccacgag      600
aacatcgaca tgcagagaga tttcacccac ctgaatcgga agaagcaagt gggcagaaca      660
aagaacatca tcgactcccc taatttccac taccactttg ccgataagga gggcaacatg      720
accatcgccg gcctgctgtt cttcgtgagc ctgttcctgg acaagaagga tgccatctgg      780
atgcagaaga agctgaaggg cttcaaggat ggcaggaacc tgcgcgagca gatgaccaat      840
gaggtgtttt gcaggtcccg catctctctg ccaaagctga agctggagaa cgtgcagaca      900
aaggactgga tgcagctgga tatgctgaat gagctggtga ggtgtcccaa gagcctgtac      960
gagcggctga gagagaagga ccgcgagtct ttcaaggtgc ctttcgatat ctttagcgac     1020
gattataacg ccgaggagga gccctttaag aataccctgg tgcggcacca ggacagattc     1080
ccttactttg tgctgaggta tttcgatctg aacgagatct tcgagcagct gcgctttcag     1140
atcgatctgg gcacctacca cttttccatc tataataaga ggatcggcga cgaggatgag     1200
```

```
gtgcgccacc tgacacacca cctgtacggc ttcgccagaa tccaggactt tgcccccag    1260 aaccagtctg aggagtggag aaagctggtg aaggacctgg atcacttcga gacaagccag    1320
gagccctaca tcagcaagac agcccctcac tatcacctgg agaatgagaa gatcggcatc    1380
aagttctgca gcgcccacaa caatctgttt ccctccctgc agaccgacaa gacatgtaac    1440
ggccggtcca agttcaatct gggcacccag ttcacagccg aggcctttct gtctgtgcac    1500
gagctgctgc ctatgatgtt ttactatctg ctgctgacca aggactactc ccggaaggag    1560
tctgccgata aggtggaggg catcatcaga aggagatct ctaacatcta cgccatctat    1620
gacgccttcg ccaacaatga gatcaatagc atcgccgatc tgaccaggcg cctgcagaac    1680
acaaatatcc tgcagggcca cctgccaaag cagatgatca gcatcctgaa gggcaggcag    1740
aaggatatgg gcaaggaggc cgagcgcaag atcggcgaga tgatcgacga tacccagcgg    1800
agactggacc tgctgtgcaa gcagacaaac cagaagatca ggatcggcaa gcgcaatgcc    1860
ggcctgctga gtccggcaa gatcgccgac tggctggtga cgatatgat gcggttccag    1920 cctgtgcaga aggatcagaa caatatccca atcaacaata gcaaggccaa ctccaccgag    1980
taccggatgc tgcagagagc cctggccctg ttcggctccg agaacttccg gctgaaggcc    2040
tacttcaacc agatgaatct ggtgggcaac gacaatcctc acccatttct ggccgagaca    2100
cagtgggagc accagacaaa catcctgtct ttctacagga attatctgga ggcccgcaag    2160
aagtacctga agggcctgaa gccccagaac tggaagcagt atcagcactt tctgatcctg    2220
aaggtgcaga aaaccaacag gaatacccctg gtgacaggct ggaagaacag cttcaatctg    2280
ccacggggca tctttacaca gcccatcaga gagtggttcg agaagcacaa caattccaag    2340
cggatctacg accagatcct gtctttcgat agagtgggct ttgtggccaa ggccatccct    2400
ctgtactttg ccgaggagta taggacaac gtgcagcctt tctacgatta tcccttcaac    2460
atcggcaatc ggctgaagcc taagaagaga cagttcctgg ataagaagga gcgcgtggag    2520
ctgtggcaga agaacaagga gctgtttaag aattacccat tgagaagaa gaaaaccgac    2580 ctggcctatc tggatttcct gagctggaag aagtttgagc gggagctgag actgatcaag    2640
aaccaggaca tcgtgacctg gctgatgttc aaggagctgt ttaatatggc cacagtggag    2700
ggcctgaaga tcggcgagat ccacctgcgg gacatcgata ccaacacagc caatgaggag    2760
tccaacaata tcctgaacag aatcatgcca atgaagctgc ccgtgaaaac ctacgagaca    2820
gacaacaagg gcaatatcct gaaggagcgg ccactggcca ccttctatat cgaggagaca    2880
gagacaaagg tgctgaagca gggcaacttt aaggccctgg tgaaggacag cgcctgaat    2940 ggcctgttct cttttgccga cacaacagat ctgaatctgg aggagcaccc catcagcaag    3000
ctgtccgtgg acctggagct gatcaagtac cagaccacaa gatcagcat cttcgagatg    3060 accctgggcc tggagaagaa gctgatcgac aagtattcca ccctgccaac agattctttt    3120
aggaacatgc tggagcggtg gctgcagtgt aaggccaata ggcccgagct gaagaactac    3180
gtgaatagcc tgatcgccgt gcgcaacgcc ttctcccaca tcagtaccc tatgtatgat    3240 gccacactgt tgccgaggt gaagaagttc acccctgtttc caagcgtgga cacaaagaag    3300
atcgagctga acatcgcccc ccagctgctg gagatcgtgg gcaaggccat caaggagatc    3360
gagaagtccg agaacaagaa t                                               3381
```

<210> SEQ ID NO 78
<211> LENGTH: 1127
<212> TYPE: PRT

<213> ORGANISM: Artificial Sequence
<220> FEATURE:
<223> OTHER INFORMATION: PbuCas13b amino acid sequence

<400> SEQUENCE: 78

```
Met Gln Lys Gln Asp Lys Leu Phe Val Asp Arg Lys Lys Asn Ala Ile
1               5                   10                  15

Phe Ala Phe Pro Lys Tyr Ile Thr Ile Met Glu Asn Lys Glu Lys Pro
                20                  25                  30

Glu Pro Ile Tyr Tyr Glu Leu Thr Asp Lys His Phe Trp Ala Ala Phe
            35                  40                  45

Leu Asn Leu Ala Arg His Asn Val Tyr Thr Thr Ile Asn His Ile Asn
        50                  55                  60

Arg Arg Leu Glu Ile Ala Glu Leu Lys Asp Asp Gly Tyr Met Met Gly
65                  70                  75                  80

Ile Lys Gly Ser Trp Asn Glu Gln Ala Lys Lys Leu Asp Lys Lys Val
                85                  90                  95

Arg Leu Arg Asp Leu Ile Met Lys His Phe Pro Phe Leu Glu Ala Ala
                100                 105                 110

Ala Tyr Glu Met Thr Asn Ser Lys Ser Pro Asn Asn Lys Glu Gln Arg
        115                 120                 125

Glu Lys Glu Gln Ser Glu Ala Leu Ser Leu Asn Asn Leu Lys Asn Val
    130                 135                 140

Leu Phe Ile Phe Leu Glu Lys Leu Gln Val Leu Arg Asn Tyr Tyr Ser
145                 150                 155                 160

His Tyr Lys Tyr Ser Glu Glu Ser Pro Lys Pro Ile Phe Glu Thr Ser
                165                 170                 175

Leu Leu Lys Asn Met Tyr Lys Val Phe Asp Ala Asn Val Arg Leu Val
            180                 185                 190

Lys Arg Asp Tyr Met His His Glu Asn Ile Asp Met Gln Arg Asp Phe
        195                 200                 205

Thr His Leu Asn Arg Lys Lys Gln Val Gly Arg Thr Lys Asn Ile Ile
    210                 215                 220

Asp Ser Pro Asn Phe His Tyr His Phe Ala Asp Lys Glu Gly Asn Met
225                 230                 235                 240

Thr Ile Ala Gly Leu Leu Phe Phe Val Ser Leu Phe Leu Asp Lys Lys
                245                 250                 255

Asp Ala Ile Trp Met Gln Lys Lys Leu Lys Gly Phe Lys Asp Gly Arg
            260                 265                 270

Asn Leu Arg Glu Gln Met Thr Asn Glu Val Phe Cys Arg Ser Arg Ile
        275                 280                 285

Ser Leu Pro Lys Leu Lys Leu Glu Asn Val Gln Thr Lys Asp Trp Met
    290                 295                 300

Gln Leu Asp Met Leu Asn Glu Leu Val Arg Cys Pro Lys Ser Leu Tyr
305                 310                 315                 320

Glu Arg Leu Arg Glu Lys Asp Arg Glu Ser Phe Lys Val Pro Phe Asp
                325                 330                 335

Ile Phe Ser Asp Asp Tyr Asn Ala Glu Glu Pro Phe Lys Asn Thr
            340                 345                 350

Leu Val Arg His Gln Asp Arg Phe Pro Tyr Phe Val Leu Arg Tyr Phe
        355                 360                 365

Asp Leu Asn Glu Ile Phe Glu Gln Leu Arg Phe Gln Ile Asp Leu Gly
    370                 375                 380

Thr Tyr His Phe Ser Ile Tyr Asn Lys Arg Ile Gly Asp Glu Asp Glu
```

-continued

```
        385                 390                 395                 400

Val Arg His Leu Thr His His Leu Tyr Gly Phe Ala Arg Ile Gln Asp
                405                 410                 415

Phe Ala Pro Gln Asn Gln Ser Glu Glu Trp Arg Lys Leu Val Lys Asp
                420                 425                 430

Leu Asp His Phe Glu Thr Ser Gln Glu Pro Tyr Ile Ser Lys Thr Ala
                435                 440                 445

Pro His Tyr His Leu Glu Asn Glu Lys Ile Gly Ile Lys Phe Cys Ser
            450                 455                 460

Ala His Asn Asn Leu Phe Pro Ser Leu Gln Thr Asp Lys Thr Cys Asn
465                 470                 475                 480

Gly Arg Ser Lys Phe Asn Leu Gly Thr Gln Phe Thr Ala Glu Ala Phe
                485                 490                 495

Leu Ser Val His Glu Leu Leu Pro Met Met Phe Tyr Tyr Leu Leu Leu
                500                 505                 510

Thr Lys Asp Tyr Ser Arg Lys Glu Ser Ala Asp Lys Val Glu Gly Ile
            515                 520                 525

Ile Arg Lys Glu Ile Ser Asn Ile Tyr Ala Ile Tyr Asp Ala Phe Ala
            530                 535                 540

Asn Asn Glu Ile Asn Ser Ile Ala Asp Leu Thr Arg Arg Leu Gln Asn
545                 550                 555                 560

Thr Asn Ile Leu Gln Gly His Leu Pro Lys Gln Met Ile Ser Ile Leu
                565                 570                 575

Lys Gly Arg Gln Lys Asp Met Gly Lys Glu Ala Glu Arg Lys Ile Gly
                580                 585                 590

Glu Met Ile Asp Asp Thr Gln Arg Arg Leu Asp Leu Leu Cys Lys Gln
            595                 600                 605

Thr Asn Gln Lys Ile Arg Ile Gly Lys Arg Asn Ala Gly Leu Leu Lys
            610                 615                 620

Ser Gly Lys Ile Ala Asp Trp Leu Val Asn Asp Met Met Arg Phe Gln
625                 630                 635                 640

Pro Val Gln Lys Asp Gln Asn Asn Ile Pro Ile Asn Asn Ser Lys Ala
                645                 650                 655

Asn Ser Thr Glu Tyr Arg Met Leu Gln Arg Ala Leu Ala Leu Phe Gly
                660                 665                 670

Ser Glu Asn Phe Arg Leu Lys Ala Tyr Phe Asn Gln Met Asn Leu Val
            675                 680                 685

Gly Asn Asp Asn Pro His Pro Phe Leu Ala Glu Thr Gln Trp Glu His
            690                 695                 700

Gln Thr Asn Ile Leu Ser Phe Tyr Arg Asn Tyr Leu Glu Ala Arg Lys
705                 710                 715                 720

Lys Tyr Leu Lys Gly Leu Lys Pro Gln Asn Trp Lys Gln Tyr Gln His
                725                 730                 735

Phe Leu Ile Leu Lys Val Gln Lys Thr Asn Arg Asn Thr Leu Val Thr
                740                 745                 750

Gly Trp Lys Asn Ser Phe Asn Leu Pro Arg Gly Ile Phe Thr Gln Pro
                755                 760                 765

Ile Arg Glu Trp Phe Glu Lys His Asn Ser Lys Arg Ile Tyr Asp
            770                 775                 780

Gln Ile Leu Ser Phe Asp Arg Val Gly Phe Val Ala Lys Ala Ile Pro
785                 790                 795                 800

Leu Tyr Phe Ala Glu Glu Tyr Lys Asp Asn Val Gln Pro Phe Tyr Asp
                805                 810                 815
```

Tyr Pro Phe Asn Ile Gly Asn Arg Leu Lys Pro Lys Arg Gln Phe
                820                 825                 830

Leu Asp Lys Lys Glu Arg Val Glu Leu Trp Gln Lys Asn Lys Glu Leu
            835                 840                 845

Phe Lys Asn Tyr Pro Ser Glu Lys Lys Thr Asp Leu Ala Tyr Leu
        850                 855                 860

Asp Phe Leu Ser Trp Lys Lys Phe Arg Glu Leu Arg Leu Ile Lys
865                 870                 875                 880

Asn Gln Asp Ile Val Thr Trp Leu Met Phe Lys Glu Leu Phe Asn Met
                885                 890                 895

Ala Thr Val Glu Gly Leu Lys Ile Gly Glu Ile His Leu Arg Asp Ile
            900                 905                 910

Asp Thr Asn Thr Ala Asn Glu Glu Ser Asn Asn Ile Leu Asn Arg Ile
        915                 920                 925

Met Pro Met Lys Leu Pro Val Lys Thr Tyr Glu Thr Asp Asn Lys Gly
    930                 935                 940

Asn Ile Leu Lys Glu Arg Pro Leu Ala Thr Phe Tyr Ile Glu Glu Thr
945                 950                 955                 960

Glu Thr Lys Val Leu Lys Gln Gly Asn Phe Lys Ala Leu Val Lys Asp
                965                 970                 975

Arg Arg Leu Asn Gly Leu Phe Ser Phe Ala Glu Thr Thr Asp Leu Asn
            980                 985                 990

Leu Glu Glu His Pro Ile Ser Lys Leu Ser Val Asp Leu Glu Leu Ile
        995                 1000                1005

Lys Tyr Gln Thr Thr Arg Ile Ser Ile Phe Glu Met Thr Leu Gly
    1010                1015                1020

Leu Glu Lys Lys Leu Ile Asp Lys Tyr Ser Thr Leu Pro Thr Asp
    1025                1030                1035

Ser Phe Arg Asn Met Leu Glu Arg Trp Leu Gln Cys Lys Ala Asn
    1040                1045                1050

Arg Pro Glu Leu Lys Asn Tyr Val Asn Ser Leu Ile Ala Val Arg
    1055                1060                1065

Asn Ala Phe Ser His Asn Gln Tyr Pro Met Tyr Asp Ala Thr Leu
    1070                1075                1080

Phe Ala Glu Val Lys Lys Phe Thr Leu Phe Pro Ser Val Asp Thr
    1085                1090                1095

Lys Lys Ile Glu Leu Asn Ile Ala Pro Gln Leu Leu Glu Ile Val
    1100                1105                1110

Gly Lys Ala Ile Lys Glu Ile Glu Lys Ser Glu Asn Lys Asn
    1115                1120                1125

<210> SEQ ID NO 79
<211> LENGTH: 36
<212> TYPE: DNA
<213> ORGANISM: Artificial Sequence
<220> FEATURE:
<223> OTHER INFORMATION: PbuCas13b direct repeat

<400> SEQUENCE: 79
gttgcatctg ccttcttttt gaaaggtaaa aacaac                                    36

<210> SEQ ID NO 80
<211> LENGTH: 2859
<212> TYPE: DNA
<213> ORGANISM: Artificial Sequence
<220> FEATURE:

<223> OTHER INFORMATION: AspCas13b nucleic acid sequence

<400> SEQUENCE: 80

```
atgtccaatg agatcggcgc cttcagagag caccagtttg cctacgcccc aggaaacgag      60
aagcaggagg aggccacctt cgccacatac ttcaacctgg ccctgtctaa tgtggagggc     120
atgatgttcg gagaggtgga gtctaaccca gacaagatcg agaagagcct ggatacccty     180
cccctgcca tcctgagaca gatcgcctcc tttatctggc tgtctaagga ggaccacccc     240
gataaggcct actccaccga ggaggtgaaa gtgatcgtga cagacctggt gcggagactg     300
tgcttctaca ggaattattt cagccactgt ttctatctgg atacacagta ctttttattcc    360
gacgagctgg tggataccac agccatcggc gagaagctgc cttacaattt ccaccacttt    420
atcaccaaca gactgttcag gtatagcctg ccagagatca cactgtttcg ctggaacgag    480
ggcgagcgga agtacgagat cctgcgggac ggcctgatct tcttttgctg tctgttcctg    540
aagaggggac aggcagagcg gtttctgaat gagctgagat tctttaagag gaccgacgag    600
gagggccgca tcaagcggac catcttcaca aagtattgca aagagagtc tcacaagcac    660
atcggcatcg aggagcagga ttccctgatc tttcaggaca tcatcggcga tctgaatagg    720
gtgcctaagg tgtgcgacgg cgtggtggat ctgagcaagg agaacgagag atacatcaag    780
aacagggaga caagcaatga gtctgatgag aacaaggccc ggtatagact gctgatcagg    840
gagaaggaca agtttcccta ctatctgatg cgctacatcg tggatttcgg cgtgctgcct    900
tgcatcacct ttaagcagaa cgactacagc acaaaggagg gccgggccag gttccactat    960
caggatgcag cagtggcaca ggaggagagg tgttacaatt ttgtggtgcg caacggcaac   1020
gtgtactatt cctatatgcc tcaggccag aacgtggtgc ggatcagcga gctgcagggc   1080
accatctccg tggaggagct gagaaatatg gtgtacgcct ctatcaatgg caaggacgtg   1140
aacaagagcg tggagcagta cctgtatcac ctgcacctgc tgtatgagaa gatcctgacc   1200
atctccggcc agacaatcaa ggagggccgg gtggacgtgg aggattacag acctctgctg   1260
gataagctgc tgctgcgccc agcctctaac ggcgaggagc tgaggcgcga gctgaggaag   1320
ctgctgccaa agcgcgtgtg cgacctgctg agcaatcggt tcgattgttc tgagggcgtg   1380
agcgccgtgg agaagaggct gaaggccatc ctgctgcgcc acgagcagct gctgctgagc   1440
cagaaccccg ccctgcacat cgacaagatc aagtccgtga tcgattacct gtatctgttc   1500
ttttctgacg atgagaagtt ccggcagcag cctaccgaga aggcccacag aggcctgaag   1560
gacgaggagt ttcagatgta ccactatctg gtgggcgact acgattctca cccactggcc   1620
ctgtggaagg agctggaggc cagcggccgg ctgaagccag agatgagaaa gctgaccagc   1680
gccacatccc tgcacggcct gtatatgctg tgcctgaagg caccgtggaa gtggtgtcgg   1740
aagcagctga tgtccatcgg caagggcaca gccaaggtgg aggccatcgc cgacagagtg   1800
ggcctgaagc tgtacgataa gctgaaggag tataccctg agcagctgga gggaggtg    1860
aagctggtgg tcatgcacgg atacgctgcc gccgccaccc caaagccaaa ggcacaggca   1920
gcaatcccat ctaagctgac agagctgcgg ttctattcct ttctgggcaa gagagagatg   1980
tctttcgccg cctttatccg gcaggacaag aaggcccaga gctgtggct gagaaatttc   2040
tataccgtgg agaacatcaa gacactgcag aagaggcagg ctgccgccga cgcagcctgc   2100
aagaagctgt ataacctggt gggagaggtg gagcgggtgc acaccaacga taaggtgctg   2160
gtgctggtgc ccagaggta tcgcgagcgg ctgctgaatg tgggcagcaa gtgtgccgtg   2220
acactggaca accccgagag gcagcagaag ctggccgacg tgtacgaggt gcagaacgcc   2280
```

```
tggctgtcca tccgcttcga cgatctggac tttaccctga cacacgtgaa cctgtctaat    2340
ctgaggaagg cctacaatct gatccccgc aagcacatcc tggccttcaa ggagtatctg    2400
gacaataggg tgaagcagaa gctgtgcgag gagtgtcgca acgtgcggag aaaggaggat    2460
ctgtgcacct gctgttcccc tcgctactct aatctgacaa gctggctgaa ggagaaccac    2520
tccgagagct ccatcgagag ggaggccgcc accatgatgc tgctggacgt ggagcgcaag    2580
ctgctgagct tcctgctgga tgagaggcgc aaggccatca tcgagtacgg caagttcatc    2640
ccattttccg ccctggtgaa ggagtgccgg ctggccgacg caggcctgtg cggcatcaga    2700
aatgacgtgc tgcacgataa cgtgatcagc tacgccgatg ccatcggcaa gctgagcgcc    2760
tattttccca aggaggcctc cgaggccgtg gagtacatcc ggagaacaaa ggaggtgcgg    2820
gagcagaggc gcgaggagct gatggccaac tctagccag                          2859
```

<210> SEQ ID NO 81
<211> LENGTH: 953
<212> TYPE: PRT
<213> ORGANISM: Artificial Sequence
<220> FEATURE:
<223> OTHER INFORMATION: AspCas13b amino acid sequence

<400> SEQUENCE: 81

```
Met Ser Asn Glu Ile Gly Ala Phe Arg Glu His Gln Phe Ala Tyr Ala
1               5                   10                  15

Pro Gly Asn Glu Lys Gln Glu Glu Ala Thr Phe Ala Thr Tyr Phe Asn
                20                  25                  30

Leu Ala Leu Ser Asn Val Glu Gly Met Met Phe Gly Glu Val Glu Ser
            35                  40                  45

Asn Pro Asp Lys Ile Glu Lys Ser Leu Asp Thr Leu Pro Pro Ala Ile
        50                  55                  60

Leu Arg Gln Ile Ala Ser Phe Ile Trp Leu Ser Lys Glu Asp His Pro
65                  70                  75                  80

Asp Lys Ala Tyr Ser Thr Glu Glu Val Lys Val Ile Val Thr Asp Leu
                85                  90                  95

Val Arg Arg Leu Cys Phe Tyr Arg Asn Tyr Phe Ser His Cys Phe Tyr
                100                 105                 110

Leu Asp Thr Gln Tyr Phe Tyr Ser Asp Glu Leu Val Asp Thr Thr Ala
            115                 120                 125

Ile Gly Glu Lys Leu Pro Tyr Asn Phe His His Phe Ile Thr Asn Arg
        130                 135                 140

Leu Phe Arg Tyr Ser Leu Pro Glu Ile Thr Leu Phe Arg Trp Asn Glu
145                 150                 155                 160

Gly Glu Arg Lys Tyr Glu Ile Leu Arg Asp Gly Leu Ile Phe Phe Cys
                165                 170                 175

Cys Leu Phe Leu Lys Arg Gly Gln Ala Glu Arg Phe Leu Asn Glu Leu
            180                 185                 190

Arg Phe Phe Lys Arg Thr Asp Glu Glu Gly Arg Ile Lys Arg Thr Ile
        195                 200                 205

Phe Thr Lys Tyr Cys Thr Arg Glu Ser His Lys His Ile Gly Ile Glu
    210                 215                 220

Glu Gln Asp Phe Leu Ile Phe Gln Asp Ile Ile Gly Asp Leu Asn Arg
225                 230                 235                 240

Val Pro Lys Val Cys Asp Gly Val Val Asp Leu Ser Lys Glu Asn Glu
                245                 250                 255
```

-continued

```
Arg Tyr Ile Lys Asn Arg Glu Thr Ser Asn Glu Ser Asp Glu Asn Lys
                260                 265                 270

Ala Arg Tyr Arg Leu Leu Ile Arg Glu Lys Asp Lys Phe Pro Tyr Tyr
            275                 280                 285

Leu Met Arg Tyr Ile Val Asp Phe Gly Val Leu Pro Cys Ile Thr Phe
        290                 295                 300

Lys Gln Asn Asp Tyr Ser Thr Lys Glu Gly Arg Gly Gln Phe His Tyr
305                 310                 315                 320

Gln Asp Ala Ala Val Ala Gln Glu Glu Arg Cys Tyr Asn Phe Val Val
                325                 330                 335

Arg Asn Gly Asn Val Tyr Tyr Ser Tyr Met Pro Gln Ala Gln Asn Val
            340                 345                 350

Val Arg Ile Ser Glu Leu Gln Gly Thr Ile Ser Val Glu Glu Leu Arg
        355                 360                 365

Asn Met Val Tyr Ala Ser Ile Asn Gly Lys Asp Val Asn Lys Ser Val
        370                 375                 380

Glu Gln Tyr Leu Tyr His Leu His Leu Leu Tyr Glu Lys Ile Leu Thr
385                 390                 395                 400

Ile Ser Gly Gln Thr Ile Lys Glu Gly Arg Val Asp Val Glu Asp Tyr
                405                 410                 415

Arg Pro Leu Leu Asp Lys Leu Leu Leu Arg Pro Ala Ser Asn Gly Glu
            420                 425                 430

Glu Leu Arg Arg Glu Leu Arg Lys Leu Leu Pro Lys Arg Val Cys Asp
        435                 440                 445

Leu Leu Ser Asn Arg Phe Asp Cys Ser Glu Gly Val Ser Ala Val Glu
    450                 455                 460

Lys Arg Leu Lys Ala Ile Leu Leu Arg His Glu Gln Leu Leu Leu Ser
465                 470                 475                 480

Gln Asn Pro Ala Leu His Ile Asp Lys Ile Lys Ser Val Ile Asp Tyr
                485                 490                 495

Leu Tyr Leu Phe Phe Ser Asp Asp Glu Lys Phe Arg Gln Gln Pro Thr
            500                 505                 510

Glu Lys Ala His Arg Gly Leu Lys Asp Glu Glu Phe Gln Met Tyr His
        515                 520                 525

Tyr Leu Val Gly Asp Tyr Asp Ser His Pro Leu Ala Leu Trp Lys Glu
    530                 535                 540

Leu Glu Ala Ser Gly Arg Leu Lys Pro Glu Met Arg Lys Leu Thr Ser
545                 550                 555                 560

Ala Thr Ser Leu His Gly Leu Tyr Met Leu Cys Leu Lys Gly Thr Val
                565                 570                 575

Glu Trp Cys Arg Lys Gln Leu Met Ser Ile Gly Lys Gly Thr Ala Lys
            580                 585                 590

Val Glu Ala Ile Ala Asp Arg Val Gly Leu Lys Leu Tyr Asp Lys Leu
        595                 600                 605

Lys Glu Tyr Thr Pro Glu Gln Leu Glu Arg Glu Val Lys Leu Val Val
    610                 615                 620

Met His Gly Tyr Ala Ala Ala Thr Pro Lys Pro Lys Ala Gln Ala
625                 630                 635                 640

Ala Ile Pro Ser Lys Leu Thr Glu Leu Arg Phe Tyr Ser Phe Leu Gly
                645                 650                 655

Lys Arg Glu Met Ser Phe Ala Phe Ile Arg Gln Asp Lys Lys Ala
            660                 665                 670

Gln Lys Leu Trp Leu Arg Asn Phe Tyr Thr Val Glu Asn Ile Lys Thr
```

```
                675                 680                 685
Leu Gln Lys Arg Gln Ala Ala Asp Ala Ala Cys Lys Lys Leu Tyr
    690                 695                 700

Asn Leu Val Gly Glu Val Arg Val His Thr Asn Asp Lys Val Leu
705                 710                 715                 720

Val Leu Val Ala Gln Arg Tyr Arg Glu Arg Leu Leu Asn Val Gly Ser
                725                 730                 735

Lys Cys Ala Val Thr Leu Asp Asn Pro Glu Arg Gln Gln Lys Leu Ala
                740                 745                 750

Asp Val Tyr Glu Val Gln Asn Ala Trp Leu Ser Ile Arg Phe Asp Asp
                755                 760                 765

Leu Asp Phe Thr Leu Thr His Val Asn Leu Ser Asn Leu Arg Lys Ala
    770                 775                 780

Tyr Asn Leu Ile Pro Arg Lys His Ile Leu Ala Phe Lys Glu Tyr Leu
785                 790                 795                 800

Asp Asn Arg Val Lys Gln Lys Leu Cys Glu Glu Cys Arg Asn Val Arg
                805                 810                 815

Arg Lys Glu Asp Leu Cys Thr Cys Cys Ser Pro Arg Tyr Ser Asn Leu
                820                 825                 830

Thr Ser Trp Leu Lys Glu Asn His Ser Glu Ser Ser Ile Glu Arg Glu
    835                 840                 845

Ala Ala Thr Met Met Leu Leu Asp Val Glu Arg Lys Leu Leu Ser Phe
850                 855                 860

Leu Leu Asp Glu Arg Arg Lys Ala Ile Ile Glu Tyr Gly Lys Phe Ile
865                 870                 875                 880

Pro Phe Ser Ala Leu Val Lys Glu Cys Arg Leu Ala Asp Ala Gly Leu
                885                 890                 895

Cys Gly Ile Arg Asn Asp Val Leu His Asp Asn Val Ile Ser Tyr Ala
                900                 905                 910

Asp Ala Ile Gly Lys Leu Ser Ala Tyr Phe Pro Lys Glu Ala Ser Glu
                915                 920                 925

Ala Val Glu Tyr Ile Arg Arg Thr Lys Glu Val Arg Glu Gln Arg Arg
    930                 935                 940

Glu Glu Leu Met Ala Asn Ser Ser Gln
945                 950

<210> SEQ ID NO 82
<211> LENGTH: 36
<212> TYPE: DNA
<213> ORGANISM: Artificial Sequence
<220> FEATURE:
<223> OTHER INFORMATION: AspCas13b direct repeat

<400> SEQUENCE: 82
gctgttatat ccttaccttt gtaagggaag tacagc                          36

<210> SEQ ID NO 83
<211> LENGTH: 3966
<212> TYPE: DNA
<213> ORGANISM: Artificial Sequence
<220> FEATURE:
<223> OTHER INFORMATION: PsmCas13b nucleic acid sequence

<400> SEQUENCE: 83
atgtctaagg agtgcaagaa gcagcgccag gagaagaagc ggagactgca gaaggccaat    60
ttctccatct ctctgaccgg caagcacgtg ttcggcgcct actttaatat ggccagaaca   120
```

```
aactttgtga aaaccatcaa ctacatcctg cctatcgccg gcgtgagggg caactatagc      180
gagaatcaga tcaacaagat gctgcacgca ctgttcctga tccaggcagg acgcaatgag      240
gagctgacca cagagcagaa gcagtgggag aagaagctgc ggctgaaccc agagcagcag      300
accaagtttc agaagctgct gttcaagcac tttccagtgc tgggaccaat gatggcagac      360
gtggcagatc acaaggccta tctgaacaag aagaagagca ccgtgcagac agaggacgag      420
acattcgcca tgctgaaggg cgtgtccctg gccgactgcc tggatatcat ctgtctgatg      480
gccgataccc tgacagagtg tagaaacttc tacacacaca aggaccctta taacaagcca      540
agccagctgg ccgatcagta cctgcaccag gagatgatcg ccaagaagct ggacaaggtg      600
gtggtggcct ccaggcgcat cctgaaggat agggagggcc tgtctgtgaa tgaggtggag      660
ttcctgaccg gcatcgatca cctgcaccag gaggtgctga aggacgagtt cggcaacgcc      720
aaggtgaagg atggcaaagt gatgaaaacc ttcgtggagt acgacgactt ctacttcaag      780
atctccggca gcggctggt gaatggctac acagtgacca caaaggacga taagcccgtg      840
aatgtgaaca ccatgctgcc tgccctgtct gacttcggcc tgctgtactt ctgcgtgctg      900
tttctgagca gcccatatgc caagctgttt atcgatgagg tgcgcctgtt cgagtactct      960
ccttttgacg ataaggagaa catgatcatg tctgagatgc tgagcatcta tcggatcaga     1020
acacccggc tgcacaagat cgactcccac gattctaagg ccaccctggc catggacatc     1080
ttcggcgagc tgcggagatg tcctatggag ctgtataacc tgctggacaa gaacgccggc     1140
cagccattct ttcacgatga ggtgaagcac ccaaactctc acccccga cgtgagcaag     1200
cggctgagat acgacgatcg cttteectaca ctggccctgc ggtatatcga tgagacagag     1260
ctgttcaagc ggatcagatt tcagctgcag ctgggcagct tccgctacaa gttttatgat     1320
aaggagaatt gcatcgacgg ccgggtgaga gtgaggcgca tccagaagga gatcaacggc     1380
tacggcagaa tgcaggaggt ggccgacaag aggatggata agtgggcga cctgatccag     1440
aagagggagg agcgcagcgt gaagctggag cacgaggagc tgtatatcaa tctgaccag     1500
ttcctggagg acaccgccga ttccacacct acgtgaccg atagacggcc cgcctataat     1560
atccacgcca accggatcgg cctgtactgg gaggactccc agaatcctaa gcagtacaag     1620
gtgtttgatg agaacggcat gtatatcccc gagctggtgg tgaccgagga caagaaggcc     1680
cctatcaaga tgccagcacc taggtgtgca ctgagcgtgt acgacctgcc agccatgctg     1740
ttctacgagt atctgcggga gcagcaggat aacgagtttc ccagcgccga gcaggtcatc     1800
atcgagtacg aggacgatta tcgcaagttc tttaaggccg tggccgaggg caagctgaag     1860
cccttcaagc ggcccaagga gttcagggac tttctgaaga aggagtaccc aaagctgcgg     1920
atggccgata tccccaagaa gctgcagctg ttttctgtgca gccacggcct gtgctacaac     1980
aataagcccg agacagtgta tgagcggctg gacagactga ccctgcagca cctggaggag     2040
agagagctgc acatccagaa caggctggag cactaccaga aggacagaga tatgatcggc     2100
aataaggaca ccagtatgg caagaagagc ttctccgatg tgcgccacgg cgccctggcc     2160
agatacctgg cacagagcat gatggagtgg cagcccacaa agctgaagga taaggagaag     2220
ggccacgaca agctgaccgg cctgaattat aacgtgctga cagcctacct ggcaacctat     2280
ggccacccac aggtgcctga ggagggcttc acccctagaa cactggagca ggtgctgatc     2340
aatgcccacc tgatcggcgg ctccaatcca caccccttta tcaacaaggt gctggcctg     2400
ggcaatagga acatcgagga gctgtacctg cactatctgg aggaggagct gaagcacatc     2460
aggtcccgca tccagtctct gagctccaac cctagcgaca aggccctgtc cgccctgcca     2520
```

```
ttcatccacc acgatcggat gagataccac gagcgcacca gcgaggagat gatggccctg    2580
gccgcacggt ataccacaat ccagctgcca gacggcctgt ttacaccta catcctggag     2640 atcctgcaga agcactatac cgagaacagc gatctgcaga acgccctgtc tcaggacgtg    2700
cctgtgaagc tgaatccaac ctgcaacgcc gcctacctga tcacactgtt ctatcagacc    2760
gtgctgaagg acaatgccca gcccttctac ctgtccgata gacctatac aagaaacaag     2820 gacggcgaga aggccgagtc tttcagcttt aagagggcct acgagctgtt ctctgtgctg    2880
aacaataaca agaaggacac attccccttt gagatgatcc ctctgtttct gaccagcgat    2940
gagatccagg agagactgtc cgccaagctg ctggacggcg atggcaatcc tgtgccagaa    3000
gtgggagaga agggcaagcc agccacagac agccagggca acaccatctg aagaggcgc     3060 atctactccg aggtggacga ttatgccgag aagctgaccg accgcgatat gaagatctcc    3120
ttcaagggcg agtgggagaa gctgcctcgg tggaagcagg ataagatcat caagcggcgg    3180
gacgagacac ggcggcagat gcgggacgag ctgctgcaga ggatgccacg ctacatccgg    3240
gacatcaagg ataatgagag gacactgcgg agatataaga cccaggatat ggtgctgttc    3300
ctgctggccg agaagatgtt taccaatatc atctccgagc agtctagcga gttcaactgg    3360
aagcagatga ggctgtctaa ggtgtgcaac gaggccttcc tgagacagac cctgaccttc    3420
cgggtgcccg tgacagtggg cgagacaaca atctacgtgg agcaggagaa tatgtctctg    3480
aagaactacg gcgagttcta tcgctttctg acagacgatc ggctgatgag cctgctgaat    3540
aacatcgtgg agacactgaa gcccaatgag aacggcgacc tggtcatcag acacacagac    3600
ctgatgagcg agctggccgc ctacgaccag tataggtcta ccatcttcat gctgatccag    3660
agcatcgaga acctgatcat cacaaataac gccgtgctgg acgatccaga cgccgatggc    3720
ttctgggtga gagaggatct gcccaagagg aataactttg cctccctgct ggagctgatc    3780
aatcagctga ataacgtgga gctgaccgac gatgagcgca agctgctggt ggccatccgg    3840
aacgccttca gccacaattc ctacaacatc gattttttcc ctgatcaagga cgtgaagcac    3900 ctgcccgagg tggccaaggg catcctgcag cacctgcagt ctatgctggg cgtggagatc    3960
accaag                                                              3966
```

<210> SEQ ID NO 84
<211> LENGTH: 1322
<212> TYPE: PRT
<213> ORGANISM: Artificial Sequence
<220> FEATURE:
<223> OTHER INFORMATION: PsmCas13b amino acid sequence

<400> SEQUENCE: 84

```
Met Ser Lys Glu Cys Lys Lys Gln Arg Gln Glu Lys Lys Arg Arg Leu
1               5                   10                  15

Gln Lys Ala Asn Phe Ser Ile Ser Leu Thr Gly Lys His Val Phe Gly
            20                  25                  30

Ala Tyr Phe Asn Met Ala Arg Thr Asn Phe Val Lys Thr Ile Asn Tyr
        35                  40                  45

Ile Leu Pro Ile Ala Gly Val Arg Gly Asn Tyr Ser Glu Asn Gln Ile
    50                  55                  60

Asn Lys Met Leu His Ala Leu Phe Leu Ile Gln Ala Gly Arg Asn Glu
65                  70                  75                  80

Glu Leu Thr Thr Glu Gln Lys Gln Trp Glu Lys Lys Leu Arg Leu Asn
                85                  90                  95
```

```
Pro Glu Gln Gln Thr Lys Phe Gln Lys Leu Leu Phe Lys His Phe Pro
            100                 105                 110

Val Leu Gly Pro Met Met Ala Asp Val Ala Asp His Lys Ala Tyr Leu
        115                 120                 125

Asn Lys Lys Lys Ser Thr Val Gln Thr Glu Asp Glu Thr Phe Ala Met
    130                 135                 140

Leu Lys Gly Val Ser Leu Ala Asp Cys Leu Asp Ile Ile Cys Leu Met
145                 150                 155                 160

Ala Asp Thr Leu Thr Glu Cys Arg Asn Phe Tyr Thr His Lys Asp Pro
                165                 170                 175

Tyr Asn Lys Pro Ser Gln Leu Ala Asp Gln Tyr Leu His Gln Glu Met
            180                 185                 190

Ile Ala Lys Lys Leu Asp Lys Val Val Ala Ser Arg Arg Ile Leu
        195                 200                 205

Lys Asp Arg Glu Gly Leu Ser Val Asn Glu Val Glu Phe Leu Thr Gly
    210                 215                 220

Ile Asp His Leu His Gln Glu Val Leu Lys Asp Glu Phe Gly Asn Ala
225                 230                 235                 240

Lys Val Lys Asp Gly Lys Val Met Lys Thr Phe Val Glu Tyr Asp Asp
                245                 250                 255

Phe Tyr Phe Lys Ile Ser Gly Lys Arg Leu Val Asn Gly Tyr Thr Val
            260                 265                 270

Thr Thr Lys Asp Asp Lys Pro Val Asn Val Asn Thr Met Leu Pro Ala
    275                 280                 285

Leu Ser Asp Phe Gly Leu Leu Tyr Phe Cys Val Leu Phe Leu Ser Lys
    290                 295                 300

Pro Tyr Ala Lys Leu Phe Ile Asp Glu Val Arg Leu Phe Glu Tyr Ser
305                 310                 315                 320

Pro Phe Asp Asp Lys Glu Asn Met Ile Met Ser Glu Met Leu Ser Ile
                325                 330                 335

Tyr Arg Ile Arg Thr Pro Arg Leu His Lys Ile Asp Ser His Asp Ser
            340                 345                 350

Lys Ala Thr Leu Ala Met Asp Ile Phe Gly Glu Leu Arg Arg Cys Pro
        355                 360                 365

Met Glu Leu Tyr Asn Leu Leu Asp Lys Asn Ala Gly Gln Pro Phe Phe
    370                 375                 380

His Asp Glu Val Lys His Pro Asn Ser His Thr Pro Asp Val Ser Lys
385                 390                 395                 400

Arg Leu Arg Tyr Asp Asp Arg Phe Pro Thr Leu Ala Leu Arg Tyr Ile
                405                 410                 415

Asp Glu Thr Glu Leu Phe Lys Arg Ile Arg Phe Gln Leu Gln Leu Gly
            420                 425                 430

Ser Phe Arg Tyr Lys Phe Tyr Asp Lys Glu Asn Cys Ile Asp Gly Arg
        435                 440                 445

Val Arg Val Arg Arg Ile Gln Lys Glu Ile Asn Gly Tyr Gly Arg Met
    450                 455                 460

Gln Glu Val Ala Asp Lys Arg Met Asp Lys Trp Gly Asp Leu Ile Gln
465                 470                 475                 480

Lys Arg Glu Glu Arg Ser Val Lys Leu Glu His Glu Glu Leu Tyr Ile
                485                 490                 495

Asn Leu Asp Gln Phe Leu Glu Asp Thr Ala Asp Ser Thr Pro Tyr Val
            500                 505                 510

Thr Asp Arg Arg Pro Ala Tyr Asn Ile His Ala Asn Arg Ile Gly Leu
```

```
                515                 520                 525
Tyr Trp Glu Asp Ser Gln Asn Pro Lys Gln Tyr Lys Val Phe Asp Glu
530                 535                 540

Asn Gly Met Tyr Ile Pro Glu Leu Val Val Thr Glu Asp Lys Lys Ala
545                 550                 555                 560

Pro Ile Lys Met Pro Ala Pro Arg Cys Ala Leu Ser Val Tyr Asp Leu
                565                 570                 575

Pro Ala Met Leu Phe Tyr Glu Tyr Leu Arg Glu Gln Gln Asp Asn Glu
                580                 585                 590

Phe Pro Ser Ala Glu Gln Val Ile Ile Glu Tyr Glu Asp Asp Tyr Arg
            595                 600                 605

Lys Phe Phe Lys Ala Val Ala Glu Gly Lys Leu Lys Pro Phe Lys Arg
            610                 615                 620

Pro Lys Glu Phe Arg Asp Phe Leu Lys Lys Glu Tyr Pro Lys Leu Arg
625                 630                 635                 640

Met Ala Asp Ile Pro Lys Lys Leu Gln Leu Phe Leu Cys Ser His Gly
                645                 650                 655

Leu Cys Tyr Asn Asn Lys Pro Glu Thr Val Tyr Glu Arg Leu Asp Arg
            660                 665                 670

Leu Thr Leu Gln His Leu Glu Glu Arg Glu Leu His Ile Gln Asn Arg
            675                 680                 685

Leu Glu His Tyr Gln Lys Asp Arg Asp Met Ile Gly Asn Lys Asp Asn
690                 695                 700

Gln Tyr Gly Lys Lys Ser Phe Ser Asp Val Arg His Gly Ala Leu Ala
705                 710                 715                 720

Arg Tyr Leu Ala Gln Ser Met Met Glu Trp Gln Pro Thr Lys Leu Lys
                725                 730                 735

Asp Lys Glu Lys Gly His Asp Lys Leu Thr Gly Leu Asn Tyr Asn Val
                740                 745                 750

Leu Thr Ala Tyr Leu Ala Thr Tyr Gly His Pro Gln Val Pro Glu Glu
            755                 760                 765

Gly Phe Thr Pro Arg Thr Leu Glu Gln Val Leu Ile Asn Ala His Leu
770                 775                 780

Ile Gly Gly Ser Asn Pro His Pro Phe Ile Asn Lys Val Leu Ala Leu
785                 790                 795                 800

Gly Asn Arg Asn Ile Glu Glu Leu Tyr Leu His Tyr Leu Glu Glu Glu
                805                 810                 815

Leu Lys His Ile Arg Ser Arg Ile Gln Ser Leu Ser Ser Asn Pro Ser
                820                 825                 830

Asp Lys Ala Leu Ser Ala Leu Pro Phe Ile His His Asp Arg Met Arg
            835                 840                 845

Tyr His Glu Arg Thr Ser Glu Glu Met Met Ala Leu Ala Ala Arg Tyr
            850                 855                 860

Thr Thr Ile Gln Leu Pro Asp Gly Leu Phe Thr Pro Tyr Ile Leu Glu
865                 870                 875                 880

Ile Leu Gln Lys His Tyr Thr Glu Asn Ser Asp Leu Gln Asn Ala Leu
                885                 890                 895

Ser Gln Asp Val Pro Val Lys Leu Asn Pro Thr Cys Asn Ala Ala Tyr
            900                 905                 910

Leu Ile Thr Leu Phe Tyr Gln Thr Val Leu Lys Asp Asn Ala Gln Pro
            915                 920                 925

Phe Tyr Leu Ser Asp Lys Thr Tyr Thr Arg Asn Lys Asp Gly Glu Lys
930                 935                 940
```

Ala Glu Ser Phe Ser Phe Lys Arg Ala Tyr Glu Leu Phe Ser Val Leu
945                 950                 955                 960

Asn Asn Asn Lys Lys Asp Thr Phe Pro Phe Glu Met Ile Pro Leu Phe
            965                 970                 975

Leu Thr Ser Asp Glu Ile Gln Glu Arg Leu Ser Ala Lys Leu Leu Asp
        980                 985                 990

Gly Asp Gly Asn Pro Val Pro Glu Val Gly Glu Lys Gly Lys Pro Ala
        995                 1000                1005

Thr Asp Ser Gln Gly Asn Thr Ile Trp Lys Arg Arg Ile Tyr Ser
    1010            1015            1020

Glu Val Asp Asp Tyr Ala Glu Lys Leu Thr Asp Arg Asp Met Lys
    1025            1030            1035

Ile Ser Phe Lys Gly Glu Trp Glu Lys Leu Pro Arg Trp Lys Gln
    1040            1045            1050

Asp Lys Ile Ile Lys Arg Arg Asp Glu Thr Arg Arg Gln Met Arg
    1055            1060            1065

Asp Glu Leu Leu Gln Arg Met Pro Arg Tyr Ile Arg Asp Ile Lys
    1070            1075            1080

Asp Asn Glu Arg Thr Leu Arg Arg Tyr Lys Thr Gln Asp Met Val
    1085            1090            1095

Leu Phe Leu Leu Ala Glu Lys Met Phe Thr Asn Ile Ile Ser Glu
    1100            1105            1110

Gln Ser Ser Glu Phe Asn Trp Lys Gln Met Arg Leu Ser Lys Val
    1115            1120            1125

Cys Asn Glu Ala Phe Leu Arg Gln Thr Leu Thr Phe Arg Val Pro
    1130            1135            1140

Val Thr Val Gly Glu Thr Thr Ile Tyr Val Glu Gln Glu Asn Met
    1145            1150            1155

Ser Leu Lys Asn Tyr Gly Glu Phe Tyr Arg Phe Leu Thr Asp Asp
    1160            1165            1170

Arg Leu Met Ser Leu Leu Asn Asn Ile Val Glu Thr Leu Lys Pro
    1175            1180            1185

Asn Glu Asn Gly Asp Leu Val Ile Arg His Thr Asp Leu Met Ser
    1190            1195            1200

Glu Leu Ala Ala Tyr Asp Gln Tyr Arg Ser Thr Ile Phe Met Leu
    1205            1210            1215

Ile Gln Ser Ile Glu Asn Leu Ile Ile Thr Asn Asn Ala Val Leu
    1220            1225            1230

Asp Asp Pro Asp Ala Asp Gly Phe Trp Val Arg Glu Asp Leu Pro
    1235            1240            1245

Lys Arg Asn Asn Phe Ala Ser Leu Leu Glu Leu Ile Asn Gln Leu
    1250            1255            1260

Asn Asn Val Glu Leu Thr Asp Asp Glu Arg Lys Leu Leu Val Ala
    1265            1270            1275

Ile Arg Asn Ala Phe Ser His Asn Ser Tyr Asn Ile Asp Phe Ser
    1280            1285            1290

Leu Ile Lys Asp Val Lys His Leu Pro Glu Val Ala Lys Gly Ile
    1295            1300            1305

Leu Gln His Leu Gln Ser Met Leu Gly Val Glu Ile Thr Lys
    1310            1315            1320

<210> SEQ ID NO 85
<211> LENGTH: 36

```
<212> TYPE: DNA
<213> ORGANISM: Artificial Sequence
<220> FEATURE:
<223> OTHER INFORMATION: PsmCas13b direct repeat

<400> SEQUENCE: 85
gttgtagaag cttatcgttt ggataggtat gacaac                                36

<210> SEQ ID NO 86
<211> LENGTH: 3285
<212> TYPE: DNA
<213> ORGANISM: Artificial Sequence
<220> FEATURE:
<223> OTHER INFORMATION: RanCas13b nucleic acid sequence

<400> SEQUENCE: 86
atggagaagc ccctgctgcc taacgtgtat accctgaagc acaagttctt ttggggcgcc      60
ttcctgaata tcgcccggca caacgccttt atcaccatct gccacatcaa tgagcagctg     120
ggcctgaaaa cccccagcaa cgacgataag atcgtggacg tggtgtgcga gacatggaac     180
aatatcctga caatgaccca cgatctgctg aagaagtccc agctgaccga gctgatcctg     240
aagcacttcc ctttctctga cagccatgtg ctaccacccc ctaagaagga gggcaagaag     300
aagggccacc agaaggagca gcagaaggag aaggagagcg aggcacagtc ccaggcagag     360
gccctgaacc catccaagct gatcgaggcc ctggagatcc tggtgaatca gctgcactct     420
ctgcggaact actatagcca ctataagcac aagaagcccg acgccgagaa ggatatcttc     480
aagcacctgt ataaggcctt cgacgcctct ctgagaatgg tgaaggagga ttataaggcc     540
cacttcaccg tgaatctgac aagggacttt gcccacctga accgcaaggg caagaacaag     600
caggacaatc ccgacttcaa cagatacaga ttcgagaagg atggcttctt taccgagtct     660
ggcctgctgt tctttacaaa tctgtttctg gacaagaggg atgcctattg gatgctgaag     720
aaggtgtccg gcttcaaggc ctctcacaag cagcgcgaga gatgaccac agaggtgttt      780 tgcaggagcc gcatcctgct gcccaagctg aggctggagt cccgctacga ccacaaccag     840
atgctgctgg atatgctgtc tgagctgagc agatgtccta agctgctgta tgagaagctg     900
agcgaggaga ataagaagca cttccaggtg gaggccgacg gctttctgga tgagatcgag     960
gaggagcaga acccattcaa ggacacccct atccggcacc aggatagatt cccctacttt    1020
gccctgaggt atctggacct gaatgagtcc ttcaagtcta tccgctttca ggtggatctg    1080
ggcacatacc actattgtat ctacgacaag aagatcggcg atgagcagga agaggcac     1140 ctgacccgca cactgctgtc cttcggccgg ctgcaggact taccgagat caacagaccc    1200 caggagtgga aggccctgac caaggacctg gattacaagg agacatccaa tcagcctttc    1260
atctctaaga ccacaccaca ctatcacatc accgacaaca agatcggctt tcggctgggc    1320
acaagcaagg agctgtaccc ctccctggag atcaaggatg gcgccaatag aatcgccaag    1380 taccttata actccggctt cgtggcccac gcctttatct ctgtgcacga gctgctgcct    1440
ctgatgttct accagcacct gaccggcaag agcgaggacc tgctgaagga gacagtgcgg    1500
cacatccaga gaatctataa ggacttcgag gaggagcgga tcaataccat cgaggatctg    1560
gagaaggcaa accagggcag actgccactg ggagcctttc ccaagcagat gctgggcctg    1620
ctgcagaata gcagcctga tctgtccgag aaggccaaga tcaagatcga agctgatc     1680 gccgagacaa agctgctgtc tcacaggctg aacacaaagc tgaagagctc ccaaaagctg    1740
ggcaagcgga gagagaagct gatcaagaca ggcgtgctgg ccgactggct ggtgaaggat    1800
```

| | |
|---|---|
| ttcatgcgct tcagcccgt ggcctacgac gcccagaatc agcctatcaa gtctagcaag | 1860 |
| gccaactcca ccgagttctg gtttatcagg cgcgccctgg ccctgtacgg aggagagaag | 1920 |
| aataggctgg agggctattt caagcagacc aacctgatcg gcaacacaaa tccacacccc | 1980 |
| ttcctgaaca gtttaattg gaaggcctgc aggaatctgg tggatttcta ccagcagtat | 2040 |
| ctggagcagc gcgagaagtt tctggaggcc atcaagaacc agccatggga gccctaccag | 2100 |
| tattgcctgc tgctgaagat ccctaaggag aacaggaaga tctggtgaa gggatgggag | 2160 |
| cagggaggaa tctctctgcc acggggcctg tttaccgagg ccatcagaga gacactgtct | 2220 |
| gaggacctga tgctgagcaa gccaatccgc aaggagatca agaagcacgg ccgggtgggc | 2280 |
| ttcatcagca gagccatcac cctgtacttt aaggagaagt atcaggataa gcaccagagc | 2340 |
| ttctacaatc tgtcctataa gctggaggca aaggcaccac tgctgaagcg ggaggagcac | 2400 |
| tacgagtatt ggcagcagaa caagcctcag tctccaaccg agagccagag gctggagctg | 2460 |
| cacacaagcg accgctggaa ggattacctg ctgtataaga gatggcagca cctggagaag | 2520 |
| aagctgcggc tgtaccggaa tcaggacgtg atgctgtggc tgatgaccct ggagctgaca | 2580 |
| aagaaccact tcaaggagct gaacctgaat tatcaccagc tgaagctgga gaatctggcc | 2640 |
| gtgaacgtgc aggaggccga tgccaagctg aaccctctga tcagaccct gcccatggtg | 2700 |
| ctgcctgtga aggtgtaccc tgccacagcc tttggcgagg tgcagtacca agaccccca | 2760 |
| atcaggacag tgtatatccg cgaggagcac accaaggccc tgaagatggg caacttcaag | 2820 |
| gccctggtga aggaccggag actgaatggc ctgttctctt ttatcaagga ggagaacgat | 2880 |
| acacagaagc acccaatcag ccagctgcgg ctgaggcgcg agctggagat ctaccagtct | 2940 |
| ctgagagtgg acgccttcaa ggagacactg agcctggagg agaagctgct gaataagcac | 3000 |
| acatccctgt cctctctgga gaacgagttt agggccctgc tggaggagtg gaagaaggag | 3060 |
| tatgccgcca gctccatggt gacagacgag cacatcgcct tcatcgccag cgtgcgcaat | 3120 |
| gccttctgcc acaaccagta ccccttctac aaggaggccc tgcacgcccc tatcccactg | 3180 |
| ttcaccgtgg cccagcccac cacagaggag aaggatggcc tgggaatcgc agaggccctg | 3240 |
| ctgaaggtgc tgagggagta ctgtgagatc gtgaagtccc agatc | 3285 |

<210> SEQ ID NO 87
<211> LENGTH: 1095
<212> TYPE: PRT
<213> ORGANISM: Artificial Sequence
<220> FEATURE:
<223> OTHER INFORMATION: RanCas13b amino acid sequence

<400> SEQUENCE: 87

Met Glu Lys Pro Leu Leu Pro Asn Val Tyr Thr Leu Lys His Lys Phe
1               5                   10                  15

Phe Trp Gly Ala Phe Leu Asn Ile Ala Arg His Asn Ala Phe Ile Thr
            20                  25                  30

Ile Cys His Ile Asn Glu Gln Leu Gly Leu Lys Thr Pro Ser Asn Asp
        35                  40                  45

Asp Lys Ile Val Asp Val Val Cys Glu Thr Trp Asn Asn Ile Leu Asn
    50                  55                  60

Asn Asp His Asp Leu Leu Lys Lys Ser Gln Leu Thr Glu Leu Ile Leu
65                  70                  75                  80

Lys His Phe Pro Phe Leu Thr Ala Met Cys Tyr His Pro Pro Lys Lys
                85                  90                  95

Glu Gly Lys Lys Lys Gly His Gln Lys Glu Gln Gln Lys Glu Lys Glu

```
              100                 105                 110
Ser Glu Ala Gln Ser Gln Ala Glu Ala Leu Asn Pro Ser Lys Leu Ile
            115                 120                 125
Glu Ala Leu Glu Ile Leu Val Asn Gln Leu His Ser Leu Arg Asn Tyr
            130                 135                 140
Tyr Ser His Tyr Lys His Lys Pro Asp Ala Glu Lys Asp Ile Phe
145                 150                 155                 160
Lys His Leu Tyr Lys Ala Phe Asp Ala Ser Leu Arg Met Val Lys Glu
                165                 170                 175
Asp Tyr Lys Ala His Phe Thr Val Asn Leu Thr Arg Asp Phe Ala His
            180                 185                 190
Leu Asn Arg Lys Gly Lys Asn Lys Gln Asp Asn Pro Asp Phe Asn Arg
            195                 200                 205
Tyr Arg Phe Glu Lys Asp Gly Phe Phe Thr Glu Ser Gly Leu Leu Phe
            210                 215                 220
Phe Thr Asn Leu Phe Leu Asp Lys Arg Asp Ala Tyr Trp Met Leu Lys
225                 230                 235                 240
Lys Val Ser Gly Phe Lys Ala Ser His Lys Gln Arg Glu Lys Met Thr
                245                 250                 255
Thr Glu Val Phe Cys Arg Ser Arg Ile Leu Leu Pro Lys Leu Arg Leu
                260                 265                 270
Glu Ser Arg Tyr Asp His Asn Gln Met Leu Leu Asp Met Leu Ser Glu
            275                 280                 285
Leu Ser Arg Cys Pro Lys Leu Leu Tyr Glu Lys Leu Ser Glu Glu Asn
            290                 295                 300
Lys Lys His Phe Gln Val Glu Ala Asp Gly Phe Leu Asp Glu Ile Glu
305                 310                 315                 320
Glu Glu Gln Asn Pro Phe Lys Asp Thr Leu Ile Arg His Gln Asp Arg
                325                 330                 335
Phe Pro Tyr Phe Ala Leu Arg Tyr Leu Asp Leu Asn Glu Ser Phe Lys
                340                 345                 350
Ser Ile Arg Phe Gln Val Asp Leu Gly Thr Tyr His Tyr Cys Ile Tyr
                355                 360                 365
Asp Lys Lys Ile Gly Asp Glu Gln Glu Lys Arg His Leu Thr Arg Thr
                370                 375                 380
Leu Leu Ser Phe Gly Arg Leu Gln Asp Phe Thr Glu Ile Asn Arg Pro
385                 390                 395                 400
Gln Glu Trp Lys Ala Leu Thr Lys Asp Leu Asp Tyr Lys Glu Thr Ser
                405                 410                 415
Asn Gln Pro Phe Ile Ser Lys Thr Thr Pro His Tyr His Ile Thr Asp
                420                 425                 430
Asn Lys Ile Gly Phe Arg Leu Gly Thr Ser Lys Glu Leu Tyr Pro Ser
                435                 440                 445
Leu Glu Ile Lys Asp Gly Ala Asn Arg Ile Ala Lys Tyr Pro Tyr Asn
            450                 455                 460
Ser Gly Phe Val Ala His Ala Phe Ile Ser Val His Glu Leu Leu Pro
465                 470                 475                 480
Leu Met Phe Tyr Gln His Leu Thr Gly Lys Ser Glu Asp Leu Leu Lys
                485                 490                 495
Glu Thr Val Arg His Ile Gln Arg Ile Tyr Lys Asp Phe Glu Glu Glu
            500                 505                 510
Arg Ile Asn Thr Ile Glu Asp Leu Glu Lys Ala Asn Gln Gly Arg Leu
            515                 520                 525
```

-continued

Pro Leu Gly Ala Phe Pro Lys Gln Met Leu Gly Leu Leu Gln Asn Lys
530                 535                 540

Gln Pro Asp Leu Ser Glu Lys Ala Lys Ile Lys Ile Glu Lys Leu Ile
545                 550                 555                 560

Ala Glu Thr Lys Leu Leu Ser His Arg Leu Asn Thr Lys Leu Lys Ser
        565                 570                 575

Ser Pro Lys Leu Gly Lys Arg Arg Glu Lys Leu Ile Lys Thr Gly Val
            580                 585                 590

Leu Ala Asp Trp Leu Val Lys Asp Phe Met Arg Phe Gln Pro Val Ala
        595                 600                 605

Tyr Asp Ala Gln Asn Gln Pro Ile Lys Ser Ser Lys Ala Asn Ser Thr
    610                 615                 620

Glu Phe Trp Phe Ile Arg Arg Ala Leu Ala Leu Tyr Gly Gly Glu Lys
625                 630                 635                 640

Asn Arg Leu Glu Gly Tyr Phe Lys Gln Thr Asn Leu Ile Gly Asn Thr
                645                 650                 655

Asn Pro His Pro Phe Leu Asn Lys Phe Asn Trp Lys Ala Cys Arg Asn
            660                 665                 670

Leu Val Asp Phe Tyr Gln Gln Tyr Leu Glu Gln Arg Glu Lys Phe Leu
        675                 680                 685

Glu Ala Ile Lys Asn Gln Pro Trp Glu Pro Tyr Gln Tyr Cys Leu Leu
690                 695                 700

Leu Lys Ile Pro Lys Glu Asn Arg Lys Asn Leu Val Lys Gly Trp Glu
705                 710                 715                 720

Gln Gly Gly Ile Ser Leu Pro Arg Gly Leu Phe Thr Glu Ala Ile Arg
                725                 730                 735

Glu Thr Leu Ser Glu Asp Leu Met Leu Ser Lys Pro Ile Arg Lys Glu
            740                 745                 750

Ile Lys Lys His Gly Arg Val Gly Phe Ile Ser Arg Ala Ile Thr Leu
        755                 760                 765

Tyr Phe Lys Glu Lys Tyr Gln Asp Lys His Gln Ser Phe Tyr Asn Leu
770                 775                 780

Ser Tyr Lys Leu Glu Ala Lys Ala Pro Leu Leu Lys Arg Glu Glu His
785                 790                 795                 800

Tyr Glu Tyr Trp Gln Gln Asn Lys Pro Gln Ser Pro Thr Glu Ser Gln
                805                 810                 815

Arg Leu Glu Leu His Thr Ser Asp Arg Trp Lys Asp Tyr Leu Leu Tyr
            820                 825                 830

Lys Arg Trp Gln His Leu Glu Lys Lys Leu Arg Leu Tyr Arg Asn Gln
        835                 840                 845

Asp Val Met Leu Trp Leu Met Thr Leu Glu Leu Thr Lys Asn His Phe
850                 855                 860

Lys Glu Leu Asn Leu Asn Tyr His Gln Leu Lys Leu Glu Asn Leu Ala
865                 870                 875                 880

Val Asn Val Gln Glu Ala Asp Ala Lys Leu Asn Pro Leu Asn Gln Thr
                885                 890                 895

Leu Pro Met Val Leu Pro Val Lys Val Tyr Pro Ala Thr Ala Phe Gly
            900                 905                 910

Glu Val Gln Tyr His Lys Thr Pro Ile Arg Thr Val Tyr Ile Arg Glu
        915                 920                 925

Glu His Thr Lys Ala Leu Lys Met Gly Asn Phe Lys Ala Leu Val Lys
930                 935                 940

Asp Arg Arg Leu Asn Gly Leu Phe Ser Phe Ile Lys Glu Glu Asn Asp
945                 950                 955                 960

Thr Gln Lys His Pro Ile Ser Gln Leu Arg Leu Arg Arg Glu Leu Glu
            965                 970                 975

Ile Tyr Gln Ser Leu Arg Val Asp Ala Phe Lys Glu Thr Leu Ser Leu
        980                 985                 990

Glu Glu Lys Leu Leu Asn Lys His  Thr Ser Leu Ser Ser  Leu Glu Asn
        995                 1000                1005

Glu Phe  Arg Ala Leu Leu Glu  Glu Trp Lys Lys Glu  Tyr Ala Ala
    1010                1015                1020

Ser Ser Met Val Thr Asp Glu  His Ile Ala Phe Ile  Ala Ser Val
    1025                1030                1035

Arg Asn Ala Phe Cys His Asn  Gln Tyr Pro Phe Tyr  Lys Glu Ala
    1040                1045                1050

Leu His Ala Pro Ile Pro Leu  Phe Thr Val Ala Gln  Pro Thr Thr
    1055                1060                1065

Glu Glu Lys Asp Gly Leu Gly  Ile Ala Glu Ala Leu  Leu Lys Val
    1070                1075                1080

Leu Arg Glu Tyr Cys Glu Ile  Val Lys Ser Gln Ile
    1085                1090                1095

<210> SEQ ID NO 88
<211> LENGTH: 36
<212> TYPE: DNA
<213> ORGANISM: Artificial Sequence
<220> FEATURE:
<223> OTHER INFORMATION: RanCas13b direct repeat

<400> SEQUENCE: 88
gttgggactg ctctcacttt gaagggtatt cacaac                                36

<210> SEQ ID NO 89
<211> LENGTH: 3372
<212> TYPE: DNA
<213> ORGANISM: Artificial Sequence
<220> FEATURE:
<223> OTHER INFORMATION: PauCas13b nucleic acid sequence

<400> SEQUENCE: 89
atggaggacg ataagaaaac cacaggcagc atctcctacg agctgaagga caagcacttc      60
tgggccgcct ttctgaacct ggcccgccac aacgtgtata tcaccatcaa ccacatcaat     120
aagctgctgg agatccggga gatcgacaac gatgagaagg tgctggacat caagaccctg     180
tggcagaagg gcaacaagga tctgaatcag aaggccaggc tgcgcgagct gatgacaaag     240
cacttcccct cctggagaca agccatctac acaaagaaca aggaggataa gaaggaggtg     300
aagcaggaga agcaggccga ggcccagtct ctggagagcc tgaaggactg cctgttcctg     360
tttctggata gctgcagga ggcccgcaat tactatagcc actacaagta ttccgagttc     420
tctaaggagc cagagtttga ggagggcctg ctggagaaga tgtataacat ctttggcaac     480
aatatccagc tggtcatcaa cgactatcag cacaacaagg atatcaatcc cgacgaggat     540
ttcaagcacc tggaccggaa gggccagttc aagtactcct tgccgataa cgagggcaat     600 atcaccgagt ccggcctgct gttcttcgtg agcctgttcc tggagaagaa ggacgccatc     660
tggatgcagc agaagctgaa cggctttaag gataacctgg agaacaagaa gaagatgaca     720
cacgaggtgt ctgccggag cagaatcctg atgcccaagc tgcgcctgga gagcacccag     780
acacaggact ggattctgct ggacatgctg aatgagctga tccggtgtcc taagtccctg     840

```
tacgagagac tgcagggcga cgatagggag aagttcaagg tgccatttga ccccgccgac      900
gaggattaca acgccgagca ggagccttt aagaataccc tgatcagaca ccaggacagg      960
ttcccatact tgtgctgag atacttcgat tacaacgaga tcttcaagaa tctgaggttt     1020
cagatcgacc tgggcaccta ccacttctct atctataaga agctgatcgg cggccagaag    1080
gaggatcgcc acctgacaca caagctgtac ggcttcgagc gcatccagga gtttgccaag    1140
cagaaccggc tgacgagtg aaggccatc gtgaaggacc tggataccta cgagacaagc      1200
aacaagcggt atatctccga gacaacacct cactataccc tggagaatca agatcggc      1260 atcaggtttc gcaacggcaa taaggagatc tgcccagcc tgaaaaccaa cgacgagaac     1320
aatgagaagt ctaagtacaa gctggataag cagtatcagg ccgaggcctt tctgtccgtg    1380
cacgagctgc tgcccatgat gttctactat ctgctgctga agaaggagaa gcctaacaat    1440
gacgagatca atgcctctat cgtggagggc ttcatcaagc gggagatcag aaacatcttc    1500
aagctgtacg acgcctttgc caatggcgag atcaacaata tcgacgatct ggagaagtat    1560 tgccgccgata agggcatccc caagagacac ctgcctaagc agatggtggc catcctgtac    1620
gacgagcaca aggatatggt gaaggaggcc aagaggaagc agaaggagat ggtgaaggat    1680
accaagaagc tgctggccac cctggagaag cagacacaga aggagaagga ggacgatggc    1740
agaaacgtga gctgctgaa gagcggcgag atcgccagat ggctggtgaa tgacatgatg    1800
aggttccagc ccgtgcagaa ggataacgag ggcaagcctc tgaacaatag caaggccaat    1860
tccaccgagt accagatgct gcagcggagc ctggccctgt ataacaatga ggagaagccc    1920
acaaggtatt ttcgccaggt gaacctgatc gagagcaaca atccccaccc tttcctgaag    1980
tggaccaagt gggaggagtg taacaacatc ctgaccttt actactctta cctgacaaag    2040
aagatcgagt tcctgaacaa gctgaagcca gaggactgga agaagaatca gtatttctg    2100 aagctgatgg agcccaagac caacagagag acactggtgc agggctggaa gaacggcttt    2160
aatctgccta ggggcatctt cacagagcca atccgcgagt ggttcaagcg gcaccagaac    2220
aatagcaagg agtacgagaa ggtggaggcc ctggacagag tgggcctggt gaccaaagtg    2280
atccccctgt tctttaagga ggagtacttc aaggataagg aggagaactt caaggaggac    2340
acacagaagg agatcaacga ttgcgtgcag ccattctaca atttccccta acgtgggc      2400 aatatccaca agcctaagga aaggactttt ctgcaccggg aggagagaat cgagctgtgg    2460
gacaagaaga aggataagtt caagggctac aaggagaaga tcaagagcaa gaagctgacc    2520
gagaaggaca aggaggagtt caggtcttat ctggagttc agagctggaa caagttcgag    2580
agggagctgc gcctggtgcg gaatcaggat atcgtgacat ggctgctgtg caaggagctg    2640
atcgacaagc tgaagatcga tgagctgaac atcgaggagc tgaagaagct gagactgaac    2700
aatatcgaca ccgatacagc caagaaggag aagaacaata tcctgaatag agtgatgcct    2760
atggagctgc cagtgaccgt gtacgagatc gacgattccc acaagatcgt gaaggacaag    2820
ccactgcaca ccatctatat caaggaggcc gagacaaagc tgctgaagca gggcaacttc    2880
aaggccctgg tgaaggatcg gagactgaat ggcctgttca gcttcgtgaa aaccaacagc    2940
gaggccgaga gcaagcgcaa tcctatctcc aagctgcggg tggagtacga gctgggcgag    3000
tatcaggagg cccggatcga gatcatccag gacatgctgg ccctggagga agctgatc      3060 aacaagtaca aggatctgcc aacaaacaag ttttccgaga tgctgaacag ctggctggag    3120
ggcaaggacg aggccgataa ggcccgcttt cagaatgacg tggatttcct gatcgccgtg    3180
```
cggaacgcct tctcccacaa tcagtaccca atgcacaaca agatcgagtt tgccaatatc    3240
aagcccttca gcctgtatac cgccaacaat tccgaggaga agggcctggg catcgccaac    3300
cagctgaagg acaagaccaa ggagacaaca gataagatca agaagatcga gaagcccatc    3360
gagacaaagg ag                                                        3372

<210> SEQ ID NO 90
<211> LENGTH: 1124
<212> TYPE: PRT
<213> ORGANISM: Artificial Sequence
<220> FEATURE:
<223> OTHER INFORMATION: PauCas13 amino acid sequence

<400> SEQUENCE: 90

Met Glu Asp Asp Lys Lys Thr Thr Gly Ser Ile Ser Tyr Glu Leu Lys
1               5                   10                  15

Asp Lys His Phe Trp Ala Ala Phe Leu Asn Leu Ala Arg His Asn Val
            20                  25                  30

Tyr Ile Thr Ile Asn His Ile Asn Lys Leu Leu Glu Ile Arg Glu Ile
        35                  40                  45

Asp Asn Asp Glu Lys Val Leu Asp Ile Lys Thr Leu Trp Gln Lys Gly
    50                  55                  60

Asn Lys Asp Leu Asn Gln Lys Ala Arg Leu Arg Glu Leu Met Thr Lys
65                  70                  75                  80

His Phe Pro Phe Leu Glu Thr Ala Ile Tyr Thr Lys Asn Lys Glu Asp
                85                  90                  95

Lys Lys Glu Val Lys Gln Glu Lys Gln Ala Glu Ala Gln Ser Leu Glu
            100                 105                 110

Ser Leu Lys Asp Cys Leu Phe Leu Phe Leu Asp Lys Leu Gln Glu Ala
        115                 120                 125

Arg Asn Tyr Tyr Ser His Tyr Lys Tyr Ser Glu Phe Ser Lys Glu Pro
    130                 135                 140

Glu Phe Glu Glu Gly Leu Leu Glu Lys Met Tyr Asn Ile Phe Gly Asn
145                 150                 155                 160

Asn Ile Gln Leu Val Ile Asn Asp Tyr Gln His Asn Lys Asp Ile Asn
                165                 170                 175

Pro Asp Glu Asp Phe Lys His Leu Asp Arg Lys Gly Gln Phe Lys Tyr
            180                 185                 190

Ser Phe Ala Asp Asn Glu Gly Asn Ile Thr Glu Ser Gly Leu Leu Phe
        195                 200                 205

Phe Val Ser Leu Phe Leu Glu Lys Lys Asp Ala Ile Trp Met Gln Gln
    210                 215                 220

Lys Leu Asn Gly Phe Lys Asp Asn Leu Glu Asn Lys Lys Met Thr
225                 230                 235                 240

His Glu Val Phe Cys Arg Ser Arg Ile Leu Met Pro Lys Leu Arg Leu
                245                 250                 255

Glu Ser Thr Gln Thr Gln Asp Trp Ile Leu Leu Asp Met Leu Asn Glu
            260                 265                 270

Leu Ile Arg Cys Pro Lys Ser Leu Tyr Glu Arg Leu Gln Gly Asp Asp
        275                 280                 285

Arg Glu Lys Phe Lys Val Pro Phe Asp Pro Ala Asp Glu Asp Tyr Asn
    290                 295                 300

Ala Glu Gln Glu Pro Phe Lys Asn Thr Leu Ile Arg His Gln Asp Arg
305                 310                 315                 320

Phe Pro Tyr Phe Val Leu Arg Tyr Phe Asp Tyr Asn Glu Ile Phe Lys

```
                    325                 330                 335
Asn Leu Arg Phe Gln Ile Asp Leu Gly Thr Tyr His Phe Ser Ile Tyr
                340                 345                 350
Lys Lys Leu Ile Gly Gly Gln Lys Glu Asp Arg His Leu Thr His Lys
                355                 360                 365
Leu Tyr Gly Phe Glu Arg Ile Gln Glu Phe Ala Lys Gln Asn Arg Pro
                370                 375                 380
Asp Glu Trp Lys Ala Ile Val Lys Asp Leu Asp Thr Tyr Glu Thr Ser
385                 390                 395                 400
Asn Lys Arg Tyr Ile Ser Glu Thr Thr Pro His Tyr His Leu Glu Asn
                405                 410                 415
Gln Lys Ile Gly Ile Arg Phe Arg Asn Gly Asn Lys Glu Ile Trp Pro
                420                 425                 430
Ser Leu Lys Thr Asn Asp Glu Asn Asn Glu Lys Ser Lys Tyr Lys Leu
                435                 440                 445
Asp Lys Gln Tyr Gln Ala Glu Ala Phe Leu Ser Val His Glu Leu Leu
                450                 455                 460
Pro Met Met Phe Tyr Tyr Leu Leu Leu Lys Lys Glu Lys Pro Asn Asn
465                 470                 475                 480
Asp Glu Ile Asn Ala Ser Ile Val Glu Gly Phe Ile Lys Arg Glu Ile
                485                 490                 495
Arg Asn Ile Phe Lys Leu Tyr Asp Ala Phe Ala Asn Gly Glu Ile Asn
                500                 505                 510
Asn Ile Asp Asp Leu Glu Lys Tyr Cys Ala Asp Lys Gly Ile Pro Lys
                515                 520                 525
Arg His Leu Pro Lys Gln Met Val Ala Ile Leu Tyr Asp Glu His Lys
                530                 535                 540
Asp Met Val Lys Glu Ala Lys Arg Lys Gln Lys Glu Met Val Lys Asp
545                 550                 555                 560
Thr Lys Lys Leu Leu Ala Thr Leu Glu Lys Gln Thr Gln Lys Glu Lys
                565                 570                 575
Glu Asp Asp Gly Arg Asn Val Lys Leu Leu Lys Ser Gly Glu Ile Ala
                580                 585                 590
Arg Trp Leu Val Asn Asp Met Met Arg Phe Gln Pro Val Gln Lys Asp
                595                 600                 605
Asn Glu Gly Lys Pro Leu Asn Asn Ser Lys Ala Asn Ser Thr Glu Tyr
                610                 615                 620
Gln Met Leu Gln Arg Ser Leu Ala Leu Tyr Asn Asn Glu Glu Lys Pro
625                 630                 635                 640
Thr Arg Tyr Phe Arg Gln Val Asn Leu Ile Glu Ser Asn Asn Pro His
                645                 650                 655
Pro Phe Leu Lys Trp Thr Lys Trp Glu Glu Cys Asn Asn Ile Leu Thr
                660                 665                 670
Phe Tyr Tyr Ser Tyr Leu Thr Lys Lys Ile Glu Phe Leu Asn Lys Leu
                675                 680                 685
Lys Pro Glu Asp Trp Lys Lys Asn Gln Tyr Phe Leu Lys Leu Met Glu
                690                 695                 700
Pro Lys Thr Asn Arg Glu Thr Leu Val Gln Gly Trp Lys Asn Gly Phe
705                 710                 715                 720
Asn Leu Pro Arg Gly Ile Phe Thr Glu Pro Ile Arg Glu Trp Phe Lys
                725                 730                 735
Arg His Gln Asn Asn Ser Lys Glu Tyr Glu Lys Val Glu Ala Leu Asp
                740                 745                 750
```

Arg Val Gly Leu Val Thr Lys Val Ile Pro Leu Phe Lys Glu Glu
    755                 760                 765

Tyr Phe Lys Asp Lys Glu Glu Asn Phe Lys Glu Asp Thr Gln Lys Glu
    770                 775                 780

Ile Asn Asp Cys Val Gln Pro Phe Tyr Asn Phe Pro Tyr Asn Val Gly
785                 790                 795                 800

Asn Ile His Lys Pro Lys Glu Lys Asp Phe Leu His Arg Glu Arg
                805                 810                 815

Ile Glu Leu Trp Asp Lys Lys Asp Lys Phe Lys Gly Tyr Lys Glu
                820                 825                 830

Lys Ile Lys Ser Lys Lys Leu Thr Glu Lys Asp Lys Glu Glu Phe Arg
                835                 840                 845

Ser Tyr Leu Glu Phe Gln Ser Trp Asn Lys Phe Glu Arg Glu Leu Arg
    850                 855                 860

Leu Val Arg Asn Gln Asp Ile Val Thr Trp Leu Leu Cys Lys Glu Leu
865                 870                 875                 880

Ile Asp Lys Leu Lys Ile Asp Glu Leu Asn Ile Glu Leu Lys Lys
                885                 890                 895

Leu Arg Leu Asn Asn Ile Asp Thr Asp Thr Ala Lys Lys Glu Lys Asn
                900                 905                 910

Asn Ile Leu Asn Arg Val Met Pro Met Glu Leu Pro Val Thr Val Tyr
                915                 920                 925

Glu Ile Asp Asp Ser His Lys Ile Val Lys Asp Lys Pro Leu His Thr
                930                 935                 940

Ile Tyr Ile Lys Glu Ala Glu Thr Lys Leu Leu Lys Gln Gly Asn Phe
945                 950                 955                 960

Lys Ala Leu Val Lys Asp Arg Arg Leu Asn Gly Leu Phe Ser Phe Val
                965                 970                 975

Lys Thr Asn Ser Glu Ala Glu Ser Lys Arg Asn Pro Ile Ser Lys Leu
                980                 985                 990

Arg Val Glu Tyr Glu Leu Gly Glu  Tyr Gln Glu Ala Arg  Ile Glu Ile
        995                 1000                1005

Ile Gln  Asp Met Leu Ala Leu  Glu Glu Lys Leu Ile  Asn Lys Tyr
    1010                1015                1020

Lys Asp  Leu Pro Thr Asn Lys  Phe Ser Glu Met Leu  Asn Ser Trp
    1025                1030                1035

Leu Glu  Gly Lys Asp Glu Ala  Asp Lys Ala Arg Phe  Gln Asn Asp
    1040                1045                1050

Val Asp  Phe Leu Ile Ala Val  Arg Asn Ala Phe Ser  His Asn Gln
    1055                1060                1065

Tyr Pro  Met His Asn Lys Ile  Glu Phe Ala Asn Ile  Lys Pro Phe
    1070                1075                1080

Ser Leu  Tyr Thr Ala Asn Asn  Ser Glu Glu Lys Gly  Leu Gly Ile
    1085                1090                1095

Ala Asn  Gln Leu Lys Asp Lys  Thr Lys Glu Thr Thr  Asp Lys Ile
    1100                1105                1110

Lys Lys  Ile Glu Lys Pro Ile  Glu Thr Lys Glu
    1115                1120

<210> SEQ ID NO 91
<211> LENGTH: 36
<212> TYPE: DNA
<213> ORGANISM: Artificial Sequence
<220> FEATURE:

<223> OTHER INFORMATION: PauCas13b direct repeat

<400> SEQUENCE: 91
gttgtatctg ccttctgttt gaaaggtaaa aacaac    36

<210> SEQ ID NO 92
<211> LENGTH: 1422
<212> TYPE: DNA
<213> ORGANISM: Artificial Sequence
<220> FEATURE:
<223> OTHER INFORMATION: CMV-BD-2xms2-PPT-exon-MMP9_intron2-2xms2-BD-
    bGHpA

<400> SEQUENCE: 92

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgcc ccattgacg caaatgggcg gtaggcgtgt | 540 |
| acggtgggag gtctatataa gcagagctgg tttagtgaac cgtcggatct tccatttcgg | 600 |
| gtgtcgtgac gtacgaatac gatctagacc ctgcatcctc tctgggacac tcaaccccct | 660 |
| cacggacagc ccgaattcga cccaagctga cgggagcaca tgaggatcac ccatgtgcca | 720 |
| cgagcgacat gaggatcacc catgtcgctt tcactagtct gtggtgtgat atccatggcg | 780 |
| gcctacttat cctgtccctt ttttttccac aggagcgcac catcttcttc aaggacgacg | 840 |
| gcaactacaa gacccgcgcc gaggtgaagt tcgagggcga cacctggtg aaccgcatcg | 900 |
| agctgaaggg catcgacttc aaggaggacg gcaacatcct gggcacaag ctggagtaca | 960 |
| actacaacag ccacaacgtc tatatcatgg ccgacaagca gaagaacggc atcaaggtga | 1020 |
| gccgggctg tgaaagctgc gggatggagc gagaaggcct gatctggctc ttgagcctgc | 1080 |
| aacggagcac atgaggatca cccatgtgcc acgagcgaca tgaggatcac ccatgtcgaa | 1140 |
| ttcgacccaa gctgactgac tgagacgagt taactgtacc gtctccgctt ctagagctcg | 1200 |
| ctgatcagcc tcgactgtgc cttcagttg ccagccatct gttgtttgcc cctccccgt | 1260 |
| gccttccttg accctggaag gtgccactcc cactgtcctt tcctaataaa atgaggaaat | 1320 |
| tgcatcgcat tgtctgagta ggtgtcattc tattctgggg ggtggggtgg ggcaggacag | 1380 |
| caaggggag gattgggaag agaatagcag gcatgctggg ga | 1422 |

<210> SEQ ID NO 93
<211> LENGTH: 5403
<212> TYPE: DNA
<213> ORGANISM: Artificial Sequence
<220> FEATURE:
<223> OTHER INFORMATION: PspCas13b-ABI1-2a-PYL1-MS2 nucleic acid
    sequence

<400> SEQUENCE: 93

| | |
|---|---|
| atgaacatcc ccgctctggt ggaaaaccag aagaagtact ttggcaccta cagcgtgatg | 60 |
| gccatgctga acgtcagac cgtgctggac cacatccaga aggtggccga tattgagggc | 120 |

```
gagcagaacg agaacaacga gaatctgtgg tttcaccccg tgatgagcca cctgtacaac    180
gccaagaacg gctacgacaa gcagcccgag aaaaccatgt tcatcatcga gcggctgcag    240
agctacttcc cattcctgaa gatcatggcc gagaaccaga gagagtacag caacggcaag    300
tacaagcaga accgcgtgga agtgaacagc aacgacatct tcgaggtgct gaagcgcgcc    360
ttcggcgtgc tgaagatgta cagggacctg accaacgcat acaagaccta cgaggaaaag    420
ctgaacgacg gctgcgagtt cctgaccagc acagagcaac ctctgagcgg catgatcaac    480
aactactaca cagtggccct gcggaacatg aacgagagat acggctacaa gacagaggac    540
ctggccttca tccaggacaa gcggttcaag ttcgtgaagg acgcctacgg caagaaaaag    600
tcccaagtga ataccggatt cttcctgagc ctgcaggact acaacggcga cacacagaag    660
aagctgcacc tgagcggagt gggaatcgcc ctgctgatct gcctgttcct ggacaagcag    720
tacatcaaca tctttctgag caggctgccc atcttctcca gctacaatgc cagagcgag     780 gaacggcgga tcatcatcag atccttcggc atcaacagca tcaagctgcc caaggaccgg    840
atccacagcg agaagtccaa caagagcgtg gccatggata tgctcaacga agtgaagcgg    900
tgccccgacg agctgttcac aacactgtct gccgagaagc agtcccggtt cagaatcatc    960
agcgacgacc acaatgaagt gctgatgaag cggagcagcg acagattcgt gcctctgctg   1020
ctgcagtata tcgattacgg caagctgttc gaccacatca ggttccacgt gaacatgggc   1080
aagctgagat acctgctgaa ggccgacaag acctgcatcg acggcagac cagagtcaga    1140 gtgatcgagc agcccctgaa cggcttcggc agactggaag aggccgagac aatgcggaag   1200
caagagaacg gcaccttcgg caacagcggc atccggatca gagacttcga gaacatgaag   1260
cgggacgacg ccaatcctgc caactatccc tacatcgtgg acacctacac acactacatc   1320
ctggaaaaca acaaggtcga gatgtttatc aacgacaaag gagacagcgc ccactgctg    1380 cccgtgatcg aggatgatag atacgtggtc aagacaatcc ccagctgccg gatgagcacc   1440
ctggaaattc cagccatggc cttccacatg tttctgttcg gcagcaagaa aaccgagaag   1500
ctgatcgtgg acgtgcacaa ccggtacaag agactgttcc aggccatgca gaaagaagaa   1560
gtgaccgccg agaatatcgc cagcttcgga atcgccgaga cgacctgcc tcagaagatc    1620 ctggatctga tcagcggcaa tgcccacggc aaggatgtgg acgccttcat cagactgacc   1680
gtggacgaca tgctgaccga caccgagcgg agaatcaaga gattcaagga cgaccggaag   1740
tccattcgga gcgccgacaa caagatggga aagagaggct tcaagcagat ctccacaggc   1800
aagctggccg acttcctggc caaggacatc gtgctgtttc agcccagcgt gaacgatggc   1860
gagaacaaga tcaccggcct gaactaccgg atcatgcaga gcgccattgc cgtgtacgat   1920
agcggcgacg attacgaggc caagcagcag ttcaagctga tgttcgagaa ggcccggctg   1980
atcggcaagg gcacaacaga gcctcatcca tttctgtaca aggtgttcgc ccgcagcatc   2040
cccgccaatg ccgtcgagtt ctacgagcgc tacctgatcg agcggaagtt ctacctgacc   2100
ggcctgtcca acgagatcaa gaaaggcaac agagtggatg tgcccttcat ccggcgggac   2160
cagaacaagt ggaaaacacc cgccatgaag accctgggca gaatctacag cgaggatctg   2220
cccgtggaac tgcccagaca gatgttcgac aatgagatca agtccacct gaagtccctg    2280 ccacagatgg aaggcatcga cttcaacaat gccaacgtga cctatctgat cgccgagtac   2340
atgaagagag tgctggacga cgacttccag accttctacc agtggaaccg caactaccgg   2400
tacatggaca tgcttaaggg cgagtacgac agaaagggct ccctgcagca ctgcttcacc   2460
```

```
agcgtggaag agagagaagg cctctggaaa gagcgggcct ccagaacaga gcggtacaga    2520
aagcaggcca gcaacaagat ccgcagcaac cggcagatga gaaacgccag cagcgaagag    2580
atcgagacaa tcctggataa gcggctgagc aacagccgga acgagtacca gaaaagcgag    2640
aaagtgatcc ggcgctacag agtgcaggat gccctgctgt ttctgctggc caaaaagacc    2700
ctgaccgaac tggccgattt cgacggcgag aggttcaaac tgaaagaaat catgcccgac    2760
gccgagaagg gaatcctgag cgagatcatg cccatgagct tcaccttcga gaaggcggc    2820 aagaagtaca ccatcaccag cgagggcatg aagctgaaga actacggcga cttctttgtg    2880
ctggctagcg acaagaggat cggcaacctg ctggaactcg tgggcagcga catcgtgtcc    2940
aaagaggata tcatggaaga gttcaacaaa tacgaccagt gcaggcccga gatcagctcc    3000
atcgtgttca acctggaaaa gtgggccttc gacacatacc ccgagctgtc tgccagagtg    3060
gaccgggaag agaaggtgga cttcaagagc atcctgaaaa tcctgctgaa caacaagaac    3120
atcaacaaag agcagagcga catcctgcgg aagatccgga acgccttcga tgcaaacaat    3180
taccccgaca aaggcgtggt ggaaatcaag gccctgcctg agatcgccat gagcatcaag    3240
aaggcctttg gggagtacgc catcatgaag ggaagcctgc aggcctatcc ctatgacgtg    3300
cccgattatg ccagcctggg cagcggctcc cccaagaaaa acgcaaggt ggaagatcct    3360 aagaaaaagc ggaaagtgga cggcattggt agtgggagca acggaggtgg aggctctgga    3420
cctaggacgc gtgtgccttt gtatggtttt acttcgattt gtggaagaag acctgagatg    3480
gaagctgctg tttcgactat accaagattc cttcaatctt cctctggttc gatgttagat    3540
ggtcggtttg atcctcaatc cgccgctcat ttcttcggtg tttacgacgg ccatggcggt    3600
tctcaggtag cgaactattg tagagagagg atgcatttgg cttttggcgga ggagatagct    3660 aaggagaaac cgatgctctg cgatggtgat acgtggctgg agaagtggaa gaaagctctt    3720
ttcaactcgt tcctgagagt tgactcggag attgagtcag ttgcgccgga gacggttggg    3780
tcaacgtcgg tggttgccgt tgttttcccg tctcacatct tcgtcgctaa ctgcggtgac    3840
tctagagccg ttctttgccg cggcaaaact gcacttccat tatccgttga ccataaaccg    3900
gatagagaag atgaagctgc gaggattgaa gccgcaggag ggaaagtgat tcagtggaat    3960
ggagctcgtg ttttcggtgt tctcgccatg tcgagatcca ttggcgatag atacttgaaa    4020
ccatccatca ttcctgatcc ggaagtgacg gctgtgaaga gagtaaaaga agatgattgt    4080
ctgattttgg cgagtgacgg ggtttgggat gtaatgacgg atgaagaagc gtgtgagatg    4140
gcaaggaagc ggattctctt gtggcacaag aaaaacgcgg tggctgggga tgcatcgttg    4200
ctcgcggatg agcggagaaa ggaagggaaa gatcctgcgg cgatgtccgc ggctgagtat    4260
ttgtcaaagc tggcgataca gagaggaagc aaagacaaca taagtgtggt ggtggttgat    4320
ttgaagggat ccggcgcaac aaacttctct ctgctgaaac aagccggaga tgtcgaagag    4380
aatcctggac cgatgggtgg gggcgcgcca actcaagacg aattcaccca actctcccaa    4440
tcaatcgccg agttccacac gtaccaactc ggtaacggcc gttgctcatc tctcctagct    4500
cagcgaatcc acgcgccgcc ggaaacagta tggtccgtgg tgagacgttt cgataggcca    4560
cagatttaca aacacttcat caaaagctgt aacgtgagtg aagatttcga gatgcgagtg    4620
ggatgcacgc gcgacgtgaa cgtgataagt ggattaccgg cgaatacgtc tcgagagaga    4680
ttagatctgt tggacgatga tcggagagtg actgggttta gtataaccgg tggtgaacat    4740
aggctgagga attataaatc ggttacgacg gttcatagat ttgagaaaga agaagaagaa    4800
gaaaggatct ggaccgttgt tttggaatct tatgttgttg atgtaccgga aggtaattcg    4860
```

```
gaggaagata cgagattgtt tgctgatacg gttattagat tgaatcttca gaaacttgct   4920
tcgatcactg aagctatgaa cgaattctca agcgctgcag gtactagtcc aaagaagaag   4980
cggaaggtcg gtggatccgg aggaggtgga agcatggctt caaactttac tcagttcgtg   5040
ctcgtggaca atggtgggac aggggatgtg acagtggctc cttctaattt cgctaatggg   5100
gtggcagagt ggatcagctc caactcacgg agccaggcct acaaggtgac atgcagcgtc   5160
aggcagtcta gtgcccagaa gagaaagtat accatcaagg tggaggtccc caaagtggct   5220
acccagacag tgggcggagt cgaactgcct gtcgccgctt ggaggtccta cctgaacatg   5280
gagctcacta tcccaatttt cgctaccaat tctgactgtg aactcatcgt gaaggcaatg   5340
caggggctcc tcaaagacgg taatcctatc ccttccgcca tcgccgctaa ctcaggtatc   5400
tac                                                                 5403
```

<210> SEQ ID NO 94
<211> LENGTH: 1801
<212> TYPE: PRT
<213> ORGANISM: Artificial Sequence
<220> FEATURE:
<223> OTHER INFORMATION: PspCas13b-ABI1-2a-PYL1-MS2 amino acid seqeunce

<400> SEQUENCE: 94

```
Met Asn Ile Pro Ala Leu Val Glu Asn Gln Lys Lys Tyr Phe Gly Thr
1               5                   10                  15

Tyr Ser Val Met Ala Met Leu Asn Ala Gln Thr Val Leu Asp His Ile
            20                  25                  30

Gln Lys Val Ala Asp Ile Glu Gly Glu Gln Asn Glu Asn Asn Glu Asn
        35                  40                  45

Leu Trp Phe His Pro Val Met Ser His Leu Tyr Asn Ala Lys Asn Gly
    50                  55                  60

Tyr Asp Lys Gln Pro Glu Lys Thr Met Phe Ile Ile Glu Arg Leu Gln
65                  70                  75                  80

Ser Tyr Phe Pro Phe Leu Lys Ile Met Ala Glu Asn Gln Arg Glu Tyr
                85                  90                  95

Ser Asn Gly Lys Tyr Lys Gln Asn Arg Val Glu Val Asn Ser Asn Asp
            100                 105                 110

Ile Phe Glu Val Leu Lys Arg Ala Phe Gly Val Leu Lys Met Tyr Arg
        115                 120                 125

Asp Leu Thr Asn Ala Tyr Lys Thr Tyr Glu Glu Lys Leu Asn Asp Gly
    130                 135                 140

Cys Glu Phe Leu Thr Ser Thr Glu Gln Pro Leu Ser Gly Met Ile Asn
145                 150                 155                 160

Asn Tyr Tyr Thr Val Ala Leu Arg Asn Met Asn Glu Arg Tyr Gly Tyr
                165                 170                 175

Lys Thr Glu Asp Leu Ala Phe Ile Gln Asp Lys Arg Phe Lys Phe Val
            180                 185                 190

Lys Asp Ala Tyr Gly Lys Lys Lys Ser Gln Val Asn Thr Gly Phe Phe
        195                 200                 205

Leu Ser Leu Gln Asp Tyr Asn Gly Asp Thr Gln Lys Lys Leu His Leu
    210                 215                 220

Ser Gly Val Gly Ile Ala Leu Leu Ile Cys Leu Phe Leu Asp Lys Gln
225                 230                 235                 240

Tyr Ile Asn Ile Phe Leu Ser Arg Leu Pro Ile Phe Ser Ser Tyr Asn
                245                 250                 255
```

-continued

Ala Gln Ser Glu Glu Arg Arg Ile Ile Ile Arg Ser Phe Gly Ile Asn
            260                 265                 270

Ser Ile Lys Leu Pro Lys Asp Arg Ile His Ser Glu Lys Ser Asn Lys
        275                 280                 285

Ser Val Ala Met Asp Met Leu Asn Glu Val Lys Arg Cys Pro Asp Glu
    290                 295                 300

Leu Phe Thr Thr Leu Ser Ala Glu Lys Gln Ser Arg Phe Arg Ile Ile
305                 310                 315                 320

Ser Asp Asp His Asn Glu Val Leu Met Lys Arg Ser Asp Arg Phe
                325                 330                 335

Val Pro Leu Leu Leu Gln Tyr Ile Asp Tyr Gly Lys Leu Phe Asp His
            340                 345                 350

Ile Arg Phe His Val Asn Met Gly Lys Leu Arg Tyr Leu Leu Lys Ala
        355                 360                 365

Asp Lys Thr Cys Ile Asp Gly Gln Thr Arg Val Arg Val Ile Glu Gln
    370                 375                 380

Pro Leu Asn Gly Phe Gly Arg Leu Glu Glu Ala Glu Thr Met Arg Lys
385                 390                 395                 400

Gln Glu Asn Gly Thr Phe Gly Asn Ser Gly Ile Arg Ile Arg Asp Phe
                405                 410                 415

Glu Asn Met Lys Arg Asp Asp Ala Asn Pro Ala Asn Tyr Pro Tyr Ile
            420                 425                 430

Val Asp Thr Tyr Thr His Tyr Ile Leu Glu Asn Asn Lys Val Glu Met
        435                 440                 445

Phe Ile Asn Asp Lys Glu Asp Ser Ala Pro Leu Leu Pro Val Ile Glu
    450                 455                 460

Asp Asp Arg Tyr Val Val Lys Thr Ile Pro Ser Cys Arg Met Ser Thr
465                 470                 475                 480

Leu Glu Ile Pro Ala Met Ala Phe His Met Phe Leu Phe Gly Ser Lys
                485                 490                 495

Lys Thr Glu Lys Leu Ile Val Asp Val His Asn Arg Tyr Lys Arg Leu
            500                 505                 510

Phe Gln Ala Met Gln Lys Glu Glu Val Thr Ala Glu Asn Ile Ala Ser
        515                 520                 525

Phe Gly Ile Ala Glu Ser Asp Leu Pro Gln Lys Ile Leu Asp Leu Ile
    530                 535                 540

Ser Gly Asn Ala His Gly Lys Asp Val Asp Ala Phe Ile Arg Leu Thr
545                 550                 555                 560

Val Asp Asp Met Leu Thr Asp Thr Glu Arg Arg Ile Lys Arg Phe Lys
                565                 570                 575

Asp Asp Arg Lys Ser Ile Arg Ser Ala Asp Asn Lys Met Gly Lys Arg
            580                 585                 590

Gly Phe Lys Gln Ile Ser Thr Gly Lys Leu Ala Asp Phe Leu Ala Lys
        595                 600                 605

Asp Ile Val Leu Phe Gln Pro Ser Val Asn Asp Gly Glu Asn Lys Ile
    610                 615                 620

Thr Gly Leu Asn Tyr Arg Ile Met Gln Ser Ala Ile Ala Val Tyr Asp
625                 630                 635                 640

Ser Gly Asp Asp Tyr Glu Ala Lys Gln Gln Phe Lys Leu Met Phe Glu
                645                 650                 655

Lys Ala Arg Leu Ile Gly Lys Gly Thr Thr Glu Pro His Pro Phe Leu
            660                 665                 670

Tyr Lys Val Phe Ala Arg Ser Ile Pro Ala Asn Ala Val Glu Phe Tyr

```
              675                 680                 685
Glu Arg Tyr Leu Ile Glu Arg Lys Phe Tyr Leu Thr Gly Leu Ser Asn
690                 695                 700
Glu Ile Lys Lys Gly Asn Arg Val Asp Val Pro Phe Ile Arg Arg Asp
705                 710                 715                 720
Gln Asn Lys Trp Lys Thr Pro Ala Met Lys Thr Leu Gly Arg Ile Tyr
                725                 730                 735
Ser Glu Asp Leu Pro Val Glu Leu Pro Arg Gln Met Phe Asp Asn Glu
                740                 745                 750
Ile Lys Ser His Leu Lys Ser Leu Pro Gln Met Glu Gly Ile Asp Phe
                755                 760                 765
Asn Asn Ala Asn Val Thr Tyr Leu Ile Ala Glu Tyr Met Lys Arg Val
770                 775                 780
Leu Asp Asp Asp Phe Gln Thr Phe Tyr Gln Trp Asn Arg Asn Tyr Arg
785                 790                 795                 800
Tyr Met Asp Met Leu Lys Gly Glu Tyr Asp Arg Lys Gly Ser Leu Gln
                805                 810                 815
His Cys Phe Thr Ser Val Glu Glu Arg Glu Gly Leu Trp Lys Glu Arg
                820                 825                 830
Ala Ser Arg Thr Glu Arg Tyr Arg Lys Gln Ala Ser Asn Lys Ile Arg
                835                 840                 845
Ser Asn Arg Gln Met Arg Asn Ala Ser Ser Glu Glu Ile Glu Thr Ile
850                 855                 860
Leu Asp Lys Arg Leu Ser Asn Ser Arg Asn Glu Tyr Gln Lys Ser Glu
865                 870                 875                 880
Lys Val Ile Arg Arg Tyr Arg Val Gln Asp Ala Leu Leu Phe Leu Leu
                885                 890                 895
Ala Lys Lys Thr Leu Thr Glu Leu Ala Asp Phe Asp Gly Glu Arg Phe
                900                 905                 910
Lys Leu Lys Glu Ile Met Pro Asp Ala Glu Lys Gly Ile Leu Ser Glu
                915                 920                 925
Ile Met Pro Met Ser Phe Thr Phe Glu Lys Gly Gly Lys Lys Tyr Thr
                930                 935                 940
Ile Thr Ser Glu Gly Met Lys Leu Lys Asn Tyr Gly Asp Phe Phe Val
945                 950                 955                 960
Leu Ala Ser Asp Lys Arg Ile Gly Asn Leu Leu Glu Leu Val Gly Ser
                965                 970                 975
Asp Ile Val Ser Lys Glu Asp Ile Met Glu Glu Phe Asn Lys Tyr Asp
                980                 985                 990
Gln Cys Arg Pro Glu Ile Ser Ser Ile Val Phe Asn Leu Glu Lys Trp
            995                 1000                1005
Ala Phe Asp Thr Tyr Pro Glu Leu Ser Ala Arg Val Asp Arg Glu
    1010                1015                1020
Glu Lys Val Asp Phe Lys Ser Ile Leu Lys Ile Leu Leu Asn Asn
    1025                1030                1035
Lys Asn Ile Asn Lys Glu Gln Ser Asp Ile Leu Arg Lys Ile Arg
    1040                1045                1050
Asn Ala Phe Asp Ala Asn Asn Tyr Pro Asp Lys Gly Val Val Glu
    1055                1060                1065
Ile Lys Ala Leu Pro Glu Ile Ala Met Ser Ile Lys Lys Ala Phe
    1070                1075                1080
Gly Glu Tyr Ala Ile Met Lys Gly Ser Leu Gln Ala Tyr Pro Tyr
    1085                1090                1095
```

```
Asp Val Pro Asp Tyr Ala Ser Leu Gly Ser Gly Ser Pro Lys Lys
    1100                1105                1110

Lys Arg Lys Val Glu Asp Pro Lys Lys Arg Lys Val Asp Gly
    1115                1120                1125

Ile Gly Ser Gly Ser Asn Gly Gly Gly Gly Ser Gly Pro Arg Thr
    1130                1135                1140

Arg Val Pro Leu Tyr Gly Phe Thr Ser Ile Cys Gly Arg Arg Pro
    1145                1150                1155

Glu Met Glu Ala Ala Val Ser Thr Ile Pro Arg Phe Leu Gln Ser
    1160                1165                1170

Ser Ser Gly Ser Met Leu Asp Gly Arg Phe Asp Pro Gln Ser Ala
    1175                1180                1185

Ala His Phe Phe Gly Val Tyr Asp Gly His Gly Gly Ser Gln Val
    1190                1195                1200

Ala Asn Tyr Cys Arg Glu Arg Met His Leu Ala Leu Ala Glu Glu
    1205                1210                1215

Ile Ala Lys Glu Lys Pro Met Leu Cys Asp Gly Asp Thr Trp Leu
    1220                1225                1230

Glu Lys Trp Lys Lys Ala Leu Phe Asn Ser Phe Leu Arg Val Asp
    1235                1240                1245

Ser Glu Ile Glu Ser Val Ala Pro Glu Thr Val Gly Ser Thr Ser
    1250                1255                1260

Val Val Ala Val Val Phe Pro Ser His Ile Phe Val Ala Asn Cys
    1265                1270                1275

Gly Asp Ser Arg Ala Val Leu Cys Arg Gly Lys Thr Ala Leu Pro
    1280                1285                1290

Leu Ser Val Asp His Lys Pro Asp Arg Glu Asp Glu Ala Ala Arg
    1295                1300                1305

Ile Glu Ala Ala Gly Gly Lys Val Ile Gln Trp Asn Gly Ala Arg
    1310                1315                1320

Val Phe Gly Val Leu Ala Met Ser Arg Ser Ile Gly Asp Arg Tyr
    1325                1330                1335

Leu Lys Pro Ser Ile Ile Pro Asp Pro Glu Val Thr Ala Val Lys
    1340                1345                1350

Arg Val Lys Glu Asp Asp Cys Leu Ile Leu Ala Ser Asp Gly Val
    1355                1360                1365

Trp Asp Val Met Thr Asp Glu Glu Ala Cys Glu Met Ala Arg Lys
    1370                1375                1380

Arg Ile Leu Leu Trp His Lys Lys Asn Ala Val Ala Gly Asp Ala
    1385                1390                1395

Ser Leu Leu Ala Asp Glu Arg Arg Lys Glu Gly Lys Asp Pro Ala
    1400                1405                1410

Ala Met Ser Ala Ala Glu Tyr Leu Ser Lys Leu Ala Ile Gln Arg
    1415                1420                1425

Gly Ser Lys Asp Asn Ile Ser Val Val Val Val Asp Leu Lys Gly
    1430                1435                1440

Ser Gly Ala Thr Asn Phe Ser Leu Leu Lys Gln Ala Gly Asp Val
    1445                1450                1455

Glu Glu Asn Pro Gly Pro Met Gly Gly Gly Ala Pro Thr Gln Asp
    1460                1465                1470

Glu Phe Thr Gln Leu Ser Gln Ser Ile Ala Glu Phe His Thr Tyr
    1475                1480                1485
```

-continued

```
Gln Leu Gly Asn Gly Arg Cys Ser Ser Leu Leu Ala Gln Arg Ile
    1490                1495                1500

His Ala Pro Pro Glu Thr Val Trp Ser Val Val Arg Arg Phe Asp
    1505                1510                1515

Arg Pro Gln Ile Tyr Lys His Phe Ile Lys Ser Cys Asn Val Ser
    1520                1525                1530

Glu Asp Phe Glu Met Arg Val Gly Cys Thr Arg Asp Val Asn Val
    1535                1540                1545

Ile Ser Gly Leu Pro Ala Asn Thr Ser Arg Glu Arg Leu Asp Leu
    1550                1555                1560

Leu Asp Asp Arg Arg Val Thr Gly Phe Ser Ile Thr Gly Gly
    1565                1570                1575

Glu His Arg Leu Arg Asn Tyr Lys Ser Val Thr Val His Arg
    1580                1585                1590

Phe Glu Lys Glu Glu Glu Glu Arg Ile Trp Thr Val Val Leu
    1595                1600                1605

Glu Ser Tyr Val Val Asp Val Pro Glu Gly Asn Ser Glu Glu Asp
    1610                1615                1620

Thr Arg Leu Phe Ala Asp Thr Val Ile Arg Leu Asn Leu Gln Lys
    1625                1630                1635

Leu Ala Ser Ile Thr Glu Ala Met Asn Glu Phe Ser Ser Ala Ala
    1640                1645                1650

Gly Thr Ser Pro Lys Lys Lys Arg Lys Val Gly Gly Ser Gly Gly
    1655                1660                1665

Gly Gly Ser Met Ala Ser Asn Phe Thr Gln Phe Val Leu Val Asp
    1670                1675                1680

Asn Gly Gly Thr Gly Asp Val Thr Val Ala Pro Ser Asn Phe Ala
    1685                1690                1695

Asn Gly Val Ala Glu Trp Ile Ser Ser Asn Ser Arg Ser Gln Ala
    1700                1705                1710

Tyr Lys Val Thr Cys Ser Val Arg Gln Ser Ser Ala Gln Lys Arg
    1715                1720                1725

Lys Tyr Thr Ile Lys Val Glu Val Pro Lys Val Ala Thr Gln Thr
    1730                1735                1740

Val Gly Gly Val Glu Leu Pro Val Ala Ala Trp Arg Ser Tyr Leu
    1745                1750                1755

Asn Met Glu Leu Thr Ile Pro Ile Phe Ala Thr Asn Ser Asp Cys
    1760                1765                1770

Glu Leu Ile Val Lys Ala Met Gln Gly Leu Leu Lys Asp Gly Asn
    1775                1780                1785

Pro Ile Pro Ser Ala Ile Ala Ala Asn Ser Gly Ile Tyr
    1790                1795                1800

<210> SEQ ID NO 95
<211> LENGTH: 3414
<212> TYPE: DNA
<213> ORGANISM: Artificial Sequence
<220> FEATURE:
<223> OTHER INFORMATION: dRfxCas13d-MS2 nucleic acid sequence

<400> SEQUENCE: 95
atgagcccca agaagaagag aaaggtggag ccagcatcg aaaaaaaaaa gtccttcgcc     60
aagggcatgg gcgtgaagtc cacactcgtg tccggctcca agtgtacat gacaaccttc    120 gccgaaggca gcgacgccag gctggaaaag atcgtggagg gcgacagcat caggagcgtg    180
```

-continued

```
aatgagggcg aggccttcag cgctgaaatg gccgataaaa acgccggcta taagatcggc    240
aacgccaaat tcagccatcc taagggctac gccgtggtgg ctaacaaccc tctgtataca    300
ggacccgtcc agcaggatat gctcggcctg aaggaaactc tggaaaagag gtacttcggc    360
gagagcgctg atggcaatga caatatttgt atccaggtga tccataacat cctggacatt    420
gaaaaaatcc tcgccgaata cattaccaac gccgcctacg ccgtcaacaa tatctccggc    480
ctggataagg acattattgg attcggcaag ttctccacag tgtataccta cgacgaattc    540
aaagaccccg agcaccatag ggccgctttc aacaataacg ataagctcat caacgccatc    600
aaggcccagt atgacgagtt cgacaacttc ctcgataacc ccagactcgg ctatttcggc    660 caggccttt t tcagcaagga gggcagaaat tacatcatca attacggcaa cgaatgctat    720
gacattctgg ccctcctgag cggactggcg cactgggtgg tcgctaacaa cgaagaagag    780
tccaggatct ccaggacctg gctctacaac ctcgataaga acctcgacaa cgaatacatc    840 tccacccctca actacctcta cgacaggatc accaatgagc tgaccaactc cttctccaag    900
aactccgccg ccaacgtgaa ctatattgcc gaaactctgg aatcaacccc tgccgaattc    960
gccgaacaat atttcagatt cagcattatg aaagagcaga aaaacctcgg attcaatatc   1020
accaagctca gggaagtgat gctggacagg aaggatatgt ccgagatcag gaaaaatcat   1080
aaggtgttcg actccatcag gaccaaggtc tacaccatga tggactttgt gatttatagg   1140
tattacatcg aagaggatgc caaggtggct gccgccaata agtccctccc cgataatgag   1200
aagtccctga gcgagaagga tatctttgtg attaacctga ggggctcctt caacgacgac   1260
cagaaggatg ccctctacta cgatgaagct aatagaattt ggagaaagct cgaaaatatc   1320
atgcacaaca tcaaggaatt taggggaaac aagacaagag agtataagaa gaaggacgcc   1380
cctagactgc ccagaatcct gcccgctggc cgtgatgttt ccgccttcag caaactcatg   1440
tatgccctga ccatgttcct ggatggcaag gagatcaacg acctcctgac caccctgatt   1500
aataaattcg ataacatcca gagcttcctg aaggtgatgc ctctcatcgg agtcaacgct   1560
aagttcgtgg aggaatacgc cttttttcaaa gactccgcca agatcgccga tgagctgagg   1620
ctgatcaagt ccttcgctag aatgggagaa cctattgccg atgccaggag ggccatgtat   1680
atcgacgcca tccgtatttt aggaaccaac ctgtcctatg atgagctcaa ggccctcgcc   1740 gacaccttt t ccctggacga gaacggaaac aagctcaaga aaggcaagca cggcatgaga   1800
aatttcatta ttaataacgt gatcagcaat aaaaaggttcc actacctgat cagatacggt   1860
gatcctgccc acctccatga gatcgccaaa aacgaggccg tggtgaagtt cgtgctcggc   1920
aggatcgctg acatccagaa aaaacagggc cagaacggca agaaccagat cgacaggtac   1980
tacgaaactt gtatcggaaa ggataagggc aagagcgtga gcgaaaaggt ggacgctctc   2040
acaaagatca tcaccggaat gaactacgac caattcgaca agaaaaggag cgtcattgag   2100
gacaccggca gggaaaacgc cgagagggag aagtttaaaa agatcatcag cctgtacctc   2160
accgtgatct accacatcct caagaatatt gtcaatatca acgccaggta cgtcatcgga   2220
ttccattgcg tcgagcgtga tgctcaactg tacaaggaga aaggctacga catcaatctc   2280
aagaaactgg aagagaaggg attcagctcc gtcaccaagc tctgcgctgg cattgatgaa   2340
actgcccccg ataagagaaa ggacgtggaa aaggagatgg ctgaaagagc caaggagagc   2400
attgacagcc tcgagagcgc caaccccaag ctgtatgcca attacatcaa atacagcgac   2460
gagaagaaag ccgaggagtt caccaggcag attaacaggg agaaggccaa aaccgccctg   2520
aacgcctacc tgaggaacac caagtggaat gtgatcatca gggaggacct cctgagaatt   2580
```

```
gacaacaaga catgtaccct gttcgcaaac aaggccgtcg ccctggaagt ggccaggtat   2640
gtccacgcct atatcaacga cattgccgag gtcaattcct acttccaact gtaccattac   2700
atcatgcaga gaattatcat gaatgagagg tacgagaaaa gcagcggaaa ggtgtccgag   2760
tacttcgacg ctgtgaatga cgagaagaag tacaacgata ggctcctgaa actgctgtgt   2820
gtgcctttcg gctactgtat ccccaggttt aagaacctga gcatcgaggc cctgttcgat   2880
aggaacgagg ccgccaagtt cgacaaggag aaaaagaagg tgtccggcaa ttccggatcc   2940
ggacctaaga aaagaggaa ggtggcggcc gcttacccat acgatgttcc agattacgct   3000
gctggatccg gaggagtgg aagcatggct tcaaacttta ctcagttcgt gctcgtggac   3060
aatggtggga caggggatgt gacagtggct ccttctaatt cgctaatgg ggtggcagag   3120 tggatcagct ccaactcacg gagccaggcc tacaaggtga catgcagcgt caggcagtct   3180
agtgcccaga agaaaagta taccatcaag gtggaggtcc ccaaagtggc tacccagaca   3240
gtgggcggag tcgaactgcc tgtcgccgct tggaggtcct acctgaacat ggagctcact   3300
atcccaattt tcgctaccaa ttctgactgt gaactcatcg tgaaggcaat gcaggggctc   3360
ctcaaagacg gtaatcctat cccttccgcc atcgccgcta actcaggtat ctac         3414
```

<210> SEQ ID NO 96
<211> LENGTH: 1138
<212> TYPE: PRT
<213> ORGANISM: Artificial Sequence
<220> FEATURE:
<223> OTHER INFORMATION: dRfxCas13d-MS2 amino acid sequence

<400> SEQUENCE: 96

```
Met Ser Pro Lys Lys Arg Lys Val Glu Ala Ser Ile Glu Lys Lys
1               5                   10                  15

Lys Ser Phe Ala Lys Gly Met Gly Val Lys Ser Thr Leu Val Ser Gly
            20                  25                  30

Ser Lys Val Tyr Met Thr Thr Phe Ala Glu Gly Ser Asp Ala Arg Leu
        35                  40                  45

Glu Lys Ile Val Glu Gly Asp Ser Ile Arg Ser Val Asn Glu Gly Glu
    50                  55                  60

Ala Phe Ser Ala Glu Met Ala Asp Lys Asn Ala Gly Tyr Lys Ile Gly
65                  70                  75                  80

Asn Ala Lys Phe Ser His Pro Lys Gly Tyr Ala Val Val Ala Asn Asn
                85                  90                  95

Pro Leu Tyr Thr Gly Pro Val Gln Gln Asp Met Leu Gly Leu Lys Glu
            100                 105                 110

Thr Leu Glu Lys Arg Tyr Phe Gly Glu Ser Ala Asp Gly Asn Asp Asn
        115                 120                 125

Ile Cys Ile Gln Val Ile His Asn Ile Leu Asp Ile Glu Lys Ile Leu
    130                 135                 140

Ala Glu Tyr Ile Thr Asn Ala Ala Tyr Ala Val Asn Asn Ile Ser Gly
145                 150                 155                 160

Leu Asp Lys Asp Ile Ile Gly Phe Gly Lys Phe Ser Thr Val Tyr Thr
                165                 170                 175

Tyr Asp Glu Phe Lys Asp Pro Glu His His Arg Ala Ala Phe Asn Asn
            180                 185                 190

Asn Asp Lys Leu Ile Asn Ala Ile Lys Ala Gln Tyr Asp Glu Phe Asp
        195                 200                 205

Asn Phe Leu Asp Asn Pro Arg Leu Gly Tyr Phe Gly Gln Ala Phe Phe
```

-continued

```
                210                 215                 220
Ser Lys Glu Gly Arg Asn Tyr Ile Ile Asn Tyr Gly Asn Glu Cys Tyr
225                 230                 235                 240

Asp Ile Leu Ala Leu Leu Ser Gly Leu Ala His Trp Val Val Ala Asn
                245                 250                 255

Asn Glu Glu Glu Ser Arg Ile Ser Arg Thr Trp Leu Tyr Asn Leu Asp
            260                 265                 270

Lys Asn Leu Asp Asn Glu Tyr Ile Ser Thr Leu Asn Tyr Leu Tyr Asp
        275                 280                 285

Arg Ile Thr Asn Glu Leu Thr Asn Ser Phe Ser Lys Asn Ser Ala Ala
    290                 295                 300

Asn Val Asn Tyr Ile Ala Glu Thr Leu Gly Ile Asn Pro Ala Glu Phe
305                 310                 315                 320

Ala Glu Gln Tyr Phe Arg Phe Ser Ile Met Lys Glu Gln Lys Asn Leu
                325                 330                 335

Gly Phe Asn Ile Thr Lys Leu Arg Glu Val Met Leu Asp Arg Lys Asp
            340                 345                 350

Met Ser Glu Ile Arg Lys Asn His Lys Val Phe Asp Ser Ile Arg Thr
        355                 360                 365

Lys Val Tyr Thr Met Met Asp Phe Val Ile Tyr Arg Tyr Tyr Ile Glu
    370                 375                 380

Glu Asp Ala Lys Val Ala Ala Ala Asn Lys Ser Leu Pro Asp Asn Glu
385                 390                 395                 400

Lys Ser Leu Ser Glu Lys Asp Ile Phe Val Ile Asn Leu Arg Gly Ser
                405                 410                 415

Phe Asn Asp Asp Gln Lys Asp Ala Leu Tyr Tyr Asp Glu Ala Asn Arg
            420                 425                 430

Ile Trp Arg Lys Leu Glu Asn Ile Met His Asn Ile Lys Glu Phe Arg
        435                 440                 445

Gly Asn Lys Thr Arg Glu Tyr Lys Lys Lys Asp Ala Pro Arg Leu Pro
    450                 455                 460

Arg Ile Leu Pro Ala Gly Arg Asp Val Ser Ala Phe Ser Lys Leu Met
465                 470                 475                 480

Tyr Ala Leu Thr Met Phe Leu Asp Gly Lys Glu Ile Asn Asp Leu Leu
                485                 490                 495

Thr Thr Leu Ile Asn Lys Phe Asp Asn Ile Gln Ser Phe Leu Lys Val
            500                 505                 510

Met Pro Leu Ile Gly Val Asn Ala Lys Phe Val Glu Glu Tyr Ala Phe
        515                 520                 525

Phe Lys Asp Ser Ala Lys Ile Ala Asp Glu Leu Arg Leu Ile Lys Ser
    530                 535                 540

Phe Ala Arg Met Gly Glu Pro Ile Ala Asp Ala Arg Arg Ala Met Tyr
545                 550                 555                 560

Ile Asp Ala Ile Arg Ile Leu Gly Thr Asn Leu Ser Tyr Asp Glu Leu
                565                 570                 575

Lys Ala Leu Ala Asp Thr Phe Ser Leu Asp Glu Asn Gly Asn Lys Leu
            580                 585                 590

Lys Lys Gly Lys His Gly Met Arg Asn Phe Ile Ile Asn Asn Val Ile
        595                 600                 605

Ser Asn Lys Arg Phe His Tyr Leu Ile Arg Tyr Gly Asp Pro Ala His
    610                 615                 620

Leu His Glu Ile Ala Lys Asn Glu Ala Val Val Lys Phe Val Leu Gly
625                 630                 635                 640
```

-continued

```
Arg Ile Ala Asp Ile Gln Lys Lys Gln Gly Gln Asn Gly Lys Asn Gln
                645                 650                 655

Ile Asp Arg Tyr Tyr Glu Thr Cys Ile Gly Lys Asp Lys Gly Lys Ser
            660                 665                 670

Val Ser Glu Lys Val Asp Ala Leu Thr Lys Ile Ile Thr Gly Met Asn
        675                 680                 685

Tyr Asp Gln Phe Asp Lys Lys Arg Ser Val Ile Glu Asp Thr Gly Arg
    690                 695                 700

Glu Asn Ala Glu Arg Glu Lys Phe Lys Lys Ile Ile Ser Leu Tyr Leu
705                 710                 715                 720

Thr Val Ile Tyr His Ile Leu Lys Asn Ile Val Asn Ile Asn Ala Arg
                725                 730                 735

Tyr Val Ile Gly Phe His Cys Val Glu Arg Asp Ala Gln Leu Tyr Lys
            740                 745                 750

Glu Lys Gly Tyr Asp Ile Asn Leu Lys Lys Leu Glu Glu Lys Gly Phe
        755                 760                 765

Ser Ser Val Thr Lys Leu Cys Ala Gly Ile Asp Glu Thr Ala Pro Asp
    770                 775                 780

Lys Arg Lys Asp Val Glu Lys Glu Met Ala Glu Arg Ala Lys Glu Ser
785                 790                 795                 800

Ile Asp Ser Leu Glu Ser Ala Asn Pro Lys Leu Tyr Ala Asn Tyr Ile
                805                 810                 815

Lys Tyr Ser Asp Glu Lys Lys Ala Glu Glu Phe Thr Arg Gln Ile Asn
            820                 825                 830

Arg Glu Lys Ala Lys Thr Ala Leu Asn Ala Tyr Leu Arg Asn Thr Lys
        835                 840                 845

Trp Asn Val Ile Ile Arg Glu Asp Leu Leu Arg Ile Asp Asn Lys Thr
    850                 855                 860

Cys Thr Leu Phe Ala Asn Lys Ala Val Ala Leu Glu Val Ala Arg Tyr
865                 870                 875                 880

Val His Ala Tyr Ile Asn Asp Ile Ala Glu Val Asn Ser Tyr Phe Gln
                885                 890                 895

Leu Tyr His Tyr Ile Met Gln Arg Ile Ile Met Asn Glu Arg Tyr Glu
            900                 905                 910

Lys Ser Ser Gly Lys Val Ser Glu Tyr Phe Asp Ala Val Asn Asp Glu
        915                 920                 925

Lys Lys Tyr Asn Asp Arg Leu Leu Lys Leu Leu Cys Val Pro Phe Gly
    930                 935                 940

Tyr Cys Ile Pro Arg Phe Lys Asn Leu Ser Ile Glu Ala Leu Phe Asp
945                 950                 955                 960

Arg Asn Glu Ala Ala Lys Phe Asp Lys Glu Lys Lys Val Ser Gly
                965                 970                 975

Asn Ser Gly Ser Gly Pro Lys Lys Arg Lys Val Ala Ala Ala Tyr
            980                 985                 990

Pro Tyr Asp Val Pro Asp Tyr Ala  Ala Gly Ser Gly  Gly Gly Ser
        995                 1000                 1005

Met Ala  Ser Asn Phe Thr Gln  Phe Val Leu Val Asp  Asn Gly Gly
    1010                1015                1020

Thr Gly  Asp Val Thr Val Ala  Pro Ser Asn Phe Ala  Asn Gly Val
    1025                1030                1035

Ala Glu  Trp Ile Ser Ser Asn  Ser Arg Ser Gln Ala  Tyr Lys Val
    1040                1045                1050
```

```
Thr Cys Ser Val Arg Gln Ser Ser Ala Gln Lys Arg Lys Tyr Thr
    1055                1060                1065
Ile Lys Val Glu Val Pro Lys Val Ala Thr Gln Thr Val Gly Gly
1070                1075                1080
Val Glu Leu Pro Val Ala Ala Trp Arg Ser Tyr Leu Asn Met Glu
1085                1090                1095
Leu Thr Ile Pro Ile Phe Ala Thr Asn Ser Asp Cys Glu Leu Ile
1100                1105                1110
Val Lys Ala Met Gln Gly Leu Leu Lys Asp Gly Asn Pro Ile Pro
    1115                1120                1125
Ser Ala Ile Ala Ala Asn Ser Gly Ile Tyr
    1130                1135
```

<210> SEQ ID NO 97
<211> LENGTH: 3411
<212> TYPE: DNA
<213> ORGANISM: Artificial Sequence
<220> FEATURE:
<223> OTHER INFORMATION: MS2-dRfxCas13d nucleic acid sequence

<400> SEQUENCE: 97

| | | | | | |
|---|---|---|---|---|---|
| atggcttcaa | actttactca | gttcgtgctc | gtggacaatg | gtgggacagg | ggatgtgaca | 60 |
| gtggctcctt | ctaatttcgc | taatggggtg | gcagagtgga | tcagctccaa | ctcacggagc | 120 |
| caggcctaca | aggtgacatg | cagcgtcagg | cagtctagtg | cccagaagag | aaagtatacc | 180 |
| atcaaggtgg | aggtccccaa | agtggctacc | cagacagtgg | gcggagtcga | actgcctgtc | 240 |
| gccgcttgga | ggtcctacct | gaacatggag | ctcactatcc | caattttcgc | taccaattct | 300 |
| gactgtgaac | tcatcgtgaa | ggcaatgcag | gggctcctca | agacggtaa | tcctatccct | 360 |
| tccgccatcg | ccgctaactc | aggtatctac | ggatccggag | gagtggaag | cagccccaag | 420 |
| aagaagagaa | aggtggaggc | cagcatcgaa | aaaaaaagt | ccttcgccaa | gggcatgggc | 480 |
| gtgaagtcca | cactcgtgtc | cggctccaaa | gtgtacatga | caaccttcgc | cgaaggcagc | 540 |
| gacgccaggc | tggaaaagat | cgtggagggc | gacagcatca | ggagcgtgaa | tgagggcgag | 600 |
| gccttcagcg | ctgaaatggc | cgataaaaac | gccggctata | gatcggcaa | cgccaaattc | 660 |
| agccatccta | agggctacgc | cgtggtggct | aacaaccctc | tgtatacagg | accgtccag | 720 |
| caggatatgc | tcggcctgaa | ggaaactctg | gaaagaggt | acttcggcga | gagcgctgat | 780 |
| ggcaatgaca | atatttgtat | ccaggtgatc | cataacatcc | tggacattga | aaaaatcctc | 840 |
| gccgaataca | ttaccaacgc | cgcctacgcc | gtcaacaata | tctccggcct | ggataaggac | 900 |
| attattggat | tcggcaagtt | ctccacagtg | tatacctacg | acgaattcaa | agaccccgag | 960 |
| caccataggg | ccgctttcaa | caataacgat | aagctcatca | cgccatcaa | ggcccagtat | 1020 |
| gacgagttcg | acaacttcct | cgataacccc | agactcggct | atttcggcca | ggcctttttc | 1080 |
| agcaaggagg | gcagaaatta | tcatcatcaat | tacggcaacg | aatgctatga | cattctggcc | 1140 |
| ctcctgagcg | gactggcgca | ctgggtggtc | gctaacaacg | aagaagagtc | caggatctcc | 1200 |
| aggacctggc | tctacaacct | cgataagaac | ctcgacaacg | aatacatctc | caccctcaac | 1260 |
| tacctctacg | acaggatcac | caatgagctg | accaactcct | tctccaagaa | ctccgccgcc | 1320 |
| aacgtgaact | atattgccga | aactctggga | atcaaccctg | ccgaattcgc | cgaacaatat | 1380 |
| ttcagattca | gcattatgaa | agagcagaaa | aacctcggat | tcaatatcac | caagctcagg | 1440 |
| gaagtgatgc | tggacaggaa | ggatatgtcc | gagatcagga | aaaatcataa | ggtgttcgac | 1500 |
| tccatcagga | ccaaggtcta | caccatgatg | gactttgtga | tttataggta | ttacatcgaa | 1560 |

```
gaggatgcca aggtggctgc cgccaataag tccctccccg ataatgagaa gtccctgagc   1620
gagaaggata tctttgtgat taacctgagg ggctccttca acgacgacca gaaggatgcc   1680
ctctactacg atgaagctaa tagaatttgg agaaagctcg aaaatatcat gcacaacatc   1740
aaggaattta ggggaaacaa gacaagagag tataagaaga aggacgcccc tagactgccc   1800
agaatcctgc ccgctggccg tgatgtttcc gccttcagca aactcatgta tgccctgacc   1860
atgttcctgg atggcaagga gatcaacgac ctcctgacca ccctgattaa taaattcgat   1920
aacatccaga gcttcctgaa ggtgatgcct ctcatcggag tcaacgctaa gttcgtggag   1980
gaatacgcct ttttcaaaga ctccgccaag atcgccgatg agctgaggct gatcaagtcc   2040
ttcgctagaa tgggagaacc tattgccgat gccaggaggg ccatgtatat cgacgccatc   2100 cgtatttttag gaaccaacct gtcctatgat gagctcaagg ccctcgccga caccttttcc   2160
ctggacgaga acggaaacaa gctcaagaaa ggcaagcacg gcatgagaaa tttcattatt   2220
aataacgtga tcagcaataa aaggttccac tacctgatca gatacggtga tcctgcccac   2280
ctccatgaga tcgccaaaaa cgaggccgtg gtgaagttcg tgctcggcag gatcgctgac   2340
atccagaaaa aacagggcca gaacggcaag aaccagatcg acaggtacta cgaaacttgt   2400
atcggaaagg ataagggcaa gagcgtgagc gaaaaggtgg acgctctcac aaagatcatc   2460
accggaatga actacgacca attcgacaag aaaaggagcg tcattgagga caccggcagg   2520
gaaaacgccg agagggagaa gtttaaaaag atcatcagcc tgtacctcac cgtgatctac   2580
cacatcctca gaatattgtc caatatcaac gccaggtacg tcatcggatt ccattgcgtc   2640
gagcgtgatg ctcaactgta caaggagaaa ggctacgaca tcaatctcaa gaaactggaa   2700
gagaagggat tcagctccgt caccaagctc tgcgctggca ttgatgaaac tgccccgat   2760 aagagaaagg acgtggaaaa ggagatggct gaaagagcca aggagagcat tgacagcctc   2820
gagagcgcca ccccaagct gtatgccaat tacatcaaat acagcgacga gaagaaagcc   2880
gaggagttca ccaggcagat taacagggag aaggccaaaa ccgccctgaa cgcctacctg   2940
aggaacacca gtggaatgt gatcatcagg gaggacctcc tgagaattga caacaagaca   3000
tgtaccctgt tcgcaaacaa ggccgtcgcc ctggaagtgg ccaggtatgt ccacgcctat   3060
atcaacgaca ttgccgaggt caattcctac ttccaactgt accattacat catgcagaga   3120
attatcatga atgagaggta cgagaaaagc agcggaaagg tgtccgagta cttcgacgct   3180
gtgaatgacg agaagaagta caacgatagg ctcctgaaac tgctgtgtgt gcctttcggc   3240
tactgtatcc ccaggtttaa gaacctgagc atcgaggccc tgttcgatag aacgaggcc   3300 gccaagttcg acaaggagaa aaagaaggtg tccggcaatt ccggatccgg acctaagaaa   3360
aagaggaagg tggcggccgc ttacccatac gatgttccag attacgctgc t            3411
```

<210> SEQ ID NO 98  
<211> LENGTH: 1137  
<212> TYPE: PRT  
<213> ORGANISM: Artificial Sequence  
<220> FEATURE:  
<223> OTHER INFORMATION: MS2-dRfxCas13d amino acid sequence

<400> SEQUENCE: 98

```
Met Ala Ser Asn Phe Thr Gln Phe Val Leu Val Asp Asn Gly Gly Thr
1               5                  10                  15

Gly Asp Val Thr Val Ala Pro Ser Asn Phe Ala Asn Gly Val Ala Glu
            20                  25                  30
```

```
Trp Ile Ser Ser Asn Ser Arg Ser Gln Ala Tyr Lys Val Thr Cys Ser
            35                  40                  45

Val Arg Gln Ser Ser Ala Gln Lys Arg Lys Tyr Thr Ile Lys Val Glu
 50                  55                  60

Val Pro Lys Val Ala Thr Gln Thr Val Gly Gly Val Glu Leu Pro Val
 65                  70                  75                  80

Ala Ala Trp Arg Ser Tyr Leu Asn Met Glu Leu Thr Ile Pro Ile Phe
            85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
            115                 120                 125

Ile Tyr Gly Ser Gly Gly Gly Ser Ser Pro Lys Lys Lys Arg Lys
            130                 135                 140

Val Glu Ala Ser Ile Glu Lys Lys Lys Ser Phe Ala Lys Gly Met Gly
145                 150                 155                 160

Val Lys Ser Thr Leu Val Ser Gly Ser Lys Val Tyr Met Thr Thr Phe
            165                 170                 175

Ala Glu Gly Ser Asp Ala Arg Leu Glu Lys Ile Val Glu Gly Asp Ser
            180                 185                 190

Ile Arg Ser Val Asn Glu Gly Glu Ala Phe Ser Ala Glu Met Ala Asp
            195                 200                 205

Lys Asn Ala Gly Tyr Lys Ile Gly Asn Ala Lys Phe Ser His Pro Lys
            210                 215                 220

Gly Tyr Ala Val Val Ala Asn Asn Pro Leu Tyr Thr Gly Pro Val Gln
225                 230                 235                 240

Gln Asp Met Leu Gly Leu Lys Glu Thr Leu Glu Lys Arg Tyr Phe Gly
            245                 250                 255

Glu Ser Ala Asp Gly Asn Asp Asn Ile Cys Ile Gln Val Ile His Asn
            260                 265                 270

Ile Leu Asp Ile Glu Lys Ile Leu Ala Glu Tyr Ile Thr Asn Ala Ala
            275                 280                 285

Tyr Ala Val Asn Asn Ile Ser Gly Leu Asp Lys Asp Ile Ile Gly Phe
            290                 295                 300

Gly Lys Phe Ser Thr Val Tyr Thr Tyr Asp Glu Phe Lys Asp Pro Glu
305                 310                 315                 320

His His Arg Ala Ala Phe Asn Asn Asn Asp Lys Leu Ile Asn Ala Ile
            325                 330                 335

Lys Ala Gln Tyr Asp Glu Phe Asp Asn Phe Leu Asp Asn Pro Arg Leu
            340                 345                 350

Gly Tyr Phe Gly Gln Ala Phe Phe Ser Lys Glu Gly Arg Asn Tyr Ile
            355                 360                 365

Ile Asn Tyr Gly Asn Glu Cys Tyr Asp Ile Leu Ala Leu Leu Ser Gly
            370                 375                 380

Leu Ala His Trp Val Val Ala Asn Asn Glu Glu Ser Arg Ile Ser
385                 390                 395                 400

Arg Thr Trp Leu Tyr Asn Leu Asp Lys Asn Leu Asp Asn Glu Tyr Ile
            405                 410                 415

Ser Thr Leu Asn Tyr Leu Tyr Asp Arg Ile Thr Asn Glu Leu Thr Asn
            420                 425                 430

Ser Phe Ser Lys Asn Ser Ala Ala Asn Val Asn Tyr Ile Ala Glu Thr
            435                 440                 445

Leu Gly Ile Asn Pro Ala Glu Phe Ala Glu Gln Tyr Phe Arg Phe Ser
```

```
            450                 455                 460
Ile Met Lys Glu Gln Lys Asn Leu Gly Phe Asn Ile Thr Lys Leu Arg
465                 470                 475                 480

Glu Val Met Leu Asp Arg Lys Asp Met Ser Glu Ile Arg Lys Asn His
                    485                 490                 495

Lys Val Phe Asp Ser Ile Arg Thr Lys Val Tyr Thr Met Met Asp Phe
                500                 505                 510

Val Ile Tyr Arg Tyr Tyr Ile Glu Glu Asp Ala Lys Val Ala Ala Ala
                515                 520                 525

Asn Lys Ser Leu Pro Asp Asn Glu Lys Ser Leu Ser Glu Lys Asp Ile
            530                 535                 540

Phe Val Ile Asn Leu Arg Gly Ser Phe Asn Asp Asp Gln Lys Asp Ala
545                 550                 555                 560

Leu Tyr Tyr Asp Glu Ala Asn Arg Ile Trp Arg Lys Leu Glu Asn Ile
                565                 570                 575

Met His Asn Ile Lys Glu Phe Arg Gly Asn Lys Thr Arg Glu Tyr Lys
                580                 585                 590

Lys Lys Asp Ala Pro Arg Leu Pro Arg Ile Leu Pro Ala Gly Arg Asp
            595                 600                 605

Val Ser Ala Phe Ser Lys Leu Met Tyr Ala Leu Thr Met Phe Leu Asp
            610                 615                 620

Gly Lys Glu Ile Asn Asp Leu Leu Thr Thr Leu Ile Asn Lys Phe Asp
625                 630                 635                 640

Asn Ile Gln Ser Phe Leu Lys Val Met Pro Leu Ile Gly Val Asn Ala
                645                 650                 655

Lys Phe Val Glu Glu Tyr Ala Phe Phe Lys Asp Ser Ala Lys Ile Ala
                660                 665                 670

Asp Glu Leu Arg Leu Ile Lys Ser Phe Ala Arg Met Gly Glu Pro Ile
            675                 680                 685

Ala Asp Ala Arg Arg Ala Met Tyr Ile Asp Ala Ile Arg Ile Leu Gly
            690                 695                 700

Thr Asn Leu Ser Tyr Asp Glu Leu Lys Ala Leu Ala Asp Thr Phe Ser
705                 710                 715                 720

Leu Asp Glu Asn Gly Asn Lys Leu Lys Lys Gly Lys His Gly Met Arg
                725                 730                 735

Asn Phe Ile Ile Asn Asn Val Ile Ser Asn Lys Arg Phe His Tyr Leu
                740                 745                 750

Ile Arg Tyr Gly Asp Pro Ala His Leu His Glu Ile Ala Lys Asn Glu
            755                 760                 765

Ala Val Val Lys Phe Val Leu Gly Arg Ile Ala Asp Ile Gln Lys Lys
            770                 775                 780

Gln Gly Gln Asn Gly Lys Asn Gln Ile Asp Arg Tyr Tyr Glu Thr Cys
785                 790                 795                 800

Ile Gly Lys Asp Lys Gly Lys Ser Val Ser Glu Lys Val Asp Ala Leu
                805                 810                 815

Thr Lys Ile Ile Thr Gly Met Asn Tyr Asp Gln Phe Asp Lys Lys Arg
                820                 825                 830

Ser Val Ile Glu Asp Thr Gly Arg Glu Asn Ala Glu Arg Glu Lys Phe
            835                 840                 845

Lys Lys Ile Ile Ser Leu Tyr Leu Thr Val Ile Tyr His Ile Leu Lys
            850                 855                 860

Asn Ile Val Asn Ile Asn Ala Arg Tyr Val Ile Gly Phe His Cys Val
865                 870                 875                 880
```

```
Glu Arg Asp Ala Gln Leu Tyr Lys Glu Lys Gly Tyr Asp Ile Asn Leu
                885                 890                 895

Lys Lys Leu Glu Glu Lys Gly Phe Ser Ser Val Thr Lys Leu Cys Ala
            900                 905                 910

Gly Ile Asp Glu Thr Ala Pro Asp Lys Arg Lys Asp Val Glu Lys Glu
        915                 920                 925

Met Ala Glu Arg Ala Lys Glu Ser Ile Asp Ser Leu Glu Ser Ala Asn
    930                 935                 940

Pro Lys Leu Tyr Ala Asn Tyr Ile Lys Tyr Ser Asp Glu Lys Lys Ala
945                 950                 955                 960

Glu Glu Phe Thr Arg Gln Ile Asn Arg Glu Lys Ala Lys Thr Ala Leu
                965                 970                 975

Asn Ala Tyr Leu Arg Asn Thr Lys Trp Asn Val Ile Ile Arg Glu Asp
            980                 985                 990

Leu Leu Arg Ile Asp Asn Lys Thr Cys Thr Leu Phe Ala Asn Lys Ala
        995                 1000                1005

Val Ala Leu Glu Val Ala Arg Tyr Val His Ala Tyr Ile Asn Asp
    1010                1015                1020

Ile Ala Glu Val Asn Ser Tyr Phe Gln Leu Tyr His Tyr Ile Met
    1025                1030                1035

Gln Arg Ile Ile Met Asn Glu Arg Tyr Glu Lys Ser Ser Gly Lys
    1040                1045                1050

Val Ser Glu Tyr Phe Asp Ala Val Asn Asp Glu Lys Lys Tyr Asn
    1055                1060                1065

Asp Arg Leu Leu Lys Leu Leu Cys Val Pro Phe Gly Tyr Cys Ile
    1070                1075                1080

Pro Arg Phe Lys Asn Leu Ser Ile Glu Ala Leu Phe Asp Arg Asn
    1085                1090                1095

Glu Ala Ala Lys Phe Asp Lys Glu Lys Lys Val Ser Gly Asn
    1100                1105                1110

Ser Gly Ser Gly Pro Lys Lys Lys Arg Lys Val Ala Ala Ala Tyr
    1115                1120                1125

Pro Tyr Asp Val Pro Asp Tyr Ala Ala
    1130                1135

<210> SEQ ID NO 99
<211> LENGTH: 57
<212> TYPE: DNA
<213> ORGANISM: Artificial Sequence
<220> FEATURE:
<223> OTHER INFORMATION: dRfxCas13d gRNA

<400> SEQUENCE: 99
aacccctacc aactggtcgg ggtttgaaac cctgtggatg aagggacaca cacatgc      57

<210> SEQ ID NO 100
<211> LENGTH: 5059
<212> TYPE: DNA
<213> ORGANISM: Artificial Sequence
<220> FEATURE:
<223> OTHER INFORMATION: AAV2_ITR-CMV-dPspCas13b-MS2-bGHpA-AAV2_ITR

<400> SEQUENCE: 100
gctgcgcgct cgctcgctca ctgaggccgc ccgggcaaag cccgggcgtc gggcgacctt      60
tggtcgcccg gcctcagtga gcgagcgagc gcgcagagag ggagtggcca actccatcac     120 tagggggttcc ttgtagttaa tgattaaccc gccatgctac ttatctacgt agccatgctc    180
```

```
tagcgggaca ttgattattg actagttatt aatagtaatc aattacgggg tcattagttc     240
atagcccata tatggagttc cgcgttacat aacttacggt aaatggcccg cctggctgac     300
cgcccaacga cccccgccca ttgacgtcaa taatgacgta tgttcccata gtaacgccaa     360
tagggacttt ccattgacgt caatgggtgg agtatttacg gtaaactgcc cacttggcag     420
tacatcaagt gtatcatatg ccaagtacgc ccctattga cgtcaatgac ggtaaatggc      480
ccgcctggca ttatgcccag tacatgacct tatgggactt tcctacttgg cagtacatct     540
acgtattagt catcgctatt accatggtga tgcggttttg gcagtacatc aatgggcgtg     600
gatagcggtt tgactcacgg ggatttccaa gtctccaccc cattgacgtc aatgggagtt     660
tgttttggca ccaaaatcaa cgggactttc caaaatgtcg taacaactcc gccccattga     720
cgcaaatggg cggtaggcgt gtacggtggg aggtctatat aagcagagct ctctggctaa     780
ctagagaacc cactgcttac tggcttatcg aaattaatac gactcactat agggagaccc     840
aagctggcta gcgtttaaac ttaagcttgc caccatgaac atccccgctc tggtggaaaa     900
ccagaagaag tactttggca cctacagcgt gatggccatg ctgaacgctc agaccgtgct     960
ggaccacatc cagaaggtgg ccgatattga gggcgagcag aacgagaaca cgagaatct   1020 gtggtttcac cccgtgatga gccacctgta caacgccaag aacggctacg acaagcagcc    1080
cgagaaaacc atgttcatca tcgagcggct gcagagctac ttcccattcc tgaagatcat    1140
ggccgagaac cagagagagt acagcaacgg caagtacaag cagaaccgcg tggaagtgaa    1200
cagcaacgac atcttcgagg tgctgaagcg cgccttcggc gtgctgaaga tgtacaggga    1260
cctgaccaac gcatacaaga cctacgagga aaagctgaac gacggctgcg agttcctgac    1320
cagcacagag caacctctga gcggcatgat caacaactac tacacagtgg ccctgcggaa    1380
catgaacgag agatacggct acaagacaga ggacctggcc ttcatccagg acaagcggtt    1440
caagttcgtg aaggacgcct acggcaagaa aaagtcccaa gtgaataccg gattcttcct    1500
gagcctgcag gactacaacg cgacacaca gaagaagctg cacctgagcg gagtgggaat    1560
cgccctgctg atctgcctgt tcctggacaa gcagtacatc aacatctttc tgagcaggct    1620
gcccatcttc tccagctaca atgcccagag cgaggaacgg cggatcatca tcagatcctt    1680
cggcatcaac agcatcaagc tgcccaagga ccggatccac agcgagaagt ccaacaagag    1740
cgtggccatg gatatgctca acgaagtgaa gcggtgcccc gacgagctgt tcacaacact    1800
gtctgccgag aagcagtccc ggttcagaat catcagcgac gaccacaatg aagtgctgat    1860
gaagcggagc agcgacagat tcgtgcctct gctgctgcag tatatcgatt acggcaagct    1920
gttcgaccac atcaggttcc acgtgaacat gggcaagctg agatacctgc tgaaggccga    1980
caagacctgc atcgacggcc agaccagagt cagagtgatc gagcagcccc tgaacggctt    2040
cggcagactg gaagaggccg agacaatgcg gaagcaagag aacggcacct tcggcaacag    2100
cggcatccgg atcagagact tcgagaacat gaagcgggac gacgccaatc ctgccaacta    2160
tccctacatc gtggacacct acacacacta catcctggaa aacaacaagg tcgagatgtt    2220
tatcaacgac aaagaggaca gcgccccact gctgcccgtg atcgaggatg atagatacgt    2280
ggtcaagaca atccccagct gccggatgag cacccctgaa attccagcca tggccttcca    2340
catgtttctg ttcggcagca gaaaaccga aagctgatc gtggacgtgc acaaccggta    2400
caagagactt ttccaggcca tgcagaaaga agaagtgacc gccgagaata tcgccagctt    2460
cggaatcgcc gagagcgacc tgcctcagaa gatcctggat ctgatcagcg gcaatgccca    2520
```

```
cggcaaggat gtggacgcct tcatcagact gaccgtggac gacatgctga ccgacaccga    2580
gcggagaatc aagagattca aggacgaccg gaagtccatt cggagcgccg acaacaagat    2640
gggaaagaga ggcttcaagc agatctccac aggcaagctg gccgacttcc tggccaagga    2700
catcgtgctg tttcagccca gcgtgaacga tggcagaaac aagatcaccg gcctgaacta    2760
ccggatcatg cagagcgcca ttgccgtgta cgatagcggc gacgattacg aggccaagca    2820
gcagttcaag ctgatgttcg agaaggcccg gctgatcggc aagggcacaa cagagccctca   2880
tccatttctg tacaaggtgt cgcccgcag catccccgcc aatgccgtcg agttctacga    2940
gcgctacctg atcgagcgga agttctacct gaccggcctg tccaacgaga tcaagaaagg    3000
caacagagtg gatgtgccct tcatccggcg ggaccagaac aagtggaaaa caccgccat    3060
gaagaccctg gcagaatct acagcgagga tctgcccgtg aactgccca gacagatgtt    3120
cgacaatgag atcaagtccc acctgaagtc cctgccacag atggaaggca tcgacttcaa    3180
caatgccaac gtgacctatc tgatcgccga gtacatgaag agagtgctgg acgacgactt    3240
ccagacctto taccagtgga accgcaacta ccggtacatg gacatgctta agggcgagta    3300
cgacagaaag ggctccctgc agcactgctt caccagcgtg aagagagag aaggcctctg    3360
gaaagagcgg gcctccagaa cagagcgta cagaaagcag gccagcaaca agatccgcag    3420
caaccggcag atgagaaacg ccagcagcga agagatcgag acaatcctgg ataagcggct    3480
gagcaacagc cggaacgagt accagaaaag cgagaaagtg atccggcgct acagagtgca    3540
ggatgccctg ctgtttctgc tggccaaaaa gaccctgacc gaactggccg atttcgacgg    3600
cgagaggttc aaactgaaag aaatcatgcc cgacgccgag aagggaatcc tgagcgagat    3660
catgcccatg agcttcacct tcgagaaagg cggcaagaag tacaccatca ccagcgaggg    3720
catgaagctg aagaactacg gcgacttctt tgtgctggct agcgacaaga ggatcggcaa    3780
cctgctggaa ctcgtgggca gcgacatcgt gtccaaagag gatatcatgg aagagttcaa    3840
caaatacgac cagtgcaggc ccgagatcag ctccatcgtg ttcaacctgg aaaagtgggc    3900
cttcgacaca taccccgagc tgtctgccag agtggaccgg aagagaaagg tggacttcaa    3960
gagcatcctg aaaatcctgc tgaacaacaa gaacatcaac aaagagcaga gcgacatcct    4020
gcggaagatc cggaacgcct tcgatgcaaa caattacccc gacaaaggcg tggtggaaat    4080
caaggccctg cctgagatcg ccatgagcat caagaaggcc tttgggagt acgccatcat    4140
gaagggaagc ctgcagccaa agaagaagcg gaaggtcggt ggatccggag gaggtggaag    4200
catggcttca aactttactc agttcgtgct cgtggacaat ggtgggacag gggatgtgac    4260
agtggctcct tctaatttcg ctaatgggt ggcagagtgg atcagctcca actcacggag    4320
ccaggcctac aaggtgacat gcagcgtcag gcagtctagt gcccagaaga gaaagtatac    4380
catcaaggtg gaggtcccca agtggctac ccagacagtg ggcggagtcg aactgcctgt    4440
cgccgcttgg aggtcctacc tgaacatgga gctcactatc ccaattttcg ctaccaattc    4500
tgactgtgaa ctcatcgtga aggcaatgca ggggctcctc aaagacggta atcctatccc    4560
ttccgccatc gccgctaact caggtatcta ctaagcggcc gctcgagtct agagggcccg    4620
tttaaacccg ctgatcagcc tcgactgtgc cttctagttg ccagccatct gttgtttgcc    4680
cctcccccgt gccttccttg accctggaag gtgccactcc cactgtcctt tcctaataaa    4740
atgaggaaat tgcatcgcat tgtctgagta ggtgtcattc tattctgggg ggtgggggtgg    4800
ggcaggacac caagggggag gattgggaag acaatagcag gcatgctggg gatgcggtgg    4860
gctctatggt cgacatctag agcatggcta cgtagataag tagcatggcg ggttaatcat    4920
```

```
taactacaag gaaccccctag tgatggagtt ggccactccc tctctgcgcg ctcgctcgct    4980
cactgaggcc gggcgaccaa aggtcgcccg acgcccgggc tttgcccggg cggcctcagt    5040
gagcgagcga gcgcgcagc                                                 5059

<210> SEQ ID NO 101
<211> LENGTH: 7146
<212> TYPE: DNA
<213> ORGANISM: Artificial Sequence
<220> FEATURE:
<223> OTHER INFORMATION: 5'LTR-EFS-dPspCas13b-MS2-2a-Blast-WPRE-3'LTR

<400> SEQUENCE: 101
gggtctctct ggttagacca gatctgagcc tgggagctct ctggctaact agggaaccca      60
ctgcttaagc ctcaataaag cttgccttga gtgcttcaag tagtgtgtgc ccgtctgttg     120
tgtgactctg gtaactagag atccctcaga ccctttttagt cagtgtggaa aatctctagc    180
agtggcgccc gaacagggac ttgaaagcga aagggaaacc agaggagctc tctcgacgca    240
ggactcggct tgctgaagcg cgcacggcaa gaggcgaggg gcggcgactg gtgagtacgc    300
caaaaatttt gactagcgga ggctagaagg agagagatgg gtgcgagagc gtcagtatta    360
agcgggggag aattagatcg cgatgggaaa aaattcggtt aaggccaggg ggaaagaaaa    420
aatataaatt aaaacatata gtatgggcaa gcagggagct agaacgattc gcagttaatc    480
ctggcctgtt agaaacatca gaaggctgta gacaaatact gggacagcta caaccatccc    540
ttcagacagg atcagaagaa cttagatcat tatataatac agtagcaacc ctctattgtg    600
tgcatcaaag gatagagata aaagacacca aggaagcttt agacaagata gaggaagagc    660
aaaacaaaag taagaccacc gcacagcaag cggccgctga tcttcagacc tggaggagga    720
gatatgaggg acaattggag aagtgaatta tataaatata agtagtaaa aattgaacca    780 ttaggagtag cacccaccaa ggcaaagaga agagtggtgc agagagaaaa aagagcagtg    840
ggaataggag ctttgttcct tgggttcttg ggagcagcag gaagcactat gggcgcagcg    900
tcaatgacgc tgacggtaca ggccagacaa ttattgtctg gtatagtgca gcagcagaac    960
aatttgctga gggctattga ggcgcaacag catctgttgc aactcacagt ctggggcatc    1020
aagcagctcc aggcaagaat cctggctgtg gaaagatacc taaaggatca acagctcctg    1080
gggatttggg gttgctctgg aaaactcatt tgcaccactg ctgtgccttg gaatgctagt    1140
tggagtaata atctctggaa cagatttgg aatcacacga cctggatgga gtgggacaga    1200
gaaattaaca attacacaag cttaatacac tccttaattg aagaatcgca aaaccagcaa    1260
gaaaagaatg aacaagaatt attggaatta gataaatggg caagtttgtg gaattggttt    1320
aacataacaa attggctgtg gtatataaaa ttattcataa tgatagtagg aggcttggta    1380
ggtttaagaa tagttttttgc tgtactttct atagtgaata gagttaggca gggatattca    1440
ccattatcgt ttcagaccca cctcccaacc ccgaggggac ccgacaggcc cgaaggaata    1500
gaagaagaag gtggagagag agacagagac agatccattc gattagtgaa cggatcggca    1560
ctgcgtgcgc caattctgca gacaaatggc agtattcatc cacaatttta aaagaaaagg    1620
ggggattggg gggtacagtg caggggaaag aatagtagac ataatagcaa cagacataca    1680
aactaaagaa ttacaaaaac aaattacaaa aattcaaaat tttcgggttt attacaggga    1740
cagcagagat ccagtttggt taattaaggt accgaattcg ctagctaggt cttgaaagga    1800
gtgggaattg gctccggtgc ccgtcagtgg gcagagcgca catcgcccac agtccccgag    1860
```

-continued

```
aagttgggggg gaggggtcgg caattgatcc ggtgcctaga gaaggtggcg cggggtaaac    1920
tgggaaagtg atgtcgtgta ctggctccgc cttttcccg agggtggggg agaaccgtat     1980
ataagtgcag tagtcgccgt gaacgttctt tttcgcaacg ggtttgccgc cagaacacag    2040
gaccggttct agagcgctgc caccatgaac atccccgctc tggtggaaaa ccagaagaag    2100
tactttggca cctacagcgt gatggccatg ctgaacgctc agaccgtgct ggaccacatc    2160
cagaaggtgg ccgatattga gggcgagcag aacgagaaca acgagaatct gtggtttcac    2220
cccgtgatga gccacctgta caacgccaag aacggctacg acaagcagcc cgagaaaacc    2280
atgttcatca tcgagcggct gcagagctac ttcccattcc tgaagatcat ggccgagaac    2340
cagagagagt acagcaacgg caagtacaag cagaaccgcg tggaagtgaa cagcaacgac    2400
atcttcgagg tgctgaagcg cgccttcggc gtgctgaaga tgtacaggga cctgaccaac    2460
gcatacaaga cctacgagga aaagctgaac gacggctgcg agttcctgac cagcacagag    2520
caacctctga gcggcatgat caacaactac tacacagtgg ccctgcggaa catgaacgag    2580
agatacggct acaagacaga ggacctggcc ttcatccagg acaagcggtt caagttcgtg    2640
aaggacgcct acggcaagaa aaagtcccaa gtgaataccg gattcttcct gagcctgcag    2700
gactacaacg gcgacacaca gaagaagctg cacctgagcg gagtgggaat cgccctgctg    2760
atctgcctgt tcctggacaa gcagtacatc aacatctttc tgagcaggct gcccatcttc    2820
tccagctaca atgcccagag cgaggaacgg cggatcatca tcagatcctt cggcatcaac    2880
agcatcaagc tgcccaagga ccggatccac agcgagaagt ccaacaagag cgtggccatg    2940
gatatgctca acgaagtgaa gcggtgcccc gacgagctgt tcacaacact gtctgccgag    3000
aagcagtccc ggttcagaat catcagcgac gaccacaatg aagtgctgat gaagcggagc    3060
agcgacagat tcgtgcctct gctgctgcag tatatcgatt acggcaagct gttcgaccac    3120
atcaggttcc acgtgaacat gggcaagctg agatacctgc tgaaggccga caagacctgc    3180
atcgacggcc agaccagagt cagagtgatc gagcagcccc tgaacggctt cggcagactg    3240
gaagaggccg agacaatgcg gaagcaagag aacggcacct tcggcaacag cggcatccgg    3300
atcagagact tcgagaacat gaagcgggac gacgccaatc tgccaactg tccctacatc     3360 gtggacacct acacacacta catcctggaa aacaacaagg tcgagatgtt tatcaacgac    3420
aaagaggaca gcgcccact gctgcccgtg atcgaggatg atagatacgt ggtcaagaca    3480
atccccagct gccggatgag caccctggaa attccagcca tggccttcca catgtttctg    3540
ttcggcagca gaaaaccga gaagctgatc gtggacgtgc acaaccggta caagagactg    3600
ttccaggcca tgcagaaaga agaagtgacc gccgagaata tcgccagctt cggaatcgcc    3660
gagagcgacc tgcctcagaa gatcctggat ctgatcagcg gcaatgccca cggcaaggat    3720
gtggacgcct tcatcagact gaccgtggac gacatgctga ccgacaccga gcggagaatc    3780
aagagattca aggacgaccg gaagtccatt cggagcgccg acaacaagat gggaaagaga    3840
ggcttcaagc agatctccac aggcaagctg gccgacttcc tggccaagga catcgtgctg    3900
tttcagccca gcgtgaacga tggcgagaac aagatcaccg gcctgaacta ccggatcatg    3960
cagagcgcca ttgccgtgta cgatagcggc gacgattacg aggccaagca gcagttcaag    4020
ctgatgttcg agaaggcccg gctgatcggc aagggcacaa cagagcctca tccatttctg    4080
tacaaggtgt tcgcccgcag catccccgcc aatgccgtcg agttctacga gcgctacctg    4140
atcgagcgga agttctacct gaccggcctg tccaacgaga tcaagaaagg caacagagtg    4200
gatgtgccct tcatccggcg ggaccagaac aagtggaaaa cacccgccat gaagaccctg    4260
```

```
ggcagaatct acagcgagga tctgcccgtg aactgccca gacagatgtt cgacaatgag    4320
atcaagtccc acctgaagtc cctgccacag atggaaggca tcgacttcaa caatgccaac    4380
gtgacctatc tgatcgccga gtacatgaag agagtgctgg acgacgactt ccagaccttc    4440
taccagtgga accgcaacta ccggtacatg gacatgctta agggcgagta cgacagaaag    4500
ggctccctgc agcactgctt caccagcgtg aagagagag aaggcctctg gaaagagcgg    4560
gcctccagaa cagagcggta cagaaagcag gccagcaaca agatccgcag caaccggcag    4620
atgagaaacg ccagcagcga agagatcgag acaatcctgg ataagcggct gagcaacagc    4680
cggaacgagt accagaaaag cgagaaagtg atccggcgct acagagtgca ggatgccctg    4740
ctgtttctgc tggccaaaaa gaccctgacc gaactggccg atttcgacgg cgagaggttc    4800
aaactgaaag aaatcatgcc cgacgccgag aagggaatcc tgagcgagat catgcccatg    4860
agcttcacct tcgagaaagg cggcaagaag tacaccatca ccagcgaggg catgaagctg    4920
aagaactacg gcgacttctt tgtgctggct agcgacaaga ggatcggcaa cctgctggaa    4980
ctcgtgggca gcgacatcgt gtccaaagag gatatcatgg aagagttcaa caaatacgac    5040
cagtgcaggc ccgagatcag ctccatcgtg ttcaacctgg aaaagtgggc cttcgacaca    5100
taccccgagc tgtctgccag agtggaccgg gaagagaagg tggacttcaa gagcatcctg    5160
aaaatcctgc tgaacaacaa gaacatcaac aaagagcaga gcgacatcct gcggaagatc    5220
cggaacgcct tcgatgcaaa caattacccc gacaaggcg tggtggaaat caaggccctg    5280
cctgagatcg ccatgagcat caagaaggcc tttgggagt acgccatcat gaagggaagc    5340
ctgcagccaa agaagaagcg gaaggtcggt ggatccggag aggtggaag catggcttca    5400 aactttactc agttcgtgct cgtggacaat ggtgggacag gggatgtgac agtggctcct    5460
tctaatttcg ctaatggggt ggcagagtgg atcagctcca actcacggag ccaggcctac    5520
aaggtgacat gcagcgtcag gcagtctagt gcccagaaga gaaagtatac catcaaggtg    5580
gaggtcccca agtggctac ccagacagtg ggcggagtcg aactgcctgt cgccgcttgg    5640
aggtcctacc tgaacatgga gctcactatc ccaatttttcg ctaccaattc tgactgtgaa    5700
ctcatcgtga aggcaatgca ggggctcctc aaagacggta atcctatccc ttccgccatc    5760
gccgctaact caggtatcta cgcaacaaac ttctctctgc tgaaacaagc cggagatgtc    5820
gaagagaatc ctggaccgat ggccaagcct ttgtctcaag aagaatccac cctcattgaa    5880
agagcaacgg ctacaatcaa cagcatcccc atctctgaag actacagcgt cgccagcgca    5940
gctctctcta gcgacggccg catcttcact ggtgtcaatg tatatcattt tactggggga    6000
ccttgtgcag aactcgtggt gctgggcact gctgctgctg cggcagctgg caacctgact    6060
tgtatcgtcg cgatcggaaa tgagaacagg gcatcttga gccctgcgg acggtgccga    6120 caggtgcttc tcgatctgca tcctgggatc aaagccatag tgaaggacag tgatggacag    6180
ccgacggcag ttgggattcg tgaattgctg ccctctggtt atgtgtggga gggctaaacg    6240
cgttaagtcg acaatcaacc tctggattac aaaatttgtg aaagattgac tggtattctt    6300
aactatgttg ctccttttac gctatgtgga tacgctgctt taatgccttt gtatcatgct    6360
attgcttccc gtatggcttt catttttctc ctccttgtata aatcctggtt gctgtctctt    6420
tatgaggagt tgtggcccgt tgtcaggcaa cgtggcgtgg tgtgcactgt gtttgctgac    6480
gcaaccccca ctggttgggg cattgccacc acctgtcagc tccttccgg gactttcgct    6540 ttcccctcc ctattgccac ggcggaactc atcgccgcct gccttgcccg ctgctggaca    6600
```

-continued

| | | | | | |
|---|---|---|---|---|---|
| ggggctcggc | tgttgggcac | tgacaattcc | gtggtgttgt | cggggaaatc | atcgtcctt 6660 |
| ccttggctgc | tcgcctgtgt | tgccacctgg | attctgcgcg | ggacgtcctt | ctgctacgtc 6720 |
| ccttcggccc | tcaatccagc | ggaccttcct | tcccgcggcc | tgctgccggc | tctgcggcct 6780 |
| cttccgcgtc | ttcgccttcg | ccctcagacg | agtcggatct | cccctttgggc | cgcctccccg 6840 |
| cgtcgacttt | aagaccaatg | acttacaagg | cagctgtaga | tcttagccac | ttttttaaaag 6900 |
| aaaaggggg | actggaaggg | ctaattcact | cccaacgaag | acaagatctg | cttttttgctt 6960 |
| gtactgggtc | tctctggtta | gaccagatct | gagcctggga | gctctctggc | taactaggga 7020 |
| acccactgct | taagcctcaa | taaagcttgc | cttgagtgct | tcaagtagtg | tgtgcccgtc 7080 |
| tgttgtgtga | ctctggtaac | tagagatccc | tcagacccctt | ttagtcagtg | tggaaaatct 7140 |
| ctagca | | | | | 7146 |